(12) United States Patent
Van Voorhis et al.

(10) Patent No.: US 11,247,972 B2
(45) Date of Patent: Feb. 15, 2022

(54) COMPOSITIONS AND METHODS FOR TREATING TOXOPLASMOSIS, CRYPTOSPORIDIOSIS, AND OTHER APICOMPLEXAN PROTOZOAN RELATED DISEASES

(71) Applicant: University of Washington through its Center for Commercialization, Seattle, WA (US)

(72) Inventors: Wesley C. Van Voorhis, Seattle, WA (US); Wilhelmus G. J. Hol, Kenmore, WA (US); Eric T. Larson, Shoreline, WA (US); Dustin James Maly, Seattle, WA (US); Ethan Merritt, Seattle, WA (US); Kayode K. Ojo, Federal Way, WA (US)

(73) Assignee: University of Washington through its Center for Commercialization, Seattle, WA (US)

( * ) Notice: Subject to any disclaimer, the term of this patent is extended or adjusted under 35 U.S.C. 154(b) by 106 days.

(21) Appl. No.: 16/740,095

(22) Filed: Jan. 10, 2020

(65) Prior Publication Data
US 2020/0223803 A1    Jul. 16, 2020

Related U.S. Application Data

(60) Continuation of application No. 15/686,839, filed on Aug. 25, 2017, now Pat. No. 10,544,104, which is a division of application No. 13/561,896, filed on Jul. 30, 2012, now Pat. No. 9,765,037, which is a continuation-in-part of application No. PCT/US2011/023047, filed on Jan. 28, 2011.

(60) Provisional application No. 61/534,285, filed on Sep. 13, 2011, provisional application No. 61/358,045, filed on Jun. 24, 2010, provisional application No. 61/299,286, filed on Jan. 28, 2010.

(51) Int. Cl.
| | | |
|---|---|---|
| *C07D 235/30* | (2006.01) | |
| *C07D 403/12* | (2006.01) | |
| *C07D 401/12* | (2006.01) | |
| *C07D 235/32* | (2006.01) | |
| *C07D 487/04* | (2006.01) | |

(52) U.S. Cl.
CPC ......... *C07D 235/30* (2013.01); *C07D 235/32* (2013.01); *C07D 401/12* (2013.01); *C07D 403/12* (2013.01); *C07D 487/04* (2013.01); *Y02A 50/30* (2018.01)

(58) Field of Classification Search
None
See application file for complete search history.

(56) References Cited

U.S. PATENT DOCUMENTS

2006/0084654 A1    4/2006    Beck et al.
2006/0235031 A1    10/2006   Arnold et al.

FOREIGN PATENT DOCUMENTS

| WO | 02/076986 A1 | 10/2002 | |
|---|---|---|---|
| WO | WO-2005097800 A1 * | 10/2005 | ............... A61P 3/10 |
| WO | 06/068760 A2 | 6/2006 | |
| WO | 07/061737 A2 | 5/2007 | |
| WO | 08/066755 A2 | 6/2008 | |
| WO | 10/006086 A2 | 1/2010 | |

OTHER PUBLICATIONS

Samie et al., Exp.Parasitol. 114, 314-322 (2006).
Ajjampur et al., J. Med. Microbiol. 57, 1364-1368 (2008).
Billker et al., Cell Host Microbe. Jun. 18, 2009;5(6):612-22.
Doerig et al., Biophysica et Biochimica Acta—Proteins and Proteomics 1754, 132-150 (2005).
Kieschnick et al., J. Biol. Chem. 276, 12369-12377 (2001).
Chen et al., Infect. Immun. 72, 6806-16 (2004).
Apsel et al. Nat Chem Biol. (2008); 4(11):691-9.
Bishop, et al. (1999) Journal of the American Chemical Society, 121(4): 627-631.
Ojo, et al., (2010) Nature Structural and Molecular Biology, 17(5): 602-607.
Lourido, et al. (2010) Nature, 465(7296): 359-362.
ISR for PCT/US11/23047, dated Jun. 8, 2011.
Montoya, et al. Principles and Practice of Infectious Diseases. Chapter 276 Mandell,B.&.D. (ed.) (Churchill Livingston, 2005).

(Continued)

*Primary Examiner* — Jeffrey S Lundgren
*Assistant Examiner* — Michael J Schmitt
(74) *Attorney, Agent, or Firm* — McDonnell Boehnen Hulbert & Berghoff LLP

(57) ABSTRACT

Compositions and methods for the treatment of toxoplasmosis, caused by the infectious eukaryotic parasite *Toxoplasma gondii* (*T. gondii*) and for the treatment of cryptosporidiosis, caused by the infectious eukaryotic parasites *Cryptosporidium parvum* (*C. parvum*) and *Cryptosporidium hominus* (*C. hominus*) are described. In particular, the present disclosure is directed to compositions and methods for inhibiting either *T. gondii* calcium dependent protein kinases (TgCDPKs) or *C. parvum* and *C. hominus* calcium dependent protein kinases (CpCDPKs) using pyrazolopyrimidine and/or imidazo[1,5-a]pyrazine inhibitors, of the formula,

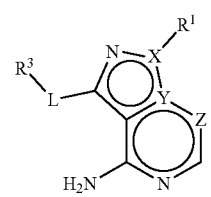

wherein the variables X, Y, Z, L, $R^1$, and $R^3$ are defined herein.

22 Claims, 26 Drawing Sheets

Specification includes a Sequence Listing.

(56) References Cited

OTHER PUBLICATIONS

Mead,P.S. et al., Emerging Infectious Diseases 5, 607-625 (1999).
Baril, L. et al. Scandinavian Journal of Infectious Diseases 31, 305-309 (1999).
Jones,J.L. et al. American Journal of Epidemiology 154, 357-365 (2001).
Wallace,M.R., et al. Jama-Journal of the American Medical Association 269, 76-77 (1993).
Vastava,P.B. et al. Neuroradiology 44, 834-838 (2002).
Hermentin,K., et al. Zentralblatt fur Bakteriologie Mikrobiologie und Hygiene Series A—Medical Microbiology Infectious Diseases Virology Parasitology 270, 534-541 (1989).
Bach,M.C, et al. Archives of Neurology 40, 596-597 (1983).
Pelphrey,P.M. et al. Journal of Medicinal Chemistry 50, 940-950 (2007).
Dannemann,B. et al. Annals of Internal Medicine 116, 33-43 (1992).
Jacobson et al. Antimicrobial Agents and Chemotherapy 40, 1360-1365 (1996).
Nagamune,K. & Sibley,L.D. Mol. Biol. Evol. 23, 1613-1627 (2006).
Lovett,J.L. & Sibley,L.D. Journal of Cell Science 116, 3009-3016 (2003).
Canduri.F., et al. Current Drug Targets 8, 389-398 (2007).
Harper,J.F. & Harmon,A. Nature Reviews Molecular Cell Biology 6, 555-566 (2005).
Raichaudhuri,A., et al. J. Biol. Chem. 281, 10399-10409 (2006).
Noble,M.E., et al. Science 303, 1800-1805 (2004).
Knight,Z.A. & Shokat,K.M. Chemistry & Biology 12, 621-637 (2005).
Cohen,M.S., et al. Science 308, 1318-1321 (2005).
Liao,J.J.. J. Med. Chem. 50, 409-424 (2007).
Bishop,A.C. et al. Nature 407, 395-401 (2000).
Zhang,C. et al. Nat. Methods 2, 435-441 (2005).
Bishop,A.C., et al. Trends Cell Biol. 11, 167-172 (2001).
Johnson,A.W. et al. European Journal of Neuroscience 28, 997-1002 (2008).
Morgan,D.J. et al. Proceedings of the National Academy of Sciences of the United States of America 105, 20740-20745 (2008).
Chen,X. et al. Neuron 46, 13-21 (2005).
Ojo,K.K. et al. Antimicrob. Agents Chemother. 52, 3710-3717 (2008).
Newman,J. et al. Acta Crystallographica Section D-Biological Crystallography 61, 1426-1431 (2005).
Cohen,A.E., et al. Journal of Applied Crystallography 35, 720-726 (2002).
McPhillips,T.M. et al.Journal of Synchrotron Radiation 9, 401-406 (2002).
Hendrickson,W.A., et al. Embo Journal 9, 1665-1672 (1990).
Otwinowski,Z. & Minor,W. Macromolecular Crystallography, Pt A 276, 307-326 (1997).
Vagin,A. & Teplyakov,A. Journal of Applied Crystallography 30, 1022-1025 (1997).
Mccoy,A.J. et al. Journal of Applied Crystallography 40, 658-674 (2007).
Terwilliger,T. Journal of Synchrotron Radiation 11, 49-52 (2004).
Emsley,P. & Cowtan,K. Acta Crystallographica Section D-Biological Crystallography 60, 2126-2132 (2004).
Murshudov,G.N., et al. Acta Crystallographica Section D Biological Crystallography 53, 240-255 (1997).
Cohen,S.X. et al. Acta Crystallographica Section D-Biological Crystallography 64, 49-60 (2008).
Schuttelkopf,et al. Acta Crystallographica Section D Biological Crystallography 60,1355-1363 (2004).
Painter,J. & Merritt,E.A. Acta Crystallographica Section DBiological Crystallography 62, 439-450 (2006).
Painter,J. & Merritt,E.A. Journal of Applied Crystallography 39, 109-111 (2006).
Lovell,S.C. et al. Proteins-Structure Function and Genetics 50, 437-450 (2003).
Bailey,S. Acta Crystallographica Section D-Biological Crystallography 50, 760-763 (1994).
Potterton,E., et al. Acta Crystallographica Section D-Biological Crystallography 59, 1131-1137 (2003).
Berman,H.M. et al. Nucleic Acids Research 28, 235-242 (2000).
Matrajt,M., et al. Molecular and Biochemical Parasitology 120, 285-289 (2002).
Striepen,B., et al. Molecular and Biochemical Parasitology 92, 325-338 (1998).
DeRocher,A., et al. Journal of Cell Science 113, 3969-3977 (2000).
Kamataki,A. et al. Molecular Microbiology 63, 1653-1668 (2007).
Fruth,I.A. & Arrizabalaga,G. International Journal for Parasitology 37, 1559-1567 (2007).
Seeber, F. & Boothroyd,J.C. Gene 169, 39-45 (1996).
White AC. Chapter 280: Cryptosporidiosis (Cryptosporidium hominis, Cryptosporidium parvum, and Other Species) in Mandell, Bennett, & Dolin: Principles and Practice of Infectious Diseases, 6th ed. Publ: Churchill Livingston (2005).
Sugi T, et al. Eukaryot. Cell 9, 667-70. (2010).
Bishop, A.C. et al. Curr. Biol. 8, 257-266 (1998).
Burchat AF, et al. Bioorg. Med. Chem. Lett., 12, 1687-1690 (2002).
Valeur, E, et al. Tet. Lett. 49, 4182-4185 (2008).
Hanke JH, et al. J. Biol. Chem., 271, 695-701 (1996).
Castellanos-Gonzalez, A, et al. J. Infect. Dis. 2008, 197, 916-923.
Gajria, B, et al. Nucleic Acids Res. 2008, 36, D553-D556.
Puiu, D, et al.Nucleic Acids Res. 2004, 32, D329-31.
Wernimont, et al. Nat. Struct. Mol. Biol. Published online May 2, 2010, (DOI. 10.1038/nsmb.1795).
Leslie, A. Acta Crystallogr., Sect. D: Biol. Crystallogr. 2006, 62, 48-57.
Evans, P. Acta Crystallogr., Sect. D: Biol. Crystallogr. 2006, 62, 72-82.
Emsley, P, et al. Acta Crystallogr., Sect. D: Biol. Crystallog. 2010, 66, 486-501.

* cited by examiner

| Species | | | | |
|---|---|---|---|---|
| T. gondii (GI:124841183) | TgCDPK1 | 122 | gyFTLVGeVYtGGELPDEI | 140 SEQ ID NO: 1 |
| C. parvum (GI:126644493) | CpCDPK1 | 146 | ssFTIVGeLYtGGELPDEI | 164 SEQ ID NO: 2 |
| T. gondii (GI:77022110) | TgCDPK3 | 147 | tnYTLVMeVYtGGELPDEI | 165 SEQ ID NO: 5 |
| E. tenella (GI:77022114) | EtCDPK1 | 117 | gyFTLVTeVYtGGELPDEI | 135 SEQ ID NO: 6 |
| P. falciparum (GI:504018306) | PfCDPK1 | 139 | kyFTLVTeFYmGGELPDQI | 157 SEQ ID NO: 7 |
| P. falciparum (GI:23498846) | PfCDPK4 | 141 | nyYTLVSdVYtGGELPDRI | 159 SEQ ID NO: 8 |
| Human (GI:4502653) | HsCDPK1 | 89 | ghLYLIMQlVYSGGELPDRI | 107 SEQ ID NO: 9 |
| X. tropicalis (GI:213608749) | XtCDPK | 83 | gfHYLVFDlVtGGELPEDI | 101 SEQ ID NO: 10 |
| M. mulatta (GI:109075456) | MmCDPK | 84 | gfHYLVFDlVtGGELPEDI | 102 SEQ ID NO: 11 |

Figure 2b

|  | NA-PP2 (nM) | intra-cellular | total | host cells |
|---|---|---|---|---|
| *CDPK1* | 0 | 164 | 467 | 471 |
| *CDPK1* | 10 | 29 | 187 | 487 |
| *CDPK1* | 1000 | 6 | 70 | 395 |
| *CDPK1 (G128M)* | 0 | 74 | 333 | 419 |
| *CDPK1 (G128M)* | 10 | 71 | 332 | 447 |
| *CDPK1 (G128M)* | 1000 | 36 | 191 | 424 |
| *GFP* | 0 | 181 | 637 | 328 |
| *GFP* | 1000 | 7 | 78 | 419 |

*Figure 10c*

| Wild type plus: | NA-PP2 (µM) | GFP+ | GFP- | host cells |
|---|---|---|---|---|
| CDPK1 | 0 | 117 | 122 | 197 |
| CDPK1 | 1 | 25 | 15 | 191 |
| CDPK1(G128M) | 0 | 104 | 113 | 174 |
| CDPK1(G128M) | 1 | 113 | 21 | 200 |
| GFP | 0 | 105 | 172 | 189 |
| GFP | 1 | 14 | 19 | 280 |

*Figure 11c*

COMPOSITIONS AND METHODS FOR TREATING TOXOPLASMOSIS, CRYPTOSPORIDIOSIS, AND OTHER APICOMPLEXAN PROTOZOAN RELATED DISEASES

CROSS-REFERENCE TO RELATED APPLICATIONS

This application is a continuation of U.S. application Ser. No. 15/686,839, filed Aug. 25, 2017, which is a divisional application of U.S. application Ser. No. 13/561,896, filed Jul. 30, 2012, which is a continuation-in-part of the International Application Serial No. PCT/US11/23047, filed on Jan. 28, 2011, which claims the benefit of the filing dates of U.S. Provisional Patent Application Ser. No. 61/299,286, filed Jan. 28, 2010, and U.S. Provisional Patent Application Ser. No. 61/358,045, filed Jun. 24, 2010, and also claims the benefit of the filing date of U.S. Provisional Patent Application Ser. No. 61/534,285 filed Sep. 13, 2011, each of which are hereby incorporated by reference in their entirety.

STATEMENT OF GOVERNMENT SUPPORT

This invention was made with government support under P01 AI067921, R01 AI080625, R01 AI050506, R01 AI089441, and R01 GM086858 awarded by The National Institutes of Health. The government has certain rights in the invention.

FIELD OF THE INVENTION

The present disclosure is generally directed to compositions and methods for treating apicomplexan protozoan related disease, such as toxoplasmosis and cryptosporidiosis.

BACKGROUND OF THE INVENTION

The apicomplexan protozoans *Cryptosporidium parvum* and *Toxoplasma gondii* are ubiquitous parasites that infect humans and domesticated animals. Recently *C. hominus* was recognized to be distinct from *C. parvum*, and does not appear to infect domesticated animals, but rather appears limited to human infections. *C. parvum* and *C. hominus* are infectious parasites of major health concern in humans as they are a common cause of illness transmitted by water. (See White A C. Chapter 280: Cryptosporidiosis (*Cryptosporidium hominis, Cryptosporidium parvum*, and Other Species) in Mandell, Bennett, & Dolin: Principles and Practice of Infectious Diseases, 6th ed. Publ: Churchill Livingston (2005)) *C. parvum* and *C. hominus* infections result in debilitating diarrhea that can be life-threatening in immunocompromised patients.

Recent studies have implicated *Cryptosporidium* spp. in around 15-20% of childhood diarrheal disease in the developing world. (See Samie et al., *Cryptosporidium* species: preliminary descriptions of the prevalence and genotype distribution among school children and hospital patients in the Venda region, Limpopo Province, South Africa. *Exp. Parasitol.* 114, 314-322 (2006); and Ajjampur et al., Closing the diarrhea diagnostic gap in Indian children by the application of molecular techniques. *J. Med. Microbiol.* 57, 1364-1368 (2008)) Currently, nitazoxanide is the only approved therapy for cryptosporidiosis but it is expensive and has not been shown to be effective in treating immunocompromised hosts. *T. gondii* may be the most common infectious eukaryotic parasite in humans, based on serosurveys. (See Montoya et al., Chapter 276: *Toxoplasma gondii* in Mandell, Bennett, &Dolin: Principles and Practice of Infectious Diseases, 6th ed. Publ: Churchill Livingston (2005)) Transmitted primarily through undercooked meat or accidental ingestion of cat feces, *T. gondii* infection presents major health concerns in immunocompromised hosts, where it causes toxoplasmic encephalitis, and in pregnancy, where it can result in severe birth defects or miscarriage. Sulfadiazine and pyrimethamine are the current therapies for toxoplasmosis, but they can cause nephrotoxicity, rash, and additional complications in pregnancy. Thus, new therapies for treating infections caused by both parasites are greatly needed.

In *T. gondii*, calcium-regulated signaling is associated with a number of cellular functions such as secretion, gliding motility and host cell invasion. (See Nagamune and Sibley, Comparative genomic and phylogenetic analyses of calcium ATPases and calcium-regulated proteins in the apicomplexa. *Mol. Biol. Evol.* 23, 1613-1627 (2006); and Billker et al., Cell Host Microbe. 2009 Jun. 18; 5(6):612-22. Calcium-dependent signaling and kinases in apicomplexan parasites) The proper control of intracellular calcium levels is important for host cell invasion and *T. gondii* use several mechanisms for the uptake and release of calcium. Furthermore, this organism contains specialized calcium-regulated signaling enzymes, including a unique family of calcium-dependent protein kinases (CDPKs) which are present in plants, ciliates and green algae but not in animals. (See Doerig et al., Protein kinases as targets for antimalarial intervention: kinomics, structure-based design, transmission-blockade, and targeting host cell enzymes. *Biophysica et Biochimica Acta—Proteins and Proteomics* 1754, 132-150 (2005)) These kinases are believed to be mediators of secretion, invasion, and gliding motility. (See Nagamune and Sibley L D, supra; Billker et al., supra; and Kieschnick et al., C. *Toxoplasma gondii* attachment to host cells is regulated by a calmodulin-like domain protein kinase. *J. Biol. Chem.* 276, 12369-12377 (2001)) *T. gondii, C. parvum*, and *C. hominus* are highly related obligate intracellular parasites. While much less is known about the role of calcium signaling in *C. parvum* and *C. hominus*, it appears that many calcium-regulated signaling processes are conserved from *T. gondii* to *C. parvum*. (See Chen et al., Apical Organelle discharge by *Cryptosporidium parvum* is temperature, cytoskeleton, and intracellular calcium dependent and required for host cell invasion. *Infect. Immun.* 72, 6806-16 (2004)) *C. parvum* and *C. hominus* also possess CDPKs that are believed to play important roles in calcium-regulated processes and they are virtually identical in these two spp. Thus inhibitors of *C. parvum* CDPKs would be expected to inhibit *C. hominus* CDPK.

The roles that CDPKs play in calcium signaling in *T. gondii, C. parvum* and *C. hominus* make this family of kinases intriguing targets for the development of anti-parasitic agents.

SUMMARY OF THE INVENTION

The present disclosure is generally directed to compositions and methods for the treatment of apicomplexan-related disorders, including but not limited to toxoplasmosis, caused by the infectious eukaryotic parasite *Toxoplasma gondii* (*T. gondii*), cryptosporidiosis, caused by the infectious eukaryotic parasites *Cryptosporidium parvum* (*C. parvum*) and *Cryptosporidium hominus* (*C. hominus*), and malaria, caused by the eukaryotic parasites *Plasmodium falciparum*

(*P. falciparum*) and *Plasmodium berghei* (*P. berghei*). In one embodiment, the present disclosure is directed to compositions and methods for inhibiting apicomplexan calcium dependent protein kinases, including but not limited to *T. gondii* calcium dependent protein kinases (TgCDPKs), *C. parvum* and *C. hominus* calcium dependent protein kinases (CpCDPKs), or *P. falciparum* and *P. berghei* calcium dependent protein kinase 4 (PfCDPKs) using pyrazolopyrimidine inhibitors, or in another embodiment, Imidazo[1,5-a]pyrazine inhibitors, both classes of compounds designed to be inactive against mammalian kinases.

In one aspect, the present disclosure provides compounds of the formula (I),

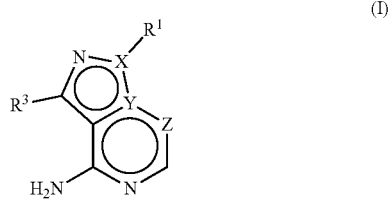

(I)

and pharmaceutically acceptable salts thereof, wherein $R^1$, $R^3$, X, Y, and Z are defined herein.

In another aspect, the present disclosure provides methods for treating an apicomplexan protozoan related disease comprising providing to a patient in need of such treatment a therapeutically effective amount of either (i) a bumped kinase inhibitor or (ii) a pharmaceutical composition comprising a bumped kinase inhibitor and a pharmaceutically acceptable excipient, carrier, or diluent.

In another aspect, the present disclosure provides methods for treating an apicomplexan protozoan related disease comprising providing to a patient in need of such treatment a therapeutically effective amount of either (i) a bumped kinase inhibitor or (ii) a pharmaceutical composition comprising a bumped kinase inhibitor and a pharmaceutically acceptable excipient, carrier, or diluent.

In another aspect, the present disclosure provides methods for treating an apicomplexan protozoan related disease comprising providing to a patient in need of such treatment a therapeutically effective amount of either a compound of formula (II) or (ii) a pharmaceutical composition comprising a compound of formula (II) and a pharmaceutically acceptable excipient, carrier, or diluent, wherein the compound of formula (II) is

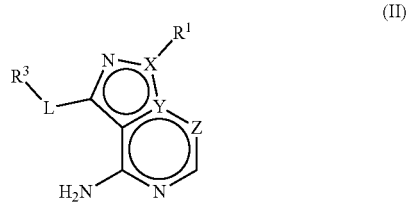

(II)

wherein $R^1$, $R^3$, L, X, Y, and Z are defined herein.

One aspect of the present disclosure provides a method of treating malaria comprising administering to a subject an effective amount of any one of compounds of the disclosure that inhibits the activity of *P. falciparum* and *P. berghei* calcium dependent protein kinase 4 (PfCDPK4).

BRIEF DESCRIPTION OF THE DRAWINGS

FIGS. 2a-2e are graphical representations of the crystal structure of calcium-free TgCDPK1. FIG. 2a: Association of the kinase domain (green) and the calmodulin-like calcium regulatory domain (orange) buries approximately 1400 $Å_2$ of accessible surface area per domain. The junction domain, connecting the kinase and regulatory domains, is shown in brown. This interaction surface between kinase and regulatory domains is entirely lost during the transition to the $Ca^{2+}$-bound form in which the regulatory domain relocates to lie along the opposite surface of the kinase domain [Wernimont et al. submitted for publication, PDB accession number 3hx4], the left side in the orientation shown. The active site is shown with bound inhibitor, NA-PP2 (magenta). FIG. 2b: Comparative analysis of the ATP binding pocket of kinases reveals the presence of a glycine in the position of the gatekeeper residue (bold) in TgCDPK1 and a *C. parvum* CDPK1 ortholog. Medium-sized side chains, threonine and serine, are found at this position in other apicomplexan CDPKs, *E. tenella* (EtCDPK1) and *P. falciparum* (PfCDPK1 and PfCDPK4). Animal CDPKs tend to have large gatekeeper residues such as phenylalanine. FIG. 2c and FIG. 2d: Stereo view of the active site with the bumped kinase inhibitors NA-PP2 (2c) and NM-PP1 (2d) bound. The orientation is as in panel 1a. Residues within 6 Å of the inhibitor are shown as sticks. The unusual glycine gatekeeper residue that permits inhibition by bumped kinase inhibitors is highlighted in cyan. Difference electron density, contoured at +3.5 σ (green mesh) and −3.5 σ (pink mesh), was calculated after omission of the inhibitor. FIG. 2e: TgCDPK1 active site in the vicinity of the gatekeeper residue. The surface of TgCDPK1 is shown in white and is slabbed through to show the adenine pocket of the ATP-binding site. The glycine at the gatekeeper position of TgCDPK1 enlarges the active site pocket and facilitates binding of bumped kinase inhibitors (NA-PP2 is magenta sticks and NM-PP1 is violet sticks). Larger amino acids, such as Met shown here (brown sticks and protruding surface) from superposition of a *C. parvum* ortholog (PDB ID 3hko; bound AMP-PNP shown as brown sticks) are more typical at this gatekeeper position, and prevent binding of compounds with large, hydrophobic "bumps" on the adenine ring. This is apparent by the brown surface protrusion of the Met clearly clashing with the "bump" of each of the BKIs in our crystal structures.

FIG. 10c shows the data used to derive the graph in FIG. 8(b). Note that cells expressing the gatekeeper mutant CDPK1(G128M) are less sensitive to the drug. The drug additionally appears to affect adhesion.

FIG. 11c shows the data used to derive the graphs. Note that the parasite line overexpressing CDPK1(G128M)-GFP was resistant to the effects of 1 μM NA-PP2, as compared to the co-cultured wild type control.

DETAILED DESCRIPTION OF THE INVENTION

Figure 1:
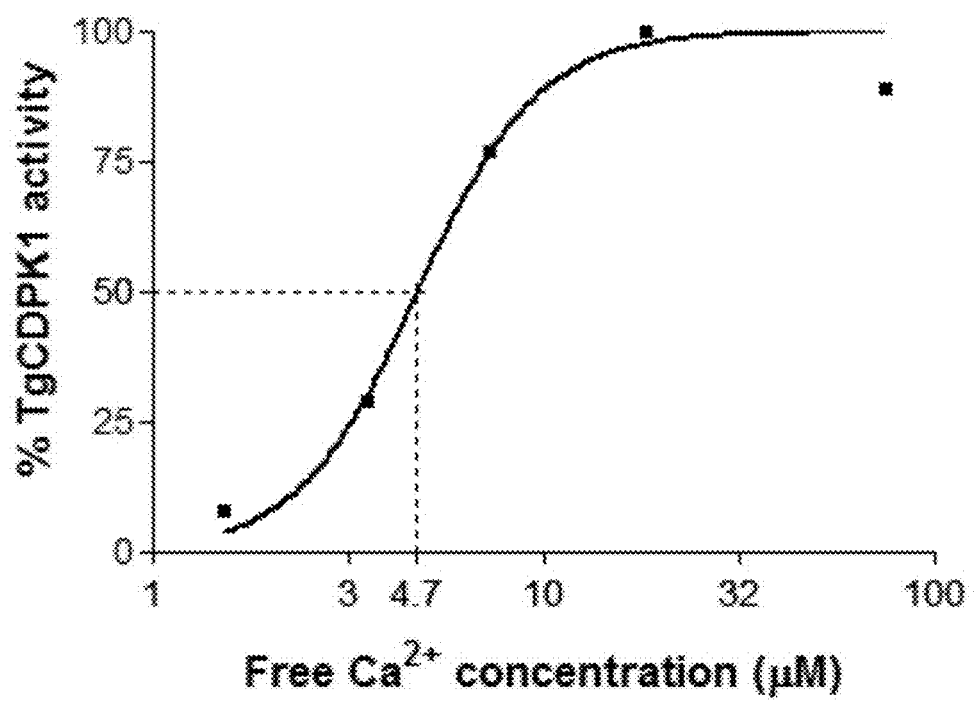
FIG. 1 is a graphical representation of calcium-dependence of TgCDPK1 activity. Enzyme activity was measured at a constant concentration of 0.5 mM EGTA with increasing concentrations of $CaCl_2$ using the luciferase based assay format. The precise quantity of free $Ca^{2+}$ was determined by measuring fluorescence intensity of Fluo-3 and Calcium green dyes (Invitrogen Corp. Carlsbad, USA) in the reaction buffer at excitation and emission wave lengths of 506 and 526 nM (Fluo-3) and 503 and 532 nM (Calcium green). No activity was observed with equimolar concentrations of EGTA and $CaCl_2$ (0 free $Ca^{2+}$) but significant kinase activity was observed by gradually increasing the $CaCl_2$ concentration in the mixture. The reaction reached maximal activity at approximately 18 μM free $CaCl_2$.

The following description provides specific details for a thorough understanding of, and enabling description for, embodiments of the disclosure. However, one skilled in the art will understand that the disclosure may be practiced without these details. In other instances, well-known structures and functions have not been shown or described in detail to avoid unnecessarily obscuring the description of the embodiments of the disclosure.

In one aspect, the present disclosure provides compounds of the formula (I),

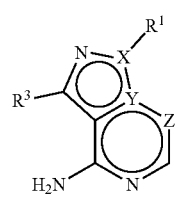
(I)

or a pharmaceutically acceptable salt thereof, wherein X, Y, and Z are defined by either: (i) X is N, Y is C, and Z is N; or (ii) X is C, Y is N, and Z is C(H);

$R^1$ is $C_{2-6}$ alkyl, $C_{1-6}$ haloalkyl, $-C_{1-4}$ alkyl-$R^{12}$, $C_{2-6}$ alkenyl, $C_{2-6}$ alkynyl, $C_{3-8}$ cycloalkyl, monocyclic heterocyclyl, monocyclic heteroaryl, or phenyl, wherein
the cycloalkyl, heterocyclyl, heteroaryl, and phenyl groups are each optionally substituted with one or two $R^{11}$ groups;

each $R^{11}$ is independently $C_{1-6}$ alkyl, $C_{1-6}$ haloalkyl, —C(O)R, —C(O)OR, —C(O)NR$_2$, —S(O)$_2$NR$_2$, or —S(O)$_2$R;

and $R^{12}$ is —OR, —SR, —NR$_2$, —C(O)R, —C(O)OR, —C(O)NR$_2$, —S(O)$_2$R, —OC(O)R, —OC(O)OR, —OC(O)NR$_2$, —N(R)C(O)R, —N(R)C(O)OR, —N(R)C(O) NR$_2$, phenyl, monocyclic heteroaryl, $C_{3-8}$ cycloalkyl, or monocyclic heterocyclyl, wherein the aryl, heteroaryl, $C_{3-8}$ cycloalkyl, and heterocyclyl groups are each optionally substituted by one, two, or three groups that are each independently halogen, cyano, nitro, $C_{1-6}$ alkyl, $C_{1-6}$ haloalkyl, —OR, —SR, —NR$_2$, —C(O)R, —C(O)OR, —C(O)NR$_2$, —S(O)$_2$R, —OC(O)R, —OC(O)OR, —OC(O)NR$_2$, —N(R)C(O) R, —N(R)C(O)OR, or —N(R)C(O)NR$_2$;

$R^3$ is one of the formulas,

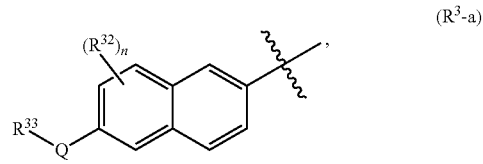
(R$^3$-a)

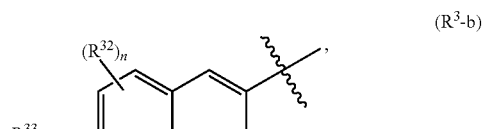
(R$^3$-b)

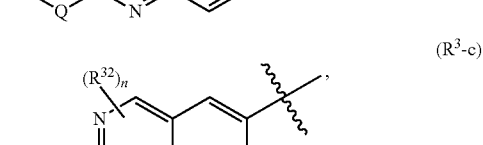
(R$^3$-c)

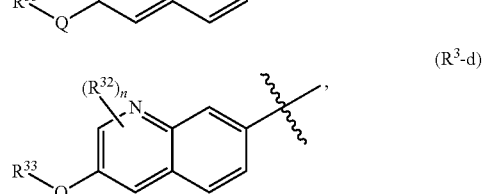
(R$^3$-d)

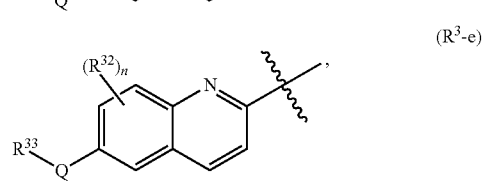
(R$^3$-e)

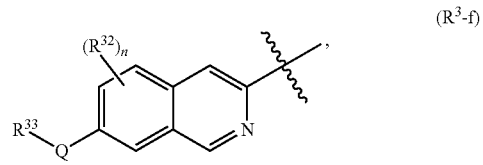
(R$^3$-f)

-continued

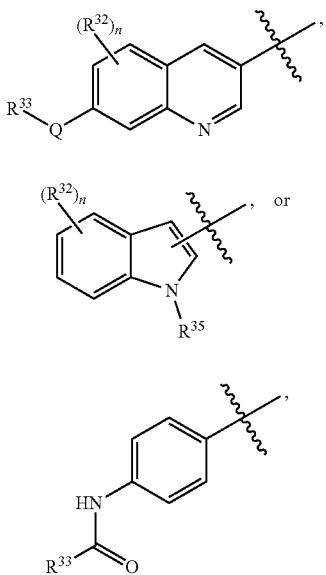

wherein n is 0, 1, or 2;

Q is —O—, —S—, or —N(R$^Q$)—, wherein R$^Q$ is hydrogen or C$_{1-6}$ alkyl; and

R$^{33}$ is C$_{1-6}$ alkyl, C$_{2-6}$ alkenyl, C$_{1-6}$ haloalkyl, C$_{3-8}$ cycloalkyl, heterocyclyl, aryl, arylC$_{1-6}$ alkyl, heteroaryl, or heteroarylC$_{1-6}$ alkyl wherein the alkyl, aryl, arylalkyl, heteroaryl, and heteroarylalkyl are optionally substituted with one, two, three, or four groups that are each independently halogen, cyano, nitro, C$_{1-6}$ alkyl, C$_{1-6}$ haloalkyl, —OR$^{20}$, —SR$^{20}$, —N(R$^{20}$)$_2$, —C(O)R$^{20}$, —C(O)OR$^{20}$, —C(O)N(R$^{20}$)$_2$, —S(O)$_2$R$^{20}$, —OC(O)R$^{20}$, —OC(O)OR$^{20}$, —OC(O)N(R$^{20}$)$_2$, —N(R$^{20}$)C(O)R$^{20}$, —N(R$^{20}$)C(O)OR$^{20}$, or —N(R$^{20}$)C(O)N(R$^{20}$)$_2$, wherein each R$^{20}$ is independently hydrogen or C$_{1-6}$ alkyl.

each R$^{32}$ is independently halogen, cyano, nitro, C$_{1-6}$ alkyl, C$_{1-6}$ haloalkyl, —OR$^{34}$, —SR$^{34}$, —N(R$^{34}$)$_2$, —C(O)R$^{34}$, —C(O)OR$^{34}$, —C(O)N(R$^{34}$)$_2$, —S(O)$_2$R$^{34}$, —OC(O)R$^{34}$, —OC(O)OR$^{34}$, —OC(O)N(R$^{34}$)$_2$, —N(R$^{34}$)C(O)R$^{34}$, —N(R$^{34}$)C(O) OR$^{34}$, or —N(R$^{34}$)C(O)N(R$^{34}$)$_2$, wherein each R$^{34}$ is independently hydrogen or C$_{1-6}$ alkyl;

and

R$^{35}$ is hydrogen or C$_{1-6}$ alkyl;

and each R is independently hydrogen, C$_{1-6}$ alkyl, C$_{2-6}$ alkenyl, C$_{1-6}$ haloalkyl, C$_{3-8}$ cycloalkyl, heterocyclyl, aryl, arylC$_{1-6}$ alkyl, heteroaryl, or heteroarylC$_{1-6}$ alkyl wherein the alkyl, aryl, arylalkyl, heteroaryl, and heteroarylalkyl are optionally substituted with one, two, three, or four groups that are each independently halogen, cyano, nitro, C$_{1-6}$ alkyl, C$_{1-6}$ haloalkyl, —OR$^o$, —SR$^o$, —N(R$^o$)$_2$, —C(O)R$^o$, —C(O)OR$^o$, —C(O)N(R$^o$)$_2$, —S(O)$_2$R$^o$, —OC(O)R$^o$, —OC(O)OR$^o$, —OC(O)N(R$^o$)$_2$, —N(R$^o$)C(O)R$^o$, —N(R$^o$)C(O)OR$^o$, or —N(R$^o$)C(O)N(R$^o$)$_2$, wherein each R$^o$ is independently hydrogen or C$_{1-6}$ alkyl, provided that the compound is not

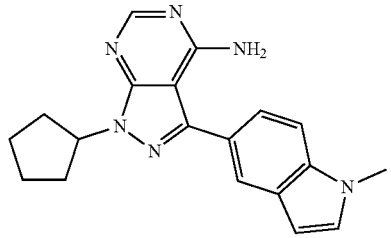

1-cyclopentyl-3-(1-methyl-1H-indol-5-yl)-1H-pyrazolo[3,4-d]pyrimidin-4-amine;

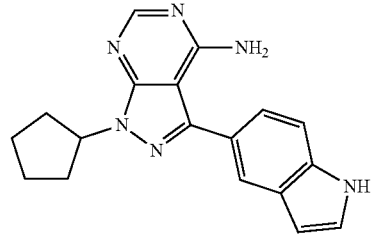

1-cyclopentyl-3-(1H-indol-5-yl)-1H-pyrazolo[3,4-d]pyrimidin-4-amine;

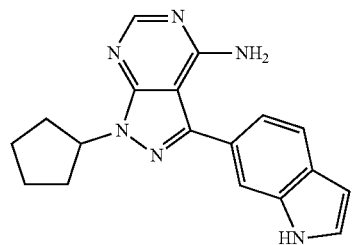

1-cyclopentyl-3-(1H-indol-6-yl)-1H-pyrazolo[3,4-d]pyrimidin-4-amine;

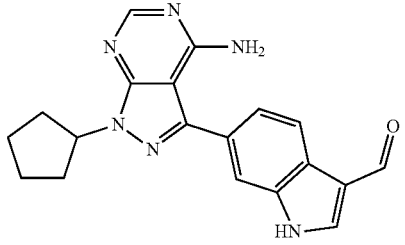

6-(4-amino-1-cyclopentyl-1H-pyrazolo[3,4-d]pyrimidin-3-yl)-1H-indole-3-carbaldehyde

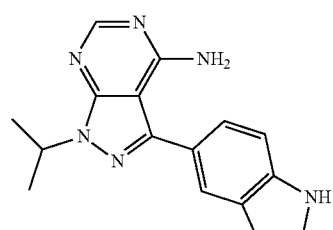

3-(1H-indol-5-yl)-1-isopropyl-1H-pyrazolo[3,4-d]pyrimidin-4-amine;

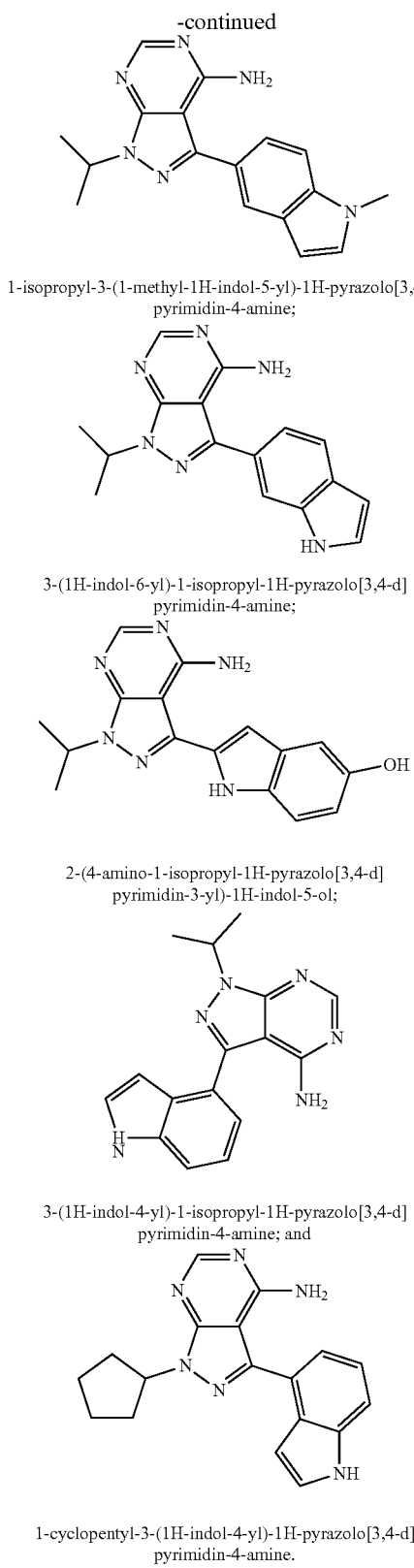

1-isopropyl-3-(1-methyl-1H-indol-5-yl)-1H-pyrazolo[3,4-d]pyrimidin-4-amine;

3-(1H-indol-6-yl)-1-isopropyl-1H-pyrazolo[3,4-d]pyrimidin-4-amine;

2-(4-amino-1-isopropyl-1H-pyrazolo[3,4-d]pyrimidin-3-yl)-1H-indol-5-ol;

3-(1H-indol-4-yl)-1-isopropyl-1H-pyrazolo[3,4-d]pyrimidin-4-amine; and 1-cyclopentyl-3-(1H-indol-4-yl)-1H-pyrazolo[3,4-d]pyrimidin-4-amine.

The disclosure further comprises subgenera of formula (I) in which the substituents are selected as any and all combinations of one or more of structural formula (I), n, Q, $R^1$, $R^3$, $R^{32}$, and $R^{33}$ as defined herein, including without limitation, the following:

Structural Formula I is One of Formulae (Ia)-(Ib):

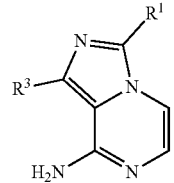
(Ia)

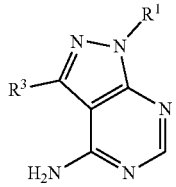
(Ib)

$R^1$ is Selected from One of the Following Groups (1a)-(1ii):

(1a) $R^1$ is $C_{2-4}$ alkyl, —$C_{1-4}$ alkyl-$R^{12}$, $C_{2-4}$ alkynyl, $C_{3-8}$ cycloalkyl, monocyclic heterocyclyl, monocyclic heteroaryl, or phenyl, wherein the cycloalkyl, heterocyclyl, heteroaryl, and phenyl groups are each optionally substituted with one or two $R^{11}$ groups.

(1b) $R^1$ is $C_{3-8}$ cycloalkyl, monocyclic heterocyclyl, monocyclic heteroaryl, or phenyl, wherein the cycloalkyl, heterocyclyl, heteroaryl, and phenyl groups are each optionally substituted with one or two $R^{11}$ groups.

(1c) $R^1$ is $C_{3-8}$ cycloalkyl; or a monocyclic heterocyclyl optionally substituted with one $R^{11}$ group.

(1d) $R^1$ is $C_{3-8}$ cycloalkyl.

(1e) $R^1$ is monocyclic heterocyclyl optionally substituted with one $R^{11}$ group.

(1f) $R^1$ is piperidinyl or tetrahydropyranyl, each optionally substituted with one $R^{11}$ group.

(1g) $R^1$ is phenyl optionally substituted with one or two $R^{11}$ groups.

(1h) $R^1$ is $C_{2-6}$ alkyl.

(1i) $R^1$ is $C_{2-4}$ alkyl.

(1j) $R^1$ is isopropyl or t-butyl.

(1k) $R^1$ is t-butyl.

(1l) $R^1$ is isopropyl.

(1m) $R^1$ is $C_{2-6}$ alkyl or —$C_{1-4}$ alkyl-$R^{12}$.

(1n) $R^1$ is —$C_{1-4}$ alkyl-$R^{12}$.

(1o) $R^1$ is —$C_{1-2}$ alkyl-$R^{12}$.

(1p) $R^1$ is —$CH_2$—$R^{12}$ (1q) Any one of groups (1m)-(1p), wherein $R^{12}$ is —C(O)OR, —C(O)$NR_2$, phenyl, monocyclic heteroaryl, $C_{3-8}$ cycloalkyl, or monocyclic heterocyclyl, wherein the phenyl, heteroaryl, $C_{3-8}$ cycloalkyl, and heterocyclyl groups are each optionally substituted by one, two, or three groups that are each independently halogen, cyano, nitro, $C_{1-6}$ alkyl, $C_{1-6}$ haloalkyl, —OR, —SR, —$NR_2$, —C(O)R, —C(O)OR, —C(O)$NR_2$, —S(O)$_2$R, —OC(O)R, —OC(O)OR, —OC(O)$NR_2$, —N(R)C(O)R, —N(R)C(O)OR, or —N(R)C(O)$NR_2$;

(1r) Any one of groups (1m)-(1p), $R^{12}$ is —C(O)OR or —C(O)$NR_2$.

(1s) Any one of groups (1m)-(1p), $R^{12}$ is phenyl, monocyclic heteroaryl, $C_{3-8}$ cycloalkyl, or monocyclic heterocyclyl, each optionally substituted by one, two, or three groups that are each independently halogen, cyano, nitro, $C_{1-6}$ alkyl, $C_{1-6}$ haloalkyl, —OR, —SR, —$NR_2$, —C(O)R, —C(O)OR, —C(O)$NR_2$, —S(O)$_2$R, —OC(O)R, —OC(O)OR, —OC(O)NR$_2$, —N(R)C(O)R, —N(R)C(O)OR, or —N(R)C(O)NR$_2$.

(1t) Any one of groups (1m)-(1p), wherein R$^{12}$ is phenyl, monocyclic heteroaryl, C$_{3-8}$ cycloalkyl, or monocyclic heterocyclyl, wherein the phenyl, heteroaryl, C$_{3-8}$ cycloalkyl, and heterocyclyl groups are each optionally substituted by one or two groups that are each independently halogen, C$_{1-6}$ alkyl, —C(O)R, —C(O)OR, —C(O)NR$_2$, —S(O)$_2$R, —OC(O)R, —OC(O)OR, —OC(O)NR$_2$, —N(R)C(O)R, —N(R)C(O)OR, or —N(R)C(O)NR$_2$.

(1u) Any one of groups (1m)-(1p), R$^{12}$ is phenyl or monocyclic heterocyclyl, each optionally substituted by one, two, or three groups that are each independently halogen, cyano, nitro, C$_{1-6}$ alkyl, C$_{1-6}$ haloalkyl, —OR, —SR, —NR$_2$, —C(O)R, —C(O)OR, —C(O)NR$_2$, —S(O)$_2$R, —OC(O)R, —OC(O)OR, —OC(O)NR$_2$, —N(R)C(O)R, —N(R)C(O)OR, or —N(R)C(O)NR$_2$.

(1v) Any one of groups (1m)-(1p), R$^{12}$ is monocyclic heterocyclyl optionally substituted by one, two, or three groups that are each independently halogen, cyano, nitro, C$_{1-6}$ alkyl, C$_{1-6}$ haloalkyl, —OR, —SR, —NR$_2$, —C(O)R, —C(O)OR, —C(O)NR$_2$, —S(O)$_2$R, —OC(O)R, —OC(O)OR, —OC(O)NR$_2$, —N(R)C(O)R, —N(R)C(O)OR, or —N(R)C(O)NR$_2$.

(1w) Any one of groups (1m)-(1p), wherein R$^{12}$ is monocyclic heterocyclyl optionally substituted by one or two groups that are each independently halogen, C$_{1-6}$ alkyl, —C(O)R, —C(O)OR, —C(O)NR$_2$, —S(O)$_2$R, —OC(O)R, —OC(O)OR, —OC(O)NR$_2$, —N(R)C(O)R, —N(R)C(O)OR, or —N(R)C(O)NR$_2$.

(1x) Any one of groups (1m)-(1p), R$^{12}$ is piperidinyl or tetrahydropyranyl, each optionally substituted by one or two groups that are each independently halogen, cyano, nitro, C$_{1-6}$ alkyl, C$_{1-6}$ haloalkyl, —OR, —SR, —NR$_2$, —C(O)R, —C(O)OR, —C(O)NR$_2$, —S(O)$_2$R, —OC(O)R, —OC(O)OR, —OC(O)NR$_2$, —N(R)C(O)R, —N(R)C(O)OR, or —N(R)C(O)NR$_2$.

(1y) Any one of groups (1m)-(1p), wherein R$^{12}$ is piperidinyl optionally substituted by one or two groups that are each independently halogen, cyano, nitro, C$_{1-6}$ alkyl, C$_{1-6}$ haloalkyl, —OR, —SR, —NR$_2$, —C(O)R, —C(O)OR, —C(O)NR$_2$, —S(O)$_2$R, —OC(O)R, —OC(O)OR, —OC(O)NR$_2$, —N(R)C(O)R, —N(R)C(O)OR, or —N(R)C(O)NR$_2$.

(1z) Any one of groups (1m)-(1p), wherein R$^{12}$ is piperidinyl optionally substituted by one or two groups that are each independently C$_{1-6}$ alkyl, —C(O)R$^A$, —C(O)OR$^A$, —C(O)N(R$^A$)$_2$, —S(O)$_2$R$^A$, —OC(O)R$^A$, —OC(O)OR$^A$, —OC(O)N(R$^A$)$_2$, —N(R$^A$)C(O)R$^A$, —N(R$^A$)C(O)OR$^A$, or —N(R$^A$)C(O)N(R$^A$)$_2$, wherein each R$^A$ is independently hydrogen, C$_{1-6}$ alkyl, C$_{2-6}$ alkenyl, C$_{1-6}$ haloalkyl, C$_{3-8}$ cycloalkyl, heterocyclyl, aryl, arylC$_{1-6}$ alkyl, heteroaryl, or heteroarylC$_{1-6}$ alkyl.

(1aa) Any one of groups (1m)-(1p), wherein R$^{12}$ is piperidinyl optionally substituted by one or two groups that are each independently C$_{1-6}$ alkyl, —C(O)R, —C(O)OR, —C(O)NR$_2$, —S(O)$_2$R, —OC(O)R, —OC(O)OR, —OC(O)NR$_2$, —N(R)C(O)R, —N(R)C(O)OR, or —N(R)C(O)NR$_2$.

(1bb) Any one of groups (1m)-(1p), wherein R$^{12}$ is piperidinyl optionally substituted by one or two groups that are each independently C$_{1-6}$ alkyl, —C(O)R$^A$, —C(O)OR$^A$, —C(O)N(R$^A$)$_2$, —S(O)$_2$R$^A$, —OC(O)R$^A$, —OC(O)OR$^A$, —OC(O)N(R$^A$)$_2$, —N(R$^A$)C(O)R$^A$, —N(R$^A$)C(O)OR$^A$, or —N(R$^A$)C(O)N(R$^A$)$_2$, wherein each R$^A$ is independently hydrogen or C$_{1-6}$ alkyl.

(1cc) Any one of groups (1m)-(1p), wherein R$^{12}$ is piperidinyl optionally substituted by one or two groups that are each independently C$_{1-6}$ alkyl, —C(O)R, —C(O)OR, —C(O)NR$_2$, or —S(O)$_2$R.

(1dd) Any one of groups (1m)-(1p), wherein R$^{12}$ is piperidinyl optionally substituted by one or two groups that are each independently C$_{1-6}$ alkyl, —C(O)R$^A$, or —S(O)$_2$R$^A$, wherein each R$^A$ is independently hydrogen or C$_{1-6}$ alkyl.

(1ee) Any one of groups (1m)-(1p), wherein R$^{12}$ is

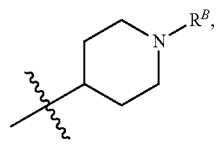

wherein R$^B$ is hydrogen, C$_{1-6}$ alkyl, —C(O)R, —C(O)OR, —C(O)NR$_2$, —S(O)$_2$R, —OC(O)R, —OC(O)OR, —OC(O)NR$_2$, —N(R)C(O)R, —N(R)C(O)OR, or —N(R)C(O)NR$_2$.

(1ff) Any one of groups (1m)-(1p), wherein R$^{12}$ is

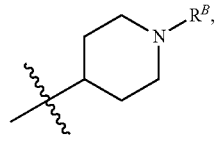

wherein R$^B$ is hydrogen, C$_{1-6}$ alkyl, —C(O)R$^A$, —C(O)OR$^A$, —C(O)N(R$^A$)$_2$, —S(O)$_2$R$^A$, —OC(O)R$^A$, —OC(O)OR$^A$, —OC(O)N(R$^A$)$_2$, —N(R$^A$)C(O)R$^A$, —N(R$^A$)C(O)OR$^A$, or —N(R$^A$)C(O)N(R$^A$)$_2$, wherein each R$^A$ is independently hydrogen, C$_{1-6}$ alkyl, C$_{2-6}$ alkenyl, C$_{1-6}$ haloalkyl, C$_{3-8}$ cycloalkyl, heterocyclyl, aryl, arylC$_{1-6}$ alkyl, heteroaryl, or heteroarylC$_{1-6}$ alkyl.

(1gg) Any one of groups (1m)-(1p), wherein R$^{12}$ is

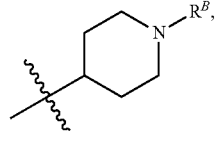

wherein R$^B$ is hydrogen, C$_{1-6}$ alkyl, —C(O)R$^A$, —C(O)OR$^A$, —C(O)N(R$^A$)$_2$, —S(O)$_2$R$^A$, —OC(O)R$^A$, —OC(O)OR$^A$, —OC(O)N(R$^A$)$_2$, —N(R$^A$)C(O)R$^A$, —N(R$^A$)C(O)OR$^A$, or —N(R$^A$)C(O)N(R$^A$)$_2$, wherein each R$^A$ is independently hydrogen or C$_{1-6}$ alkyl.

(1hh) Any one of groups (1m)-(1p), wherein R$^{12}$ is

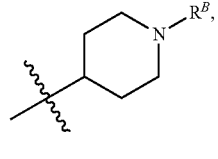

wherein $R^B$ is hydrogen, $C_{1-6}$ alkyl, —C(O)R, —C(O)OR, —C(O)NR$_2$, or —S(O)$_2$R.

(1ii) Any one of groups (1m)-(1p), wherein $R^{12}$ is

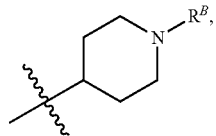

wherein $R^B$ is hydrogen, $C_{1-6}$ alkyl, —C(O)$R^A$, or —S(O)$_2$ $R^A$, wherein each $R^A$ is independently hydrogen or $C_{1-6}$ alkyl.

$R^3$ is Selected from One of the Following Groups (2a)-(2Aa):

(2a) $R^3$ is one of groups ($R^3$-a) through ($R^3$-g) as defined above.

(2b) $R^3$ is one of groups ($R^3$-b) through ($R^3$-g) as defined above.

(2c) $R^3$ is

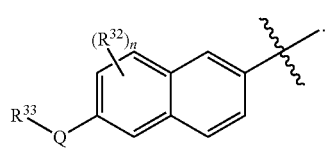

(2d) $R^3$ is

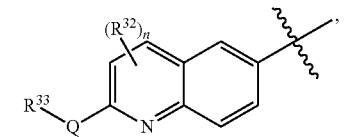, or

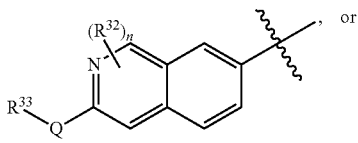

(2e) $R^3$ is

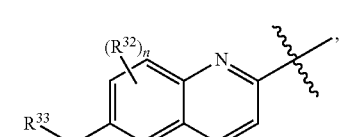, or

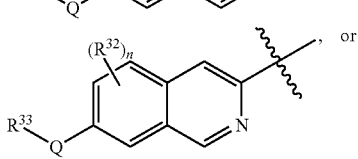

-continued

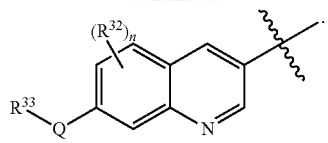

(2f) $R^3$ is

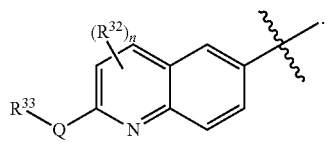

(2i) $R^3$ is

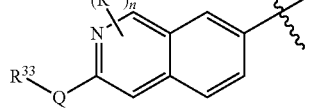

(2g) $R^3$ is

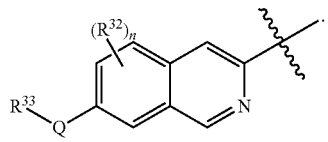

(2j) $R^3$ is

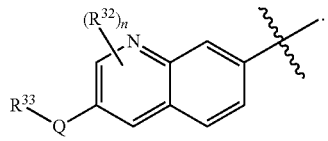

(2h) $R^3$ is (2k) $R^3$ is

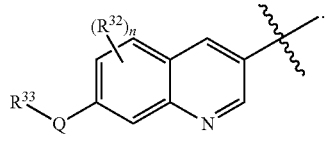

(2l) R³ is

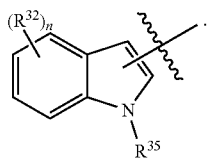

(2m) R³ is

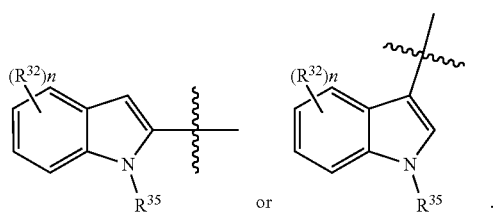 or (2n) R³ is

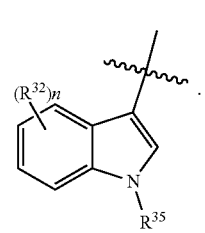

(2o) R³ is

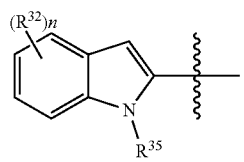

(2p) R³ is

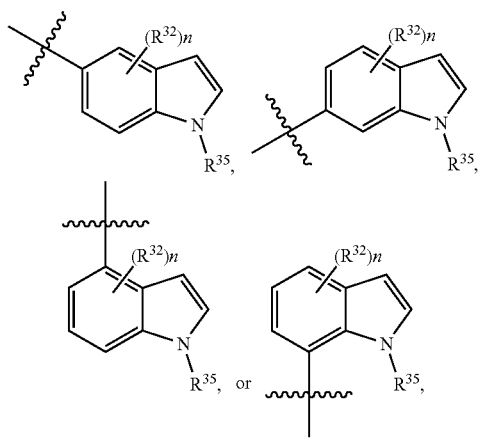

(2q) R³ is

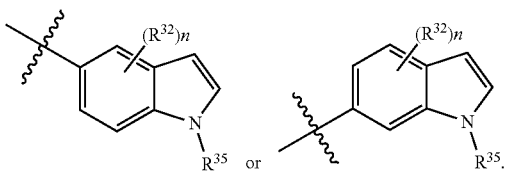 or (2r) R³ is

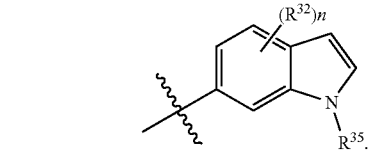

(2s) R³ is

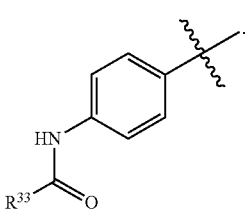

(2t) R³ is

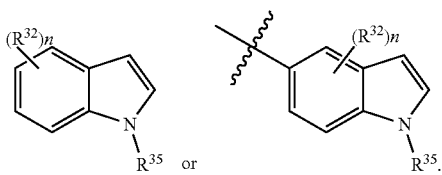

(2u) Any one of groups (2l)-(2t), wherein R³⁵ is hydrogen or methyl.
(2v) Any one of groups (2l)-(2t), wherein R³⁵ is methyl.
(2w) Any one of groups (2l)-(2t), wherein R³⁵ is hydrogen.
(2x) R³ is (2y) Group (2x) wherein R³³ is $C_{1-6}$ alkyl, $C_{2-6}$ alkenyl, $C_{1-6}$ haloalkyl, $C_{3-8}$ cycloalkyl, aryl, or aryl$C_{1-6}$ alkyl.
(2z) Group (2x) wherein R³³ is $C_{1-6}$ alkyl, $C_{1-6}$ haloalkyl, $C_{3-8}$ cycloalkyl, phenyl, or benzyl.
(2aa) Group (2x) wherein R³³ is $C_{1-4}$ alkyl, $C_{1-4}$ haloalkyl, $C_{5-6}$ cycloalkyl, phenyl, or benzyl.

Q is Selected from One of the Following Groups (3a)-(3e):
(3a) Q is —O— or —N(R$^Q$)—.
(3b) Q is —O— or —N(H)—.

(3c) Q is —O—.
(3d) Q is —N($R^Q$)—.
(3e) Q is —N(H)—.

n and $R^{32}$ are Selected from One of the Following Groups (4a)-(4x):
(4a) n is 0.
(4b) n is 0 or 1 and $R^{32}$ is as defined for formula (I).
(4c) n is 0 or 1 and $R^{32}$ is halogen, cyano, nitro, $C_{1-6}$ alkyl, or $C_{1-6}$ haloalkyl.
(4d) n is 0 or 1 and $R^{32}$ is halogen, $C_{1-6}$ alkyl, or $C_{1-6}$ haloalkyl.
(4e) n is 0 or 1 and each $R^{32}$ is —$OR^{34}$, —$SR^{34}$, —$N(R^{34})_2$, —$C(O)R^{34}$, —$C(O)OR^{34}$, —$C(O)N(R^{34})_2$, —$S(O)_2R^{34}$, —$OC(O)R^{34}$, —$OC(O)OR^{34}$, —$OC(O)N(R^{34})_2$, —$N(R^{34})C(O)R^{34}$, —$N(R^{34})C(O)OR^{34}$, or —$N(R^{34})C(O)N(R^{34})_2$, wherein each $R^{34}$ is independently hydrogen or $C_{1-6}$ alkyl.
(4f) n is 0 or 1 and $R^{32}$ is —$OR^{34}$, —$SR^{34}$, —$N(R^{34})_2$, wherein each $R^{34}$ is independently hydrogen or $C_{1-6}$ alkyl.
(4g) n is 0 or 1 and $R^{32}$ is —$C(O)R^{34}$, —$C(O)OR^{34}$, —$C(O)N(R^{34})_2$, or —$S(O)_2R^{34}$, wherein each $R^{34}$ is independently hydrogen or $C_{1-6}$ alkyl.
(4h) n is as defined for formula (I) and each $R^{32}$ is independently halogen, cyano, nitro, $C_{1-6}$ alkyl, or $C_{1-6}$ haloalkyl.
(4i) n is as defined for formula (I) and each $R^{32}$ is independently halogen, $C_{1-6}$ alkyl, or $C_{1-6}$ haloalkyl.
(4j) n is as defined for formula (I) and each $R^{32}$ is independently —$OR^{34}$, —$SR^{34}$, —$N(R^{34})_2$, —$C(O)R^{34}$, —$C(O)OR^{34}$, —$C(O)N(R^{34})_2$, —$S(O)_2R^{34}$, —$OC(O)R^{34}$, —$OC(O)OR^{34}$, —$OC(O)N(R^{34})_2$, —$N(R^{34})C(O)R^{34}$, —$N(R^{34})C(O)OR^{34}$, or —$N(R^{34})C(O)N(R^{34})_2$, wherein each $R^{34}$ is independently hydrogen or $C_{1-6}$ alkyl.
(4k) n is as defined for formula (I) and each $R^{32}$ is independently —$OR^{34}$, —$SR^{34}$, —$N(R^{34})_2$, wherein each $R^{34}$ is independently hydrogen or $C_{1-6}$ alkyl.
(4l) n is as defined for formula (I) and each $R^{32}$ is independently —$C(O)R^{34}$, —$C(O)OR^{34}$, —$C(O)N(R^{34})_2$, or —$S(O)_2R^{34}$, wherein each $R^{34}$ is independently hydrogen or $C_{1-6}$ alkyl.
(4m) n is 1 or 2 and each $R^{32}$ is as defined for formula (I).
(4n) n is 1 or 2 and each $R^{32}$ is independently halogen, cyano, nitro, $C_{1-6}$ alkyl, or $C_{1-6}$ haloalkyl.
(4o) n is 1 or 2 and each $R^{32}$ is independently halogen, $C_{1-6}$ alkyl, or $C_{1-6}$ haloalkyl.
(4p) n is 1 or 2 and each $R^{32}$ is independently —$OR^{34}$, —$SR^{34}$, —$N(R^{34})_2$, —$C(O)R^{34}$, —$C(O)OR^{34}$, —$C(O)N(R^{34})_2$, —$S(O)_2R^{34}$, —$OC(O)R^{34}$, —$OC(O)OR^{34}$, —$OC(O)N(R^{34})_2$, —$N(R^{34})C(O)R^{34}$, —$N(R^{34})C(O)OR^{34}$, or —$N(R^{34})C(O)N(R^{34})_2$, wherein each $R^{34}$ is independently hydrogen or $C_{1-6}$ alkyl.
(4q) n is 1 or 2 and each $R^{32}$ is independently —$OR^{34}$, —$SR^{34}$, —$N(R^{34})_2$, wherein each $R^{34}$ is independently hydrogen or $C_{1-6}$ alkyl.
(4r) n is 1 or 2 and each $R^{32}$ is independently —$C(O)R^{34}$, —$C(O)OR^{34}$, —$C(O)N(R^{34})_2$, or —$S(O)_2R^{34}$, wherein each $R^{34}$ is independently hydrogen or $C_{1-6}$ alkyl.
(4s) n is 1 and $R^{32}$ is as defined for formula (I).
(4t) n is 1 and $R^{32}$ is halogen, cyano, nitro, $C_{1-6}$ alkyl, or $C_{1-6}$ haloalkyl.
(4u) n is 1 and $R^{32}$ is halogen, $C_{1-6}$ alkyl, or $C_{1-6}$ haloalkyl.
(4v) n is 1 and $R^{32}$ is —$OR^{34}$, —$SR^{34}$, —$N(R^{34})_2$, —$C(O)R^{34}$, —$C(O)OR^{34}$, —$C(O)N(R^{34})_2$, —$S(O)_2R^{34}$, —$OC(O)R^{34}$, —$OC(O)OR^{34}$, —$OC(O)N(R^{34})_2$, —$N(R^{34})C(O)R^{34}$, —$N(R^{34})C(O)OR^{34}$, or —$N(R^{34})C(O)N(R^{34})_2$, wherein each $R^{34}$ is independently hydrogen or $C_{1-6}$ alkyl.
(4w) n is 1 and $R^{32}$ is -$OR^{34}$, —$SR^{34}$, —$N(R^{34})_2$, wherein each $R^{34}$ is independently hydrogen or $C_{1-6}$ alkyl.
(4x) n is 1 and $R^{32}$ is —$C(O)R^{34}$, —$C(O)OR^{34}$, —$C(O)N(R^{34})_2$, or —$S(O)_2R^{34}$, wherein each $R^{34}$ is independently hydrogen or $C_{1-6}$ alkyl.

$R^{33}$ is Selected from One of the Following Groups (5a)-(5t):
(5a) $R^{33}$ is $C_{1-6}$ alkyl, $C_{2-6}$ alkenyl, aryl$C_{1-6}$ alkyl, or heteroaryl$C_{1-6}$ alkyl, wherein the arylalkyl and heteroarylalkyl are optionally substituted with one, two, three, or four groups that are each independently halogen, cyano, nitro, $C_{1-6}$ alkyl, $C_{1-6}$ haloalkyl, —$OR^{20}$, —$SR^{20}$, —$N(R^{20})_2$, —$C(O)R^{20}$, —$C(O)OR^{20}$, —$C(O)N(R^{20})_2$, —$S(O)_2R^{20}$, —O $C(O)R^{20}$, —$OC(O)OR^{20}$, —$OC(O)N(R^{20})_2$, —$N(R^{20})C(O)R^{20}$, —$N(R^{20})C(O)OR^{20}$, or —$N(R^{20})C(O)N(R^{20})_2$, wherein each $R^{20}$ is independently hydrogen or $C_{1-6}$ alkyl.
(5b) $R^{33}$ is $C_{1-6}$ alkyl, $C_{2-6}$ alkenyl, aryl$C_{1-6}$ alkyl, or heteroaryl$C_{1-6}$ alkyl, wherein the arylalkyl and heteroarylalkyl are each substituted with one, two, three, or four groups that are each independently halogen, cyano, nitro, $C_{1-6}$ alkyl, $C_{1-6}$ haloalkyl, —$OR^{20}$, —$SR^{20}$, —$N(R^{20})_2$, —$C(O)R^{20}$, —$C(O)OR^{20}$, —$C(O)N(R^{20})_2$, —$S(O)_2R^{20}$, —O $C(O)R^{20}$, —$OC(O)OR^{20}$, —$OC(O)N(R^{20})_2$, —$N(R^{20})C(O)R^{20}$, —$N(R^{20})C(O)OR^{20}$, or —$N(R^{20})C(O)N(R^{20})_2$, wherein each $R^{20}$ is independently hydrogen or $C_{1-6}$ alkyl.
(5c) $R^{33}$ is $C_{1-6}$ alkyl, $C_{2-6}$ alkenyl, aryl$C_{1-6}$ alkyl, or heteroaryl$C_{1-6}$ alkyl, wherein the arylalkyl and heteroarylalkyl are optionally substituted with one or two groups that are each independently halogen, $C_{1-6}$ alkyl, or $C_{1-6}$ haloalkyl.
(5d) $R^{33}$ is $C_{1-6}$ alkyl, $C_{2-6}$ alkenyl, aryl$C_{1-6}$ alkyl, or heteroaryl$C_{1-6}$ alkyl, wherein the arylalkyl and heteroarylalkyl are each substituted with one or two groups that are each independently halogen, $C_{1-6}$ alkyl, or $C_{1-6}$ haloalkyl.
(5e) $R^{33}$ is $C_{2-6}$ alkenyl, aryl$C_{1-6}$ alkyl, or heteroaryl$C_{1-6}$ alkyl, wherein the arylalkyl and heteroarylalkyl are optionally substituted with one, two, three, or four groups that are each independently halogen, cyano, nitro, $C_{1-6}$ alkyl, $C_{1-6}$ haloalkyl, —$OR^{20}$, —$SR^{20}$, —$N(R^{20})_2$, —$C(O)R^{20}$, —$C(O)OR^{20}$, —$C(O)N(R^{20})_2$, —$S(O)_2R^{20}$, —O $C(O)R^{20}$, —$OC(O)OR^{20}$, —$OC(O)N(R^{20})_2$, —$N(R^{20})C(O)R^{20}$, —$N(R^{20})C(O)OR^{20}$, or —$N(R^{20})C(O)N(R^{20})_2$, wherein each $R^{20}$ is independently hydrogen or $C_{1-6}$ alkyl.
(5f) $R^{33}$ is $C_{2-6}$ alkenyl, aryl$C_{1-6}$ alkyl, or heteroaryl$C_{1-6}$ alkyl, wherein the arylalkyl and heteroarylalkyl are each substituted with one, two, three, or four groups that are each independently halogen, cyano, nitro, $C_{1-6}$ alkyl, $C_{1-6}$ haloalkyl, —$OR^{20}$, —$SR^{20}$, —$N(R^{20})_2$, —$C(O)R^{20}$, —$C(O)OR^{20}$, —$C(O)N(R^{20})_2$, —$S(O)_2R^{20}$, —O $C(O)R^{20}$, —$OC(O)OR^{20}$, —$OC(O)N(R^{20})_2$, —$N(R^{20})C(O)R^{20}$, —$N(R^{20})C(O)OR^{20}$, or —$N(R^{20})C(O)N(R^{20})_2$, wherein each $R^{20}$ is independently hydrogen or $C_{1-6}$ alkyl.
(5g) $R^{33}$ is $C_{2-6}$ alkenyl, aryl$C_{1-6}$ alkyl, or heteroaryl$C_{1-6}$ alkyl, wherein the arylalkyl and heteroarylalkyl are optionally substituted with one or two groups that are each independently halogen, $C_{1-6}$ alkyl, or $C_{1-6}$ haloalkyl.
(5h) $R^{33}$ is $C_{2-6}$ alkenyl, aryl$C_{1-6}$ alkyl, or heteroaryl$C_{1-6}$ alkyl, wherein the arylalkyl and heteroarylalkyl are each substituted with one or two groups that are each independently halogen, $C_{1-6}$ alkyl, or $C_{1-6}$ haloalkyl.

(5i) $R^{33}$ is aryl$C_{1-6}$ alkyl or heteroaryl$C_{1-6}$ alkyl, each are optionally substituted with one, two, three, or four groups that are each independently halogen, cyano, nitro, $C_{1-6}$ alkyl, $C_{1-6}$ haloalkyl, —$OR^{20}$, —$SR^{20}$, —$N(R^{20})_2$, —$C(O)R^{20}$, —$C(O)OR^{20}$, —$C(O)N(R^{20})_2$, —$S(O)_2R^{20}$, —$OC(O)R^{20}$, —$OC(O)OR^{20}$, —$OC(O)N(R^{20})_2$, —$N(R^{20})C(O)R^{20}$, —$N(R^{20})C(O)OR^{20}$, or —$N(R^{20})C(O)N(R^{20})_2$, wherein each $R^{20}$ is independently hydrogen or $C_{1-6}$ alkyl.

(5j) $R^{33}$ is aryl$C_{1-6}$ alkyl or heteroaryl$C_{1-6}$ alkyl, each are each substituted with one, two, three, or four groups that are each independently halogen, cyano, nitro, $C_{1-6}$ alkyl, $C_{1-6}$ haloalkyl, —$OR^{20}$, —$SR^{20}$, —$N(R^{20})_2$, —$C(O)R^{20}$, —$C(O)OR^{20}$, —$C(O)N(R^{20})_2$, —$S(O)_2R^{20}$, —$O\,C(O)R^{20}$, —$OC(O)OR^{20}$, —$OC(O)N(R^{20})_2$, —$N(R^{20})C(O)R^{20}$, —$N(R^{20})C(O)OR^{20}$, or —$N(R^{20})C(O)N(R^{20})_2$, wherein each $R^{20}$ is independently hydrogen or $C_{1-6}$ alkyl (5k) $R^{33}$ is aryl$C_{1-6}$ alkyl or heteroaryl$C_{1-6}$ alkyl, each optionally substituted with one or two groups that are each independently halogen, $C_{1-6}$ alkyl, or $C_{1-6}$ haloalkyl.

(5l) $R^{33}$ is aryl$C_{1-6}$ alkyl or heteroaryl$C_{1-6}$ alkyl, each substituted with one or two groups that are each independently halogen, $C_{1-6}$ alkyl, or $C_{1-6}$ haloalkyl.

(5m) $R^{33}$ is aryl$C_{1-6}$ alkyl optionally substituted with one, two, three, or four groups that are each independently halogen, cyano, nitro, $C_{1-6}$ alkyl, $C_{1-6}$ haloalkyl, —$OR^{20}$, —$SR^{20}$, —$N(R^{20})_2$, —$C(O)R^{20}$, —$C(O)OR^{20}$, —$C(O)N(R^{20})_2$, —$S(O)_2R^{20}$, —$O\,C(O)R^{20}$, —$OC(O)OR^{20}$, —$OC(O)N(R^{20})_2$, —$N(R^{20})C(O)R^{20}$, —$N(R^{20})C(O)OR^{20}$, or —$N(R^{20})C(O)N(R^{20})_2$, wherein each $R^{20}$ is independently hydrogen or $C_{1-6}$ alkyl.

(5n) $R^{33}$ is aryl$C_{1-6}$ alkyl substituted with one, two, three, or four groups that are each independently halogen, cyano, nitro, $C_{1-6}$ alkyl, $C_{1-6}$ haloalkyl, —$OR^{20}$, —$SR^{20}$, —$N(R^{20})_2$, —$C(O)R^{20}$, —$C(O)OR^{20}$, —$C(O)N(R^{20})_2$, —$S(O)_2R^{20}$, —$OC(O)R^{20}$, —$OC(O)OR^{20}$, —$OC(O)N(R^{20})_2$, —$N(R^{20})C(O)R^{20}$, —$N(R^{20})C(O)OR^{20}$, or —$N(R^{20})C(O)N(R^{20})_2$, wherein each $R^{20}$ is independently hydrogen or $C_{1-6}$ alkyl (5o) $R^{33}$ is aryl$C_{1-6}$ alkyl optionally substituted with one or two groups that are each independently halogen, $C_{1-6}$ alkyl, or $C_{1-6}$ haloalkyl.

(5p) $R^{33}$ is aryl$C_{1-6}$ alkyl substituted with one or two groups that are each independently halogen, $C_{1-6}$ alkyl, or $C_{1-6}$ haloalkyl.

(5q) $R^{33}$ is benzyl optionally substituted with one, two, three, or four groups that are each independently halogen, cyano, nitro, $C_{1-6}$ alkyl, $C_{1-6}$ haloalkyl, —$OR^{20}$, —$SR^{20}$, —$N(R^{20})_2$, —$C(O)R^{20}$, —$C(O)OR^{20}$, —$C(O)N(R^{20})_2$, —$S(O)_2R^{20}$, —$OC(O)R^{20}$, —$OC(O)OR^{20}$, —$OC(O)N(R^{20})_2$, —$N(R^{20})C(O)R^{20}$, —$N(R^{20})C(O)OR^{20}$, or —$N(R^{20})C(O)N(R^{20})_2$, wherein each $R^{20}$ is independently hydrogen or $C_{1-6}$ alkyl.

(5r) $R^{33}$ is benzyl substituted with one, two, three, or four groups that are each independently halogen, cyano, nitro, $C_{1-6}$ alkyl, $C_{1-6}$ haloalkyl, —$OR^{20}$, —$SR^{20}$, —$N(R^{20})_2$, —$C(O)R^{20}$, —$C(O)OR^{20}$, —$C(O)N(R^{20})_2$, —$S(O)_2R^{20}$, —$OC(O)R^{20}$, —$OC(O)OR^{20}$, —$OC(O)N(R^{20})_2$, —$N(R^{20})C(O)R^{20}$, —$N(R^{20})C(O)OR^{20}$, or —$N(R^{20})C(O)N(R^{20})_2$, wherein each $R^{20}$ is independently hydrogen or $C_{1-6}$ alkyl.

(5s) $R^{33}$ is benzyl optionally substituted with one or two groups that are each independently halogen, $C_{1-6}$ alkyl, or $C_{1-6}$ haloalkyl.

(5t) $R^{33}$ is benzyl substituted with one or two groups that are each independently halogen, $C_{1-6}$ alkyl, or $C_{1-6}$ haloalkyl.

Particular embodiments of this aspect of the invention include compounds of any one of the formulae (I), (Ia), and (Ib), each as defined in each of the following rows, wherein each entry is a group number as defined above (e.g., (3c) refers to Q is —O—), a dash "-" indicates that the variable is as defined for formula (I) or defined according to any one of the applicable variable definitions (1a)-(5t) [e.g., when $R^1$ is a dash, it can be either as defined for Formula (I) or any one of definitions (1a)-(1ii)]; and an "x" indicates that the variable is not applicable to the articular embodiment (e.g., when $R^3$ is (2o), then Q and $R^{33}$ are not necessary):

| | $R^1$ | $R^3$ | $R^{33}$ | n & $R^{32}$ | Q |
|---|---|---|---|---|---|
| (1)-1 | 1h | 2b | 5a | 4c | 3a |
| (1)-2 | 1n | 2b | 5a | 4c | 3a |
| (1)-3 | 1p | 2b | 5a | 4c | 3a |
| (1)-4 | 1aa | 2b | 5a | 4c | 3a |
| (1)-5 | 1h | 2b | 5e | 4c | 3a |
| (1)-6 | 1n | 2b | 5e | 4c | 3a |
| (1)-7 | 1p | 2b | 5e | 4c | 3a |
| (1)-8 | 1aa | 2b | 5e | 4c | 3a |
| (1)-9 | 1h | 2b | 5i | 4c | 3a |
| (1)-10 | 1n | 2b | 5i | 4c | 3a |
| (1)-11 | 1p | 2b | 5i | 4c | 3a |
| (1)-12 | 1aa | 2b | 5i | 4c | 3a |
| (1)-13 | 1h | 2b | 5q | 4c | 3a |
| (1)-14 | 1n | 2b | 5q | 4c | 3a |
| (1)-15 | 1p | 2b | 5q | 4c | 3a |
| (1)-16 | 1aa | 2b | 5q | 4c | 3a |
| (1)-17 | 1h | 2c | 5a | 4c | 3a |
| (1)-18 | 1n | 2c | 5a | 4c | 3a |
| (1)-19 | 1p | 2c | 5a | 4c | 3a |
| (1)-20 | 1aa | 2c | 5a | 4c | 3a |
| (1)-21 | 1h | 2c | 5e | 4c | 3a |
| (1)-22 | 1n | 2c | 5e | 4c | 3a |
| (1)-23 | 1p | 2c | 5e | 4c | 3a |
| (1)-24 | 1aa | 2c | 5e | 4c | 3a |
| (1)-25 | 1h | 2c | 5i | 4c | 3a |
| (1)-26 | 1n | 2c | 5i | 4c | 3a |
| (1)-27 | 1p | 2c | 5i | 4c | 3a |
| (1)-28 | 1aa | 2c | 5i | 4c | 3a |
| (1)-29 | 1h | 2c | 5q | 4c | 3a |
| (1)-30 | 1n | 2c | 5q | 4c | 3a |
| (1)-31 | 1p | 2c | 5q | 4c | 3a |
| (1)-32 | 1aa | 2c | 5q | 4c | 3a |
| (1)-33 | 1h | 2b | 5a | 4n | 3a |
| (1)-34 | 1n | 2b | 5a | 4n | 3a |
| (1)-35 | 1p | 2b | 5a | 4n | 3a |
| (1)-36 | 1aa | 2b | 5a | 4n | 3a |
| (1)-37 | 1h | 2b | 5e | 4n | 3a |
| (1)-38 | 1n | 2b | 5e | 4n | 3a |
| (1)-39 | 1p | 2b | 5e | 4n | 3a |
| (1)-40 | 1aa | 2b | 5e | 4n | 3a |
| (1)-41 | 1h | 2b | 5i | 4n | 3a |
| (1)-42 | 1n | 2b | 5i | 4n | 3a |
| (1)-43 | 1p | 2b | 5i | 4n | 3a |
| (1)-44 | 1aa | 2b | 5i | 4n | 3a |
| (1)-45 | 1h | 2b | 5q | 4n | 3a |
| (1)-46 | 1n | 2b | 5q | 4n | 3a |
| (1)-47 | 1p | 2b | 5q | 4n | 3a |
| (1)-48 | 1aa | 2b | 5q | 4n | 3a |
| (1)-49 | 1h | 2c | 5a | 4n | 3a |
| (1)-50 | 1n | 2c | 5a | 4n | 3a |
| (1)-51 | 1p | 2c | 5a | 4n | 3a |
| (1)-52 | 1aa | 2c | 5a | 4n | 3a |
| (1)-53 | 1h | 2c | 5e | 4n | 3a |
| (1)-54 | 1n | 2c | 5e | 4n | 3a |
| (1)-55 | 1p | 2c | 5e | 4n | 3a |
| (1)-56 | 1aa | 2c | 5e | 4n | 3a |

| | R¹ | R³ | R³³ | n & R³² | Q |
|---|---|---|---|---|---|
| (1)-57 | 1h | 2c | 5i | 4n | 3a |
| (1)-58 | 1n | 2c | 5i | 4n | 3a |
| (1)-59 | 1p | 2c | 5i | 4n | 3a |
| (1)-60 | 1aa | 2c | 5i | 4n | 3a |
| (1)-61 | 1h | 2c | 5q | 4n | 3a |
| (1)-62 | 1n | 2c | 5q | 4n | 3a |
| (1)-63 | 1p | 2c | 5q | 4n | 3a |
| (1)-64 | 1aa | 2c | 5q | 4n | 3a |
| (1)-65 | 1h | 2b | 5a | 4c | 3c |
| (1)-66 | 1n | 2b | 5a | 4c | 3c |
| (1)-67 | 1p | 2b | 5a | 4c | 3c |
| (1)-68 | 1aa | 2b | 5a | 4c | 3c |
| (1)-69 | 1h | 2b | 5e | 4c | 3c |
| (1)-70 | 1n | 2b | 5e | 4c | 3c |
| (1)-71 | 1p | 2b | 5e | 4c | 3c |
| (1)-72 | 1aa | 2b | 5e | 4c | 3c |
| (1)-73 | 1h | 2b | 5i | 4c | 3c |
| (1)-74 | 1n | 2b | 5i | 4c | 3c |
| (1)-75 | 1p | 2b | 5i | 4c | 3c |
| (1)-76 | 1aa | 2b | 5i | 4c | 3c |
| (1)-77 | 1h | 2b | 5q | 4c | 3c |
| (1)-78 | 1n | 2b | 5q | 4c | 3c |
| (1)-79 | 1p | 2b | 5q | 4c | 3c |
| (1)-80 | 1aa | 2b | 5q | 4c | 3c |
| (1)-81 | 1h | 2c | 5a | 4c | 3c |
| (1)-82 | 1n | 2c | 5a | 4c | 3c |
| (1)-83 | 1p | 2c | 5a | 4c | 3c |
| (1)-84 | 1aa | 2c | 5a | 4c | 3c |
| (1)-85 | 1h | 2c | 5e | 4c | 3c |
| (1)-86 | 1n | 2c | 5e | 4c | 3c |
| (1)-87 | 1p | 2c | 5e | 4c | 3c |
| (1)-88 | 1aa | 2c | 5e | 4c | 3c |
| (1)-89 | 1h | 2c | 5i | 4c | 3c |
| (1)-90 | 1n | 2c | 5i | 4c | 3c |
| (1)-91 | 1p | 2c | 5i | 4c | 3c |
| (1)-92 | 1aa | 2c | 5i | 4c | 3c |
| (1)-93 | 1h | 2c | 5q | 4c | 3c |
| (1)-94 | 1n | 2c | 5q | 4c | 3c |
| (1)-95 | 1p | 2c | 5q | 4c | 3c |
| (1)-96 | 1aa | 2c | 5q | 4c | 3c |
| (1)-97 | 1h | 2b | 5a | 4n | 3c |
| (1)-98 | 1n | 2b | 5a | 4n | 3c |
| (1)-99 | 1p | 2b | 5a | 4n | 3c |
| (1)-100 | 1aa | 2b | 5a | 4n | 3c |
| (1)-101 | 1h | 2b | 5e | 4n | 3c |
| (1)-102 | 1n | 2b | 5e | 4n | 3c |
| (1)-103 | 1p | 2b | 5e | 4n | 3c |
| (1)-104 | 1aa | 2b | 5e | 4n | 3c |
| (1)-105 | 1h | 2b | 5i | 4n | 3c |
| (1)-106 | 1n | 2b | 5i | 4n | 3c |
| (1)-107 | 1p | 2b | 5i | 4n | 3c |
| (1)-108 | 1aa | 2b | 5i | 4n | 3c |
| (1)-109 | 1h | 2b | 5q | 4n | 3c |
| (1)-110 | 1n | 2b | 5q | 4n | 3c |
| (1)-111 | 1p | 2b | 5q | 4n | 3c |
| (1)-112 | 1aa | 2b | 5q | 4n | 3c |
| (1)-113 | 1h | 2c | 5a | 4n | 3c |
| (1)-114 | 1n | 2c | 5a | 4n | 3c |
| (1)-115 | 1p | 2c | 5a | 4n | 3c |
| (1)-116 | 1aa | 2c | 5a | 4n | 3c |
| (1)-117 | 1h | 2c | 5e | 4n | 3c |
| (1)-118 | 1n | 2c | 5e | 4n | 3c |
| (1)-119 | 1p | 2c | 5e | 4n | 3c |
| (1)-120 | 1aa | 2c | 5e | 4n | 3c |
| (1)-121 | 1h | 2c | 5i | 4n | 3c |
| (1)-122 | 1n | 2c | 5i | 4n | 3c |
| (1)-123 | 1p | 2c | 5i | 4n | 3c |
| (1)-124 | 1aa | 2c | 5i | 4n | 3c |
| (1)-125 | 1h | 2c | 5q | 4n | 3c |
| (1)-126 | 1n | 2c | 5q | 4n | 3c |
| (1)-127 | 1p | 2c | 5q | 4n | 3c |
| (1)-128 | 1aa | 2c | 5q | 4n | 3c |
| (1)-129 | 1h | 2b | — | — | — |
| (1)-130 | 1n | 2b | — | — | — |
| (1)-131 | 1p | 2b | — | — | — |
| (1)-132 | 1aa | 2b | — | — | — |
| (1)-133 | 1h | 2c | — | — | — |
| (1)-134 | 1n | 2c | — | — | — |
| (1)-135 | 1p | 2c | — | — | — |
| (1)-136 | 1aa | 2c | — | — | — |
| (1)-137 | 1h | 2b | — | — | 3c |
| (1)-138 | 1n | 2b | — | — | 3c |
| (1)-139 | 1p | 2b | — | — | 3c |
| (1)-140 | 1aa | 2b | — | — | 3c |
| (1)-141 | 1h | 2c | — | — | 3c |
| (1)-142 | 1n | 2c | — | — | 3c |
| (1)-143 | 1p | 2c | — | — | 3c |
| (1)-144 | 1aa | 2c | — | — | 3c |
| (1)-145 | 1h | 2b | — | — | 3a |
| (1)-146 | 1n | 2b | — | — | 3a |
| (1)-147 | 1p | 2b | — | — | 3a |
| (1)-148 | 1aa | 2b | — | — | 3a |
| (1)-149 | 1h | 2c | — | — | 3a |
| (1)-150 | 1n | 2c | — | — | 3a |
| (1)-151 | 1p | 2c | — | — | 3a |
| (1)-152 | 1aa | 2c | — | — | 3a |
| (1)-153 | — | — | 5a | — | 3a |
| (1)-154 | — | — | 5e | — | 3a |
| (1)-155 | — | — | 5i | — | 3a |
| (1)-156 | — | — | 5q | — | 3a |
| (1)-157 | — | — | 5a | — | 3c |
| (1)-158 | — | — | 5e | — | 3a |
| (1)-159 | — | — | 5i | — | 3a |
| (1)-160 | — | — | 5q | — | 3a |
| (1)-161 | — | 2b | 5a | — | 3a |
| (1)-162 | — | 2b | 5e | — | 3a |
| (1)-163 | — | 2b | 5i | — | 3a |
| (1)-164 | — | 2b | 5q | — | 3a |
| (1)-165 | — | 2b | 5a | — | 3c |
| (1)-166 | — | 2b | 5e | — | 3a |
| (1)-167 | — | 2b | 5i | — | 3a |
| (1)-168 | — | 2b | 5q | — | 3a |
| (1)-169 | — | 2c | 5a | — | 3a |
| (1)-170 | — | 2c | 5e | — | 3a |
| (1)-171 | — | 2c | 5i | — | 3a |
| (1)-172 | — | 2c | 5q | — | 3a |
| (1)-173 | — | 2c | 5a | — | 3c |
| (1)-174 | — | 2c | 5e | — | 3a |
| (1)-175 | — | 2c | 5i | — | 3a |
| (1)-176 | — | 2c | 5q | — | 3a |
| (1)-177 | 1h | 2o | x | 4c | x |
| (1)-178 | 1n | 2o | x | 4c | x |
| (1)-179 | 1p | 2o | x | 4c | x |
| (1)-180 | 1aa | 2o | x | 4c | x |
| (1)-185 | 1h | 2o | x | 4n | x |
| (1)-186 | 1n | 2o | x | 4n | x |
| (1)-187 | 1p | 2o | x | 4n | x |
| (1)-188 | 1aa | 2o | x | 4n | x |
| (1)-189 | 1h | 2r | x | 4n | x |
| (1)-190 | 1n | 2r | x | 4n | x |
| (1)-191 | 1p | 2r | x | 4n | x |
| (1)-192 | 1aa | 2r | x | 4n | x |
| (1)-181 | 1h | 2r | x | 4c | x |
| (1)-182 | 1n | 2r | x | 4c | x |
| (1)-183 | 1p | 2r | x | 4c | x |
| (1)-184 | 1aa | 2r | x | 4c | x |
| (1)-193 | 1h | 2o | x | — | x |
| (1)-194 | 1n | 2o | x | — | x |
| (1)-195 | 1p | 2o | x | — | x |
| (1)-196 | 1aa | 2o | x | — | x |
| (1)-197 | 1h | 2r | x | — | x |
| (1)-198 | 1n | 2r | x | — | x |
| (1)-199 | 1p | 2r | x | — | x |
| (1)-200 | 1aa | 2r | x | — | x |

In one embodiment, the compound is one of the compounds in Table A:

TABLE A

| Structure | Name |
|---|---|
| 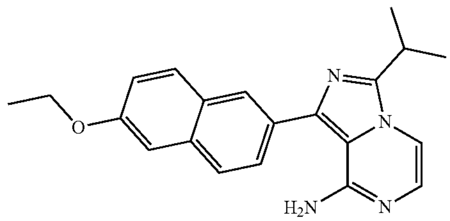 [SMILES: CCOc1ccc2cc(-c3nc(C(C)C)n4ccnc(N)c34)ccc2c1] | 1-(6-ethoxynaphthalen-2-yl)-3-isopropylimidazo[1,5-a]pyrazin-8-amine; |
| 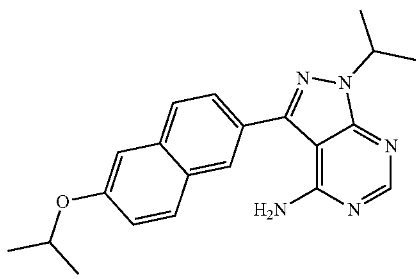 [SMILES: CC(C)Oc1ccc2cc(-c3nn(C(C)C)c4ncnc(N)c34)ccc2c1] | 3-(6-isopropoxynaphthalen-2-yl)-1-isopropyl-1H-pyrazolo[3,4-d]pyrimidin-4-amine; |
| 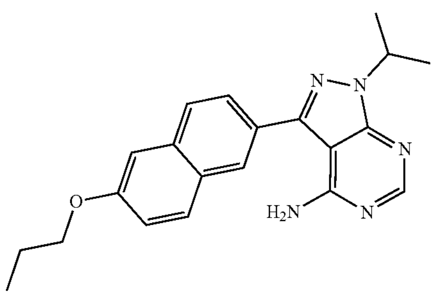 [SMILES: CCCOc1ccc2cc(-c3nn(C(C)C)c4ncnc(N)c34)ccc2c1] | 1-isopropyl-3-(6-propoxynaphthalen-2-yl)-1H-pyrazolo[3,4-d]pyrimidin-4-amine; |
| 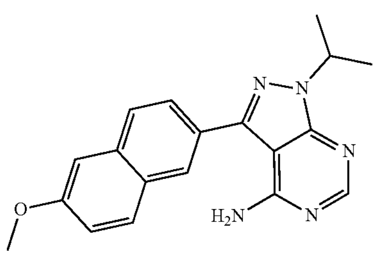 [SMILES: COc1ccc2cc(-c3nn(C(C)C)c4ncnc(N)c34)ccc2c1] | 1-isopropyl-3-(6-methoxynaphthalen-2-yl)-1H-pyrazolo[3,4-d]pyrimidin-4-amine; |
| 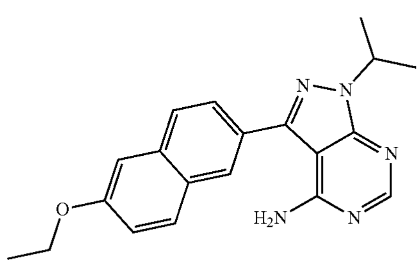 [SMILES: CCOc1ccc2cc(-c3nn(C(C)C)c4ncnc(N)c34)ccc2c1] | 3-(6-ethoxynaphthalen-2-yl)-1-isopropyl-1H-pyrazolo[3,4-d]pyrimidin-4-amine; |
| 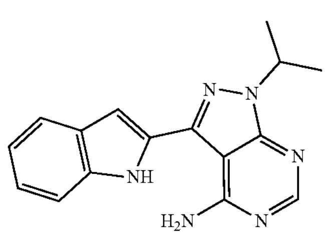 [SMILES: CC(C)n1nc(-c2cc3ccccc3[nH]2)c2c(N)ncnc21] | 3-(1H-indol-2-yl)-1-isopropyl-1H-pyrazolo[3,4-d]pyrimidin-4-amine; |

TABLE A-continued

| Structure | Name |
|---|---|
| | 1-isopropyl-3-(4-methyl-1H-indol-2-yl)-1H-pyrazolo[3,4-d]pyrimidin-4-amine; |
| | 3-(4-chloro-1H-indol-2-yl)-1-isopropyl-1H-pyrazolo[3,4-d]pyrimidin-4-amine; |
| | 1-isopropyl-3-(5-methoxy-1H-indol-2-yl)-1H-pyrazolo[3,4-d]pyrimidin-4-amine; |
| | 3-(naphthalen-2-yl)-1-(piperidin-4-ylmethyl)-1H-pyrazolo[3,4-d]pyrimidin-4-amine |
| | 3-(6-methoxynaphthalen-2-yl)-1-(piperidin-4-ylmethyl)-1H-pyrazolo[3,4-d]pyrimidin-4-amine; |
| | 3-(6-ethoxynaphthalen-2-yl)-1-(piperidin-4-ylmethyl)-1H-pyrazolo[3,4-d]pyrimidin-4-amine; |
| | 3-(6-ethoxynaphthalen-2-yl)-1-((1-methylpiperidin-4-yl)methyl)-1H-pyrazolo[3,4-d]pyrimidin-4-amine |

TABLE A-continued

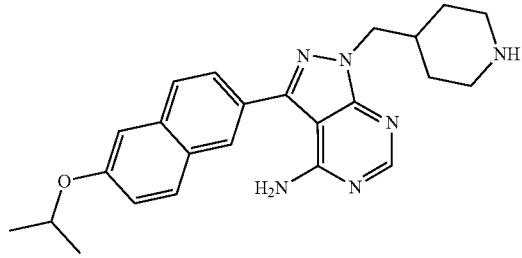 [SMILES: CC(C)Oc1ccc2cc(-c3nn(CC4CCNCC4)c4ncnc(N)c34)ccc2c1]

3-(6-isopropoxynaphthalen-2-yl)-1-(piperidin-4-ylmethyl)-1H-pyrazolo[3,4-d]pyrimidin-4-amine;

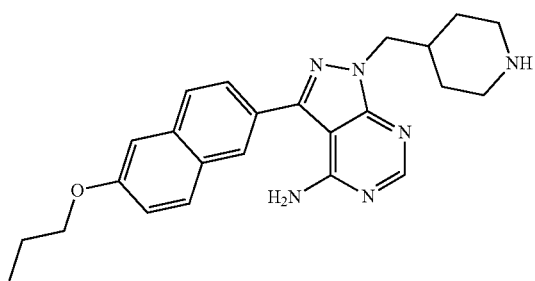 [SMILES: CCCOc1ccc2cc(-c3nn(CC4CCNCC4)c4ncnc(N)c34)ccc2c1]

1-(piperidin-4-ylmethyl)-3-(6-propoxynaphthalen-2-yl)-1H-pyrazolo[3,4-d]pyrimidin-4-amine;

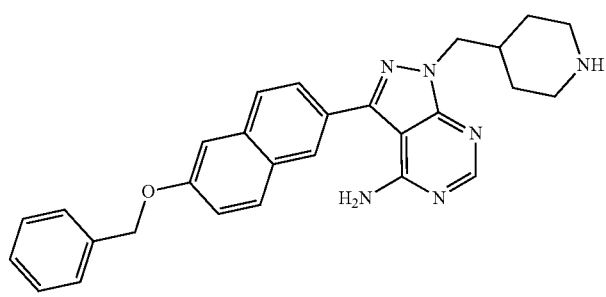 [SMILES: Nc1ncnc2c1c(-c1ccc3cc(OCc4ccccc4)ccc3c1)nn2CC1CCNCC1]

3-(6-(benzyloxy)naphthalen-2-yl)-1-(piperidin-4-ylmethyl)-1H-pyrazolo[3,4-d]pyrimidin-4-amine;

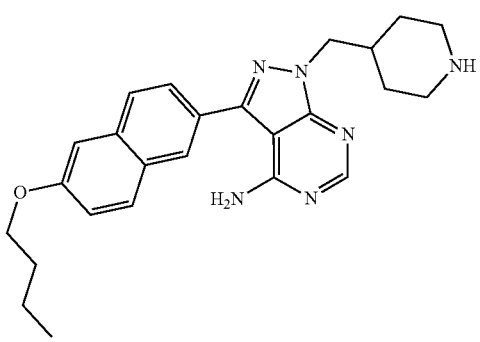 [SMILES: CCCCOc1ccc2cc(-c3nn(CC4CCNCC4)c4ncnc(N)c34)ccc2c1]

3-(6-butoxynaphthalen-2-yl)-1-(piperidin-4-ylmethyl)-1H-pyrazolo[3,4-d]pyrimidin-4-amine;

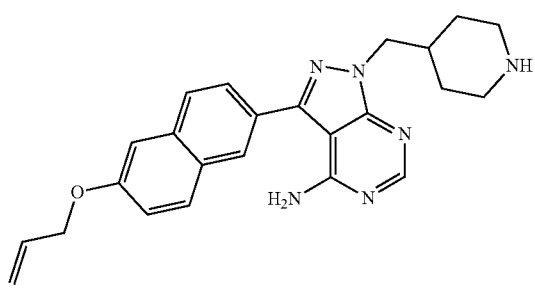 [SMILES: C=CCOc1ccc2cc(-c3nn(CC4CCNCC4)c4ncnc(N)c34)ccc2c1]

3-(6-(allyloxy)naphthalen-2-yl)-1-(piperidin-4-ylmethyl)-1H-pyrazolo[3,4-d]pyrimidin-4-amine;

TABLE A-continued

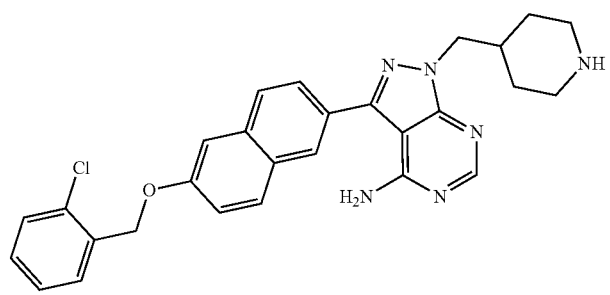 [SMILES: Nc1ncnc2c1c(-c1ccc3cc(OCc4ccccc4Cl)ccc3c1)nn2CC1CCNCC1]
3-(6-(2-chlorobenzyloxy)naphthalen-2-yl)-1-(piperidin-4-ylmethyl)-1H-pyrazolo[3,4-d]pyrimidin-4-amine

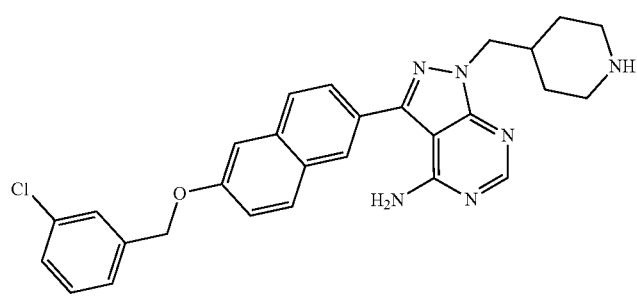 [SMILES: Nc1ncnc2c1c(-c1ccc3cc(OCc4cccc(Cl)c4)ccc3c1)nn2CC1CCNCC1]
3-(6-(3-chlorobenzyloxy)naphthalen-2-yl)-1-(piperidin-4-ylmethyl)-1H-pyrazolo[3,4-d]pyrimidin-4-amine;

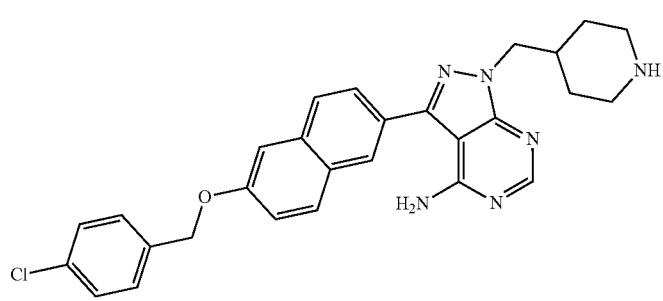 [SMILES: Nc1ncnc2c1c(-c1ccc3cc(OCc4ccc(Cl)cc4)ccc3c1)nn2CC1CCNCC1]
3-(6-(4-chlorobenzyloxy)naphthalen-2-yl)-1-(piperidin-4-ylmethyl)-1H-pyrazolo[3,4-d]pyrimidin-4-amine;

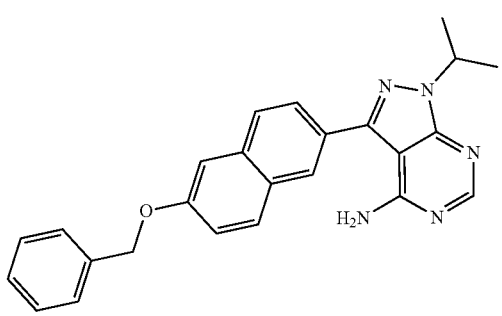 [SMILES: CC(C)n1nc(-c2ccc3cc(OCc4ccccc4)ccc3c2)c2c(N)ncnc21]
3-(6-(benzyloxy)naphthalen-2-yl)-1-isopropyl-1H-pyrazolo[3,4-d]pyrimidin-4-amine;

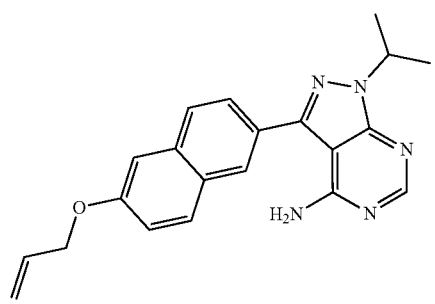 [SMILES: C=CCOc1ccc2cc(-c3nn(C(C)C)c4ncnc(N)c34)ccc2c1]
3-(6-(allyloxy)naphthalen-2-yl)-1-isopropyl-1H-pyrazolo[3,4-d]pyrimidin-4-amine;

TABLE A-continued

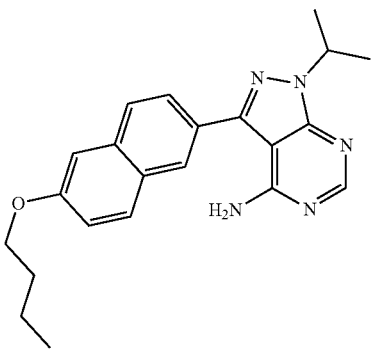 [SMILES: CCCCOc1ccc2cc(-c3nn(C(C)C)c4ncnc(N)c34)ccc2c1]

3-(6-butoxynaphthalen-2-yl)-1-isopropyl-1H-pyrazolo[3,4-d]pyrimidin-4-amine;

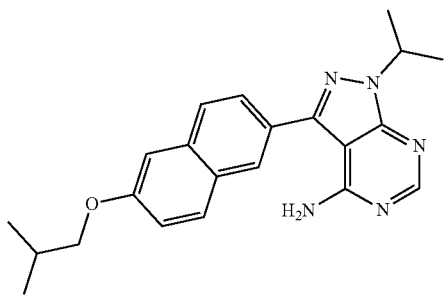 [SMILES: CC(C)COc1ccc2cc(-c3nn(C(C)C)c4ncnc(N)c34)ccc2c1]

3-(6-isobutoxynaphthalen-2-yl)-1-isopropyl-1H-pyrazolo[3,4-d]pyrimidin-4-amine;

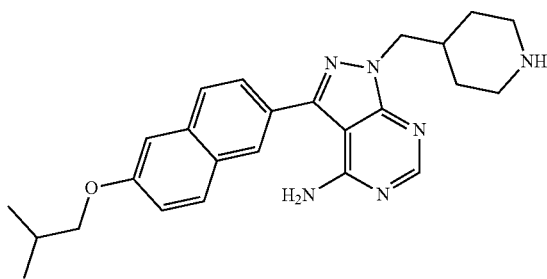 [SMILES: CC(C)COc1ccc2cc(-c3nn(CC4CCNCC4)c4ncnc(N)c34)ccc2c1]

3-(6-isobutoxynaphthalen-2-yl)-1-(piperidin-4-ylmethyl)-1H-pyrazolo[3,4-d]pyrimidin-4-amine;

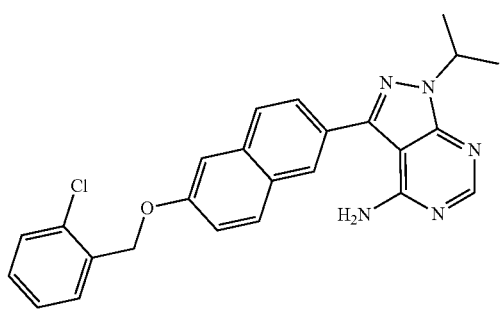 [SMILES: CC(C)n1nc(-c2ccc3cc(OCc4ccccc4Cl)ccc3c2)c2c(N)ncnc21]

3-(6-(2-chlorobenzyloxy)naphthalen-2-yl)-1-isopropyl-1H-pyrazolo[3,4-d]pyrimidin-4-amine;

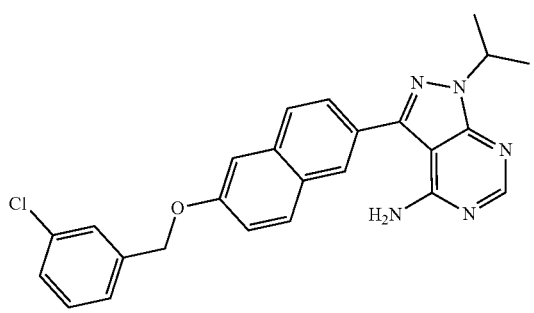 [SMILES: CC(C)n1nc(-c2ccc3cc(OCc4cccc(Cl)c4)ccc3c2)c2c(N)ncnc21]

3-(6-(3-chlorobenzyloxy)naphthalen-2-yl)-1-isopropyl-1H-pyrazolo[3,4-d]pyrimidin-4-amine;

TABLE A-continued
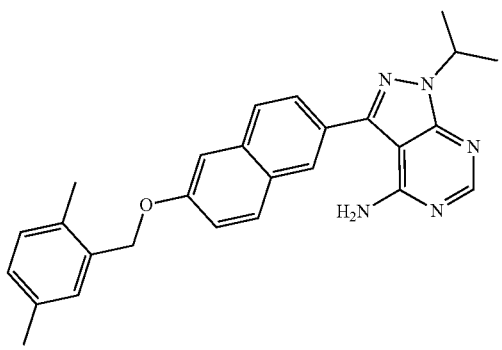 [SMILES: Cc1ccc(C)c(COc2ccc3cc(-c4nn(C(C)C)c5ncnc(N)c45)ccc3c2)c1]
3-(6-(2,5-dimethylbenzyloxy)naphthalen-2-yl)-1-isopropyl-1H-pyrazolo[3,4-d]pyrimidin-4-amine;
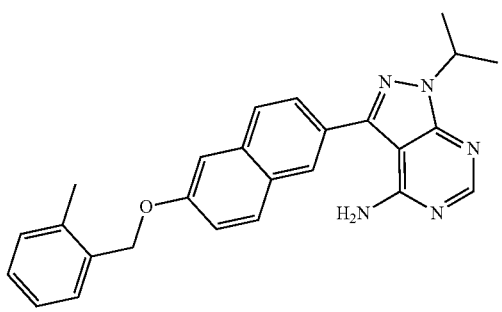 [SMILES: Cc1ccccc1COc1ccc2cc(-c3nn(C(C)C)c4ncnc(N)c34)ccc2c1]
1-isopropyl-3-(6-(2-methylbenzyloxy)naphthalen-2-yl)-1H-pyrazolo[3,4-d]pyrimidin-4-amine;
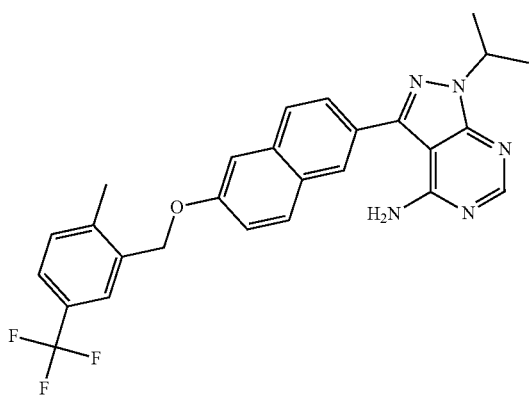 [SMILES: Cc1ccc(C(F)(F)F)cc1COc1ccc2cc(-c3nn(C(C)C)c4ncnc(N)c34)ccc2c1]
1-isopropyl-3-(6-(2-methyl-5-(trifluoromethyl)benzyloxy)naphthalen-2-yl)-1H-pyrazolo[3,4-d]pyrimidin-4-amine;
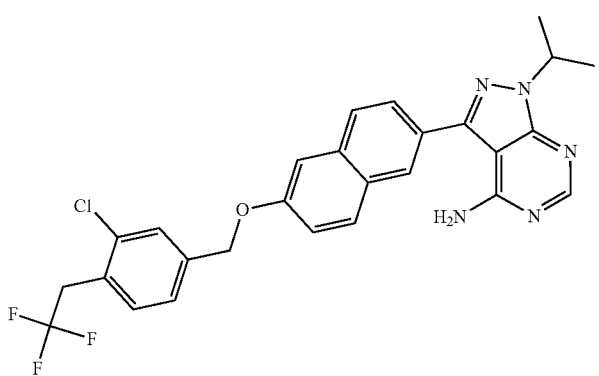 [SMILES: CC(C)n1nc(-c2ccc3cc(OCc4ccc(CC(F)(F)F)c(Cl)c4)ccc3c2)c2c(N)ncnc21]
3-(6-(3-chloro-4-(2,2,2-trifluoroethyl)benzyloxy)naphthalen-2-yl)-1-isopropyl-1H-pyrazolo[3,4-d]pyrimidin-4-amine;

TABLE A-continued

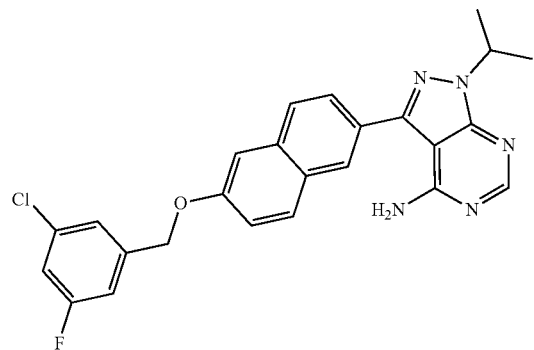 [SMILES: CC(C)n1nc(-c2ccc3cc(OCc4cc(F)cc(Cl)c4)ccc3c2)c2c(N)ncnc21]

3-(6-(3-chloro-5-fluorobenzyloxy)naphthalen-2-yl)-1-isopropyl-1H-pyrazolo[3,4-d]pyrimidin-4-amine;

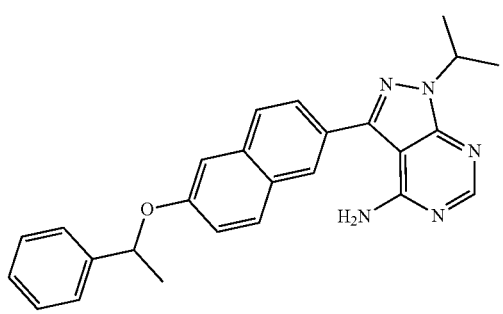 [SMILES: CC(Oc1ccc2cc(-c3nn(C(C)C)c4ncnc(N)c34)ccc2c1)c1ccccc1]

1-isopropyl-3-(6-(1-phenylethoxy)naphthalen-2-yl)-1H-pyrazolo[3,4-d]pyrimidin-4-amine;

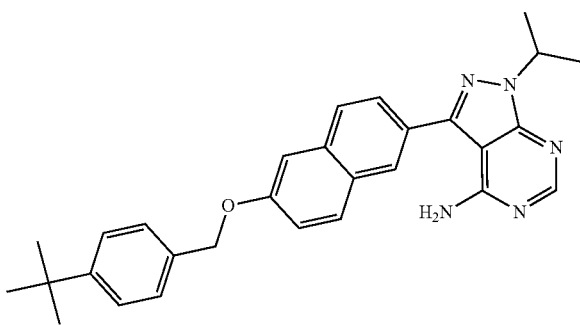 [SMILES: CC(C)n1nc(-c2ccc3cc(OCc4ccc(C(C)(C)C)cc4)ccc3c2)c2c(N)ncnc21]

3-(6-(4-tert-butylbenzyloxy)naphthalen-2-yl)-1-isopropyl-1H-pyrazolo[3,4-d]pyrimidin-4-amine;

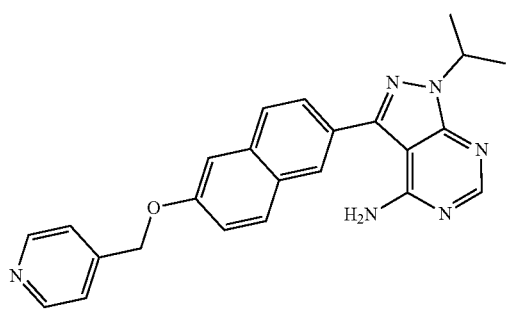 [SMILES: CC(C)n1nc(-c2ccc3cc(OCc4ccncc4)ccc3c2)c2c(N)ncnc21]

1-isopropyl-3-(6-(pyridin-4-ylmethoxy)naphthalen-2-yl)-1H-pyrazolo[3,4-d]pyrimidin-4-amine;

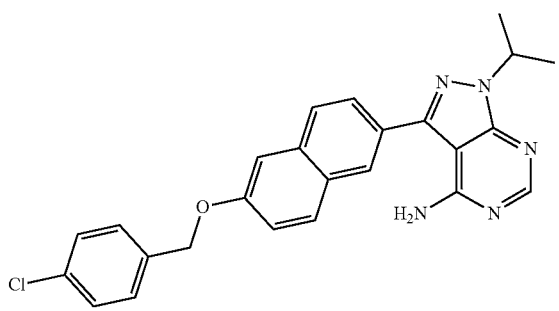 [SMILES: CC(C)n1nc(-c2ccc3cc(OCc4ccc(Cl)cc4)ccc3c2)c2c(N)ncnc21]

3-(6-(4-chlorobenzyloxy)naphthalen-2-yl)-1-isopropyl-1H-pyrazolo[3,4-d]pyrimidin-4-amine;

TABLE A-continued

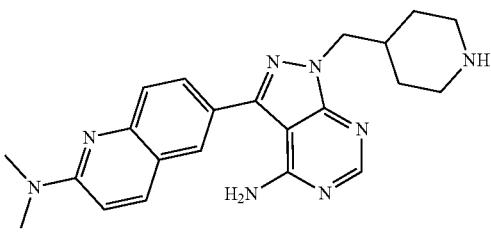 [SMILES: CN(C)c1ccc2cc(-c3nn(CC4CCNCC4)c4ncnc(N)c34)ccc2n1]

6-(4-amino-1-(piperidin-4-ylmethyl)-1H-pyrazolo[3,4-d]pyrimidin-3-yl)-N,N-dimethylquinolin-2-amine;

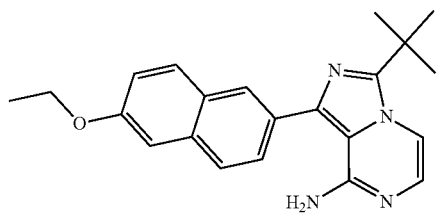 [SMILES: CCOc1ccc2cc(-c3nc(C(C)(C)C)n4ccnc(N)c34)ccc2c1]

3-tert-butyl-1-(6-ethoxynaphthalen-2-yl)imidazo[1,5-a]pyrazin-8-amine;

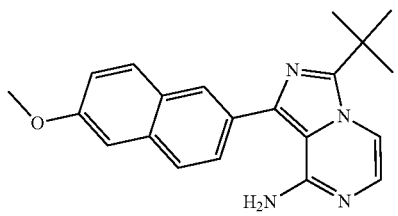 [SMILES: COc1ccc2cc(-c3nc(C(C)(C)C)n4ccnc(N)c34)ccc2c1]

3-tert-butyl-1-(6-methoxynaphthalen-2-yl)imidazo[1,5-a]pyrazin-8-amine;

and a pharmaceutically acceptable salts thereof.

In another embodiment, the present disclosure provides compounds of the formula (III),

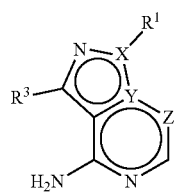

(III)

or a pharmaceutically acceptable salt thereof, wherein

X, Y, and Z are defined by either: (i) X is N, Y is C, and Z is N; or (ii) X is C, Y is N, and Z is C(H);

$R^1$ is $C_{2-6}$ alkyl or $-C_{1-4}$ alkyl-$R^{12}$, wherein $R^{12}$ is a monocyclic heterocyclyl optionally substituted by one, two, or three groups that are each independently halogen, cyano, nitro, $C_{1-6}$ alkyl, $C_{1-6}$ haloalkyl, —OR, —SR, —NR$_2$, —C(O)R, —C(O)OR, —C(O)NR$_2$, —S(O)$_2$R, —OC(O)R, —OC(O)OR, —OC(O)NR$_2$, —N(R)C(O)R, —N(R)C(O)OR, or —N(R)C(O)NR$_2$;

$R^3$ is one of the formulas,

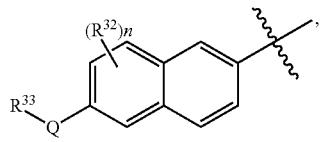

(R$^3$-a)

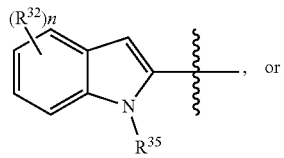

(R$^3$-j)

, or

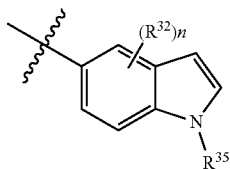

(R$^3$-k)

wherein n is 0, 1, or 2;

Q is —O— or —N(R$^Q$)—, wherein R$^Q$ is hydrogen or $C_{1-6}$ alkyl; and $R^{33}$ is $C_{1-6}$ alkyl, $C_{2-6}$ alkenyl, aryl$C_{1-6}$ alkyl, or heteroaryl$C_{1-6}$ alkyl wherein the arylalkyl and heteroarylalkyl are optionally substituted with one, two, three, or four groups that are each independently halogen, $C_{1-6}$ alkyl, $C_{1-6}$ haloalkyl, —OR$^{20}$, —SR$^{20}$, or —N(R$^{20}$)$_2$, wherein each R$^{20}$ is independently hydrogen or $C_{1-6}$ alkyl.

each $R^{32}$ is independently halogen, $C_{1-6}$ alkyl, or —OR$^{34}$, wherein R$^{34}$ is $C_{1-6}$ alkyl;

and $R^{35}$ is hydrogen or $C_{1-6}$ alkyl;

and each R is independently hydrogen or $C_{1-6}$ alkyl.

The disclosure further comprises subgenera of formula (III) in which the substituents are selected as any and all combinations of one or more of structural formula (III), n, Q, $R^1$, $R^3$, $R^{32}$, and $R^{33}$ as defined herein, including without limitation, the following:

Structural Formula III is One of Formulae (IIIa)-(IIIb):

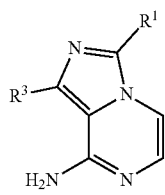
(IIIa)

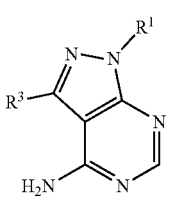
(IIIb)

$R^1$ is Selected from One of the Following Groups (8a)-(8u):
- (8a) $R^1$ is $C_{2-6}$ alkyl.
- (8b) $R^1$ is $C_{2-4}$ alkyl.
- (8c) $R^1$ is isopropyl or t-butyl.
- (8d) $R^1$ is t-butyl.
- (8e) $R^1$ is isopropyl.
- (8f) $R^1$ is —$C_{1-4}$ alkyl-$R^{12}$.
- (8g) $R^1$ is —$C_{1-2}$ alkyl-$R^{12}$.
- (8h) $R^1$ is —$CH_2$—$R^{12}$.
- (8i) Any one of groups (8f)-(8h), wherein $R^{12}$ is monocyclic heterocyclyl optionally substituted by one or two groups that are each independently halogen, $C_{1-6}$ alkyl, —C(O)R, —C(O)OR, —C(O)$NR_2$, —S(O)$_2$R, —OC(O)R, —OC(O)OR, —OC(O)$NR_2$, —N(R)C(O)R, —N(R)C(O)OR, or —N(R)C(O)$NR_2$.
- (8j) Any one of groups (8f)-(8h), $R^{12}$ is piperidinyl or tetrahydropyranyl, each optionally substituted by one or two groups that are each independently halogen, cyano, nitro, $C_{1-6}$ alkyl, $C_{1-6}$ haloalkyl, —OR, —SR, —$NR_2$, —C(O)R, —C(O)OR, —C(O)$NR_2$, —S(O)$_2$R, —OC(O)R, —OC(O)OR, —OC(O)$NR_2$, —N(R)C(O)R, —N(R)C(O)OR, or —N(R)C(O)$NR_2$.
- (8k) Any one of groups (8f)-(8h), wherein $R^{12}$ is piperidinyl optionally substituted by one or two groups that are each independently halogen, cyano, nitro, $C_{1-6}$ alkyl, $C_{1-6}$ haloalkyl, —OR, —SR, —$NR_2$, —C(O)R, —C(O)OR, —C(O)$NR_2$, —S(O)$_2$R, —OC(O)R, —OC(O)OR, —OC(O)$NR_2$, —N(R)C(O)R, —N(R)C(O)OR, or —N(R)C(O)$NR_2$.
- (8l) Any one of groups (8f)-(8h), wherein $R^{12}$ is piperidinyl optionally substituted by one or two groups that are each independently $C_{1-6}$ alkyl, —C(O)$R^A$, —C(O)$OR^A$, —C(O)N($R^A$)$_2$, —S(O)$_2R^A$, —OC(O)$R^A$, —OC(O)$OR^A$, —OC(O)N($R^A$)$_2$, —N($R^A$)C(O)$R^A$, —N($R^A$)C(O)$OR^A$, or —N($R^A$)C(O)N($R^A$)$_2$, wherein each $R^A$ is independently hydrogen, $C_{1-6}$ alkyl, $C_{2-6}$ alkenyl, $C_{1-6}$ haloalkyl, $C_{3-8}$ cycloalkyl, heterocyclyl, aryl, aryl$C_{1-6}$ alkyl, heteroaryl, or heteroaryl$C_{1-6}$ alkyl.
- (8m) Any one of groups (8f)-(8h), wherein $R^{12}$ is piperidinyl optionally substituted by one or two groups that are each independently $C_{1-6}$ alkyl, —C(O)R, —C(O)OR, —C(O)$NR_2$, —S(O)$_2$R, —OC(O)R, —OC(O)OR, —OC(O)$NR_2$, —N(R)C(O)R, —N(R)C(O)OR, or —N(R)C(O)$NR_2$.
- (8n) Any one of groups (8f)-(8h), wherein $R^{12}$ is piperidinyl optionally substituted by one or two groups that are each independently $C_{1-6}$ alkyl, —C(O)$R^A$, —C(O)$OR^A$, —C(O)N($R^A$)$_2$, —S(O)$_2R^A$, —OC(O)$R^A$, —OC(O)$OR^A$, —OC(O)N($R^A$)$_2$, —N($R^A$)C(O)$R^A$, —N($R^A$)C(O)$OR^A$, or —N($R^A$)C(O)N($R^A$)$_2$, wherein each $R^A$ is independently hydrogen or $C_{1-6}$ alkyl.
- (8o) Any one of groups (8f)-(8h), wherein $R^{12}$ is piperidinyl optionally substituted by one or two groups that are each independently $C_{1-6}$ alkyl, —C(O)R, —C(O)OR, —C(O)$NR_2$, or —S(O)$_2$R.
- (8p) Any one of groups (8f)-(8h), wherein $R^{12}$ is piperidinyl optionally substituted by one or two groups that are each independently $C_{1-6}$ alkyl, —C(O)$R^A$, or —S(O)$_2R^A$, wherein each $R^A$ is independently hydrogen or $C_{1-6}$ alkyl.
- (8q) Any one of groups (8f)-(8h), wherein $R^{12}$ is

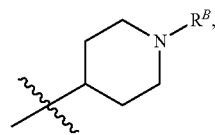

wherein $R^B$ is hydrogen, $C_{1-6}$ alkyl, —C(O)R, —C(O)OR, —C(O)$NR_2$, —S(O)$_2$R, —OC(O)R, —OC(O)OR, —OC(O)$NR_2$, —N(R)C(O)R, —N(R)C(O)OR, or —N(R)C(O)$NR_2$.

- (8r) Any one of groups (8f)-(8h), wherein $R^{12}$ is

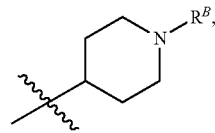

wherein $R^B$ is hydrogen, $C_{1-6}$ alkyl, —C(O)$R^A$, —C(O)$OR^A$, —C(O)N($R^A$)$_2$, —S(O)$_2R^A$, —OC(O)$R^A$, —OC(O)$OR^A$, —OC(O)N($R^A$)$_2$, —N($R^A$)C(O)$R^A$, —N($R^A$)C(O)$OR^A$, or —N($R^A$)C(O)N($R^A$)$_2$, wherein each $R^A$ is independently hydrogen, $C_{1-6}$ alkyl, $C_{2-6}$ alkenyl, $C_{1-6}$ haloalkyl, $C_{3-8}$ cycloalkyl, heterocyclyl, aryl, aryl$C_{1-6}$ alkyl, heteroaryl, or heteroaryl$C_{1-6}$ alkyl.

- (8s) Any one of groups (8f)-(8h), wherein $R^{12}$ is

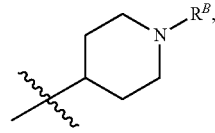

wherein $R^B$ is hydrogen, $C_{1-6}$ alkyl, —C(O)$R^A$, —C(O)$OR^A$, —C(O)N($R^A$)$_2$, —S(O)$_2R^A$, —OC(O)$R^A$, —OC(O)$OR^A$, —OC(O)N($R^A$)$_2$, —N($R^A$)C(O)$R^A$, —N($R^A$)C(O)$OR^A$, or —N($R^A$)C(O)N($R^A$)$_2$, wherein each $R^A$ is independently hydrogen or $C_{1-6}$ alkyl.

(8t) Any one of groups (8f)-(8h), wherein $R^{12}$ is

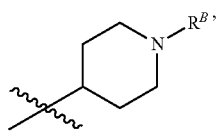

wherein $R^B$ is hydrogen, $C_{1-6}$ alkyl, —C(O)R, —C(O)OR, —C(O)NR$_2$, or —S(O)$_2$R.

(8u) Any one of groups (8f)-(8h), wherein $R^{12}$ is

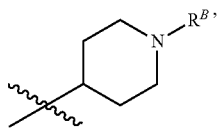

wherein $R^B$ is hydrogen, $C_{1-6}$ alkyl, —C(O)R$^A$, or —S(O)$_2$R$^A$, wherein each $R^A$ is independently hydrogen or $C_{1-6}$ alkyl.

$R^3$ is Selected from One of the Following Groups (9a)-(9g):

(9a) $R^3$ is

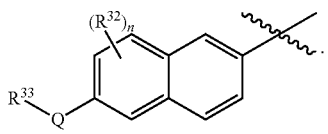

(9b) $R^3$ is

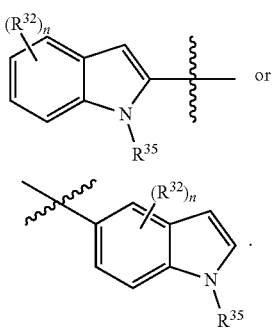 or (9c) $R^3$ is

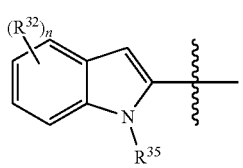

(9d) $R^3$ is

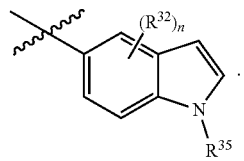

(9e) Any one of groups (9b)-(9d), wherein $R^{35}$ is hydrogen or methyl.
(9f) Any one of groups (9b)-(9d), wherein $R^{35}$ is methyl.
(9g) Any one of groups (9b)-(9d), wherein $R^{35}$ is hydrogen.

Q is Selected from One of the Following Groups (10a)-(10d):
(10a) Q is —O— or —N(H)—.
(10b) Q is —O—.
(10c) Q is —N(R$^Q$)—.
(10d) Q is —N(H)—.

n and $R^{32}$ are Selected from One of the Following Groups (11a)-(11c):
(11a) n is 0.
(11b) n is 0 or 1 and $R^{32}$ is as defined for formula (III).
(11c) n is 1 or 2 and $R^{32}$ is as defined for formula (III).

$R^{33}$ is Selected from One of the Following Groups (12a)-(12j):
(12a) $R^{33}$ is $C_{1-6}$ alkyl, $C_{2-6}$ alkenyl, aryl$C_{1-6}$ alkyl, or heteroaryl$C_{1-6}$ alkyl, wherein the arylalkyl and heteroarylalkyl are optionally substituted with one or two groups that are each independently halogen, $C_{1-6}$ alkyl, or $C_{1-6}$ haloalkyl.
(12b) $R^{33}$ is $C_{1-6}$ alkyl, $C_{2-6}$ alkenyl, aryl$C_{1-6}$ alkyl, or heteroaryl$C_{1-6}$ alkyl, wherein the arylalkyl and heteroarylalkyl are each substituted with one or two groups that are each independently halogen, $C_{1-6}$ alkyl, or $C_{1-6}$ haloalkyl.
(12c) $R^{33}$ is $C_{2-6}$ alkenyl, aryl$C_{1-6}$ alkyl, or heteroaryl$C_{1-6}$ alkyl, wherein the arylalkyl and heteroarylalkyl are optionally substituted with one or two groups that are each independently halogen, $C_{1-6}$ alkyl, or $C_{1-6}$ haloalkyl.
(12d) $R^{33}$ is $C_{2-6}$ alkenyl, aryl$C_{1-6}$ alkyl, or heteroaryl$C_{1-6}$ alkyl, wherein the arylalkyl and heteroarylalkyl are each substituted with one or two groups that are each independently halogen, $C_{1-6}$ alkyl, or $C_{1-6}$ haloalkyl.
(12e) $R^{33}$ is aryl$C_{1-6}$ alkyl or heteroaryl$C_{1-6}$ alkyl, each optionally substituted with one or two groups that are each independently halogen, $C_{1-6}$ alkyl, or $C_{1-6}$ haloalkyl.
(12f) $R^{33}$ is aryl$C_{1-6}$ alkyl or heteroaryl$C_{1-6}$ alkyl, each substituted with one or two groups that are each independently halogen, $C_{1-6}$ alkyl, or $C_{1-6}$ haloalkyl.
(12g) $R^{33}$ is aryl$C_{1-6}$ alkyl optionally substituted with one or two groups that are each independently halogen, $C_{1-6}$ alkyl, or $C_{1-6}$ haloalkyl.
(12h) $R^{33}$ is aryl$C_{1-6}$ alkyl substituted with one or two groups that are each independently halogen, $C_{1-6}$ alkyl, or $C_{1-6}$ haloalkyl.
(12i) $R^{33}$ is benzyl optionally substituted with one or two groups that are each independently halogen, $C_{1-6}$ alkyl, or $C_{1-6}$ haloalkyl.
(12j) $R^{33}$ is benzyl substituted with one or two groups that are each independently halogen, $C_{1-6}$ alkyl, or $C_{1-6}$ haloalkyl.

Particular embodiments of this aspect of the invention include compounds of any one of the formulae (III), (IIIa), and (IIIb), each as defined in each of the following rows, wherein each entry is a group number as defined above (e.g., (10b) refers to Q is —O—), and a dash "-" indicates that the variable is as defined for formula (III) or defined according to any one of the applicable variable definitions (8a)-(12j) [e.g., when $R^1$ is a dash, it can be either as defined for Formula (III) or any one of definitions (8a)-(8u)]; and an "x" indicates that the variable is not applicable to the particular embodiment (e.g., when $R^3$ is (9c), then Q and $R^{33}$ are not necessary):

|  | $R^1$ | $R^3$ | $R^{33}$ | n & $R^{32}$ | Q |
|---|---|---|---|---|---|
| (3)-1 | 8a | 9a | 12a | — | 10b |
| (3)-2 | 8f | 9a | 12a | — | 10b |
| (3)-3 | 8g | 9a | 12a | — | 10b |
| (3)-4 | 8h | 9a | 12a | — | 10b |
| (3)-5 | 8m | 9a | 12a | — | 10b |
| (3)-6 | 8a | 9a | 12c | — | 10b |
| (3)-7 | 8f | 9a | 12c | — | 10b |
| (3)-8 | 8g | 9a | 12c | — | 10b |
| (3)-9 | 8h | 9a | 12c | — | 10b |
| (3)-10 | 8m | 9a | 12c | — | 10b |
| (3)-11 | 8a | 9a | 12e | — | 10b |
| (3)-12 | 8f | 9a | 12e | — | 10b |
| (3)-13 | 8g | 9a | 12e | — | 10b |
| (3)-14 | 8h | 9a | 12e | — | 10b |
| (3)-15 | 8m | 9a | 12e | — | 10b |
| (3)-16 | 8a | 9a | 12i | — | 10b |
| (3)-17 | 8f | 9a | 12i | — | 10b |
| (3)-18 | 8g | 9a | 12i | — | 10b |
| (3)-19 | 8h | 9a | 12i | — | 10b |
| (3)-20 | 8m | 9a | 12i | — | 10b |
| (3)-21 | 8a | 9c | x | — | x |
| (3)-22 | 8f | 9c | x | — | x |
| (3)-23 | 8g | 9c | x | — | x |
| (3)-24 | 8h | 9c | x | — | x |
| (3)-25 | 8m | 9c | x | — | x |
| (3)-26 | 8a | 9d | x | — | x |
| (3)-27 | 8f | 9d | x | — | x |
| (3)-28 | 8g | 9d | x | — | x |
| (3)-29 | 8h | 9d | x | — | x |
| (3)-30 | 8m | 9d | x | — | x |
| (3)-31 | 8a | 9a | — | — | — |
| (3)-32 | 8f | 9a | — | — | — |
| (3)-33 | 8g | 9a | — | — | — |
| (3)-34 | 8h | 9a | — | — | — |
| (3)-35 | 8m | 9a | — | — | — |
| (3)-36 | 8a | 9a | — | — | 10b |
| (3)-37 | 8f | 9a | — | — | 10b |
| (3)-38 | 8g | 9a | — | — | 10b |
| (3)-39 | 8h | 9a | — | — | 10b |
| (3)-40 | 8m | 9a | — | — | 10b |
| (3)-41 | — | — | 12a | — | 10b |
| (3)-42 | — | — | 12c | — | 10b |
| (3)-43 | — | — | 12e | — | 10b |
| (3)-44 | — | — | 12i | — | 10b |
| (3)-45 | — | 9a | 12a | — | 10b |
| (3)-46 | — | 9a | 12c | — | 10b |
| (3)-47 | — | 9a | 12e | — | 10b |
| (3)-48 | — | 9a | 12i | — | 10b |

Particular embodiments of this aspect of the invention include compounds of any one of the formula (IIIb), each as defined in each of the following rows, wherein each entry is a group number as defined above (e.g., (10b) refers to Q is —O—). In addition, any one of groups (8f)-(8h) can be either as defined for Formula (IIIb) or any one of definitions (8f)-(8u):

|  | $R^1$ | $R^3$ | $R^{33}$ | n & $R^{32}$ | Q |
|---|---|---|---|---|---|
| (3)-49 | 8f | 9a | 12a | 11a | 10a |
| (3)-50 | 8g | 9a | 12a | 11a | 10a |
| (3)-51 | 8h | 9a | 12a | 11a | 10a |
| (3)-52 | 8f | 9a | 12b | 11a | 10a |
| (3)-53 | 8g | 9a | 12b | 11a | 10a |
| (3)-54 | 8h | 9a | 12b | 11a | 10a |
| (3)-55 | 8f | 9a | 12a | 11a | 10b |
| (3)-56 | 8g | 9a | 12a | 11a | 10b |
| (3)-57 | 8h | 9a | 12a | 11a | 10b |
| (3)-58 | 8f | 9a | 12b | 11a | 10b |
| (3)-59 | 8g | 9a | 12b | 11a | 10b |
| (3)-60 | 8h | 9a | 12b | 11a | 10b |
| (3)-61 | 8f | 9a | 12a | 11b | 10a |
| (3)-62 | 8g | 9a | 12a | 11b | 10a |
| (3)-63 | 8h | 9a | 12a | 11b | 10a |
| (3)-64 | 8f | 9a | 12b | 11b | 10a |
| (3)-65 | 8g | 9a | 12b | 11b | 10a |
| (3)-66 | 8h | 9a | 12b | 11b | 10a |
| (3)-67 | 8f | 9a | 12a | 11b | 10b |
| (3)-68 | 8g | 9a | 12a | 11b | 10b |
| (3)-69 | 8h | 9a | 12a | 11b | 10b |
| (3)-70 | 8f | 9a | 12b | 11b | 10b |
| (3)-71 | 8g | 9a | 12b | 11b | 10b |
| (3)-72 | 8h | 9a | 12b | 11b | 10b |

In an embodiment of the preceding embodiments of formulas (I) and (III), the compound is not

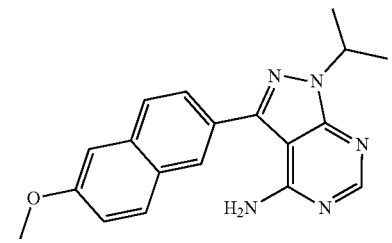

1-isopropyl-3-(6-methoxynaphthalen-2-yl)-1H-pyrazolo[3,4-d]pyrimidin-4-amine

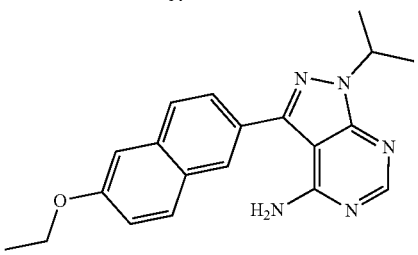

3-(6-ethoxynapthalen-2-yl)-1-isopropyl-1H-pyrazolo[3,4-d]pyrimidin-4-amine

Methods for Use

Clinical toxoplasmosis is caused by the actively dividing tachyzoite form of the parasite, which exits its host cell and invades a new cell every few days. TgCDPK1 has a unique ATP-binding site with a small gatekeeper residue, as opposed to the large gatekeeper residues present in mammalian protein kinases. This key difference in gatekeeper residues between mammalian kinases and TgCDPK1 allowed us to use bumped kinase inhibitors (BKIs) to selectively inhibit TgCDPK1 without untoward effects on the mammalian host cell.

Accordingly, the disclosure provides methods for treating an apicomplexan protozoan related disease comprising providing to a patient in need of such treatment a therapeutically effective amount of either (i) a bumped kinase inhibitor or (ii) a pharmaceutical composition comprising a bumped kinase inhibitor and a pharmaceutically acceptable excipient, carrier, or diluent.

Figure 14:
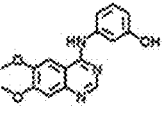
FIG. 14 shows in vitro activities of previously-described kinase inhibitors against TgCDPK1. Values shown are the average of three assays.

In one embodiment, the bumped kinase inhibitor is selected from one of the compounds of FIG. 14, or a pharmaceutically acceptable salt thereof.

In another embodiment, the bumped kinase inhibitor is according to of the formula (I) as defined above, or any embodiment thereof.

In another embodiment, the bumped kinase inhibitor is of the formula (II),

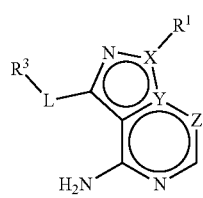

(II)

or a pharmaceutically acceptable salt thereof, wherein
X, Y, and Z are defined by either: (i) X is N, Y is C, and Z is N; or (ii) X is C, Y is N, and Z is C(H);
$R^1$ is $C_{1-6}$ alkyl, $C_{1-6}$ haloalkyl, $C_{2-6}$ alkenyl, $C_{2-6}$ alkynyl, —$C_{1-6}$ alkyl-$R^{12}$, $C_{3-8}$ cycloalkyl, monocyclic heterocyclyl, monocyclic heteroaryl, or phenyl, wherein
  the cycloalkyl, monocyclic heterocyclyl, monocyclic heteroaryl, and phenyl groups are each optionally substituted with one or two $R^{11}$ groups;
  each $R^{11}$ is independently $C_{1-6}$ alkyl, $C_{1-6}$ haloalkyl, —C(O)R, —C(O)OR, —C(O)$NR_2$, —S(O)$NR_2$, or —S(O)$_2$R;
and
$R^{12}$ is —OR, —SR, —$NR_2$, —C(O)R, —C(O)OR, —C(O)$NR_2$, —S(O)$_2$R, —OC(O)R, —OC(O)OR, —OC(O)$NR_2$, —N(R)C(O)R, —N(R)C(O)OR, —N(R)C(O)$NR_2$, phenyl, monocyclic heteroaryl, $C_{3-8}$ cycloalkyl, or monocyclic heterocyclyl, wherein the phenyl, heteroaryl, $C_{3-8}$ cycloalkyl, and heterocyclyl groups are each optionally substituted by one, two, or three groups that are each independently halogen, cyano, nitro, $C_{1-6}$ alkyl, $C_{1-6}$ haloalkyl, —OR, —SR, —$NR_2$, —C(O)R, —C(O)OR, —C(O)$NR_2$, —S(O)$_2$R, —OC(O)R, —OC(O)OR, —OC(O)$NR_2$, —N(R)C(O)R, —N(R)C(O)OR, or —N(R)C(O)$NR_2$;
L is a bond or —$CH_2$—;
$R^3$ is aryl or heteroaryl, each optionally substituted with one, two, or three $R^{31}$ groups, wherein each $R^{31}$ is independently halogen, cyano, nitro, $C_{1-6}$ alkyl, $C_{1-6}$ haloalkyl, aryl, heteroaryl, $C_{3-8}$ cycloalkyl, heterocyclyl, aryl$C_{1-6}$ alkyl, heteroaryl$C_{1-6}$ alkyl, —OR, —SR, —$NR_2$, —C(O)R, —C(O)OR, —C(O)$NR_2$, —S(O)$_2$R, —OC(O)R, —OC(O)OR, —OC(O)$NR_2$, —N(R)C(O)R, —N(R)C(O)OR, —N(R)C(O)$NR_2$ or —N(R)S(O)$_2$R, wherein the aryl, heteroaryl, $C_{3-8}$ cycloalkyl, heterocyclyl, arylalkyl, and heteroarylalkyl groups are optionally substituted with one or two $R^{10}$ groups;
each R is independently hydrogen, $C_{1-6}$ alkyl, $C_{2-6}$ alkenyl, $C_{1-6}$ haloalkyl, $C_{3-8}$ cycloalkyl, heterocyclyl, aryl, aryl$C_{1-6}$ alkyl, heteroaryl, or heteroaryl$C_{1-6}$ alkyl wherein the alkyl, aryl, arylalkyl, heteroaryl, and heteroarylalkyl are optionally substituted with one, two, three, or four $R^{10}$ groups;
and
each $R^{10}$ is independently halogen, cyano, nitro, $C_{1-6}$ alkyl, $C_{1-6}$ haloalkyl, —$OR^o$, —$SR^o$, —N($R^o$)$_2$, —C(O)$R^o$, —C(O)O$R^o$, —C(O)N($R^o$)$_2$, —S(O)$_2R^o$, —OC(O)$R^o$, —OC(O)O$R^o$, —OC(O)N($R^o$)$_2$, —N($R^o$)C(O)$R^o$, —N($R^o$)C(O)O$R^o$, or —N($R^o$)C(O)N($R^o$)$_2$, wherein each $R^o$ is independently hydrogen or $C_{1-6}$ alkyl.

The disclosure further comprises subgenera of formula (II) in which the substituents are selected as any and all combinations of one or more of structural formula (II), $R^1$, and $R^3$, as defined herein, including without limitation, the following:

Structural Formula II is One of Formulae (IIa)-(IIh):

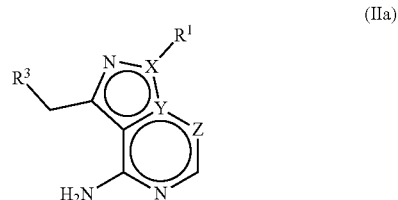

(IIa)

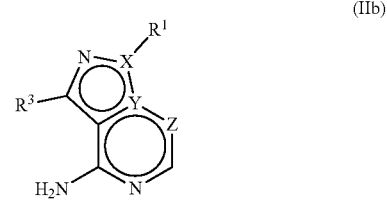

(IIb)

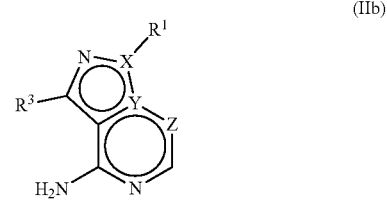

(IIc)

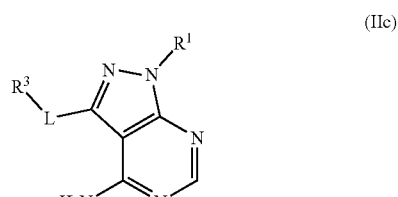

(IId)

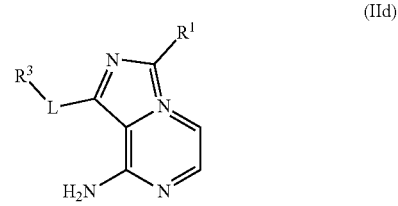

(IIe)

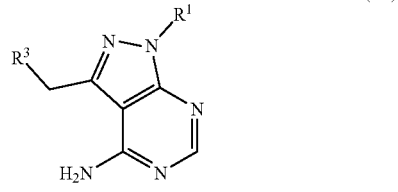

(IIf)

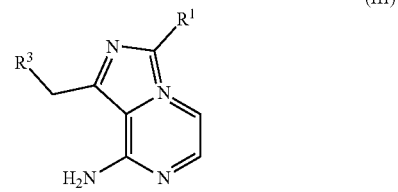

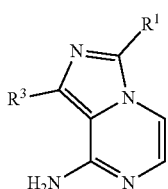

(IIg)

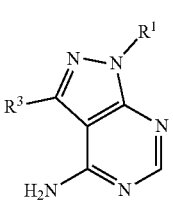

(IIh)

$R^1$ is Selected from One of the Following Groups (6a)-(6ii):
- (6a) $R^1$ is $C_{1-4}$ alkyl, —$C_{1-4}$ alkyl-$R^{12}$, $C_{2-4}$ alkynyl, $C_{3-8}$ cycloalkyl, monocyclic heterocyclyl, monocyclic heteroaryl, or phenyl, wherein the cycloalkyl, heterocyclyl, heteroaryl, and phenyl groups are each optionally substituted with one or two $R^{11}$ groups.
- (6b) $R^1$ is $C_{3-8}$ cycloalkyl, monocyclic heterocyclyl, monocyclic heteroaryl, or phenyl, wherein the cycloalkyl, heterocyclyl, heteroaryl, and phenyl groups are each optionally substituted with one or two $R^{11}$ groups.
- (6c) $R^1$ is $C_{3-8}$ cycloalkyl; or a monocyclic heterocyclyl optionally substituted with one $R^{11}$ group.
- (6d) $R^1$ is $C_{3-8}$ cycloalkyl.
- (6e) $R^1$ is monocyclic heterocyclyl optionally substituted with one $R^{11}$ group.
- (6f) $R^1$ is piperidinyl or tetrahydropyranyl, each optionally substituted with one $R^{11}$ group.
- (6g) $R^1$ is phenyl optionally substituted with one or two $R^{11}$ groups.
- (6h) $R^1$ is $C_{2-6}$ alkyl.
- (6i) $R^1$ is $C_{1-4}$ alkyl.
- (6j) $R^1$ is isopropyl or t-butyl.
- (6k) $R^1$ is t-butyl.
- (6l) $R^1$ is isopropyl.
- (6m) $R^1$ is $C_{2-6}$ alkyl or —$C_{1-4}$ alkyl-$R^{12}$.
- (6n) $R^1$ is —$C_{1-4}$ alkyl-$R^{12}$.
- (6o) $R^1$ is —$C_{1-2}$ alkyl-$R^{12}$.
- (6p) $R^1$ is —$CH_2$—$R^{12}$.
- (6q) Any one of groups (6m)-(6p), wherein $R^{12}$ is —C(O)OR, —C(O)NR$_2$, phenyl, monocyclic heteroaryl, $C_{3-8}$ cycloalkyl, or monocyclic heterocyclyl, wherein the phenyl, heteroaryl, $C_{3-8}$ cycloalkyl, and heterocyclyl groups are each optionally substituted by one, two, or three groups that are each independently halogen, cyano, nitro, $C_{1-6}$ alkyl, $C_{1-6}$ haloalkyl, —OR, —SR, —NR$_2$, —C(O)R, —C(O)OR, —C(O)NR$_2$, —S(O)$_2$R, —OC(O)R, —OC(O)OR, —OC(O)NR$_2$, —N(R)C(O)R, —N(R)C(O)OR, or —N(R)C(O)NR$_2$;
- (6r) Any one of groups (6m)-(6p), $R^{12}$ is —C(O)OR or —C(O)NR$_2$.
- (6s) Any one of groups (6m)-(6p), $R^{12}$ is phenyl, monocyclic heteroaryl, $C_{3-8}$ cycloalkyl, or monocyclic heterocyclyl, each optionally substituted by one, two, or three groups that are each independently halogen, cyano, nitro, $C_{1-6}$ alkyl, $C_{1-6}$ haloalkyl, —OR, —SR, —NR$_2$, —C(O)R, —C(O)OR, —C(O)NR$_2$, —S(O)$_2$R, —OC(O)R, —OC(O)OR, —OC(O)NR$_2$, —N(R)C(O)R, —N(R)C(O)OR, or —N(R)C(O)NR$_2$.
- (6t) Any one of groups (6m)-(6p), wherein $R^{12}$ is phenyl, monocyclic heteroaryl, $C_{3-8}$ cycloalkyl, or monocyclic heterocyclyl, wherein the phenyl, heteroaryl, $C_{3-8}$ cycloalkyl, and heterocyclyl groups are each optionally substituted by one or two groups that are each independently halogen, $C_{1-6}$ alkyl, —C(O)R, —C(O)OR, —C(O)NR$_2$, —S(O)$_2$R, —OC(O)R, —OC(O)OR, —OC(O)NR$_2$, —N(R)C(O)R, —N(R)C(O)OR, or —N(R)C(O)NR$_2$.
- (6u) Any one of groups (6m)-(6p), $R^{12}$ is phenyl or monocyclic heterocyclyl, each optionally substituted by one, two, or three groups that are each independently halogen, cyano, nitro, $C_{1-6}$ alkyl, $C_{1-6}$ haloalkyl, —OR, —SR, —NR$_2$, —C(O)R, —C(O)OR, —C(O)NR$_2$, —S(O)$_2$R, —OC(O)R, —OC(O)OR, —OC(O)NR$_2$, —N(R)C(O)R, —N(R)C(O)OR, or —N(R)C(O)NR$_2$.
- (6v) Any one of groups (6m)-(6p), $R^{12}$ is monocyclic heterocyclyl optionally substituted by one, two, or three groups that are each independently halogen, cyano, nitro, $C_{1-6}$ alkyl, $C_{1-6}$ haloalkyl, —OR, —SR, —NR$_2$, —C(O)R, —C(O)OR, —C(O)NR$_2$, —S(O)$_2$R, —OC(O)R, —OC(O)OR, —OC(O)NR$_2$, —N(R)C(O)R, —N(R)C(O)OR, or —N(R)C(O)NR$_2$.
- (6w) Any one of groups (6m)-(6p), wherein $R^{12}$ is monocyclic heterocyclyl optionally substituted by one or two groups that are each independently halogen, $C_{1-6}$ alkyl, —C(O)R, —C(O)OR, —C(O)NR$_2$, —S(O)$_2$R, —OC(O)R, —OC(O)OR, —OC(O)NR$_2$, —N(R)C(O)R, —N(R)C(O)OR, or —N(R)C(O)NR$_2$.
- (6x) Any one of groups (6m)-(6p), $R^{12}$ is piperidinyl or tetrahydropyranyl, each optionally substituted by one or two groups that are each independently halogen, cyano, nitro, $C_{1-6}$ alkyl, $C_{1-6}$ haloalkyl, —OR, —SR, —NR$_2$, —C(O)R, —C(O)OR, —C(O)NR$_2$, —S(O)$_2$R, —OC(O)R, —OC(O)OR, —OC(O)NR$_2$, —N(R)C(O)R, —N(R)C(O)OR, or —N(R)C(O)NR$_2$.
- (6y) Any one of groups (6m)-(6p), wherein $R^{12}$ is piperidinyl optionally substituted by one or two groups that are each independently halogen, cyano, nitro, $C_{1-6}$ alkyl, $C_{1-6}$ haloalkyl, —OR, —SR, —NR$_2$, —C(O)R, —C(O)OR, —C(O)NR$_2$, —S(O)$_2$R, —OC(O)R, —OC(O)OR, —OC(O)NR$_2$, —N(R)C(O)R, —N(R)C(O)OR, or —N(R)C(O)NR$_2$.
- (6z) Any one of groups (6m)-(6p), wherein $R^{12}$ is piperidinyl optionally substituted by one or two groups that are each independently $C_{1-6}$ alkyl, —C(O)$R^A$, —C(O)O$R^A$, —C(O)N($R^A$)$_2$, —S(O)$_2R^A$, —OC(O)$R^A$, —OC(O)O$R^A$, —OC(O)N($R^A$)$_2$, —N($R^A$)C(O)$R^A$, —N($R^A$)C(O)O$R^A$, or —N($R^A$)C(O)N($R^A$)$_2$, wherein each $R^A$ is independently hydrogen, $C_{1-6}$ alkyl, $C_{2-6}$ alkenyl, $C_{1-6}$ haloalkyl, $C_{3-8}$ cycloalkyl, heterocyclyl, aryl, aryl$C_{1-6}$ alkyl, heteroaryl, or heteroaryl$C_{1-6}$ alkyl.
- (6aa) Any one of groups (6m)-(6p), wherein $R^{12}$ is piperidinyl optionally substituted by one or two groups that are each independently $C_{1-6}$ alkyl, —C(O)R, —C(O)OR, —C(O)NR$_2$, —S(O)$_2$R, —OC(O)R, —OC(O)OR, —OC(O)NR$_2$, —N(R)C(O)R, —N(R)C(O)OR, or —N(R)C(O)NR$_2$.
- (6bb) Any one of groups (6m)-(6p), wherein $R^{12}$ is piperidinyl optionally substituted by one or two groups that are each independently $C_{1-6}$ alkyl, —C(O)$R^A$, —C(O)O$R^A$, —C(O)N($R^A$)$_2$, —S(O)$_2R^A$, —OC(O)$R^A$, —OC(O)O$R^A$, —OC(O)N($R^A$)$_2$, —N($R^A$) C(O)$R^A$, —N($R^A$)C(O)O$R^A$, or —N($R^A$)C(O)N($R^A$)$_2$, wherein each $R^A$ is independently hydrogen or $C_{1-6}$ alkyl.

(6cc) Any one of groups (6m)-(6p), wherein $R^{12}$ is piperidinyl optionally substituted by one or two groups that are each independently $C_{1-6}$ alkyl, —C(O)R, —C(O)OR, —C(O)NR$_2$, or —S(O)$_2$R.

(6dd) Any one of groups (6m)-(6p), wherein $R^{12}$ is piperidinyl optionally substituted by one or two groups that are each independently $C_{1-6}$ alkyl, —C(O)R$^A$, or —S(O)$_2$R$^A$, wherein each $R^A$ is independently hydrogen or $C_{1-6}$ alkyl.

(6ee) Any one of groups (6m)-(6p), wherein $R^{12}$ is

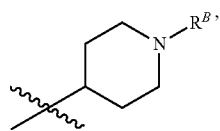

wherein $R^B$ is hydrogen, $C_{1-6}$ alkyl, —C(O)R, —C(O)OR, —C(O)NR$_2$, —S(O)$_2$R, —OC(O)R, —OC(O)OR, —OC(O)NR$_2$, —N(R)C(O)R, —N(R)C(O)OR, or —N(R)C(O)NR$_2$.

(6ff) Any one of groups (6m)-(6p), wherein $R^{12}$ is

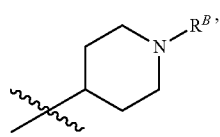

wherein $R^B$ is hydrogen, $C_{1-6}$ alkyl, —C(O)R$^A$, —C(O)OR$^A$, —C(O)N(R$^A$)$_2$, —S(O)$_2$R$^A$, —OC(O)R$^A$, —OC(O)OR$^A$, —OC(O)N(R$^A$)$_2$, —N(R$^A$)C(O)R$^A$, —N(R$^A$)C(O)OR$^A$, or —N(R$^A$)C(O)N(R$^A$)$_2$, wherein each $R^A$ is independently hydrogen, $C_{1-6}$ alkyl, $C_{2-6}$ alkenyl, $C_{1-6}$ haloalkyl, $C_{3-8}$ cycloalkyl, heterocyclyl, aryl, arylC$_{1-6}$ alkyl, heteroaryl, or heteroarylC$_{1-6}$ alkyl.

(6gg) Any one of groups (6m)-(6p), wherein $R^{12}$ is

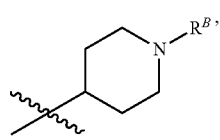

wherein $R^B$ is hydrogen, $C_{1-6}$ alkyl, —C(O)R$^A$, —C(O)OR$^A$, —C(O)N(R$^A$)$_2$, —S(O)$_2$R$^A$, —OC(O)R$^A$, —OC(O)OR$^A$, —OC(O)N(R$^A$)$_2$, —N(R$^A$)C(O)R$^A$, —N(R$^A$)C(O)OR$^A$, or —N(R$^A$)C(O)N(R$^A$)$_2$, wherein each $R^A$ is independently hydrogen or $C_{1-6}$ alkyl.

(6hh) Any one of groups (6m)-(6p), wherein $R^{12}$ is

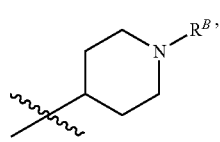

wherein $R^B$ is hydrogen, $C_{1-6}$ alkyl, —C(O)R, —C(O)OR, —C(O)NR$_2$, or —S(O)$_2$R.

(6ii) Any one of groups (6m)-(6p), wherein $R^{12}$ is

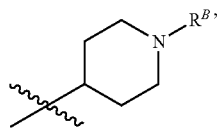

wherein $R^B$ is hydrogen, $C_{1-6}$ alkyl, —C(O)R$^A$, or —S(O)$_2$R$^A$, wherein each $R^A$ is independently hydrogen or $C_{1-6}$ alkyl.

$R^3$ is Selected from One of the Following Groups (7a)-(7x):

(7a) $R^3$ is naphthyl, quinolinyl, pyridyl, pyrimidinyl, indolyl, benzodioxolyl, 2,3-dihydrobenzodioxinyl, dibenzothienyl, chromanyl, or phenyl, each optionally substituted with one, two, or three $R^{31}$ groups.

(7b) $R^3$ is naphthyl, quinolinyl, indolyl, benzodioxolyl, 2,3-dihydrobenzodioxinyl, or chromanyl, each optionally substituted with one, two, or three $R^{31}$ groups.

(7c) $R^3$ is quinolinyl, pyridyl, pyrimidinyl, or indolyl, each optionally substituted with one, two, or three $R^{31}$ groups.

(7d) $R^3$ is quinolinyl or indolyl, each optionally substituted with one, two, or three $R^{31}$ groups.

(7e) $R^3$ is quinolinyl optionally substituted with one, two, or three $R^{31}$ groups.

(7f) $R^3$ is pyridyl or pyrimidinyl, each optionally substituted with one, two, or three $R^{31}$ groups.

(7g) $R^3$ is phenyl substituted with one, two, or three $R^{31}$ groups.

(7h) $R^3$ is phenyl optionally substituted with one or two $R^{31}$ groups, and substituted with one group that is halogen, $C_{1-6}$ alkyl, —OR, —SR, —NR$_2$, —N(R)C(O)R, or —N(R)S(O)$_2$R.

(7i) $R^3$ is phenyl optionally substituted with one or two $R^{31}$ groups, and substituted with one group that is —OR or —N(R)C(O)R.

(7j) $R^3$ is phenyl optionally substituted with one or two $R^{31}$ groups, and substituted with one group that is —OR$^{10}$, wherein $R^{10}$ is benzyl optionally substituted with one, two, three, or four groups that are each independently halogen, $C_{1-6}$ alkyl, $C_{1-6}$ haloalkyl, or —OR$^O$.

(7k) $R^3$ is phenyl optionally substituted with one or two $R^{31}$ groups, and substituted with one group that is —N(H)C(O)R$^{20}$, wherein $R^{20}$ is $C_{1-6}$ alkyl, $C_{2-6}$ alkenyl, $C_{1-6}$ haloalkyl, aryl, or arylC$_{1-6}$ alkyl.

(7l) $R^3$ is naphthyl optionally substituted with one, two, or three $R^{31}$ groups.

(7m) $R^3$ is naphthyl optionally substituted with one or two $R^{31}$ groups and substituted with one group that is —OR$^{15}$, wherein $R^{15}$ is $C_{1-6}$ alkyl or benzyl, wherein the benzyl is optionally substituted with one, two, three, or four groups that are each independently halogen, $C_{1-6}$ alkyl, $C_{1-6}$ haloalkyl, or —OR$^O$.

(7n) $R^3$ is naphth-1-yl optionally substituted with one, two, or three $R^{31}$ groups.

(7o) $R^3$ is naphth-1-yl optionally substituted with one or two $R^{31}$ groups and substituted with one group that is —OR$^{15}$, wherein $R^{15}$ is $C_{1-6}$ alkyl or benzyl, wherein the benzyl is optionally substituted with one, two, three, or four groups that are each independently halogen, $C_{1-6}$ alkyl, $C_{1-6}$ haloalkyl, or —OR$^O$.

(7p) $R^3$ is naphth-2-yl optionally substituted with one, two, or three $R^{31}$ groups.

(7q) $R^3$ is naphth-2-yl optionally substituted with one or two $R^{31}$ groups and substituted with one group that is —OR$^{15}$, wherein R$^{15}$ is C$_{1-6}$ alkyl or benzyl, wherein the benzyl is optionally substituted with one, two, three, or four groups that are each independently halogen, C$_{1-6}$ alkyl, C$_{1-6}$ haloalkyl, or —OR$^0$.

(7r) R$^3$ is

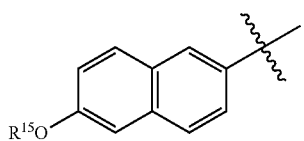

(7s) R$^3$ is indolyl optionally substituted with one, two, or three R$^{31}$ groups.
(7t) R$^3$ is indol-2-yl optionally substituted with one, two, or three R$^{31}$ groups.
(7u) R$^3$ is indol-3-yl optionally substituted with one, two, or three R$^{31}$ groups.
(7v) R$^3$ is indol-5-yl optionally substituted with one, two, or three R$^{31}$ groups.
(7w) R$^3$ is indol-6-yl optionally substituted with one, two, or three R$^{31}$ groups.
(7x) Any one of groups (2a)-(2aa) as defined above for formula (I).

Other particular embodiments of this aspect of the invention include compounds of any one of the formulae (II), (IIa)-(IIh), each as defined in each of the following rows, wherein each entry is a group number as defined above (e.g., (7w) refers to R$^3$ is indol-6-yl optionally substituted with one, two, or three R$^{31}$ groups), and a dash "-" indicates that the variable is as defined for formula (II) or defined according to any one of the applicable variable definitions (6a)-(7x) [e.g., when R$^1$ is a dash, it can be either as defined for Formula (II) or any one of definitions (6a)-(6ii)]:

| | R$^1$ | R$^3$ |
|---|---|---|
| (2)-1 | 6c | 7a |
| (2)-2 | 6c | 7c |
| (2)-3 | 6c | 7e |
| (2)-4 | 6c | 7g |
| (2)-5 | 6c | 7k |
| (2)-6 | 6c | 7l |
| (2)-7 | 6c | 7m |
| (2)-8 | 6c | 7s |
| (2)-9 | 6c | 7t |
| (2)-10 | 6c | 7v |
| (2)-11 | 6f | 7a |
| (2)-12 | 6f | 7c |
| (2)-13 | 6f | 7e |
| (2)-14 | 6f | 7g |
| (2)-15 | 6f | 7k |
| (2)-16 | 6f | 7l |
| (2)-17 | 6f | 7m |
| (2)-18 | 6f | 7s |
| (2)-19 | 6f | 7t |
| (2)-20 | 6f | 7v |
| (2)-21 | 6h | 7a |
| (2)-22 | 6h | 7c |
| (2)-23 | 6h | 7e |
| (2)-24 | 6h | 7g |
| (2)-25 | 6h | 7k |
| (2)-26 | 6h | 7l |
| (2)-27 | 6h | 7m |
| (2)-28 | 6h | 7s |
| (2)-29 | 6h | 7t |
| (2)-30 | 6h | 7v |
| (2)-31 | 6n | 7a |
| (2)-32 | 6n | 7c |
| (2)-33 | 6n | 7e |
| (2)-34 | 6n | 7g |
| (2)-35 | 6n | 7k |
| (2)-36 | 6n | 7l |
| (2)-37 | 6n | 7m |
| (2)-38 | 6n | 7s |
| (2)-39 | 6n | 7t |
| (2)-40 | 6n | 7v |
| (2)-41 | 6o | 7a |
| (2)-42 | 6o | 7c |
| (2)-43 | 6o | 7e |
| (2)-44 | 6o | 7g |
| (2)-45 | 6o | 7k |
| (2)-46 | 6o | 7l |
| (2)-47 | 6o | 7m |
| (2)-48 | 6o | 7s |
| (2)-49 | 6o | 7t |
| (2)-50 | 6o | 7v |
| (2)-51 | 6p | 7a |
| (2)-52 | 6p | 7c |
| (2)-53 | 6p | 7e |
| (2)-54 | 6p | 7g |
| (2)-55 | 6p | 7k |
| (2)-56 | 6p | 7l |
| (2)-57 | 6p | 7m |
| (2)-58 | 6p | 7s |
| (2)-59 | 6p | 7t |
| (2)-60 | 6p | 7v |
| (2)-61 | 6aa | 7a |
| (2)-62 | 6aa | 7c |
| (2)-63 | 6aa | 7e |
| (2)-64 | 6aa | 7g |
| (2)-65 | 6aa | 7k |
| (2)-66 | 6aa | 7l |
| (2)-67 | 6aa | 7m |
| (2)-68 | 6aa | 7s |
| (2)-69 | 6aa | 7t |
| (2)-70 | 6aa | 7v |

In another embodiment, the compound of formula (II) is one of compounds of Table B,

TABLE B

| Cmpd # | Structure | Name |
|---|---|---|
| 1 | 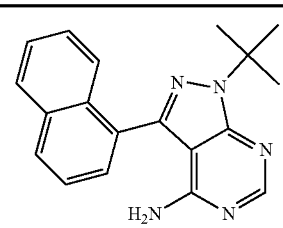 | 1-tert-butyl-3-(naphthalen-1-yl)-1H-pyrazolo[3,4-d]pyrimidin-4-amine |

TABLE B-continued

| Cmpd # | Structure | Name |
|---|---|---|
| 2 | 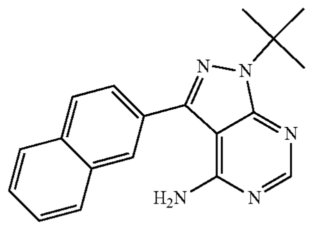 [SMILES: CC(C)(C)n1nc(-c2ccc3ccccc3c2)c2c(N)ncnc21] | 1-tert-butyl-3-(naphthalen-2-yl)-1H-pyrazolo[3,4-d]pyrimidin-4-amine |
| 3 | 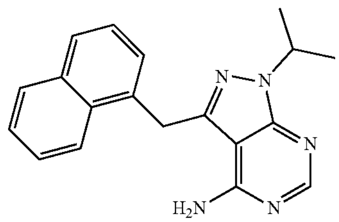 [SMILES: CC(C)n1nc(Cc2cccc3ccccc23)c2c(N)ncnc21] | 1-isopropyl-3-(naphthalen-1-ylmethyl)-1H-pyrazolo[3,4-d]pyrimidin-4-amine |
| 5a | 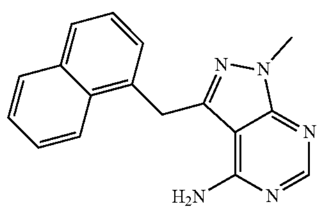 [SMILES: Cn1nc(Cc2cccc3ccccc23)c2c(N)ncnc21] | 1-methyl-3-(naphthalen-1-ylmethyl)-1H-pyrazolo[3,4-d]pyrimidin-4-amine |
| 5b | 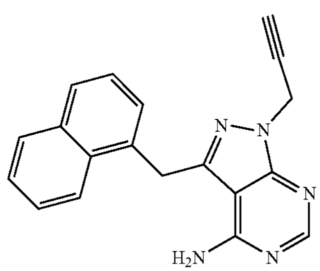 [SMILES: C#CCn1nc(Cc2cccc3ccccc23)c2c(N)ncnc21] | 3-(naphthalen-1-ylmethyl)-1-(prop-2-ynyl)-1H-pyrazolo[3,4-d]pyrimidin-4-amine |
| 5c | 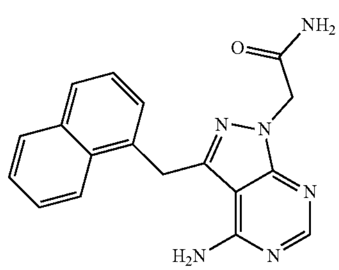 [SMILES: NC(=O)Cn1nc(Cc2cccc3ccccc23)c2c(N)ncnc21] | 2-(4-amino-3-(naphthalen-1-ylmethyl)-1H-pyrazolo[3,4-d]pyrimidin-1-yl)acetamide |
| 5d | 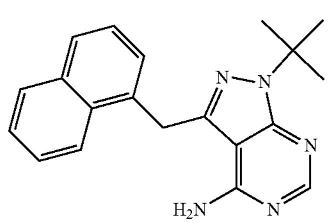 [SMILES: CC(C)(C)n1nc(Cc2cccc3ccccc23)c2c(N)ncnc21] | 1-tert-butyl-3-(naphthalen-1-ylmethyl)-1H-pyrazolo[3,4-d]pyrimidin-4-amine |

TABLE B-continued

| Cmpd # | Structure | Name |
| --- | --- | --- |
| 5e | 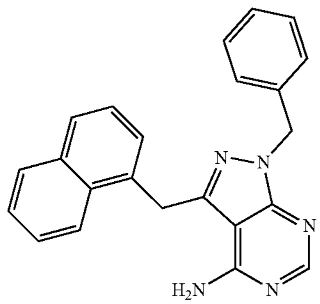 [SMILES: Nc1ncnc2c1c(Cc1cccc3ccccc13)nn2Cc1ccccc1] | 1-benzyl-3-(naphthalen-1-ylmethyl)-1H-pyrazolo[3,4-d]pyrimidin-4-amine |
| 5f | 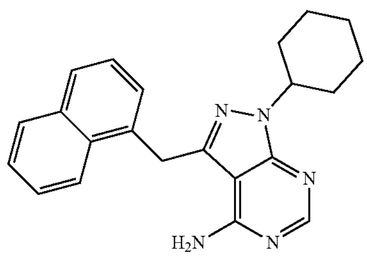 | 1-cyclohexyl-3-(naphthalen-1-ylmethyl)-1H-pyrazolo[3,4-d]pyrimidin-4-amine |
| 5g | 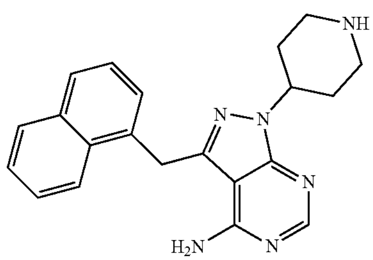 [SMILES: Nc1ncnc2c1c(Cc1cccc3ccccc13)nn2C1CCNCC1] | 3-(naphthalen-1-ylmethyl)-1-(piperidin-4-yl)-1H-pyrazolo[3,4-d]pyrimidin-4-amine |
| 5i | 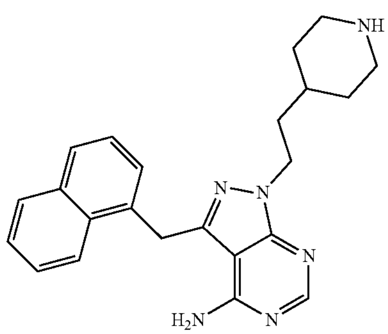 [SMILES: Nc1ncnc2c1c(Cc1cccc3ccccc13)nn2CCC1CCNCC1] | 3-(naphthalen-1-ylmethyl)-1-(2-(piperidin-4-yl)ethyl)-1H-pyrazolo[3,4-d]pyrimidin-4-amine |
| 5h | 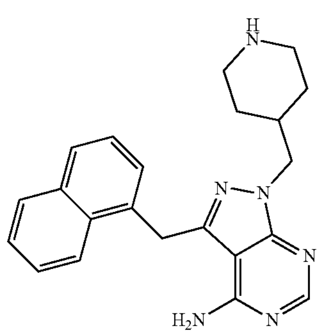 [SMILES: Nc1ncnc2c1c(Cc1cccc3ccccc13)nn2CC1CCNCC1] | 3-(naphthalen-1-ylmethyl)-1-(piperidin-4-ylmethyl)-1H-pyrazolo[3,4-d]pyrimidin-4-amine |

TABLE B-continued

| Cmpd # | Structure | Name |
| --- | --- | --- |
| 5j | 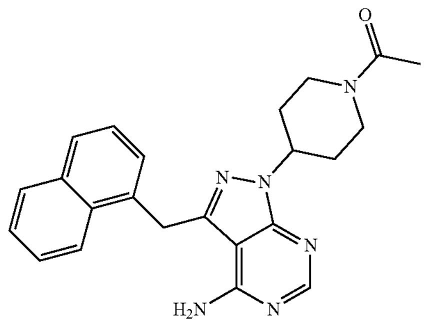 [SMILES: CC(=O)N1CCC(n2nc(Cc3cccc4ccccc34)c3c(N)ncnc32)CC1] | 1-(4-(4-amino-3-(naphthalen-1-ylmethyl)-1H-pyrazolo[3,4-d]pyrimidin-1-yl)piperidin-1-yl)ethanone |
| 5p | 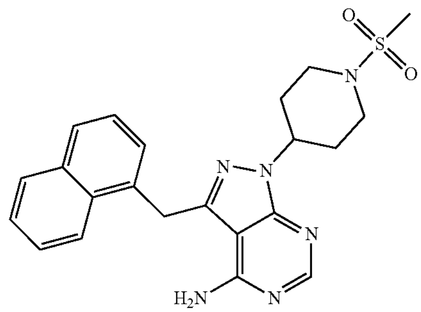 [SMILES: CS(=O)(=O)N1CCC(n2nc(Cc3cccc4ccccc34)c3c(N)ncnc32)CC1] | 1-(1-(methylsulfonyl)piperidin-4-yl)-3-(naphthalen-1-ylmethyl)-1H-pyrazolo[3,4-d]pyrimidin-4-amine |
| 5m | 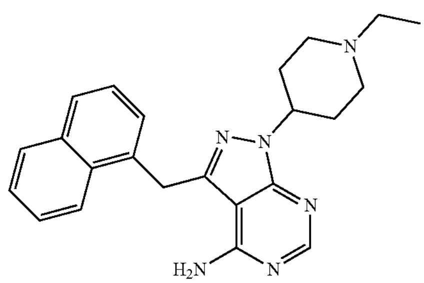 [SMILES: CCN1CCC(n2nc(Cc3cccc4ccccc34)c3c(N)ncnc32)CC1] | 1-(1-ethylpiperidin-4-yl)-3-(naphthalen-1-ylmethyl)-1H-pyrazolo[3,4-d]pyrimidin-4-amine |
| 5k | 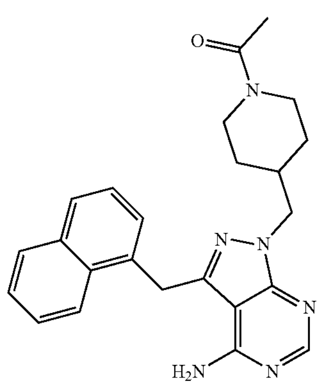 [SMILES: CC(=O)N1CCC(Cn2nc(Cc3cccc4ccccc34)c3c(N)ncnc32)CC1] | 1-(4-((4-amino-3-(naphthalen-1-ylmethyl)-1H-pyrazolo[3,4-d]pyrimidin-1-yl)methyl)piperidin-1-yl)ethanone |

TABLE B-continued

| Cmpd # | Structure | Name |
|---|---|---|
| 5q | 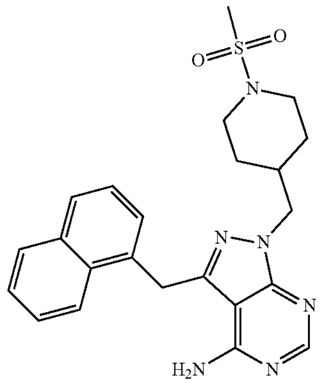 [SMILES: CS(=O)(=O)N1CCC(Cn2nc(Cc3cccc4ccccc34)c3c(N)ncnc32)CC1] | 1-((1-(methylsulfonyl)piperidin-4-yl)methyl)-3-(naphthalen-1-ylmethyl)-1H-pyrazolo[3,4-d]pyrimidin-4-amine |
| 5n | 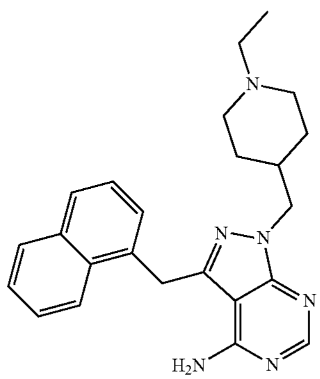 [SMILES: CCN1CCC(Cn2nc(Cc3cccc4ccccc34)c3c(N)ncnc32)CC1] | 1-((1-ethylpiperidin-4-yl)methyl)-3-(naphthalen-1-ylmethyl)-1H-pyrazolo[3,4-d]pyrimidin-4-amine |
| 5l | 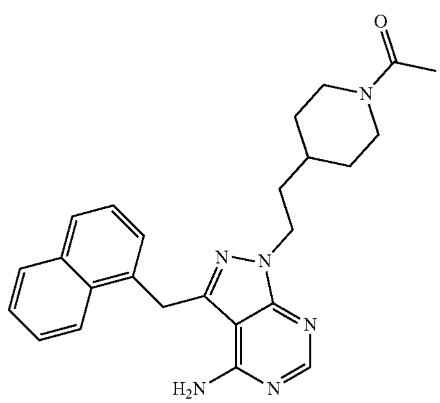 [SMILES: CC(=O)N1CCC(CCn2nc(Cc3cccc4ccccc34)c3c(N)ncnc32)CC1] | 1-(4-(2-(4-amino-3-(naphthalen-1-ylmethyl)-1H-pyrazolo[3,4-d]pyrimidin-1-yl)ethyl)piperidin-1-yl)ethanone |
| 5r | 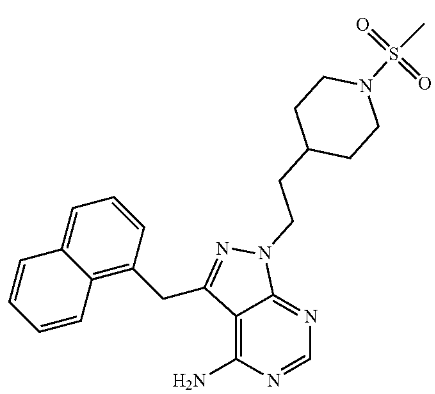 [SMILES: CS(=O)(=O)N1CCC(CCn2nc(Cc3cccc4ccccc34)c3c(N)ncnc32)CC1] | 1-(2-(1-(methylsulfonyl)piperidin-4-yl)ethyl)-3-(naphthalen-1-ylmethyl)-1H-pyrazolo[3,4-d]pyrimidin-4-amine |

TABLE B-continued

| Cmpd # | Structure | Name |
|---|---|---|
| 5o | 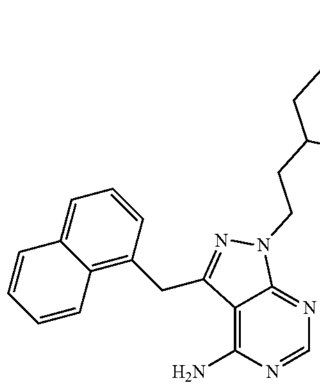 | 1-(2-(1-ethylpiperidin-4-yl)ethyl)-3-(naphthalen-1-ylmethyl)-1H-pyrazolo[3,4-d]pyrimidin-4-amine |
| 7a | 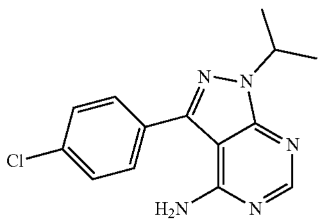 [SMILES: CC(C)n1nc(-c2ccc(Cl)cc2)c2c(N)ncnc21] | 3-(4-chlorophenyl)-1-isopropyl-1H-pyrazolo[3,4-d]pyrimidin-4-amine |
| 7b | 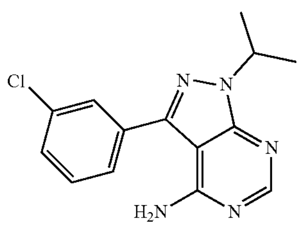 [SMILES: CC(C)n1nc(-c2cccc(Cl)c2)c2c(N)ncnc21] | 3-(3-chlorophenyl)-1-isopropyl-1H-pyrazolo[3,4-d]pyrimidin-4-amine |
| 7c | 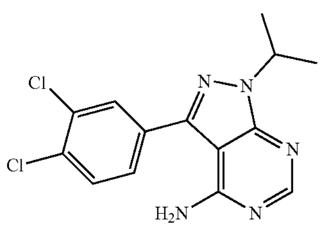 [SMILES: CC(C)n1nc(-c2ccc(Cl)c(Cl)c2)c2c(N)ncnc21] | 3-(3,4-dichlorophenyl)-1-isopropyl-1H-pyrazolo[3,4-d]pyrimidin-4-amine |
| 7d | 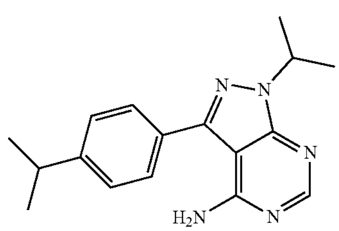 [SMILES: CC(C)c1ccc(-c2nn(C(C)C)c3ncnc(N)c23)cc1] | 1-isopropyl-3-(4-isopropylphenyl)-1H-pyrazolo[3,4-d]pyrimidin-4-amine |
| 7e | 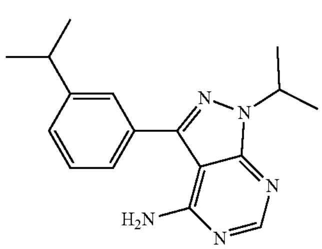 [SMILES: CC(C)c1cccc(-c2nn(C(C)C)c3ncnc(N)c23)c1] | 1-isopropyl-3-(3-isopropylphenyl)-1H-pyrazolo[3,4-d]pyrimidin-4-amine |

TABLE B-continued

| Cmpd # | Structure | Name |
|---|---|---|
| 7f | 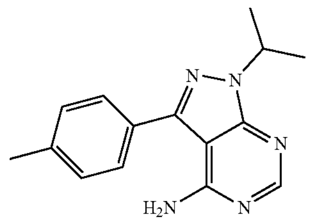 [SMILES: Cc1ccc(-c2nn(C(C)C)c3ncnc(N)c23)cc1] | 1-isopropyl-3-p-tolyl-1H-pyrazolo[3,4-d]pyrimidin-4-amine |
| 7g | 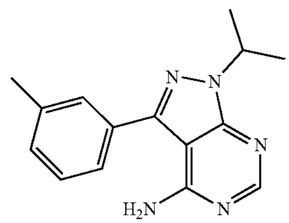 [SMILES: Cc1cccc(-c2nn(C(C)C)c3ncnc(N)c23)c1] | 1-isopropyl-3-m-tolyl-1H-pyrazolo[3,4-d]pyrimidin-4-amine |
| 7h | 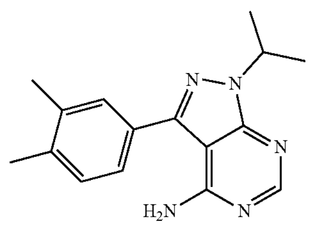 [SMILES: Cc1ccc(-c2nn(C(C)C)c3ncnc(N)c23)cc1C] | 3-(3,4-dimethylphenyl)-1-isopropyl-1H-pyrazolo[3,4-d]pyrimidin-4-amine |
| 7i | 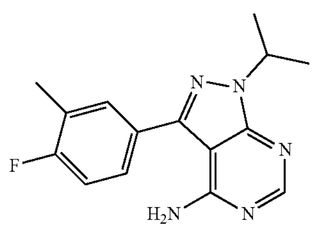 [SMILES: Cc1cc(-c2nn(C(C)C)c3ncnc(N)c23)ccc1F] | 3-(4-fluoro-3-methylphenyl)-1-isopropyl-1H-pyrazolo[3,4-d]pyrimidin-4-amine |
| 7j | 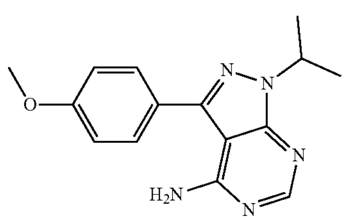 [SMILES: COc1ccc(-c2nn(C(C)C)c3ncnc(N)c23)cc1] | 1-isopropyl-3-(4-methoxyphenyl)-1H-pyrazolo[3,4-d]pyrimidin-4-amine |
| 7k | 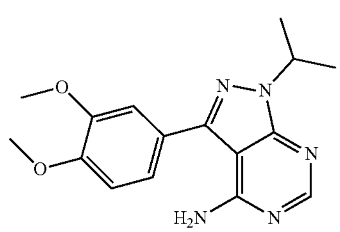 [SMILES: COc1ccc(-c2nn(C(C)C)c3ncnc(N)c23)cc1OC] | 3-(3,4-dimethoxyphenyl)-1-isopropyl-1H-pyrazolo[3,4-d]pyrimidin-4-amine |
| 7l | 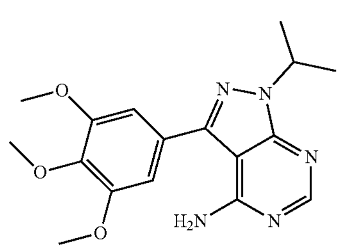 [SMILES: COc1cc(-c2nn(C(C)C)c3ncnc(N)c23)cc(OC)c1OC] | 1-isopropyl-3-(3,4,5-trimethoxyphenyl)-1H-pyrazolo[3,4-d]pyrimidin-4-amine |

TABLE B-continued

| Cmpd # | Structure | Name |
|---|---|---|
| 7m | 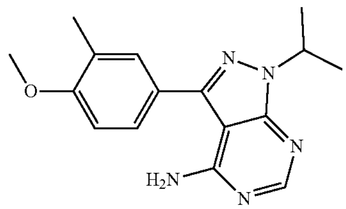 [SMILES: COc1ccc(-c2nn(C(C)C)c3ncnc(N)c23)cc1C] | 1-isopropyl-3-(4-methoxy-3-methylphenyl)-1H-pyrazolo[3,4-d]pyrimidin-4-amine |
| 7n | 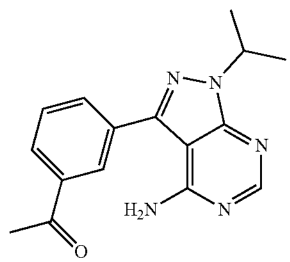 [SMILES: CC(=O)c1cccc(-c2nn(C(C)C)c3ncnc(N)c23)c1] | 1-(3-(4-amino-1-isopropyl-1H-pyrazolo[3,4-d]pyrimidin-3-yl)phenyl)ethanone |
| 7o | 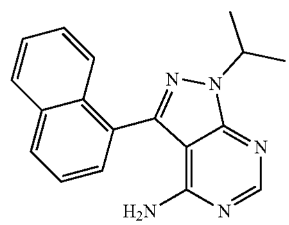 [SMILES: CC(C)n1nc(-c2cccc3ccccc23)c2c(N)ncnc21] | 1-isopropyl-3-(naphthalen-1-yl)-1H-pyrazolo[3,4-d]pyrimidin-4-amine |
| 7p | 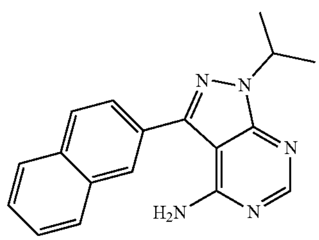 [SMILES: CC(C)n1nc(-c2ccc3ccccc3c2)c2c(N)ncnc21] | 1-isopropyl-3-(naphthalen-2-yl)-1H-pyrazolo[3,4-d]pyrimidin-4-amine |
| 7q | 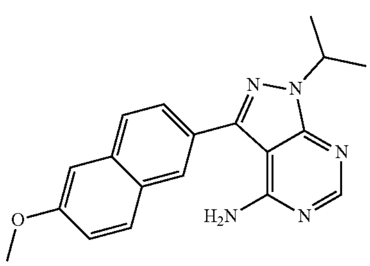 [SMILES: COc1ccc2cc(-c3nn(C(C)C)c4ncnc(N)c34)ccc2c1] | 1-isopropyl-3-(6-methoxynaphthalen-2-yl)-1H-pyrazolo[3,4-d]pyrimidin-4-amine |
| 7r | 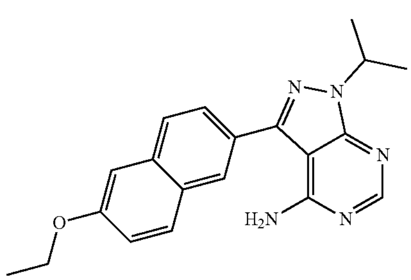 [SMILES: CCOc1ccc2cc(-c3nn(C(C)C)c4ncnc(N)c34)ccc2c1] | 3-(6-ethoxynaphthalen-2-yl)-1-isopropyl-1H-pyrazolo[3,4-d]pyrimidin-4-amine |

TABLE B-continued

| Cmpd # | Structure | Name |
|---|---|---|
| 7s | 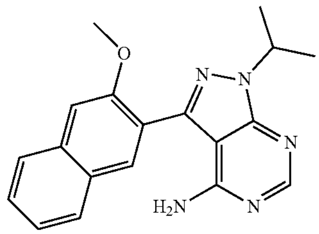 [SMILES: COc1cc2ccccc2cc1-c1nn(C(C)C)c2ncnc(N)c12] | 1-isopropyl-3-(3-methoxynaphthalen-2-yl)-1H-pyrazolo[3,4-d]pyrimidin-4-amine |
| 7t | 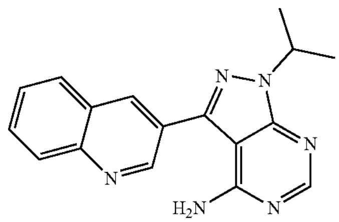 [SMILES: CC(C)n1nc(-c2cnc3ccccc3c2)c2c(N)ncnc21] | 1-isopropyl-3-(quinolin-3-yl)-1H-pyrazolo[3,4-d]pyrimidin-4-amine |
| 7u | 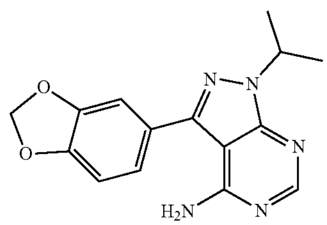 [SMILES: CC(C)n1nc(-c2ccc3c(c2)OCO3)c2c(N)ncnc21] | 3-(benzo[d][1,3]dioxol-5-yl)-1-isopropyl-1H-pyrazolo[3,4-d]pyrimidin-4-amine |
| 7v | 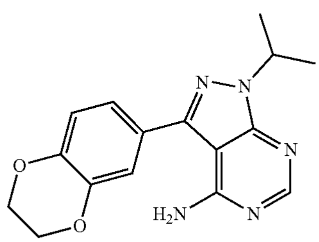 [SMILES: CC(C)n1nc(-c2ccc3c(c2)OCCO3)c2c(N)ncnc21] | 3-(2,3-dihydrobenzo[b][1,4]dioxin-6-yl)-1-isopropyl-1H-pyrazolo[3,4-d]pyrimidin-4-amine |
| 7w | 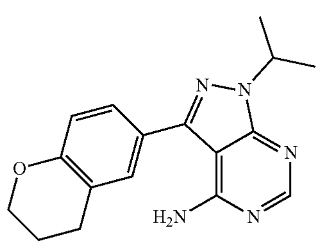 [SMILES: CC(C)n1nc(-c2ccc3c(c2)CCCO3)c2c(N)ncnc21] | 3-(chroman-6-yl)-1-isopropyl-1H-pyrazolo[3,4-d]pyrimidin-4-amine |
| 7x | 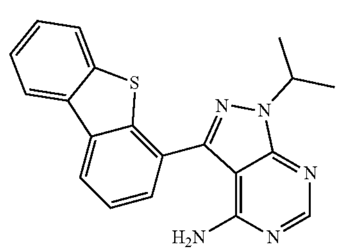 [SMILES: CC(C)n1nc(-c2cccc3c2sc2ccccc23)c2c(N)ncnc21] | 3-(dibenzo[b,d]thiophen-4-yl)-1-isopropyl-1H-pyrazolo[3,4-d]pyrimidin-4-amine |

TABLE B-continued

| Cmpd # | Structure | Name |
| --- | --- | --- |
| 7y | 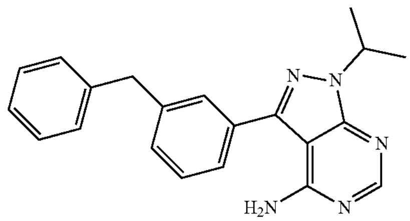 [SMILES: CC(C)n1nc(-c2cccc(Cc3ccccc3)c2)c2c(N)ncnc21] | 3-(3-benzylphenyl)-1-isopropyl-1H-pyrazolo[3,4-d]pyrimidin-4-amine |
| 7z | 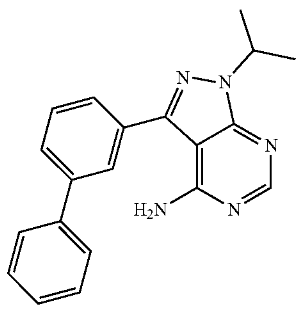 [SMILES: CC(C)n1nc(-c2cccc(-c3ccccc3)c2)c2c(N)ncnc21] | 3-(biphenyl-3-yl)-1-isopropyl-1H-pyrazolo[3,4-d]pyrimidin-4-amine |
| 7aa | 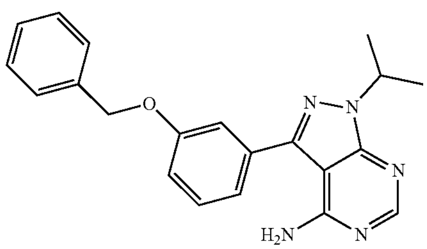 [SMILES: CC(C)n1nc(-c2cccc(OCc3ccccc3)c2)c2c(N)ncnc21] | 3-(3-(benzyloxy)phenyl)-1-isopropyl-1H-pyrazolo[3,4-d]pyrimidin-4-amine |
| 7ab | 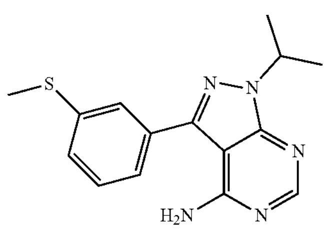 [SMILES: CSc1cccc(-c2nn(C(C)C)c3ncnc(N)c23)c1] | 1-isopropyl-3-(3-(methylthio)phenyl)-1H-pyrazolo[3,4-d]pyrimidin-4-amine |
| 8 | 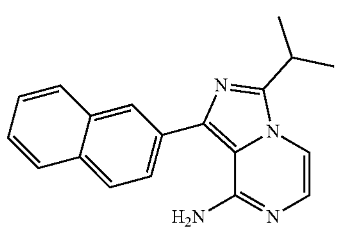 [SMILES: CC(C)c1nc(-c2ccc3ccccc3c2)c2c(N)nccn12] | 3-isopropyl-1-(naphthalen-2-yl)imidazo[1,5-a]pyrazin-8-amine |
| 9 | 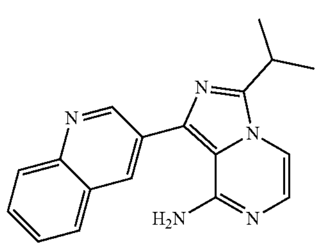 [SMILES: CC(C)c1nc(-c2cnc3ccccc3c2)c2c(N)nccn12] | 3-isopropyl-1-(quinolin-3-yl)imidazo[1,5-a]pyrazin-8-amine |

TABLE B-continued

| Cmpd # | Structure | Name |
|---|---|---|
| 10 | 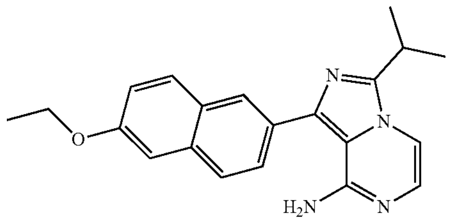 [SMILES: CCOc1ccc2cc(-c3nc(C(C)C)n4ccnc(N)c34)ccc2c1] | 1-(6-ethoxynaphthalen-2-yl)-3-isopropylimidazo[1,5-a]pyrazin-8-amine |
| 11 | 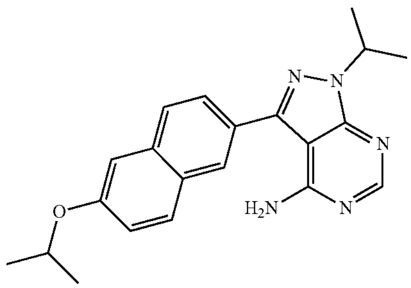 [SMILES: CC(C)Oc1ccc2cc(-c3nn(C(C)C)c4ncnc(N)c34)ccc2c1] | 3-(6-isopropoxynaphthalen-2-yl)-1-isopropyl-1H-pyrazolo[3,4-d]pyrimidin-4-amine |
| 12 | 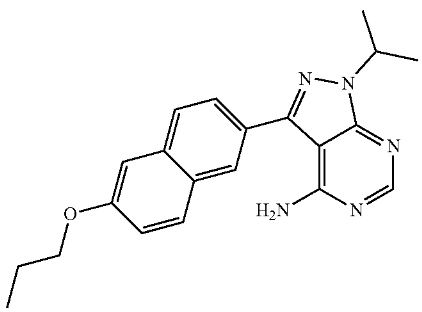 [SMILES: CCCOc1ccc2cc(-c3nn(C(C)C)c4ncnc(N)c34)ccc2c1] | 1-isopropyl-3-(6-propoxynaphthalen-2-yl)-1H-pyrazolo[3,4-d]pyrimidin-4-amine |
| 13 | 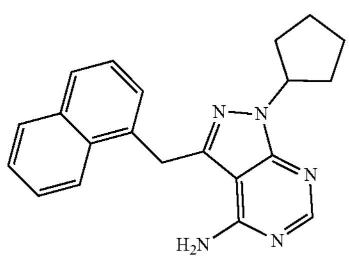 [SMILES: Nc1ncnc2c1c(Cc1cccc3ccccc13)nn2C1CCCC1] | 1-cyclopentyl-3-(naphthalen-1-ylmethyl)-1H-pyrazolo[3,4-d]pyrimidin-4-amine |
| 14 | 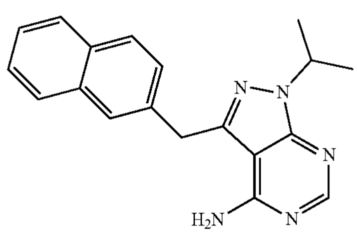 [SMILES: CC(C)n1nc(Cc2ccc3ccccc3c2)c2c(N)ncnc21] | 1-isopropyl-3-(naphthalen-2-ylmethyl)-1H-pyrazolo[3,4-d]pyrimidin-4-amine |
| 15 | 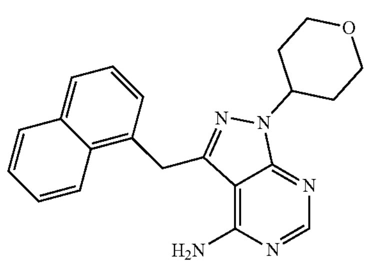 [SMILES: Nc1ncnc2c1c(Cc1cccc3ccccc13)nn2C1CCOCC1] | 3-(naphthalen-1-ylmethyl)-1-(tetrahydro-2H-pyran-4-yl)-1H-pyrazolo[3,4-d]pyrimidin-4-amine |

TABLE B-continued

| Cmpd # | Structure | Name |
|---|---|---|
| 16 | 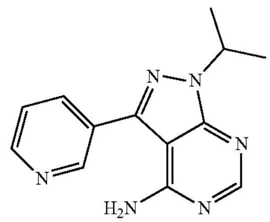 | 1-isopropyl-3-(pyridin-3-yl)-1H-pyrazolo[3,4-d]pyrimidin-4-amine |
| 17 | 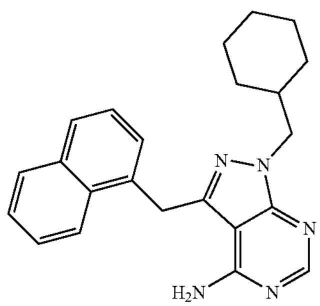 [SMILES: Nc1ncnc2c1c(Cc1cccc3ccccc13)nn2CC1CCCCC1] | 1-(cyclohexylmethyl)-3-(naphthalen-1-ylmethyl)-1H-pyrazolo[3,4-d]pyrimidin-4-amine |
| 18 | 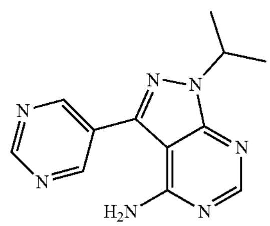 [SMILES: CC(C)n1nc(-c2cncnc2)c2c(N)ncnc21] | 1-isopropyl-3-(pyrimidin-5-yl)-1H-pyrazolo[3,4-d]pyrimidin-4-amine |
| 19 | 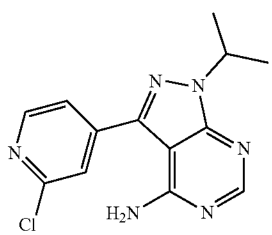 [SMILES: CC(C)n1nc(-c2ccnc(Cl)c2)c2c(N)ncnc21] | 3-(2-chloropyridin-4-yl)-1-isopropyl-1H-pyrazolo[3,4-d]pyrimidin-4-amine |
| 20 | 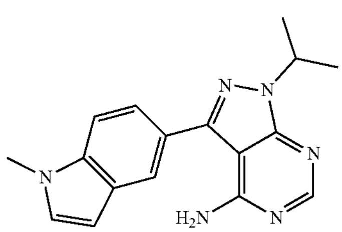 [SMILES: CC(C)n1nc(-c2ccc3c(ccn3C)c2)c2c(N)ncnc21] | 1-isopropyl-3-(1-methyl-1H-indol-5-yl)-1H-pyrazolo[3,4-d]pyrimidin-4-amine |
| 21 | 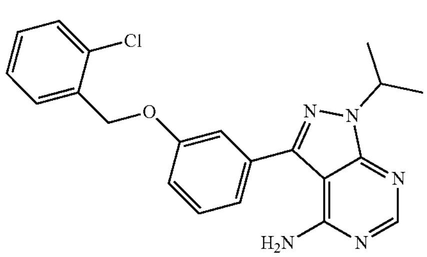 [SMILES: CC(C)n1nc(-c2cccc(OCc3ccccc3Cl)c2)c2c(N)ncnc21] | 3-(3-(2-chlorobenzyloxy)phenyl)-1-isopropyl-1H-pyrazolo[3,4-d]pyrimidin-4-amine |

TABLE B-continued

| Cmpd # | Structure | Name |
|---|---|---|
| 22 | 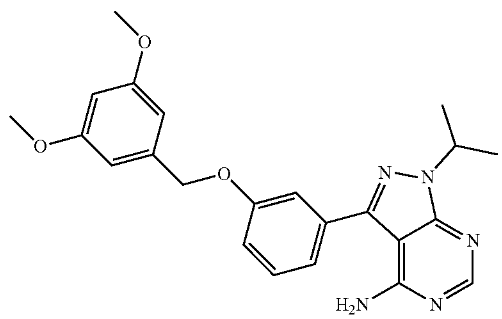 [SMILES: COc1cc(COc2cccc(-c3nn(C(C)C)c4ncnc(N)c34)c2)cc(OC)c1] | 3-(3-(3,5-dimethoxybenzyloxy)phenyl)-1-isopropyl-1H-pyrazolo[3,4-d]pyrimidin-4-amine |
| 23 | 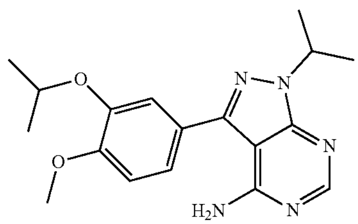 [SMILES: COc1ccc(-c2nn(C(C)C)c3ncnc(N)c23)cc1OC(C)C] | 3-(3-isopropoxy-4-methoxyphenyl)-1-isopropyl-1H-pyrazolo[3,4-d]pyrimidin-4-amine |
| 24 | 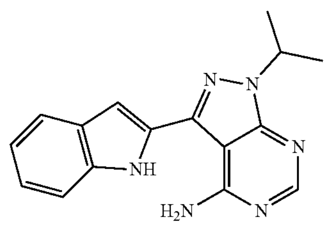 [SMILES: CC(C)n1nc(-c2cc3ccccc3[nH]2)c2c(N)ncnc21] | 3-(1H-indol-2-yl)-1-isopropyl-1H-pyrazolo[3,4-d]pyrimidin-4-amine |
| 25 | 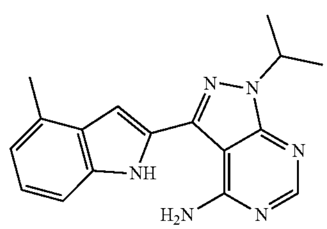 [SMILES: Cc1cccc2[nH]c(-c3nn(C(C)C)c4ncnc(N)c34)cc12] | 1-isopropyl-3-(4-methyl-1H-indol-2-yl)-1H-pyrazolo[3,4-d]pyrimidin-4-amine |
| 26 | 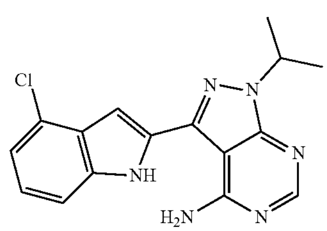 [SMILES: CC(C)n1nc(-c2cc3c(Cl)cccc3[nH]2)c2c(N)ncnc21] | 3-(4-chloro-1H-indol-2-yl)-1-isopropyl-1H-pyrazolo[3,4-d]pyrimidin-4-amine |
| 27 | 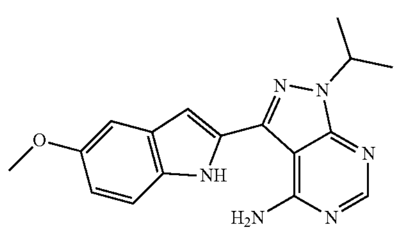 [SMILES: COc1ccc2[nH]c(-c3nn(C(C)C)c4ncnc(N)c34)cc2c1] | 1-isopropyl-3-(5-methoxy-1H-indol-2-yl)-1H-pyrazolo[3,4-d]pyrimidin-4-amine |

TABLE B-continued

| Cmpd # | Structure | Name |
|---|---|---|
| 28 | 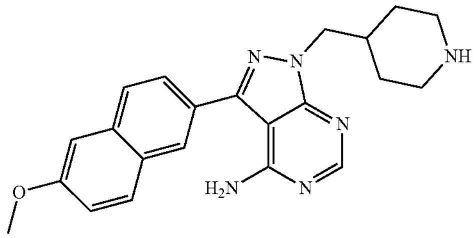 [SMILES: COc1ccc2cc(-c3nn(CC4CCNCC4)c4ncnc(N)c34)ccc2c1] | 3-(6-methoxynaphthalen-2-yl)-1-(piperidin-4-ylmethyl)-1H-pyrazolo[3,4-d]pyrimidin-4-amine |
| 29 | 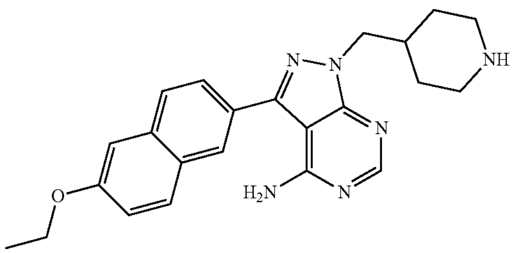 [SMILES: CCOc1ccc2cc(-c3nn(CC4CCNCC4)c4ncnc(N)c34)ccc2c1] | 3-(6-ethoxynaphthalen-2-yl)-1-(piperidin-4-ylmethyl)-1H-pyrazolo[3,4-d]pyrimidin-4-amine |
| 30 | 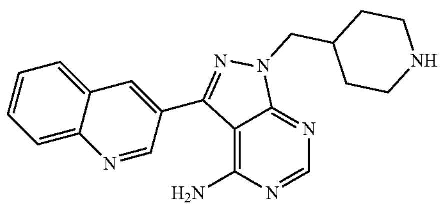 [SMILES: Nc1ncnc2c1c(-c1cnc3ccccc3c1)nn2CC1CCNCC1] | 1-(piperidin-4-ylmethyl)-3-(quinolin-3-yl)-1H-pyrazolo[3,4-d]pyrimidin-4-amine |
| 31 | 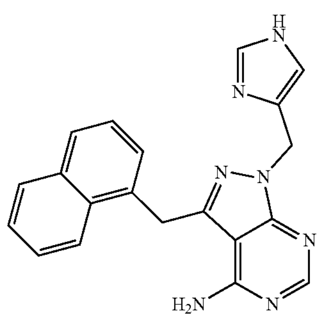 [SMILES: Nc1ncnc2c1c(Cc1cccc3ccccc13)nn2Cc1c[nH]cn1] | 1-((1H-imidazol-4-yl)methyl)-3-(naphthalen-1-ylmethyl)-1H-pyrazolo[3,4-d]pyrimidin-4-amine |
| 32 | 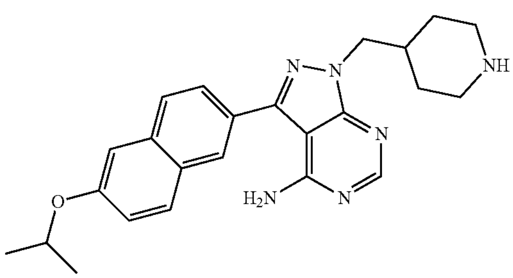 [SMILES: CC(C)Oc1ccc2cc(-c3nn(CC4CCNCC4)c4ncnc(N)c34)ccc2c1] | 3-(6-isopropoxynaphthalen-2-yl)-1-(piperidin-4-ylmethyl)-1H-pyrazolo[3,4-d]pyrimidin-4-amine |
| 33 | 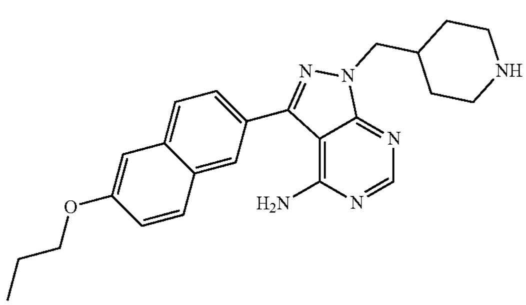 [SMILES: CCCOc1ccc2cc(-c3nn(CC4CCNCC4)c4ncnc(N)c34)ccc2c1] | 1-(piperidin-4-ylmethyl)-3-(6-propoxynaphthalen-2-yl)-1H-pyrazolo[3,4-d]pyrimidin-4-amine |

TABLE B-continued

| Cmpd # | Structure | Name |
|---|---|---|
| 34 | 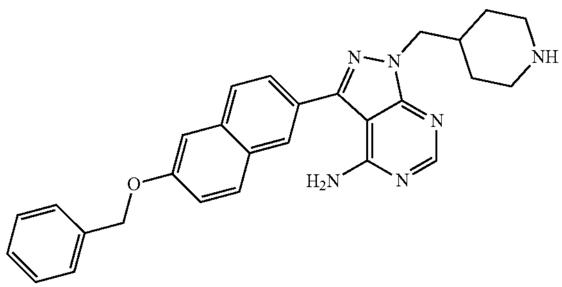 [SMILES: Nc1ncnc2c1c(-c1ccc3cc(OCc4ccccc4)ccc3c1)nn2CC1CCNCC1] | 3-(6-(benzyloxy)naphthalen-2-yl)-1-(piperidin-4-ylmethyl)-1H-pyrazolo[3,4-d]pyrimidin-4-amine |
| 35 | 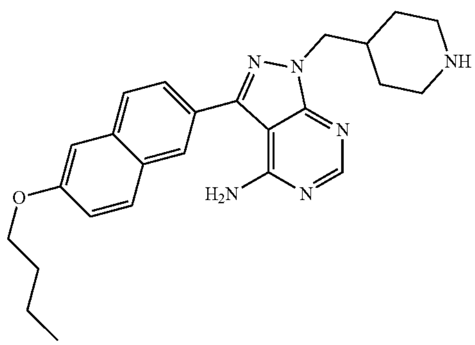 [SMILES: CCCCOc1ccc2cc(-c3nn(CC4CCNCC4)c4ncnc(N)c34)ccc2c1] | 3-(6-butoxynaphthalen-2-yl)-1-(piperidin-4-ylmethyl)-1H-pyrazolo[3,4-d]pyrimidin-4-amine |
| 36 | 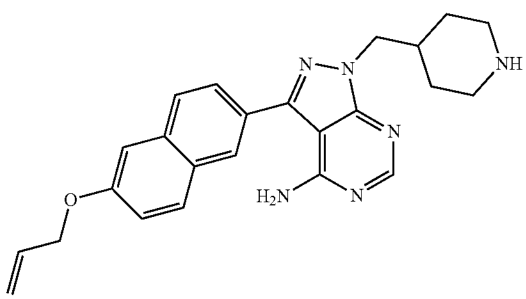 [SMILES: C=CCOc1ccc2cc(-c3nn(CC4CCNCC4)c4ncnc(N)c34)ccc2c1] | 3-(6-(allyloxy)naphthalen-2-yl)-1-(piperidin-4-ylmethyl)-1H-pyrazolo[3,4-d]pyrimidin-4-amine |
| 37 | 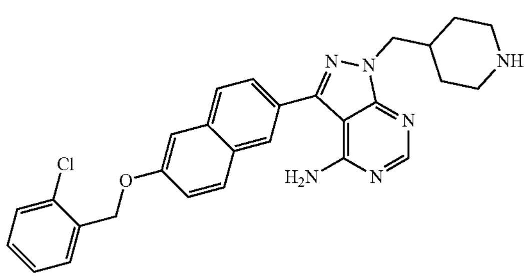 [SMILES: Nc1ncnc2c1c(-c1ccc3cc(OCc4ccccc4Cl)ccc3c1)nn2CC1CCNCC1] | 3-(6-(2-chlorobenzyloxy)naphthalen-2-yl)-1-(piperidin-4-ylmethyl)-1H-pyrazolo[3,4-d]pyrimidin-4-amine |
| 38 | 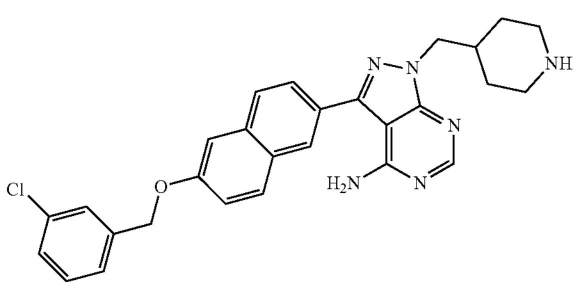 [SMILES: Nc1ncnc2c1c(-c1ccc3cc(OCc4cccc(Cl)c4)ccc3c1)nn2CC1CCNCC1] | 3-(6-(3-chlorobenzyloxy)naphthalen-2-yl)-1-(piperidin-4-ylmethyl)-1H-pyrazolo[3,4-d]pyrimidin-4-amine |

TABLE B-continued

| Cmpd # | Structure | Name |
|---|---|---|
| 39 | 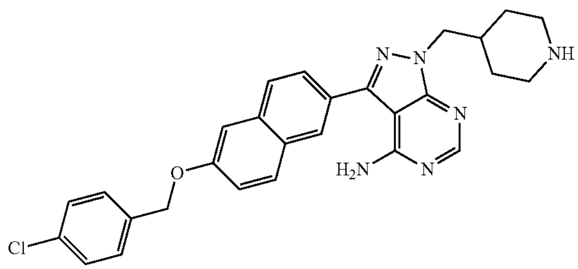 [SMILES: Nc1ncnc2c1c(-c1ccc3cc(OCc4ccc(Cl)cc4)ccc3c1)nn2CC1CCNCC1] | 3-(6-(4-chlorobenzyloxy)naphthalen-2-yl)-1-(piperidin-4-ylmethyl)-1H-pyrazolo[3,4-d]pyrimidin-4-amine |
| 40 | 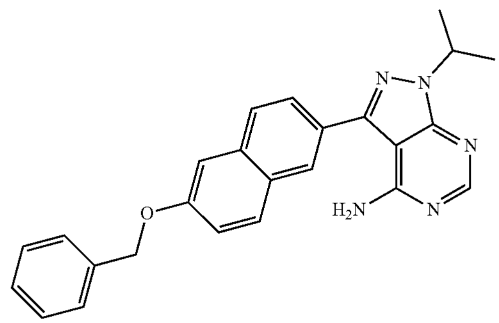 [SMILES: CC(C)n1nc(-c2ccc3cc(OCc4ccccc4)ccc3c2)c2c(N)ncnc21] | 3-(6-(benzyloxy)naphthalen-2-yl)-1-isopropyl-1H-pyrazolo[3,4-d]pyrimidin-4-amine |
| 41 | 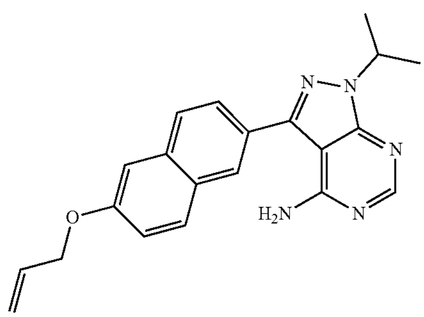 [SMILES: C=CCOc1ccc2cc(-c3nn(C(C)C)c4ncnc(N)c34)ccc2c1] | 3-(6-(allyloxy)naphthalen-2-yl)-1-isopropyl-1H-pyrazolo[3,4-d]pyrimidin-4-amine |
| 42 | 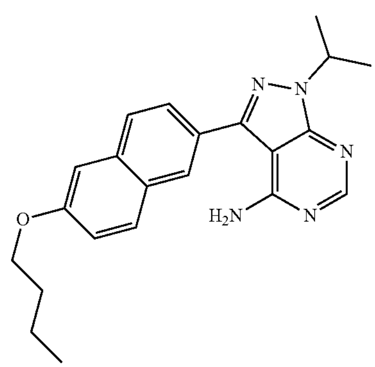 [SMILES: CCCCOc1ccc2cc(-c3nn(C(C)C)c4ncnc(N)c34)ccc2c1] | 3-(6-butoxynaphthalen-2-yl)-1-isopropyl-1H-pyrazolo[3,4-d]pyrimidin-4-amine |
| 43 | 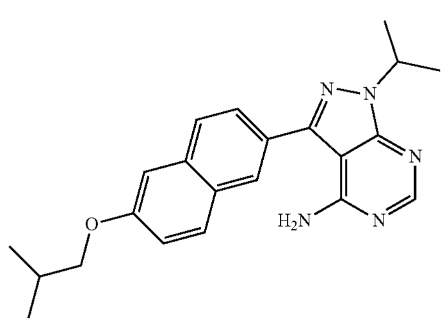 [SMILES: CC(C)COc1ccc2cc(-c3nn(C(C)C)c4ncnc(N)c34)ccc2c1] | 3-(6-isobutoxynaphthalen-2-yl)-1-isopropyl-1H-pyrazolo[3,4-d]pyrimidin-4-amine |

TABLE B-continued

| Cmpd # | Structure | Name |
|---|---|---|
| 44 | 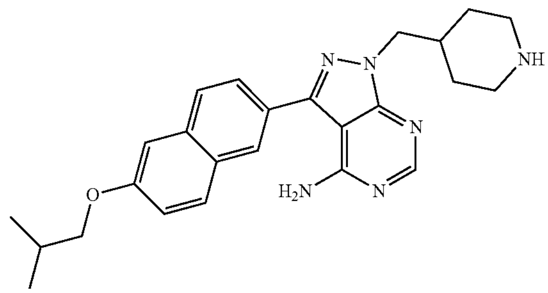 [SMILES: CC(C)COc1ccc2cc(-c3nn(CC4CCNCC4)c4ncnc(N)c34)ccc2c1] | 3-(6-isobutoxynaphthalen-2-yl)-1-(piperidin-4-ylmethyl)-1H-pyrazolo[3,4-d]pyrimidin-4-amine |
| 45 | 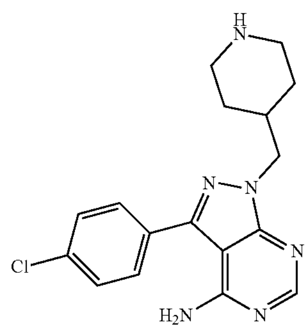 [SMILES: Nc1ncnc2c1c(-c1ccc(Cl)cc1)nn2CC1CCNCC1] | 3-(4-chlorophenyl)-1-(piperidin-4-ylmethyl)-1H-pyrazolo[3,4-d]pyrimidin-4-amine |
| 46 | 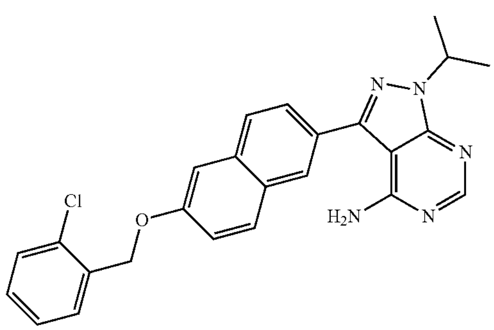 [SMILES: CC(C)n1nc(-c2ccc3cc(OCc4ccccc4Cl)ccc3c2)c2c(N)ncnc21] | 3-(6-(2-chlorobenzyloxy)naphthalen-2-yl)-1-isopropyl-1H-pyrazolo[3,4-d]pyrimidin-4-amine |
| 47 | 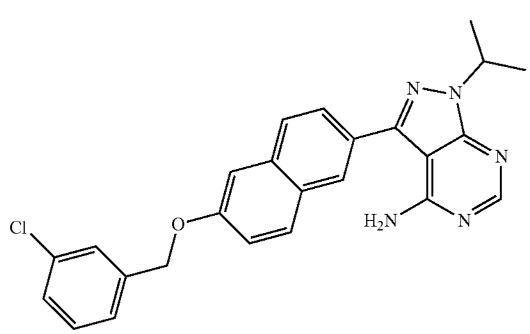 [SMILES: CC(C)n1nc(-c2ccc3cc(OCc4cccc(Cl)c4)ccc3c2)c2c(N)ncnc21] | 3-(6-(3-chlorobenzyloxy)naphthalen-2-yl)-1-isopropyl-1H-pyrazolo[3,4-d]pyrimidin-4-amine |

TABLE B-continued

| Cmpd # | Structure | Name |
|---|---|---|
| 48 | 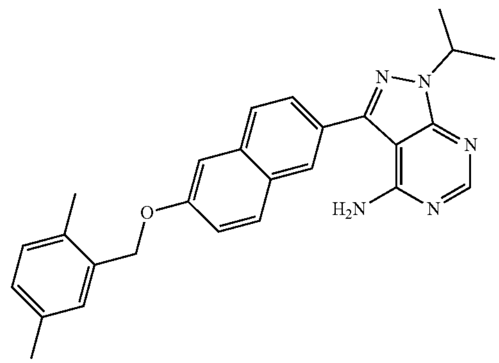 [SMILES: Cc1ccc(C)c(COc2ccc3cc(-c4nn(C(C)C)c5ncnc(N)c45)ccc3c2)c1] | 3-(6-(2,5-dimethylbenzyloxy)naphthalen-2-yl)-1-isopropyl-1H-pyrazolo[3,4-d]pyrimidin-4-amine |
| 49 | 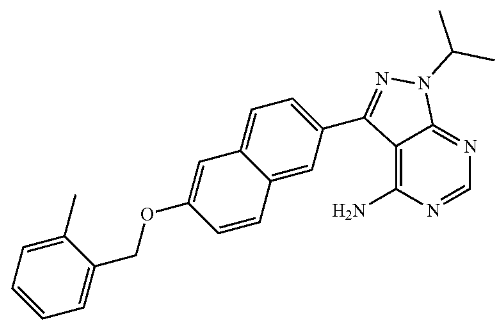 [SMILES: Cc1ccccc1COc1ccc2cc(-c3nn(C(C)C)c4ncnc(N)c34)ccc2c1] | 1-isopropyl-3-(6-(2-methylbenzyloxy)naphthalen-2-yl)-1H-pyrazolo[3,4-d]pyrimidin-4-amine |
| 50 | 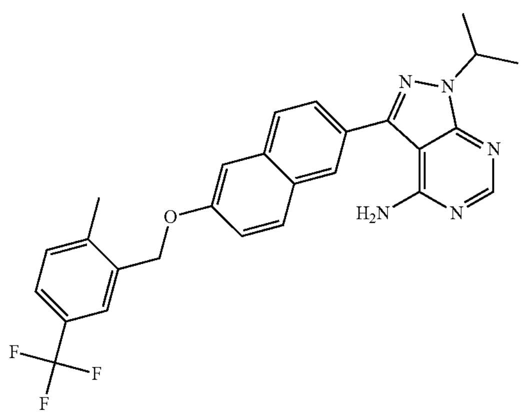 [SMILES: Cc1ccc(C(F)(F)F)cc1COc1ccc2cc(-c3nn(C(C)C)c4ncnc(N)c34)ccc2c1] | 1-isopropyl-3-(6-(2-methyl-5-(trifluoromethyl)benzyloxy)naphthalen-2-yl)-1H-pyrazolo[3,4-d]pyrimidin-4-amine |
| 51 | 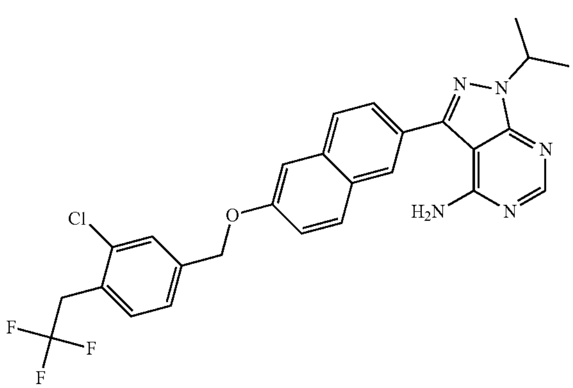 [SMILES: CC(C)n1nc(-c2ccc3cc(OCc4ccc(CC(F)(F)F)c(Cl)c4)ccc3c2)c2c(N)ncnc21] | 3-(6-(3-chloro-4-(2,2,2-trifluoroethyl)benzyloxy)naphthalen-2-yl)-1-isopropyl-1H-pyrazolo[3,4-d]pyrimidin-4-amine |

TABLE B-continued

| Cmpd # | Structure | Name |
|---|---|---|
| 52 | 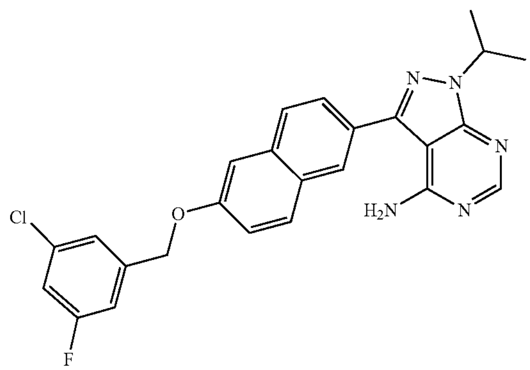 [SMILES: CC(C)n1nc(-c2ccc3cc(OCc4cc(F)cc(Cl)c4)ccc3c2)c2c(N)ncnc21] | 3-(6-(3-chloro-5-fluorobenzyloxy)naphthalen-2-yl)-1-isopropyl-1H-pyrazolo[3,4-d]pyrimidin-4-amine |
| 53 | 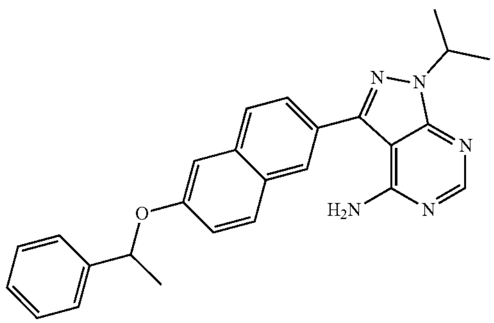 [SMILES: CC(Oc1ccc2cc(-c3nn(C(C)C)c4ncnc(N)c34)ccc2c1)c1ccccc1] | 1-isopropyl-3-(6-(1-phenylethoxy)naphthalen-2-yl)-1H-pyrazolo[3,4-d]pyrimidin-4-amine |
| 54 | 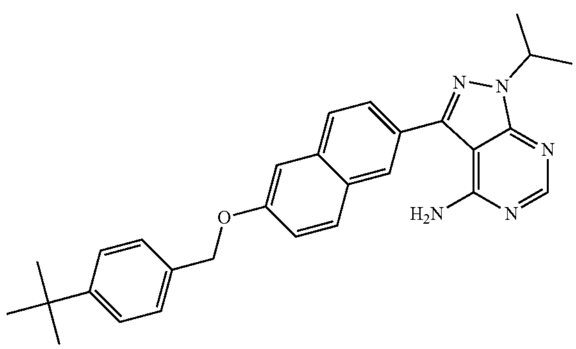 [SMILES: CC(C)n1nc(-c2ccc3cc(OCc4ccc(C(C)(C)C)cc4)ccc3c2)c2c(N)ncnc21] | 3-(6-(4-tert-butylbenzyloxy)naphthalen-2-yl)-1-isopropyl-1H-pyrazolo[3,4-d]pyrimidin-4-amine |
| 55 | 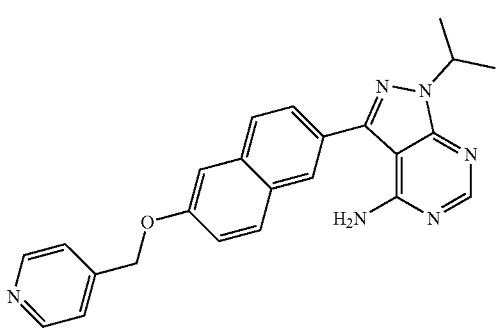 [SMILES: CC(C)n1nc(-c2ccc3cc(OCc4ccncc4)ccc3c2)c2c(N)ncnc21] | 1-isopropyl-3-(6-(pyridin-4-ylmethoxy)naphthalen-2-yl)-1H-pyrazolo[3,4-d]pyrimidin-4-amine |

TABLE B-continued

| Cmpd # | Structure | Name |
| --- | --- | --- |
| 56 | 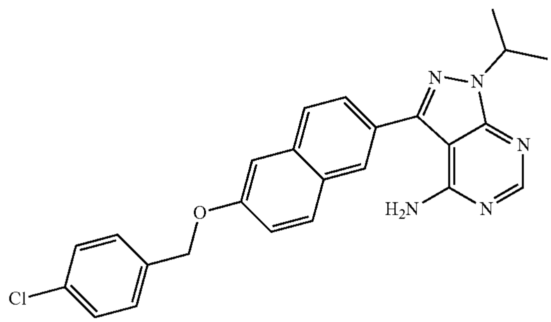 [SMILES: CC(C)n1nc(-c2ccc3cc(OCc4ccc(Cl)cc4)ccc3c2)c2c(N)ncnc21] | 3-(6-(4-chlorobenzyloxy)naphthalen-2-yl)-1-isopropyl-1H-pyrazolo[3,4-d]pyrimidin-4-amine |
| 57 | 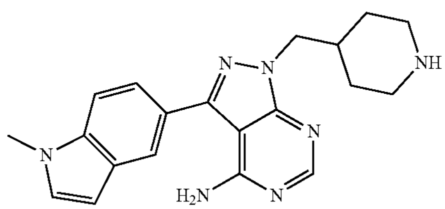 [SMILES: Cn1ccc2cc(-c3nn(CC4CCNCC4)c4ncnc(N)c34)ccc21] | 3-(1-methyl-1H-indol-5-yl)-1-(piperidin-4-ylmethyl)-1H-pyrazolo[3,4-d]pyrimidin-4-amine |
| 58 | 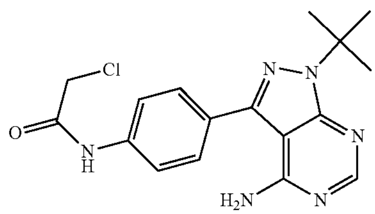 [SMILES: CC(C)(C)n1nc(-c2ccc(NC(=O)CCl)cc2)c2c(N)ncnc21] | N-(4-(4-amino-1-tert-butyl-1H-pyrazolo[3,4-d]pyrimidin-3-yl)phenyl)-2-chloroacetamide |
| 59 | 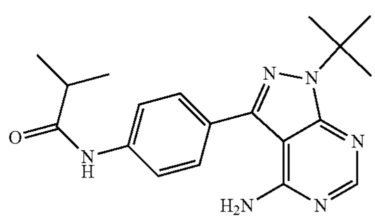 [SMILES: CC(C)C(=O)Nc1ccc(-c2nn(C(C)(C)C)c3ncnc(N)c23)cc1] | N-(4-(4-amino-1-tert-butyl-1H-pyrazolo[3,4-d]pyrimidin-3-yl)phenyl)isobutyramide |
| 60 | 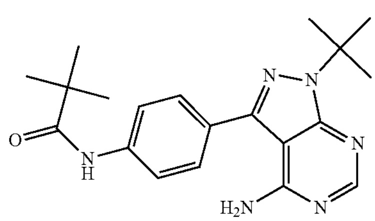 [SMILES: CC(C)(C)C(=O)Nc1ccc(-c2nn(C(C)(C)C)c3ncnc(N)c23)cc1] | N-(4-(4-amino-1-tert-butyl-1H-pyrazolo[3,4-d]pyrimidin-3-yl)phenyl)pivalamide |
| 61 | 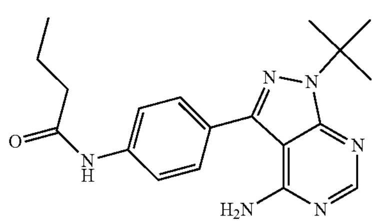 [SMILES: CCCC(=O)Nc1ccc(-c2nn(C(C)(C)C)c3ncnc(N)c23)cc1] | N-(4-(4-amino-1-tert-butyl-1H-pyrazolo[3,4-d]pyrimidin-3-yl)phenyl)butyramide |

TABLE B-continued

| Cmpd # | Structure | Name |
|---|---|---|
| 62 | 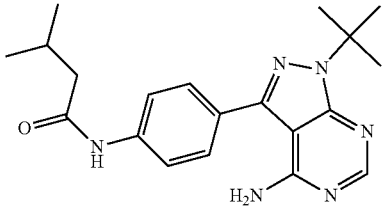 [SMILES: CC(C)CC(=O)Nc1ccc(-c2nn(C(C)(C)C)c3ncnc(N)c23)cc1] | N-(4-(4-amino-1-tert-butyl-1H-pyrazolo[3,4-d]pyrimidin-3-yl)phenyl)-3-methylbutanamide |
| 63 | 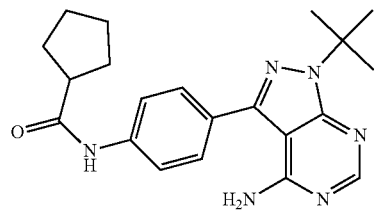 [SMILES: CC(C)(C)n1nc(-c2ccc(NC(=O)C3CCCC3)cc2)c2c(N)ncnc21] | N-(4-(4-amino-1-tert-butyl-1H-pyrazolo[3,4-d]pyrimidin-3-yl)phenyl)cyclopentanecarboxamide |
| 64 | 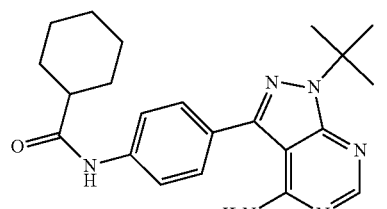 | N-(4-(4-amino-1-tert-butyl-1H-pyrazolo[3,4-d]pyrimidin-3-yl)phenyl)cyclohexanecarboxamide |
| 65 | 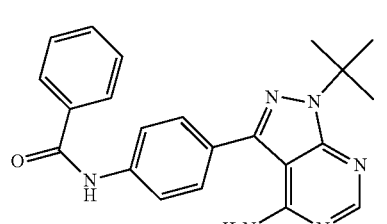 | N-(4-(4-amino-1-tert-butyl-1H-pyrazolo[3,4-d]pyrimidin-3-yl)phenyl)benzamide |
| 66 | 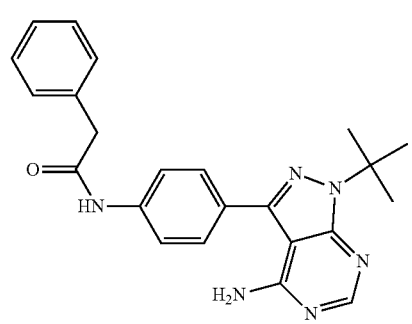 [SMILES: CC(C)(C)n1nc(-c2ccc(NC(=O)Cc3ccccc3)cc2)c2c(N)ncnc21] | N-(4-(4-amino-1-tert-butyl-1H-pyrazolo[3,4-d]pyrimidin-3-yl)phenyl)-2-phenylacetamide |
| 67 | 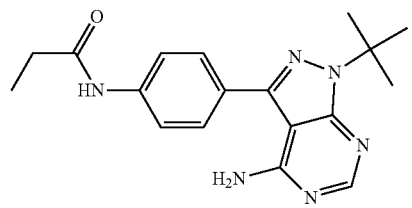 [SMILES: CCC(=O)Nc1ccc(-c2nn(C(C)(C)C)c3ncnc(N)c23)cc1] | N-(4-(4-amino-1-tert-butyl-1H-pyrazolo[3,4-d]pyrimidin-3-yl)phenyl)propionamide |

TABLE B-continued

| Cmpd # | Structure | Name |
|---|---|---|
| 68 | 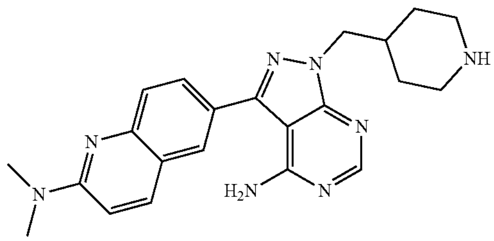 [SMILES: CN(C)c1ccc2cc(-c3nn(CC4CCNCC4)c4ncnc(N)c34)ccc2n1] | 6-(4-amino-1-(piperidin-4-ylmethyl)-1H-pyrazolo[3,4-d]pyrimidin-3-yl)-N,N-dimethylquinolin-2-amine |
| 69 | 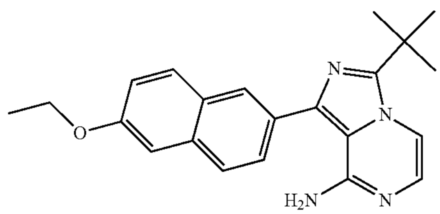 [SMILES: CCOc1ccc2cc(-c3nc(C(C)(C)C)n4ccnc(N)c34)ccc2c1] | 3-tert-butyl-1-(6-ethoxynaphthalen-2-yl)imidazo[1,5-a]pyrazin-8-amine |
| 70 | 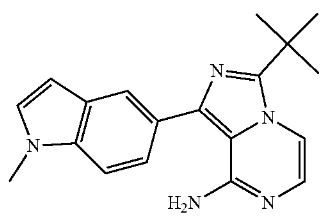 [SMILES: Cn1ccc2cc(-c3nc(C(C)(C)C)n4ccnc(N)c34)ccc21] | 3-tert-butyl-1-(1-methyl-1H-indol-5-yl)imidazo[1,5-a]pyrazin-8-amine |
| 71 | 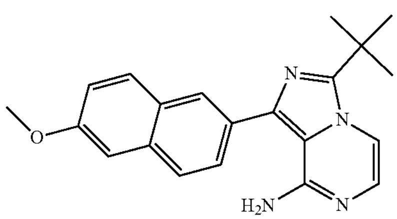 [SMILES: COc1ccc2cc(-c3nc(C(C)(C)C)n4ccnc(N)c34)ccc2c1] | 3-tert-butyl-1-(6-methoxynaphthalen-2-yl)imidazo[1,5-a]pyrazin-8-amine |
| 72 | 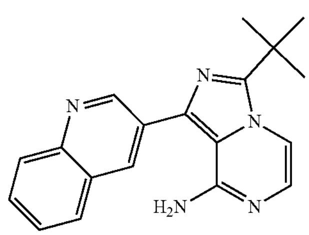 [SMILES: CC(C)(C)c1nc(-c2cnc3ccccc3c2)c2c(N)nccn12] | 3-tert-butyl-1-(quinolin-3-yl)imidazo[1,5-a]pyrazin-8-amine |
| 73 | 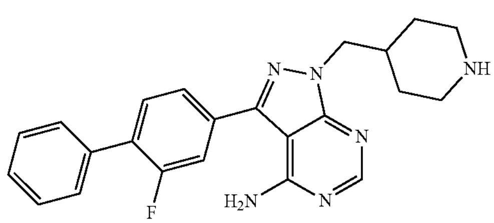 [SMILES: Nc1ncnc2c1c(-c1ccc(-c3ccccc3)c(F)c1)nn2CC1CCNCC1] | 3-(2-fluorobiphenyl-4-yl)-1-(piperidin-4-ylmethyl)-1H-pyrazolo[3,4-d]pyrimidin-4-amine |

TABLE B-continued

| Cmpd # | Structure | Name |
|---|---|---|
| 74 | 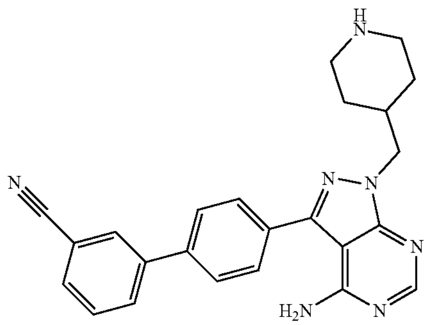 [SMILES: N#Cc1cccc(-c2ccc(-c3nn(CC4CCNCC4)c4ncnc(N)c34)cc2)c1] | 4'-(4-amino-1-(piperidin-4-ylmethyl)-1H-pyrazolo[3,4-d]pyrimidin-3-yl)biphenyl-3-carbonitrile |
| 75 | 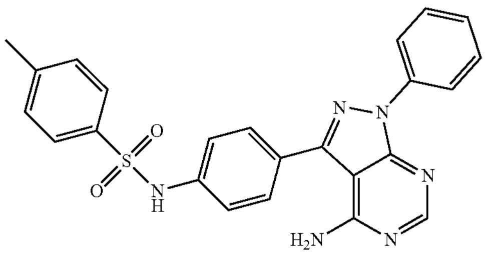 [SMILES: Cc1ccc(S(=O)(=O)Nc2ccc(-c3nn(-c4ccccc4)c4ncnc(N)c34)cc2)cc1] | N-(4-(4-amino-1-phenyl-1H-pyrazolo[3,4-d]pyrimidin-3-yl)phenyl)-4-methylbenzenesulfonamide |
| 76 | 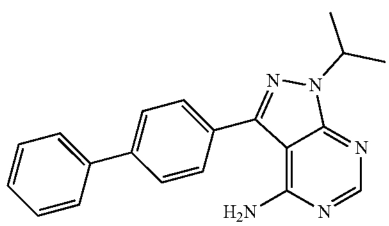 [SMILES: CC(C)n1nc(-c2ccc(-c3ccccc3)cc2)c2c(N)ncnc21] | 3-(biphenyl-4-yl)-1-isopropyl-1H-pyrazolo[3,4-d]pyrimidin-4-amine |
| 77 | 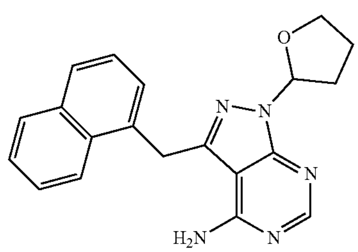 [SMILES: Nc1ncnc2c1c(Cc1cccc3ccccc13)nn2C1CCCO1] | 3-(naphthalen-1-ylmethyl)-1-(tetrahydrofuran-2-yl)-1H-pyrazolo[3,4-d]pyrimidin-4-amine |
| 78 | 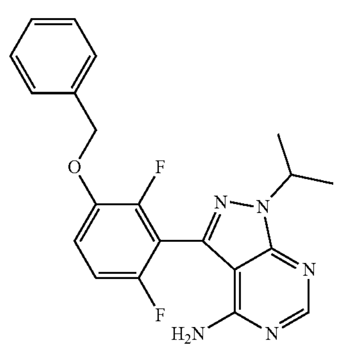 [SMILES: CC(C)n1nc(-c2c(F)ccc(OCc3ccccc3)c2F)c2c(N)ncnc21] | 3-(3-(benzyloxy)-2,6-difluorophenyl)-1-isopropyl-1H-pyrazolo[3,4-d]pyrimidin-4-amine |

TABLE B-continued

| Cmpd # | Structure | Name |
|---|---|---|
| 79 | 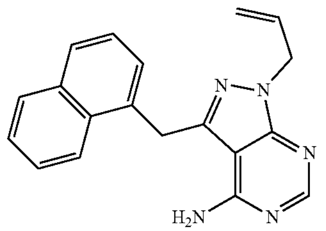 [SMILES: C=CCn1nc(Cc2cccc3ccccc23)c2c(N)ncnc21] | 1-allyl-3-(naphthalen-1-ylmethyl)-1H-pyrazolo[3,4-d]pyrimidin-4-amine |
| 80 | 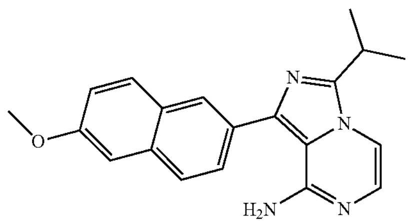 [SMILES: COc1ccc2cc(-c3nc(C(C)C)n4ccnc(N)c34)ccc2c1] | 3-isopropyl-1-(6-methoxynaphthalen-2-yl)imidazo[1,5-a]pyrazin-8-amine |
| 147 | 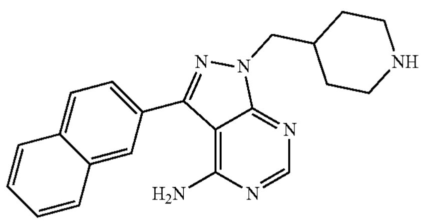 [SMILES: Nc1ncnc2c1c(-c1ccc3ccccc3c1)nn2CC1CCNCC1] | 3-(naphthalen-2-yl)-1-(piperidin-4-ylmethyl)-1H-pyrazolo[3,4-d]pyrimidin-4-amine |
| 150 | | 3-(6-ethoxynaphthalen-2-yl)-1-((1-methylpiperidin-4-yl)methyl)-1H-pyrazolo[3,4-d]pyrimidin-4-amine | and pharmaceutically acceptable salts thereof.

In another embodiment, the bumped kinase inhibitor is of the formula (IV),

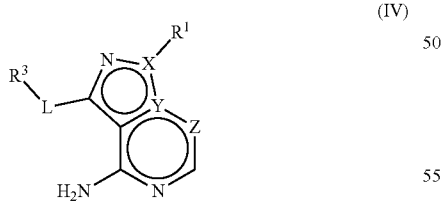

(IV)

or a pharmaceutically acceptable salt thereof, wherein

X, Y, and Z are defined by either: (i) X is N, Y is C, and Z is N; or (ii) X is C, Y is N, and Z is C(H);

$R^1$ is $C_{1-6}$ alkyl, $C_{2-6}$ alkynyl, —$C_{1-6}$ alkyl-$R^{12}$, $C_{3-8}$ cycloalkyl, monocyclic heterocyclyl, or phenyl, wherein
the monocyclic heterocyclyl and phenyl groups are each optionally substituted with one or two $R^{11}$ groups;
each $R^{11}$ is independently $C_{1-6}$ alkyl, $C_{1-6}$ haloalkyl, —C(O)R, or —S(O)$_2$R;

and $R^{12}$ is —C(O)OR, —C(O)NR$_2$, phenyl, monocyclic heteroaryl, $C_{3-8}$ cycloalkyl, or monocyclic heterocyclyl, wherein the phenyl, heteroaryl, $C_{3-8}$ cycloalkyl, and heterocyclyl groups are each optionally substituted by one, two, or three groups that are each independently halogen, cyano, nitro, $C_{1-6}$ alkyl, $C_{1-6}$ haloalkyl, —OR, —SR, —NR$_2$, —C(O)R, —C(O)OR, —C(O)NR$_2$, —S(O)$_2$R, —OC(O)R, —OC(O)OR, —OC(O)NR$_2$, —N(R)C(O)R, —N(R)C(O)OR, or —N(R)C(O)NR$_2$;

L is a bond or —CH$_2$—;

$R^3$ is aryl or heteroaryl, each optionally substituted with one, two, or three $R^{31}$ groups, wherein each $R^{31}$ is independently halogen, $C_{1-6}$ alkyl, $C_{1-6}$ haloalkyl, phenyl, benzyl, —OR, —SR, —NR$_2$, —C(O)R, —C(O)OR, —C(O)NR$_2$, —OC(O)R, —N(R)C(O)R, or —N(R)S(O)$_2$R, wherein the phenyl and benzyl groups are optionally substituted with one or two $R^{10}$ groups;

each R is independently hydrogen, $C_{1-6}$ alkyl, $C_{2-6}$ alkenyl, $C_{1-6}$ haloalkyl, $C_{3-8}$ cycloalkyl, aryl, aryl$C_{1-6}$ alkyl, or heteroaryl$C_{1-6}$ alkyl wherein the alkyl, aryl, arylalkyl, heteroaryl, and heteroarylalkyl are optionally substituted with one or two $R^{10}$ groups;

and each $R^{10}$ is independently halogen, cyano, $C_{1-6}$ alkyl, $C_{1-6}$ haloalkyl, —$OR^o$, —$SR^o$, or —$N(R^o)_2$, wherein each $R^o$ is independently hydrogen or $C_{1-6}$ alkyl.

The disclosure further comprises subgenera of formula (IV) in which the substituents are selected as any and all combinations of one or more of structural formula (IV), $R^1$, and $R^3$, as defined herein, including without limitation, the following:

Structural Formula II is one of formulae (IVa)-(IVh):

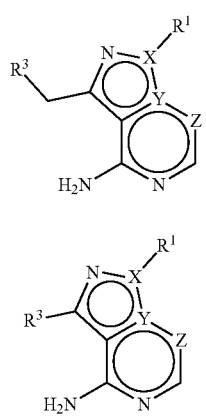

(IVa)

(IVb)

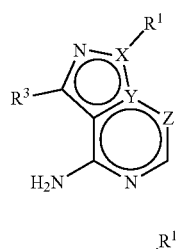

(IVc)

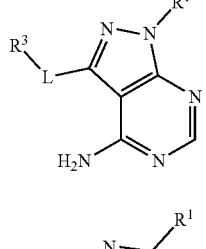

(IVd)

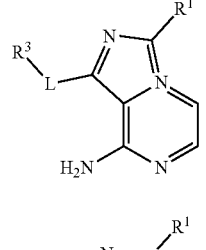

(IVe)

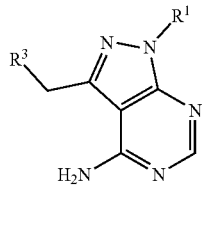

(IVf)

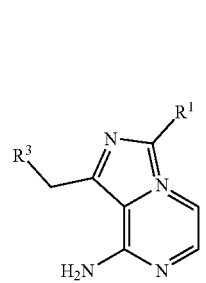

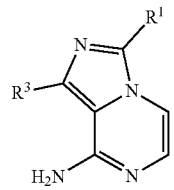

(IVg)

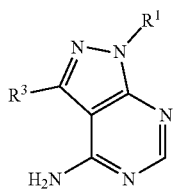

(IVh)

$R^1$ is Selected from One of the Following Groups (13a)-(13ff):

(13a) $R^1$ is $C_{3-8}$ cycloalkyl; or a monocyclic heterocyclyl optionally substituted with one $R^{11}$ group.

(13b) $R^1$ is $C_{3-8}$ cycloalkyl.

(13c) $R^1$ is monocyclic heterocyclyl optionally substituted with one $R^{11}$ group.

(13d) $R^1$ is piperidinyl or tetrahydropyranyl, each optionally substituted with one $R^{11}$ group.

(13e) $R^1$ is phenyl optionally substituted with one or two $R^{11}$ groups.

(13f) $R^1$ is $C_{2-6}$ alkyl.

(13g) $R^1$ is $C_{1-4}$ alkyl.

(13h) $R^1$ is isopropyl or t-butyl.

(13i) $R^1$ is t-butyl.

(13j) $R^1$ is isopropyl.

(13k) $R^1$ is $C_{2-6}$ alkyl or —$C_{1-4}$ alkyl-$R^{12}$.

(13l) $R^1$ is —$C_{1-4}$ alkyl-$R^{12}$.

(13m) $R^1$ is —$C_{1-2}$ alkyl-$R^{12}$.

(13n) $R^1$ is —$CH_2$—$R^{12}$.

(13o) Any one of groups (13k)-(13n), $R^{12}$ is —C(O)OR or —C(O)NR$_2$.

(13p) Any one of groups (13k)-(13n), $R^{12}$ is phenyl, monocyclic heteroaryl, $C_{3-8}$ cycloalkyl, or monocyclic heterocyclyl, each optionally substituted by one, two, or three groups that are each independently halogen, cyano, nitro, $C_{1-6}$ alkyl, $C_{1-6}$ haloalkyl, —OR, —SR, —NR$_2$, —C(O)R, —C(O)OR, —C(O)NR$_2$, —S(O)$_2$R, —OC(O)R, —OC(O)OR, —OC(O)NR$_2$, —N(R)C(O)R, —N(R)C(O)OR, or —N(R)C(O)NR$_2$.

(13q) Any one of groups (13k)-(13n), wherein $R^{12}$ is phenyl, monocyclic heteroaryl, $C_{3-8}$ cycloalkyl, or monocyclic heterocyclyl, wherein the phenyl, heteroaryl, $C_{3-8}$ cycloalkyl, and heterocyclyl groups are each optionally substituted by one or two groups that are each independently halogen, $C_{1-6}$ alkyl, —C(O)R, —C(O)OR, —C(O)NR$_2$, —S(O)$_2$R, —OC(O)R, —OC(O)OR, —OC(O)NR$_2$, —N(R)C(O)R, —N(R)C(O)OR, or —N(R)C(O)NR$_2$.

(13r) Any one of groups (13k)-(13n), $R^{12}$ is phenyl or monocyclic heterocyclyl, each optionally substituted by one, two, or three groups that are each independently halogen, cyano, nitro, $C_{1-6}$ alkyl, $C_{1-6}$ haloalkyl, —OR, —SR, —NR$_2$, —C(O)R, —C(O)OR, —C(O)NR$_2$, —S(O)$_2$R, —OC(O)R, —OC(O)OR, —OC(O)NR$_2$, —N(R)C(O)R, —N(R)C(O)OR, or —N(R)C(O)NR$_2$.

(13s) Any one of groups (13k)-(13n), $R^{12}$ is monocyclic heterocyclyl optionally substituted by one, two, or three groups that are each independently halogen, cyano, nitro, $C_{1-6}$ alkyl, $C_{1-6}$ haloalkyl, —OR, —SR, —NR$_2$, —C(O)R, —C(O)OR, —C(O)NR$_2$, —S(O)$_2$R, —OC(O)R, —OC(O)OR, —OC(O)NR$_2$, —N(R)C(O)R, —N(R)C(O)OR, or —N(R)C(O)NR$_2$.

(13t) Any one of groups (13k)-(13n), wherein $R^{12}$ is monocyclic heterocyclyl optionally substituted by one or two groups that are each independently halogen, $C_{1-6}$ alkyl, —C(O)R, —C(O)OR, —C(O)NR$_2$, —S(O)$_2$R, —OC(O)R, —OC(O)OR, —OC(O)NR$_2$, —N(R)C(O)R, —N(R)C(O)OR, or —N(R)C(O)NR$_2$.

(13u) Any one of groups (13k)-(13n), $R^{12}$ is piperidinyl or tetrahydropyranyl, each optionally substituted by one or two groups that are each independently halogen, cyano, nitro, $C_{1-6}$ alkyl, $C_{1-6}$ haloalkyl, —OR, —SR, —NR$_2$, —C(O)R, —C(O)OR, —C(O)NR$_2$, —S(O)$_2$R, —OC(O)R, —OC(O)OR, —OC(O)NR$_2$, —N(R)C(O)R, —N(R)C(O)OR, or —N(R)C(O)NR$_2$.

(13v) Any one of groups (13k)-(13n), wherein $R^{12}$ is piperidinyl optionally substituted by one or two groups that are each independently halogen, cyano, nitro, $C_{1-6}$ alkyl, $C_{1-6}$ haloalkyl, —OR, —SR, —NR$_2$, —C(O)R, —C(O)OR, —C(O)NR$_2$, —S(O)$_2$R, —OC(O)R, —OC(O)OR, —OC(O)NR$_2$, —N(R)C(O)R, —N(R)C(O)OR, or —N(R)C(O)NR$_2$.

(13w) Any one of groups (13k)-(13n), wherein $R^{12}$ is piperidinyl optionally substituted by one or two groups that are each independently $C_{1-6}$ alkyl, —C(O)R$^A$, —C(O)OR$^A$, —C(O)N(R$^A$)$_2$, —S(O)$_2$R$^A$, —OC(O)R$^A$, —OC(O)OR$^A$, —OC(O)N(R$^A$)$_2$, —N(R$^A$)C(O)R$^A$, —N(R$^A$)C(O)OR$^A$, or —N(R$^A$)C(O)N(R$^A$)$_2$, wherein each R$^A$ is independently hydrogen, $C_{1-6}$ alkyl, $C_{2-6}$ alkenyl, $C_{1-6}$ haloalkyl, $C_{3-8}$ cycloalkyl, heterocyclyl, aryl, arylC$_{1-6}$ alkyl, heteroaryl, or heteroarylC$_{1-6}$ alkyl.

(13x) Any one of groups (13k)-(13n), wherein $R^{12}$ is piperidinyl optionally substituted by one or two groups that are each independently $C_{1-6}$ alkyl, —C(O)R, —C(O)OR, —C(O)NR$_2$, —S(O)$_2$R, —OC(O)R, —OC(O)OR, —OC(O)NR$_2$, —N(R)C(O)R, —N(R)C(O)OR, or —N(R)C(O)NR$_2$.

(13y) Any one of groups (13k)-(13n), wherein $R^{12}$ is piperidinyl optionally substituted by one or two groups that are each independently $C_{1-6}$ alkyl, —C(O)R$^A$, —C(O)OR$^A$, —C(O)N(R$^A$)$_2$, —S(O)$_2$R$^A$, —OC(O)R$^A$, —OC(O)OR$^A$, —OC(O)N(R$^A$)$_2$, —N(R$^A$)C(O)R$^A$, —N(R$^A$)C(O)OR$^A$, or —N(R$^A$)C(O)N(R$^A$)$_2$, wherein each R$^A$ is independently hydrogen or $C_{1-6}$ alkyl.

(13z) Any one of groups (13k)-(13n), wherein $R^{12}$ is piperidinyl optionally substituted by one or two groups that are each independently $C_{1-6}$ alkyl, —C(O)R, —C(O)OR, —C(O)NR$_2$, or —S(O)$_2$R.

(13aa) Any one of groups (13k)-(13n), wherein $R^{12}$ is piperidinyl optionally substituted by one or two groups that are each independently $C_{1-6}$ alkyl, —C(O)R$^A$, or —S(O)$_2$R$^A$, wherein each R$^A$ is independently hydrogen or $C_{1-6}$ alkyl.

(13bb) Any one of groups (13k)-(13n), wherein $R^{12}$ is

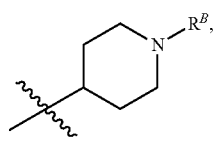

wherein $R^B$ is hydrogen, $C_{1-6}$ alkyl, —C(O)R, —C(O)OR, —C(O)NR$_2$, —S(O)$_2$R, —OC(O)R, —OC(O)OR, —OC(O)NR$_2$, —N(R)C(O)R, —N(R)C(O)OR, or —N(R)C(O)NR$_2$.

(13cc) Any one of groups (13k)-(13n), wherein $R^{12}$ is

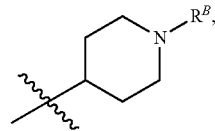

wherein $R^B$ is hydrogen, $C_{1-6}$ alkyl, —C(O)R$^A$, —C(O)OR$^A$, —C(O)N(R$^A$)$_2$, —S(O)$_2$R$^A$, —OC(O)R$^A$, —OC(O)OR$^A$, —OC(O)N(R$^A$)$_2$, —N(R$^A$)C(O)R$^A$, —N(R$^A$)C(O)OR$^A$, or —N(R$^A$)C(O)N(R$^A$)$_2$, wherein each R$^A$ is independently hydrogen, $C_{1-6}$ alkyl, $C_{2-6}$ alkenyl, $C_{1-6}$ haloalkyl, $C_{3-8}$ cycloalkyl, heterocyclyl, aryl, arylC$_{1-6}$ alkyl, heteroaryl, or heteroarylC$_{1-6}$ alkyl.

(13dd) Any one of groups (13k)-(13n), wherein $R^{12}$ is

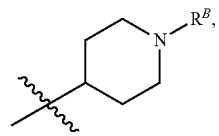

wherein $R^B$ is hydrogen, $C_{1-6}$ alkyl, —C(O)R$^A$, —C(O)OR$^A$, —C(O)N(R$^A$)$_2$, —S(O)$_2$R$^A$, —OC(O)R$^A$, —OC(O)OR$^A$, —OC(O)N(R$^A$)$_2$, —N(R$^A$)C(O)R$^A$, —N(R$^A$)C(O)OR$^A$, or —N(R$^A$)C(O)N(R$^A$)$_2$, wherein each R$^A$ is independently hydrogen or $C_{1-6}$ alkyl.

(13ee) Any one of groups (13k)-(13n), wherein $R^{12}$ is

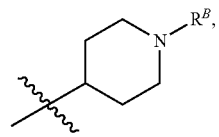

wherein $R^B$ is hydrogen, $C_{1-6}$ alkyl, —C(O)R, —C(O)OR, —C(O)NR$_2$, or —S(O)$_2$R.

(13ff) Any one of groups (13k)-(13n), wherein $R^{12}$ is

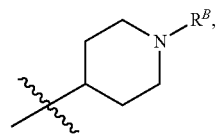

wherein $R^B$ is hydrogen, $C_{1-6}$ alkyl, —C(O)R$^A$, or —S(O)$_2$R$^A$, wherein each R$^A$ is independently hydrogen or $C_{1-6}$ alkyl.

$R^3$ is Selected from One of the Following Groups (14a)-(14x):

(14a) $R^3$ is naphthyl, quinolinyl, pyridyl, pyrimidinyl, indolyl, benzodioxolyl, 2,3-dihydrobenzodioxinyl, dibenzothienyl, chromanyl, or phenyl, each optionally substituted with one, two, or three $R^{31}$ groups.

(14b) $R^3$ is naphthyl, quinolinyl, indolyl, benzodioxolyl, 2,3-dihydrobenzodioxinyl, or chromanyl, each optionally substituted with one, two, or three $R^{31}$ groups.

(14c) $R^3$ is quinolinyl, pyridyl, pyrimidinyl, or indolyl, each optionally substituted with one, two, or three $R^{31}$ groups.

(14d) $R^3$ is quinolinyl or indolyl, each optionally substituted with one, two, or three $R^{31}$ groups.

(14e) $R^3$ is quinolinyl optionally substituted with one, two, or three $R^{31}$ groups.

(14f) $R^3$ is pyridyl or pyrimidinyl, each optionally substituted with one, two, or three $R^{31}$ groups.

(14g) $R^3$ is phenyl substituted with one, two, or three $R^{31}$ groups.

(14h) $R^3$ is phenyl optionally substituted with one or two $R^{31}$ groups, and substituted with one group that is halogen, $C_{1-6}$ alkyl, —OR, —SR, —$NR_2$, —N(R)C(O)R, or —N(R)S(O)$_2$R.

(14i) $R^3$ is phenyl optionally substituted with one or two $R^{31}$ groups, and substituted with one group that is —OR or —N(R)C(O)R.

(14j) $R^3$ is phenyl optionally substituted with one or two $R^{31}$ groups, and substituted with one group that is —OR$^{10}$, wherein $R^{10}$ is benzyl optionally substituted with one, two, three, or four groups that are each independently halogen, $C_{1-6}$ alkyl, $C_{1-6}$ haloalkyl, or —OR$^0$.

(14k) $R^3$ is phenyl optionally substituted with one or two $R^{31}$ groups, and substituted with one group that is —N(H)C(O)R$^{20}$, wherein $R^{20}$ is $C_{1-6}$ alkyl, $C_{2-6}$ alkenyl, $C_{1-6}$ haloalkyl, aryl, or aryl$C_{1-6}$ alkyl.

(14l) $R^3$ is naphthyl optionally substituted with one, two, or three $R^{31}$ groups.

(14m) $R^3$ is naphthyl optionally substituted with one or two $R^{31}$ groups and substituted with one group that is —OR$^{15}$, wherein $R^{15}$ is $C_{1-6}$ alkyl or benzyl, wherein the benzyl is optionally substituted with one or two groups that are each independently halogen, $C_{1-6}$ alkyl, $C_{1-6}$ haloalkyl, or —OR$^0$.

(14n) $R^3$ is naphth-1-yl optionally substituted with one, two, or three $R^{31}$ groups.

(14o) $R^3$ is naphth-1-yl optionally substituted with one or two $R^{31}$ groups and substituted with one group that is —OR$^{15}$, wherein $R^{15}$ is $C_{1-6}$ alkyl or benzyl, wherein the benzyl is optionally substituted with one or two groups that are each independently halogen, $C_{1-6}$ alkyl, $C_{1-6}$ haloalkyl, or —OR$^0$.

(14p) $R^3$ is naphth-2-yl optionally substituted with one, two, or three $R^{31}$ groups.

(14q) $R^3$ is naphth-2-yl optionally substituted with one or two $R^{31}$ groups and substituted with one group that is —OR$^{15}$, wherein $R^{15}$ is $C_{1-6}$ alkyl or benzyl, wherein the benzyl is optionally substituted with one or two groups that are each independently halogen, $C_{1-6}$ alkyl, $C_{1-6}$ haloalkyl, or —OR$^0$.

(14r) $R^3$ is

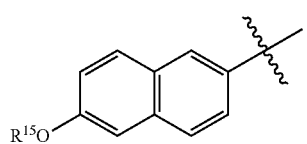

(14s) $R^3$ is indolyl optionally substituted with one, two, or three $R^{31}$ groups.

(14t) $R^3$ is indol-2-yl optionally substituted with one, two, or three $R^{31}$ groups.

(14u) $R^3$ is indol-3-yl optionally substituted with one, two, or three $R^{31}$ groups.

(14v) $R^3$ is indol-5-yl optionally substituted with one, two, or three $R^{31}$ groups.

(14w) $R^3$ is indol-6-yl optionally substituted with one, two, or three $R^{31}$ groups.

(14x) Any one of groups (2a)-(2aa) as defined above for formula (I).

Other particular embodiments of this aspect of the invention include compounds of any one of the formulae (IV), (IVa)-(IVh), each as defined in each of the following rows, wherein each entry is a group number as defined above (e.g., (14w) refers to $R^3$ is indol-6-yl optionally substituted with one, two, or three $R^{31}$ groups), and a dash "-" indicates that the variable is as defined for formula (IV) or defined according to any one of the applicable variable definitions (13a)-(14x) [e.g., when $R^1$ is a dash, it can be either as defined for Formula (IV) or any one of definitions (13a)-(13ff)]:

|        | $R^1$ | $R^3$ |
|--------|-------|-------|
| (4)-1  | 13a   | 14b   |
| (4)-2  | 13a   | 14d   |
| (4)-3  | 13a   | 14e   |
| (4)-4  | 13a   | 14g   |
| (4)-5  | 13a   | 14i   |
| (4)-6  | 13a   | 14k   |
| (4)-7  | 13a   | 14m   |
| (4)-8  | 13a   | 14q   |
| (4)-9  | 13a   | 14t   |
| (4)-10 | 13a   | 14v   |
| (4)-11 | 13f   | 14b   |
| (4)-12 | 13f   | 14d   |
| (4)-13 | 13f   | 14e   |
| (4)-14 | 13f   | 14g   |
| (4)-15 | 13f   | 14i   |
| (4)-16 | 13f   | 14k   |
| (4)-17 | 13f   | 14m   |
| (4)-18 | 13f   | 14q   |
| (4)-19 | 13f   | 14t   |
| (4)-20 | 13f   | 14v   |
| (4)-21 | 13l   | 14b   |
| (4)-22 | 13l   | 14d   |
| (4)-23 | 13l   | 14e   |
| (4)-24 | 13l   | 14g   |
| (4)-25 | 13l   | 14i   |
| (4)-26 | 13l   | 14k   |
| (4)-27 | 13l   | 14m   |
| (4)-28 | 13l   | 14q   |
| (4)-29 | 13l   | 14t   |
| (4)-30 | 13l   | 14v   |
| (4)-31 | 13v   | 14b   |
| (4)-32 | 13v   | 14d   |
| (4)-33 | 13v   | 14e   |
| (4)-34 | 13v   | 14g   |
| (4)-35 | 13v   | 14i   |
| (4)-36 | 13v   | 14k   |
| (4)-37 | 13v   | 14m   |
| (4)-38 | 13v   | 14q   |
| (4)-39 | 13v   | 14t   |
| (4)-40 | 13v   | 14v   |
| (4)-41 | 13bb  | 14b   |
| (4)-42 | 13bb  | 14d   |
| (4)-43 | 13bb  | 14e   |
| (4)-44 | 13bb  | 14g   |
| (4)-45 | 13bb  | 14i   |
| (4)-46 | 13bb  | 14k   |
| (4)-47 | 13bb  | 14m   |
| (4)-48 | 13bb  | 14q   |
| (4)-49 | 13bb  | 14t   |
| (4)-50 | 13bb  | 14v   |

Particular embodiments of this aspect of the invention include compounds of any one of the formula (IVb) or (IVh), each as defined in each of the following rows, wherein each entry is a group number as defined above (e.g., (13n) refers to R¹ is —CH₂—R¹²). In addition, any one of groups (13k)-(13n) can be either as defined for Formula (IV) or any one of definitions (13p)-(13ff):

|        | R¹  | R³  |
|--------|-----|-----|
| (4)-51 | 13k | 14a |
| (4)-52 | 13k | 14b |
| (4)-53 | 13k | 14l |
| (4)-54 | 13k | 14m |
| (4)-55 | 13k | 14p |
| (4)-56 | 13k | 14q |
| (4)-57 | 13k | 14r |
| (4)-58 | 13l | 14a |
| (4)-59 | 13l | 14b |
| (4)-60 | 13l | 14l |
| (4)-61 | 13l | 14m |
| (4)-62 | 13l | 14p |
| (4)-63 | 13l | 14q |
| (4)-64 | 13l | 14r |
| (4)-65 | 13m | 14a |
| (4)-66 | 13m | 14b |
| (4)-67 | 13m | 14l |
| (4)-68 | 13m | 14m |
| (4)-69 | 13m | 14p |
| (4)-70 | 13m | 14q |
| (4)-71 | 13m | 14r |
| (4)-72 | 13n | 14a |
| (4)-73 | 13n | 14b |
| (4)-74 | 13n | 14l |
| (4)-1  | 13n | 14m |
| (4)-2  | 13n | 14p |
| (4)-3  | 13n | 14q |
| (4)-1  | 13n | 14r |

In an embodiment of any of the preceding, the compound of formula (II) and (IV) is not one of the following compounds

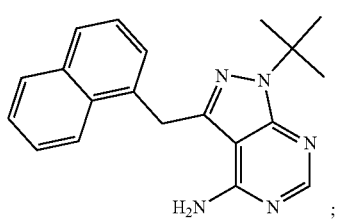

1-tert-butyl-3-(naphthalen-1-ylmethyl)-
1H-pyrazolo[3,4-d]pyrimidin-4-amine

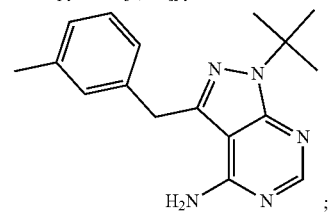

1-tert-butyl-3-(3-methylbenzyl)-1H-
pyrazolo[3,4-d]pyrimidin-4-amine

-continued

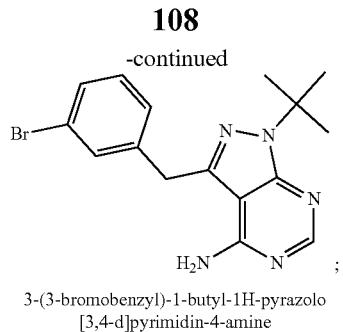

3-(3-bromobenzyl)-1-butyl-1H-pyrazolo
[3,4-d]pyrimidin-4-amine

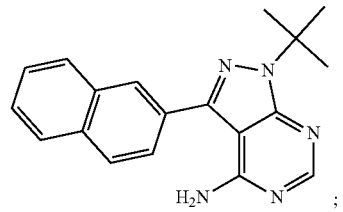

1-tert-butyl-3-(naphthalen-2-yl)-1H-
pyrazolo[3,4-d]pyrimidin-4-amine

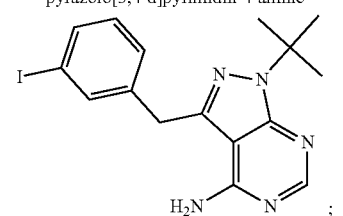

1-tert-butyl-3-(3-iodobenzyl)-1H-pyrazolo
[3,4-d]pyrimidin-4-amine

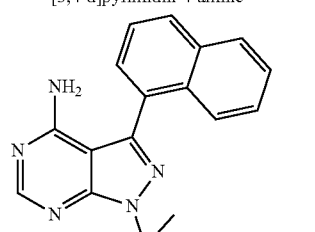

1-tert-butyl-3-(naphthalen-1-yl)-1H-
pyrazolo[3,4-d]pyrimidin-4-amine

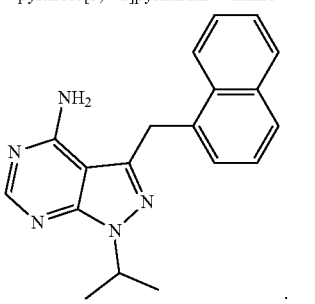

1-isopropyl-3-(naphthalen-1-ylmethyl)-
1H-pyrazolo[3,4-d]pyrimidin-4-amine

One embodiment of the present disclosure provide a method of treating a subject in need of treatment for an apicomplexan-related disease comprising administering an effective amount of a compound of any of formulas (I)-(IV) or any embodiment thereof, that inhibits the activity of an apicomplexan calcium dependent protein kinase (CDPK).

Particular embodiments of the present disclosure provide a method of treating cryptosporidiosis in a subject comprising administering an effective amount of a compound of any of formulas (I)-(IV) or any embodiment thereof, that inhibits the activity of *Cryptosporidium parvum* and *C. hominus* calcium dependent protein kinase 1 (CpCDPK1).

Other particular embodiments of the present disclosure provide a method of treating cryptosporidiosis in a subject comprising administering an effective amount of a compound of any of formulas (I)-(IV) or any embodiment thereof, that inhibits the activity of *T. gondii*, calcium dependent protein kinase 1 (TgCDPK1).

Other particular embodiments of the present disclosure provide a method of treating cryptosporidiosis in a subject comprising administering an effective amount of a compound of any of formulas (I)-(IV) or any embodiment thereof, that inhibits the activity of *P. falciparum* or *P. berghei* calcium dependent protein kinase 4 (PfCDPK4 or PbCDPK4).

Optionally, the compound of any one of formulas (I)-(IV) or any embodiment thereof, can be administered in combination with a second agent, such as agents specific for use against the specific apicomplexan-related disorder being treated.

In one embodiment, the apicomplexan protozoan related disease is toxoplasmosis. As understood by one of ordinary skill in the art, toxoplasmosis can encompass a number of pathologies, including, but not limited to, encephalitis, retinitis, lymphadenopathy, disseminated disease, and hepatitis. Toxoplasmosis infects most genera of warm-blooded animals, including humans, but the primary host is the felid (cat) family.

Cats are the definitive host for the *Toxoplasma* organism. Infection with this protozoan parasite is fairly common, but actual disease caused by this parasite is relatively rare in cats. Cats can become infected by *Toxoplasma* by eating any of the three infective stages of the parasites. The most common route of infection is probably by ingestion of tissue cysts in infected prey or in other raw meat. *Toxoplasma* multiply in the small intestines and in approximately two to three weeks the oocysts are excreted in the infected cat's feces. In another example, cats may be treated prophylactically for toxoplasmosis (e.g, a gastrointestinal infection) provided by providing a therapeutically effective amount of a compounds of any one of formulas (I)-(IV) or to eliminate the chance that they would shed infectious *Toxoplasmodia* oocyts and infect their owners. In another embodiment, infected cats may be treated by providing a therapeutically effective amount of a compound of any one of formulas (I)-(IV) to treat toxoplasmosis. As will be understood by those of skill in the art, similar prophylactic and therapeutic methods for limiting development of or treating toxoplasmosis can be used in any animal that can be infected by *Toxoplasma* sp.

Animals are infected by eating infected meat, by ingestion of feces of a cat that has itself recently been infected, or by transmission from mother to fetus. While cats are often blamed for spreading toxoplasmosis, contact with raw meat is a more significant source of human infections in many countries, and fecal contamination of hands is a greater risk factor. Infection has two stages (1) acute toxoplasmosis; and (2) latent toxoplasmosis. During acute toxoplasmosis, symptoms are often influenza-like: swollen lymph nodes, or muscle aches and pains that last for a month or more. Rarely, a patient with a fully functioning immune system may develop eye damage from toxoplasmosis. Young children (15 years old or younger) and immunocompromised patients, such as those with HIV/AIDS, those taking certain types of chemotherapy, or those who have recently received an organ transplant, may develop severe toxoplasmosis. In an embodiment, a young child can be 14 years old or younger; or 13 years old or younger; or 12 years old or younger; or 11 years old or younger; or 10 years old or younger; or 9 years old or younger; or 8 years old or younger; or 7 years old or younger; or 6 years old or younger; or 5 years old or younger; or 4 years old or younger; or 3 years old or younger; or 2 years old or younger; or 1 year old or younger. This can cause damage to the brain (encephalitis) or the eyes (necrotizing retinochoroiditis). Infants infected via placental transmission may be born with either of these problems, or with nasal malformations, although these complications are rare in newborns. In most immunocompetent patients, the infection enters a latent phase, during which only bradyzoites are present, forming cysts in nervous and muscle tissue. Most infants who are infected while in the womb have no symptoms at birth but may develop symptoms later in life. The most common current therapy for toxoplasmosis is sulfadiazine/pyrimethamine combination therapy, but therapy is often limited by allergic reactions to the sulfa component, anemia and pancytopenia induced by blocking the folate pathway. When sulfadiazine cannot be used, clindamycin may be combined with pyrimethamine but most experts feel it does not work as well as sulfadiazine. Spiramycin has been used for toxoplasmosis during pregnancy but has issues with low efficacy and is no longer available in the United States. Thus few therapeutic alternatives are available.

In another embodiment, the apicomplexan protozoan related disease is cryptosporidiosis. Cryptosporidiosis is caused by infection with the single-celled parasite (not bacterium) *Cryptosporidium parvum*. This parasite is found in many mammals including lambs, calves, goat kids, piglets and humans. Research so far has shown two basic types, the bovine type which affects most species, and a second human type which causes disease in humans only. Outbreaks of human disease, where large numbers of people are affected, are usually water-borne and usually associated with the bovine type of *cryptosporidium*. Individual sporadic cases of cryptosporidiosis in humans are mostly (around 60%) associated with the human type of *cryptosporidium*.

Cryptosporidiosis affects the intestines of mammals and is typically an acute short-term infection. It is spread through the fecal-oral route, often through contaminated water; the main symptom is self-limiting diarrhea in people with intact immune systems. In immunocompromised individuals, such as HIV/AIDS patients, the symptoms are particularly severe and often fatal. *Cryptosporidium* is the organism most commonly isolated in HIV positive patients presenting with diarrhea. Cryptosporidiosis is one of the most common waterborne diseases and is found worldwide. The parasite is transmitted by environmentally hardy microbial cysts (oocysts) that, once ingested, exist in the small intestine and result in an infection of intestinal epithelial tissue. Infection is through contaminated material such as earth, water, uncooked or cross-contaminated food that has been in contact with the feces of an infected individual or animal. It is especially prevalent amongst those in regular contact with bodies of fresh water including recreational water such as swimming pools. Other potential sources include insufficiently treated or insufficiently filtered water supplies, contaminated food, or exposure to feces. Symptoms appear from two to ten days after infection, and last for up to two weeks or more. In immunocompetent people, the disease can be asymptomatic or cause acute diarrhea or persistent diarrhea that can last for a few weeks. There is often stomach pain or cramping and a low fever. Other symptoms may include nausea, vomiting, malabsorption, and dehydration.

Individuals who are asymptomatic (have no symptoms) are nevertheless infective. Immunocompromised people, as well as very young or very old people, can develop a more severe form of cryptosporidiosis. When *Cryptosporidium* spreads beyond the intestine, as it can predominantly in patients with AIDS, it can reach the lungs, middle ear, pancreas, and stomach. Thus, one symptom is pain in the right upper quadrant. The parasite can infect the biliary tract, causing biliary cryptosporidiosis. This can result in cholecystitis and cholangitis. Current treatment is symptomatic, with fluid rehydration, electrolyte correction and management of any pain. Nitazoxanide has been FDA-approved for treatment of diarrhea caused by *Cryptosporidium* in people with healthy immune systems and is available by prescription, however it only shortens the duration of diarrhea by a couple of days. The effectiveness of nitazoxanide in immunosuppressed individuals is unclear and multiple trials have shown no benefit.

The inhibitors described herein may have use in other apicoplexa protozoan related diseases, such as coccidiosis caused by *Eimeria* spp., cause infections and disease in poultry; which causes Babesiosis which is caused by *Babesia* spp. and results in a malaria-like disease, and malaria in humans and animals caused by *Plasmodium* spp.

*Plasmodium* calcium dependent protein kinase 4 (CDPK4) is essential for exflaggelation of microgametes, sexual reproduction and infection of the mosquito host and is a potential drug target to block mosquito transmission. *Plasmodium* transmission-blocking compounds that act via inhibition of PfCDPK4 have great promise in the armamentarium of malaria control. *Plasmodium* CDPK4 has a unique ATP binding site which renders CDPK4 differentially sensitive to bumped kinase inhibitors (BKIs). TgCDPK1 and CpCDPK1 have ATP-binding pockets with an atypically small gatekeeper residue, glycine. *P. falciparum* CDPK4 (PfCDPK4) has a serine residue at the gatekeeper position, smaller than any gatekeeper in mammalian kinases, and an overall ATP-binding pocket that is very similar to TgCDPK1 and CpCDPK1. BKIs inhibit *P. falciparum* CDPK4 (PfCDPK4) and prevents the exflagellation of malaria microgametes. Administration of BKIs to mice stops the transmission of *P. berghei* to mosquitoes. Finally, addition of BKIs to blood containing *P. falciparum* gametocytes stops exflagellation of microgametocytes and blocks the infection of mosquitoes. BKIs are non-toxic, selective inhibitors that block malaria transmission to mosquitos, have favorable oral pharmacokinetic (PK) properties, have a low likelihood of generating resistance.

Thus, other particular embodiments of the present disclosure provide a method for treating malaria comprising administering an effective amount of a compound of any of formulas (I)-(IV) or any embodiment thereof, that inhibits the activity of Plasmodium falciparum and *P. berghei* calcium dependent protein kinases. In one embodiment, the compound can be administered in combination with a second agent. In another embodiment, the subject has malaria, and the second agent is an anti-malarial therapeutic. The subject can be human. In further embodiments, the subject is a mammal other than a human, such as a cat or livestock (e.g., pigs, sheep, goats, cattle).

As used herein, the term "subject", "individual," or "patient," used interchangeably, refers to any animal, including mammals, preferably mice, rats, other rodents, rabbits, dogs, cats, birds, swine, horses, livestock (e.g., pigs, sheep, goats, cattle), primates or humans.

As used here, a subject "in need thereof" refers to a subject that has the disorder or disease to be treated or is predisposed to or otherwise at risk of developing the disease or disorder.

As used here, the terms "treatment" and "treating" means
(i) inhibiting the progression of the disease;
(ii) prophylactic use for example, preventing or limiting development of a disease, condition or disorder in an individual who may be predisposed or otherwise at risk to the disease, condition or disorder but does not yet experience or display the pathology or symptomatology of the disease;
(iii) inhibiting the disease; for example, inhibiting a disease, condition or disorder in an individual who is experiencing or displaying the pathology or symptomatology of the disease, condition or disorder;
(iv) Ameliorating the referenced disease state, for example, ameliorating a disease, condition or disorder in an individual who is experiencing or displaying the pathology or symptomatology of the disease, condition or disorder (i.e., reversing or improving the pathology and/or symptomatology) such as decreasing the severity of disease;
(v) eliciting the referenced biological effect, or
(vi) limiting transmission of the disease.

In various preferred embodiments, the individual may be immunocompromised (having an immune system that has been impaired by disease or treatment, such as an HIV infected patient, and AIDS patient, or a patient receiving chemotherapy or an organ transplant), a pregnant female, fifteen years old or younger, fifty-five years old or older, exposed to contaminated water supplies, and/or exposed to other sources of contamination (fecal matter, blood transfusion, earth, food, etc.) The methods may further comprise administering the compounds disclosed herein to subjects at risk of acquiring an apicomplexan-related disease, such as those with compromised immune systems or that are extremely young in high risk areas.

In other embodiments, the compounds described herein can be used in prophylactic manner. Cryptosporidiosis is usually seen in calves between one and two weeks of age and presents with diarrhea, colic and pain, depression, loss of appetite, and weight loss. Thus, in one embodiment, calves may be treated prophylactically by providing an effective amount of a compound of any one of formulas (I)-(IV) to limit the contraction or transmission of cryptosporidiosis. In a preferred embodiment, the administering is done within the first 7-8 days after birth (day 1, 2, 3, 4, 5, 6, 7, or 8) when calves are most susceptible to Cryptosporidia infection. Such treatments may be repeated as necessary as would be understood by one skilled in the art.

In another embodiment, infected cattle may be treated by providing a therapeutically effective amount of a compound of any one of formulas (I)-(IV) to treat cryptosporidiosis. Such treatments may be repeated as necessary as would be understood by one skilled in the art. In this embodiment, the compounds of the invention may be administered together with electrolytes if cattle become dehydrated. If disease is severe, halfuginone can be used in combination with the compounds of the invention to reduce disease severity and prevent spread to other animals.

In another example, lambs are susceptible to cryptosporidiosis and may be provided a therapeutically effective amount of a compounds of any one of formulas (I)-(IV) to limit the contraction or transmission of cryptosporidiosis.

In another example, any or all members of a herd (e.g., cattle, goats, lambs, etc.), may be provided a therapeutically effective amount of a compound of any one of formulas (I)-(IV) to limit the contraction or transmission of toxoplasmosis or cryptosporidiosis or to rid the herd of cattle of toxoplasmosis or cryptosporidiosis.

In another embodiment, goat kids may be treated prophylactically by providing an effective amount of a compound of any one of formulas (I)-(IV) to limit the contraction or transmission of cryptosporidiosis. In a preferred embodiment, the administering is done within the first 7-8 days after birth (day 1, 2, 3, 4, 5, 6, 7, or 8) when kids are most susceptible to cryptosporidiosis. Such treatments may be repeated as necessary as would be understood by one skilled in the art. The extent to which a kid is infected seems to be dependent on its age and immune status. Younger animals are much more susceptible to infection than adults. In studies done with lambs, five-day-old lambs had diarrhea for 9-10 days and suffered from a high rate of mortality. Sixty-day-old lambs showed no symptoms when they were infected, and adult sheep completely resisted infection. There is an indication that adults develop an immunity to *Cryptosporidium*, yet this immunity does not seem to be passed to their offspring.

Immune-depressed goats are very susceptible to the disease. This refers to the total immune status, not just protection from cryptosporidiosis. Many situations can cause animals to lack immunity. Animals with severe infections are more susceptible to secondary infections. The most common problem with kids is receiving a deficient amount of colostral antibodies following birth. Whether caused by disease, an imbalanced ration or improper management, animals lacking adequate immunity are much more susceptible to cryptosporidiosis.

In another embodiment, infected goats may be treated by providing a therapeutically effective amount of a compound of any one of formulas (I)-(IV) to treat cryptosporidiosis. In a preferred embodiment, the goat is a kid.

In another example, pigs are susceptible to cryptosporidiosis and may be provided a therapeutically effective amount of a compound of any one of formulas (I)-(IV) to limit the contraction or transmission of cryptosporidiosis. In a preferred embodiment, the administering is done within the first 21 days after birth (day 1, 2, 3, 4, 5, 6, 7, 8, 9, 10, 11, 12, 13, 14, 15, 16, 17, 18, 19, 20, or 21) when piglets are most susceptible to cryptosporidiosis and/or most likely In another embodiment, infected pigs may be treated by providing a therapeutically effective amount of a compound of any one of formulas (I)-(IV) to treat cryptosporidiosis. In a preferred embodiment, the pig is a piglet.

In another example, birds, such as turkeys and chickens, are susceptible to cryptosporidiosis and may be provided an effective amount of a compounds of any one of formulas (I)-(IV) to prevent the contraction or transmission of cryptosporidiosis. In particular, *Cryptosporidium baileyi* can cause respiratory disease in chickens and turkeys. The same species causes infections of the hindgut and cloacal bursa in chickens, turkeys, and ducks. *C. meleagridis* also infects both species. A further species causes respiratory disease in quail. The oocysts are excreted ready sporulated in the faeces and infection occurs by inhalation and ingestion. Signs of cryptosporidiosis in poultry include snick, cough, swollen sinuses, low weight gain, and diarrhea. In another embodiment, infected birds may be treated by providing a therapeutically effective amount of a compound of any one of formulas (I)-(IV) to treat cryptosporidiosis.

In another example, birds, such as turkeys and chickens, are susceptible to coccidiosis due to *Eimeria* infections and may be provided an effective amount of a compounds of any one of formulas (I)-(IV) to limit the contraction or transmission of coccidiosis, a parasitic disease caused by the development and multiplication of coccidia in the epithelial cells of the intestine. *Eimeria* infections are ubiquitous; they are found wherever chickens or turkeys are reared (traditional, industrial, label or organic/bio farms). Particular strains of *Eimeria* known to infect birds include, but are not limited to, *Eimeria acervulina. Eimeria adenoeides, Eimeria brunette, Eimeria colchici, Eimeria curvata, Eimeria dispersa, Eimeria duodenali, Eimeria fraterculae, Eimeria gallopavonis, Eimeria praecox, Eimeria maxima, Eimeria meleagrimitis, Eimeria mitis, Eimeria necatrix, Eimeria phasiani, Eimeria procera*, and *Eimeria tenella*. In another embodiment, infected birds may be treated by providing a therapeutically effective amount of a compound of any one of formulas (I)-(IV) to treat coccidiosis In another example, mammals, such as goats, sheep, llamas, alpacas, cattle, rabbits, and mice, are susceptible to coccidiosis and may be provided an effective amount of a compounds of any one of formulas (I)-(IV) to limit the contraction or spreading of *Eimeria*. Particular strains of *Eimeria* known to infect mammals include, but are not limited to, *Eimeria ahsata, Eimeria alabamensis, Eimeria alijevi, Eimeria apsheronica, Eimeria arloingi, Eimeria arundeli, Eimeria bakuensis, Eimeria bovis, Eimeria cameli, Eimeria caprina, Eimeria caprovina, Eimeria christenseni, Eimeria clethrionomyis, Eimeria coecicola, Eimeria contorta, Eimeria couesii, Eimeria crandallis, Eimeria dammahensis, Eimeria dowleri, Eimeria exigua, Eimeria falciformis, Eimeria farasanii, Eimeria ferrisi, Eimeria flavescens, Eimeria gallatii, Eimeria granulosa, Eimeria hirci, Eimeria intestinalis, Eimeria irresidua, Eimeria intricata, Eimeria jolchijevi, Eimeria krijgsmanni, Eimeria larimerensis, Eimeria macusaniensis, Eimeria magna, Eimeria marconii, Eimeria media, Eimeria melanuri, Eimeria myoxi, Eimeria nagpurensis, Eimeria ninakohlyakimovae, Eimeria ovinoidalis, Eimeria pallida, Eimeria palustris, Eimeria papillata, Eimeria perforans, Eimeria phocae, Eimeria pileata, Eimeria pipistrellu, Eimeria piriformis, Eimeria prionotemni, Eimeria punctate, Eimeria roobroucki, Eimeria saudiensis, Eimeria sealanderi, Eimeria separate, Eimeria stiedae, Eimeria ursini, Eimeria vermiformis, Eimeria weybridgensis, Eimeria wobati*, and *Eimeria zuernii*. In another embodiment, infected mammals may be treated by providing a therapeutically effective amount of a compound of any one of formulas (I)-(IV) to treat coccidiosis The usual age range for animals suffering from coccidiosis is from three weeks to one year of age, but cattle remain susceptible to coccidiosis throughout their lives or until they develop acquired immunity. The susceptibility of the animals is influenced by nutritional status (colostrum supply), stress (overstocking, transport, climate, hygiene, etc.), immune status and the occurrence of concurrent diseases.

Infections with multiple *Eimeria* species (pathogenic and non-pathogenic) are common in real life situations. The most important species related to the clinical manifestation of the disease in the stable are *Eimeria bovis* and *Eimeria zuernii*, although other pathogenic coccidia species may also affect the cattle in the stables, such as *Eimeria alabamensis* (animals fed on contaminated hay), which is commonly associated with diarrheic problems in animals that are released to pasture.

"Carrier hosts" shed relatively fewer oocysts and the susceptible "multiplier hosts" pick up the infection and shed many-fold oocysts into the environment. Exposure to multiplier hosts leads to subclinical or mildly clinical infection in animals exposed to a large number of oocysts in the environment. Calves exposed to a large number of oocysts are likely to develop severe coccidiosis. In feedlots where few oocysts are present, stress factors such as weaning, diet, temperature extremes and other variables may make the calves more susceptible to infection and under such conditions the reproductive potential of coccidia in the gut greatly increases.

In goats, although the infection can occur in any goat herd raised under semi and intensive management practices, it is most frequently observed in kids 2 to 4 weeks postweaning. The infection occurs by ingesting the pathogenic sporulated oocyst (sporulated is a form of resistance of the Coccidia). Oocysts can be found in the water or in feed supplies contaminated with feces. Once ingested, oocysts penetrate the cells lining the intestine where they go through several stages of development and cause inflammation and destruction of intestinal cells. Stress is the predisposing factor in kids during the postweaning period. Outbreaks can occur during stressful conditions such as after shipping or when animals are relocated. Outbreaks can also occur during sudden weather changes, after a change in concentrated feed practices, when animals are recovering from a disease, or in worm burden cases. Although coccidiosis can occur year around, a higher incidence occurs during postweaning.

The compounds disclosed herein can be used to treat coccidiosis in combination with standard treatments such as, but not limited to, replacing fluids by administering liquid nutritional supplement orally by nipple bottle until the animal is rehydrated. Animals that have lost 5 percent of their body weight may require intravenous (IV) and/or electrolyte therapy. Treatment may include IV or subcutaneously (SC) fluid therapy with a physiologically balanced electrolyte such as Ringer's, Plasmalyte-A, or Normosol-R. Administer the solution (2 to 5 milliliters per pound) one to three times daily until the animal is rehydrated. Sulfas such as Albon™, Sulmet™, or Di-Methox™, can also be mixed in the drinking water or as a drench for individual goats. An alternative is CORID™ (amprolium).

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician, which includes one or more of the following: (1) preventing the disease; for example, preventing a disease, condition or disorder in an individual who may be predisposed to the disease, condition or disorder but does not yet experience or display the pathology or symptomatology of the disease; (2) inhibiting the disease; for example, inhibiting a disease, condition or disorder in an individual who is experiencing or displaying the pathology or symptomatology of the disease, condition or disorder; and (3) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

Methods for Identifying a Compound

As disclosed herein, the inventors have identified compounds for use in treating apicomplexan-related disorders. While not being bound by a specific mechanism of action, the inventors believe that the inhibitory activity is based on selective inhibition of apicomplexan protein kinases, specifically selective inhibitors against apicomplexan calcium-dependent protein kinases (CDPKs). The inventors have further identified a specific region of such CDPKs that the inhibitors bind to, exemplified by SEQ ID NO:1 (from the *T. gondii*, CDPK (SEQ ID NO: 13); (TgCDPK))) and SEQ ID NO:2 (from the *C. parvum* CDPK (CpCDPK)(SEQ ID NOs: 14, 15, 16, 17)). Thus, another aspect of the present disclosure provides a method of identifying a compound for treating an apicomplexan-related disease, including but not limited to those disclosed above, and most preferably toxoplasmosis and cryptosporidiosis. The method comprises (a) contacting a polypeptide comprising an amino acid sequence according to SEQ ID NO. 1 or SEQ ID NO:2 with a compound to be tested for the ability to bind to the polypeptide under conditions suitable for binding to the polypeptide, and (b) identifying compounds that bind to the polypeptide. Suitable conditions for such binding can be determined by one of skill in the art based on the teachings herein. For example, the methods may comprise suitable wash steps to remove unbound compounds. The methods may be conducted in vitro, or the binding may be assayed in cells using appropriate reporter molecules.

In one embodiment, the method comprises contacting the compound with the recited peptide. In another embodiment, the compound is contacted with TgCDPK or CpCDPK. In a further embodiment, the compound is contacted with TgCDPK or CpCDPK under conditions for crystallizing the complex, as described in the examples that follow. In all of these embodiments, the method may further comprise comparing binding of the compound to a control. Any suitable control can be used. In one embodiment, the control comprises comparing binding of the polypeptide to binding of the compound to a control polypeptide. Any suitable control polypeptide may be used. In one embodiment, the control polypeptide may comprise a mutated CDPK active region, such as TgCDPK1 G128M (described below), or corresponding *C. parvum* CDPK mutated at the gatekeeper glycine residue (CpCDPK residue 150) (as described in detail herein). For example, the gatekeeper glycine residue in any TgCDPK or CpCDPK may be mutated as described herein to replace the glycine residue with alanine, arginine, asparagine, aspartic acid, cysteine, glutamic acid, glutamine, histidine, isoleucine, leucine, lysine, methionine, phenylalanine, proline, serine, threonine, tryptophan, tyrosine, or valine. In these embodiments, those compounds that show selective binding to the polypeptide and little to no binding to the control peptide are identified as selective inhibitors against apicomplexan CDPKs. Exemplary methods according to this aspect of the invention are described in the examples that follow.

In a further embodiment, the methods may comprise a verification step (c), comprising applying a compound selected in (b) to the relevant apicomplexan species, such Toxoplasma gondii of *C. parvum*, to test for inhibitory activity. Exemplary such assays for inhibitory activity are described in the examples herein.

When the test compounds comprise polypeptide sequences, such polypeptides may be chemically synthesized or recombinantly expressed. Recombinant expression can be accomplished using standard methods in the art, as disclosed above. Such expression vectors can comprise bacterial or viral expression vectors, and such host cells can be prokaryotic or eukaryotic. Synthetic polypeptides, prepared using the well-known techniques of solid phase, liquid phase, or peptide condensation techniques, or any combination thereof, can include natural and unnatural amino acids. Amino acids used for peptide synthesis may be standard Boc (Nα-amino protected Nu-t-butyloxycarbonyl)

amino acid resin with standard deprotecting, neutralization, coupling and wash protocols, or standard base-labile Nα-amino protected 9-fluorenylmethoxycarbonyl (Fmoc) amino acids. Both Fmoc and Boc Nα-amino protected amino acids can be obtained from Sigma, Cambridge Research Biochemical, or other chemical companies familiar to those skilled in the art. In addition, the polypeptides can be synthesized with other Nα-protecting groups that are familiar to those skilled in this art. Solid phase peptide synthesis may be accomplished by techniques familiar to those in the art and provided, such as by using automated synthesizers.

When the test compounds comprise antibodies, such antibodies can be polyclonal or monoclonal. The antibodies can be humanized, fully human, or murine forms of the antibodies. Such antibodies can be made by well-known methods, such as described in Harlow and Lane, Antibodies; A Laboratory Manual, Cold Spring Harbor Laboratory, Cold Spring Harbor, N.Y., (1988).

When the test compounds comprise nucleic acid sequences, such nucleic acids may be chemically synthesized or recombinantly expressed as well. Recombinant expression techniques are well known to those in the art (See, for example, Sambrook, et al., 1989, supra). The nucleic acids may be DNA or RNA, and may be single stranded or double. Similarly, such nucleic acids can be chemically or enzymatically synthesized by manual or automated reactions, using standard techniques in the art. If synthesized chemically or by in vitro enzymatic synthesis, the nucleic acid may be purified prior to introduction into the cell. For example, the nucleic acids can be purified from a mixture by extraction with a solvent or resin, precipitation, electrophoresis, chromatography, or a combination thereof. Alternatively, the nucleic acids may be used with no or a minimum of purification to avoid losses due to sample processing.

When the test compounds comprise compounds other than polypeptides, antibodies, or nucleic acids, such compounds can be made by any of the variety of methods in the art for conducting organic chemical synthesis.

Pharmaceutical Compositions

The pharmaceutical compositions described herein generally comprise a combination of a compound described herein and a pharmaceutically acceptable carrier, diluent, or excipient. Such compositions are substantially free of non-pharmaceutically acceptable components, i.e., contain amounts of non-pharmaceutically acceptable components lower than permitted by US regulatory requirements at the time of filing this application. In some embodiments of this aspect, if the compound is dissolved or suspended in water, the composition further optionally comprises an additional pharmaceutically acceptable carrier, diluent, or excipient. In other embodiments, the pharmaceutical compositions described herein are solid pharmaceutical compositions (e.g., tablet, capsules, etc.).

These compositions can be prepared in a manner well known in the pharmaceutical art, and can be administered by a variety of routes, depending upon whether local or systemic treatment is desired and upon the area to be treated. Administration may be topical (including ophthalmic and to mucous membranes including intranasal, vaginal and rectal delivery), pulmonary (e.g., by inhalation or insufflation of powders or aerosols, including by nebulizer; intratracheal, intranasal, epidermal and transdermal), ocular, oral or parenteral. Methods for ocular delivery can include topical administration (eye drops), subconjunctival, periocular or intravitreal injection or introduction by balloon catheter or ophthalmic inserts surgically placed in the conjunctival sac. Parenteral administration includes intravenous, intraarterial, subcutaneous, intraperitoneal or intramuscular injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Also, pharmaceutical compositions can contain, as the active ingredient, one or more of the compounds described herein above in combination with one or more pharmaceutically acceptable carriers. In making the compositions described herein, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions described herein can be formulated so as to provide quick, sustained or delayed release of the active ingredient after administration to the patient by employing procedures known in the art.

The compositions can be formulated in a unit dosage form, each dosage containing from about 5 to about 100 mg, more usually about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound described herein. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, 0.1 to about 500 mg of the active ingredient of a compound described herein.

The tablets or pills can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of the compounds can vary according to, for example, the particular use for which the treatment is made, the manner of administration of the compound, the health and condition of the patient, and the judgment of the prescribing physician. The proportion or concentration of a compound described herein in a pharmaceutical composition can vary depending upon a number of factors including dosage, chemical characteristics (e.g., hydrophobicity), and the route of administration. For example, the compounds described herein can be provided in an aqueous physiological buffer solution containing about 0.1 to about 10% w/v of the compound for parenteral administration. Some typical dose ranges are from about 1 μg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compounds described herein can also be formulated in combination with one or more additional active ingredients which can include any pharmaceutical agent such as anti-viral agents, vaccines, antibodies, immune enhancers, immune suppressants, anti-inflammatory agents and the like.

Definitions

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to". Words using the singular or plural number also include the plural or singular number, respectively. Additionally, the words "herein," "above" and "below" and words of similar import, when used in this application, shall refer to this application as a whole and not to any particular portions of this application.

Terms used herein may be preceded and/or followed by a single dash, "-", or a double dash, "=", to indicate the bond order of the bond between the named substituent and its parent moiety; a single dash indicates a single bond and a double dash indicates a double bond. In the absence of a single or double dash it is understood that a single bond is formed between the substituent and its parent moiety; further, substituents are intended to be read "left to right" unless a dash indicates otherwise. For example, $C_1$-$C_6$alkoxycarbonyloxy and —OC(O)$C_1$-$C_6$alkyl indicate the same functionality; similarly arylalkyl and -alkylaryl indicate the same functionality.

The term "alkenyl" as used herein, means a straight or branched chain hydrocarbon containing from 2 to 10 carbons, unless otherwise specified, and containing at least one carbon-carbon double bond. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, 3-decenyl, and 3,7-dimethylocta-2,6-dienyl.

The term "alkyl" as used herein, means a straight or branched chain hydrocarbon containing from 1 to 10 carbon atoms, unless otherwise specified. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl. When an "alkyl" group is a linking group between two other moieties, then it may also be a straight or branched chain; examples include, but are not limited to —CH$_2$—, —CH$_2$CH$_2$—, —CH$_2$CH$_2$CHC (CH$_3$)—, —CH$_2$CH(CH$_2$CH$_3$)CH$_2$—.

The term "alkynyl" as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "aryl," as used herein, means a phenyl (i.e., monocyclic aryl), a bicyclic ring system containing at least one phenyl ring or an aromatic bicyclic ring containing only carbon atoms in the aromatic bicyclic ring system or a multicyclic aryl ring system, provided that the bicyclic or multicyclic aryl ring system does not contain a heteroaryl ring when fully aromatic. The bicyclic aryl can be azulenyl, naphthyl, or a phenyl fused to a monocyclic cycloalkyl, a monocyclic cycloalkenyl, or a monocyclic heterocyclyl. The bicyclic aryl is attached to the parent molecular moiety through any carbon atom contained within the phenyl portion of the bicyclic system, or any carbon atom with the napthyl or azulenyl ring. The fused monocyclic cycloalkyl or monocyclic heterocyclyl portions of the bicyclic aryl are optionally substituted with one or two oxo and/or thia groups. Representative examples of the bicyclic aryls include, but are not limited to, azulenyl, naphthyl, dihydroinden-1-yl, dihydroinden-2-yl, dihydroinden-3-yl, dihydroinden-4-yl, 2,3-dihydroindol-4-yl, 2,3-dihydroindol-5-yl, 2,3-dihydroindol-6-yl, 2,3-dihydroindol-7-yl, inden-1-yl, inden-2-yl, inden-3-yl, inden-4-yl, dihydronaphthalen-2-yl, dihydronaphthalen-3-yl, dihydronaphthalen-4-yl, dihydronaphthalen-1-yl, 5,6,7,8-tetrahydronaphthalen-1-yl, 5,6,7,8-tetrahydronaphthalen-2-yl, 2,3-dihydrobenzofuran-4-yl, 2,3-dihydrobenzofuran-5-yl, 2,3-dihydrobenzofuran-6-yl, 2,3-dihydrobenzofuran-7-yl, benzo[d][1,3]dioxol-4-yl, benzo[d][1,3]dioxol-5-yl, 2H-chromen-2-On-5-yl, 2H-chromen-2-On-6-yl, 2H-chromen-2-On-7-yl, 2H-chromen-2-On-8-yl, isoindoline-1,3-dion-4-yl, isoindoline-1,3-dion-5-yl, inden-1-On-4-yl, inden-1-On-5-yl, inden-1-On-6-yl, inden-1-On-7-yl, 2,3-dihydrobenzo[b][1,4]dioxan-5-yl, 2,3-dihydrobenzo[b][1,4]dioxan-6-yl, 2H-benzo[b][1,4]oxazin3(4H)-On-5-yl, 2H-benzo[b][1,4]oxazin3(4H)-On-6-yl, 2H-benzo[b][1,4]oxazin3(4H)-On-7-yl, 2H-benzo[b][1,4]oxazin3(4H)-On-8-yl, benzo[d]oxazin-2(3H)-On-5-yl, benzo[d]oxazin-2(3H)-On-6-yl, benzo[d]oxazin-2(3H)-On-7-yl, benzo[d]oxazin-2(3H)-On-8-yl, quinazolin-4(3H)-On-5-yl, quinazolin-4(3H)-On-6-yl, quinazolin-4(3H)-On-7-yl, quinazolin-4(3H)-On-8-yl, quinoxalin-2(1H)-On-5-yl, quinoxalin-2(1H)-On-6-yl, quinoxalin-2(1H)-On-7-yl, quinoxalin-2(1H)-On-8-yl, benzo[d]thiazol-2(3H)-On-4-yl, benzo[d]thiazol-2(3H)-On-5-yl, benzo[d]thiazol-2(3H)-On-6-yl, and, benzo[d]thiazol-2(3H)-On-7-yl. In certain embodiments, the bicyclic aryl is (i) naphthyl or (ii) a phenyl ring fused to either a 5 or 6 membered monocyclic cycloalkyl, a 5 or 6 membered monocyclic cycloalkenyl, or a 5 or 6 membered monocyclic heterocyclyl, wherein the fused cycloalkyl, cycloalkenyl, and heterocyclyl groups are optionally substituted with one or two groups which are independently oxo or thia. Multicyclic aryl groups are a phenyl ring (base ring) fused to either (i) one ring system selected from the group consisting of a bicyclic aryl, a bicyclic cycloalkyl, a bicyclic cycloalkenyl, and a bicyclic heterocyclyl; or (ii) two other ring systems independently selected from the group consisting of a phenyl, a bicyclic aryl, a monocyclic or bicyclic cycloalkyl, a monocyclic or bicyclic cycloalkenyl, and a monocyclic or bicyclic heterocyclyl, provided that when the base ring is fused to a bicyclic cycloalkyl, bicyclic cycloalkenyl, or bicyclic heterocyclyl, then the base ring is fused to the base ring of the a bicyclic cycloalkyl, bicyclic cycloalkenyl, or bicyclic heterocyclyl. The multicyclic aryl is attached to the parent molecular moiety through any carbon atom contained within the base ring. In certain embodiments, multicyclic aryl groups are a phenyl ring (base ring) fused to either (i) one ring system selected from the group consisting of a bicyclic aryl, a bicyclic cycloalkyl, a bicyclic cycloalkenyl, and a bicyclic heterocyclyl; or (ii) two other ring systems independently selected from the group consisting of a phenyl, a monocyclic cycloalkyl, a monocyclic cycloalkenyl, and a monocyclic heterocyclyl, provided that when the base ring is fused to a bicyclic cycloalkyl, bicyclic cycloalkenyl, or bicyclic heterocyclyl, then the base ring is fused to the base ring of the a bicyclic cycloalkyl, bicyclic cycloalkenyl, or bicyclic heterocyclyl. Examples of multicyclic aryl groups include but are not limited to anthracen-9-yl and phenanthren-9-yl.

The term "arylalkyl" and "-alkylaryl" as used herein, means an aryl group, as defined herein, appended to the parent molecular moiety through an alkyl group, as defined herein. Representative examples of arylalkyl include, but are not limited to, benzyl, 2-phenylethyl, 3-phenylpropyl, and 2-naphth-2-ylethyl.

The terms "cyano" and "nitrile" as used herein, mean a —CN group.

The term "cycloalkyl" as used herein, means a monocyclic, bicyclic, or a multicyclic cycloalkyl ring system. Monocyclic ring systems are cyclic hydrocarbon groups containing from 3 to 8 carbon atoms, where such groups can be saturated or unsaturated, but not aromatic. In certain embodiments, cycloalkyl groups are fully saturated. Examples of monocyclic cycloalkyls include cyclopropyl, cyclobutyl, cyclopentyl, cyclopentenyl, cyclohexyl, cyclohexenyl, cycloheptyl, and cyclooctyl. Bicyclic cycloalkyl ring systems are bridged monocyclic rings or fused bicyclic rings. Bridged monocyclic rings contain a monocyclic cycloalkyl ring where two non-adjacent carbon atoms of the monocyclic ring are linked by an alkylene bridge of between one and three additional carbon atoms (i.e., a bridging group of the form —(CH$_2$)$_w$—, where w is 1, 2, or 3). Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. Fused bicyclic cycloalkyl ring systems contain a monocyclic cycloalkyl ring fused to either a phenyl, a monocyclic cycloalkyl, a monocyclic cycloalkenyl, a monocyclic heterocyclyl, or a monocyclic heteroaryl. The bridged or fused bicyclic cycloalkyl is attached to the parent molecular moiety through any carbon atom contained within the monocyclic cycloalkyl ring. Cycloalkyl groups are optionally substituted with one or two groups which are independently oxo or thia. In certain embodiments, the fused bicyclic cycloalkyl is a 5 or 6 membered monocyclic cycloalkyl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused bicyclic cycloalkyl is optionally substituted by one or two groups which are independently oxo or thia. Multicyclic cycloalkyl ring systems are a monocyclic cycloalkyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other rings systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. The multicyclic cycloalkyl is attached to the parent molecular moiety through any carbon atom contained within the base ring. In certain embodiments, multicyclic cycloalkyl ring systems are a monocyclic cycloalkyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other rings systems independently selected from the group consisting of a phenyl, a monocyclic heteroaryl, a monocyclic cycloalkyl, a monocyclic cycloalkenyl, and a monocyclic heterocyclyl. Examples of multicyclic cycloalkyl groups include, but are not limited to tetradecahydrophenanthrenyl, perhydrophenothiazin-1-yl, and perhydrophenoxazin-1-yl.

"Cycloalkenyl" as used herein refers to a monocyclic, bicyclic, or a multicyclic cycloalkenyl ring system. Monocyclic ring systems are cyclic hydrocarbon groups containing from 3 to 8 carbon atoms, where such groups are unsaturated (i.e., containing at least one annular carbon-carbon double bond), but not aromatic. Examples of monocyclic ring systems include cyclopentenyl and cyclohexenyl. Bicyclic cycloalkenyl rings are bridged monocyclic rings or a fused bicyclic rings. Bridged monocyclic rings contain a monocyclic cycloalkenyl ring where two non-adjacent carbon atoms of the monocyclic ring are linked by an alkylene bridge of between one and three additional carbon atoms (i.e., a bridging group of the form —$(CH_2)_w$—, where w is 1, 2, or 3). Representative examples of bicyclic cycloalkenyls include, but are not limited to, norbornenyl and bicyclo[2.2.2]oct-2-enyl. Fused bicyclic cycloalkenyl ring systems contain a monocyclic cycloalkenyl ring fused to either a phenyl, a monocyclic cycloalkyl, a monocyclic cycloalkenyl, a monocyclic heterocyclyl, or a monocyclic heteroaryl. The bridged or fused bicyclic cycloalkenyl is attached to the parent molecular moiety through any carbon atom contained within the monocyclic cycloalkenyl ring. Cycloalkenyl groups are optionally substituted with one or two groups which are independently oxo or thia. Multicyclic cycloalkenyl rings contain a monocyclic cycloalkenyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two rings systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. The multicyclic cycloalkenyl is attached to the parent molecular moiety through any carbon atom contained within the base ring. IN certain embodiments, multicyclic cycloalkenyl rings contain a monocyclic cycloalkenyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two rings systems independently selected from the group consisting of a phenyl, a monocyclic heteroaryl, a monocyclic cycloalkyl, a monocyclic cycloalkenyl, and a monocyclic heterocyclyl.

The term "halo" or "halogen" as used herein, means —Cl, —Br, —I or —F.

The term "haloalkyl" as used herein, means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "heteroaryl," as used herein, means a monocyclic, bicyclic, or a multicyclic heteroaryl ring system. The monocyclic heteroaryl can be a 5 or 6 membered ring. The 5 membered ring consists of two double bonds and one, two, three or four nitrogen atoms and optionally one oxygen or sulfur atom. The 6 membered ring consists of three double bonds and one, two, three or four nitrogen atoms. The 5 or 6 membered heteroaryl is connected to the parent molecular moiety through any carbon atom or any nitrogen atom contained within the heteroaryl. Representative examples of monocyclic heteroaryl include, but are not limited to, furyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. The bicyclic heteroaryl consists of a monocyclic heteroaryl fused to a phenyl, a monocyclic cycloalkyl, a monocyclic cycloalkenyl, a monocyclic heterocyclyl, or a monocyclic heteroaryl. The fused cycloalkyl or heterocyclyl portion of the bicyclic heteroaryl group is optionally substituted with one or two groups which are independently oxo or thia. When the bicyclic heteroaryl contains a fused cycloalkyl, cycloalkenyl, or heterocyclyl ring, then the bicyclic heteroaryl group is connected to the parent molecular moiety through any carbon or nitrogen atom contained within the monocyclic heteroaryl portion of the bicyclic ring system. When the bicyclic heteroaryl is a monocyclic heteroaryl fused to a phenyl ring or a monocyclic heteroaryl, then the bicyclic heteroaryl group is connected to the parent molecular moiety through any carbon atom or nitrogen atom within the bicyclic ring system. Representative examples of bicyclic heteroaryl include, but are not limited to, benzimidazolyl, benzofuranyl, benzothienyl, benzoxadiazolyl, benzoxathiadiazolyl, benzothiazolyl, cinnolinyl, 5,6-dihydroquinolin-2-yl, 5,6-dihydroisoquinolin-1-yl, furopyridinyl, indazolyl, indolyl, isoquinolinyl, naphthyridinyl, quinolinyl, purinyl, 5,6,7,8-tetrahydroquinolin-2-yl, 5,6,7,8-tetrahydroquinolin-3-yl, 5,6,7,8-tetrahydroquinolin-4-yl, 5,6,7,8-tetrahydroisoquinolin-1-yl, thienopyridinyl, 4,5,6,7-tetrahydrobenzo[c][1,2,5]oxadiazolyl, and 6,7-dihydrobenzo[c][1,2,5]oxadiazol-4(5H)-onyl. In certain embodiments, the fused bicyclic heteroaryl is a 5 or 6 membered monocyclic heteroaryl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused cycloalkyl, cycloalkenyl, and heterocyclyl groups are optionally substituted with one or two groups which are independently oxo or thia. The multicyclic heteroaryl group is a monocyclic heteroaryl ring (base ring) fused to either (i) one ring system selected from the group consisting of a bicyclic aryl, a bicyclic heteroaryl, a bicyclic heterocyclyl, a bicyclic cycloalkenyl, and a bicyclic cycloalkyl; or (ii) two ring systems selected from the group consisting of a phenyl, a bicyclic aryl, a monocyclic or bicyclic heteroaryl, a monocyclic or bicyclic heterocyclyl, a monocyclic or bicyclic cycloalkenyl, and a monocyclic or bicyclic cycloalkyl. The multicyclic heteroaryl group is connected to the parent molecular moiety through any carbon atom or nitrogen atom contained within the base ring. In certain embodiments, multicyclic heteroaryl groups are a monocyclic heteroaryl ring (base ring) fused to either (i) one ring system selected from the group consisting of a bicyclic aryl, a bicyclic heteroaryl, a bicyclic heterocyclyl, a bicyclic cycloalkenyl, and a bicyclic cycloalkyl; or (ii) two ring systems selected from the group consisting of a phenyl, a monocyclic heteroaryl, a monocyclic heterocyclyl, a monocyclic cycloalkenyl, and a monocyclic cycloalkyl. Examples of multicyclic heteroaryls include, but are not limited to 5H-[1,2,4]triazino [5,6-b]indol-5-yl, 2,3,4,9-tetrahydro-1H-carbazol-9-yl, 9H-pyrido[3,4-b]indol-9-yl, 9H-carbazol-9-yl, acridin-9-yl, The term "heteroarylalkyl" and "-alkylheteroaryl" as used herein, means a heteroaryl, as defined herein, appended to the parent molecular moiety through an alkyl group, as defined herein. Representative examples of heteroarylalkyl include, but are not limited to, fur-3-ylmethyl, 1H-imidazol-2-ylmethyl, 1H-imidazol-4-ylmethyl, 1-(pyridin-4-yl)ethyl, pyridin-3-ylmethyl, pyridin-4-ylmethyl, pyrimidin-5-ylmethyl, 2-(pyrimidin-2-yl)propyl, thien-2-ylmethyl, and thien-3-ylmethyl.

The term "heterocyclyl" as used herein, means a monocyclic, bicyclic, or multicyclic heterocycle. The monocyclic heterocycle is a 3, 4, 5, 6 or 7 membered ring containing at least one heteroatom independently selected from the group consisting of O, N, and S where the ring is saturated or unsaturated, but not aromatic. The 3 or 4 membered ring contains 1 heteroatom selected from the group consisting of O, N and S. The 5 membered ring can contain zero or one double bond and one, two or three heteroatoms selected from the group consisting of O, N and S. The 6 or 7 membered ring contains zero, one or two double bonds and one, two or three heteroatoms selected from the group consisting of O, N and S. The monocyclic heterocycle is connected to the parent molecular moiety through any carbon atom or any nitrogen atom contained within the monocyclic heterocycle. Representative examples of monocyclic heterocycle include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to either a phenyl, a monocyclic cycloalkyl, a monocyclic cycloalkenyl, a monocyclic heterocycle, or a monocyclic heteroaryl. The bicyclic heterocycle is connected to the parent molecular moiety through any carbon atom or any nitrogen atom contained within the monocyclic heterocycle portion of the bicyclic ring system. Representative examples of bicyclic heterocyclyls include, but are not limited to, 2,3-dihydrobenzofuran-2-yl, 2,3-dihydrobenzofuran-3-yl, indolin-1-yl, indolin-2-yl, indolin-3-yl, 2,3-dihydrobenzothien-2-yl, decahydroquinolinyl, decahydroisoquinolinyl, octahydro-1H-indolyl, and octahydrobenzofuranyl. Heterocyclyl groups are optionally substituted with one or two groups which are independently oxo or thia. In certain embodiments, the bicyclic heterocyclyl is a 5 or 6 membered monocyclic heterocyclyl ring fused to phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the bicyclic heterocyclyl is optionally substituted by one or two groups which are independently oxo or thia. Multicyclic heterocyclyl ring systems are a monocyclic heterocyclyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other rings systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. The multicyclic heterocyclyl is attached to the parent molecular moiety through any carbon atom or nitrogen atom contained within the base ring. In certain embodiments, multicyclic heterocyclyl ring systems are a monocyclic heterocyclyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other rings systems independently selected from the group consisting of a phenyl, a monocyclic heteroaryl, a monocyclic cycloalkyl, a monocyclic cycloalkenyl, and a monocyclic heterocyclyl. Examples of multicyclic heterocyclyl groups include, but are not limited to 10H-phenothiazin-10-yl, 9,10-dihydroacridin-9-yl, 9,10-dihydroacridin-10-yl, 10H-phenoxazin-10-yl, 10,11-dihydro-5H-dibenzo[b,f]azepin-5-yl, 1,2,3,4-tetrahydropyrido[4,3-g]isoquinolin-2-yl, 12H-benzo[b]phenoxazin-12-yl, and dodecahydro-1H-carbazol-9-yl.

The term "nitro" as used herein, means a —NO$_2$ group.

The term "oxo" as used herein means a =O group.

The term "saturated" as used herein means the referenced chemical structure does not contain any multiple carbon-carbon bonds. For example, a saturated cycloalkyl group as defined herein includes cyclohexyl, cyclopropyl, and the like.

The term "thia" as used herein means a =S group.

The term "unsaturated" as used herein means the referenced chemical structure contains at least one multiple carbon-carbon bond, but is not aromatic. For example, a unsaturated cycloalkyl group as defined herein includes cyclohexenyl, cyclopentenyl, cyclohexadienyl, and the like.

As used herein, the phrase "pharmaceutically acceptable salt" refers to both pharmaceutically acceptable acid and base addition salts and solvates. Such pharmaceutically acceptable salts include salts of acids such as hydrochloric, phosphoric, hydrobromic, sulfuric, sulfinic, formic, toluenesulfonic, methanesulfonic, nitric, benzoic, citric, tartaric, maleic, hydroiodic, alkanoic such as acetic, HOOC—(CH$_2$)$_n$—COOH where n is 0-4, and the like. Non-toxic pharmaceutical base addition salts include salts of bases such as sodium, potassium, calcium, ammonium, and the like. Those skilled in the art will recognize a wide variety of non-toxic pharmaceutically acceptable addition salts.

Synthetic Methods

The two exemplary synthetic routes described below can be used to generate derivatives that contain varying substituents at the 1- and 3-positions of the pyrazolopyrimidine core (Schemes 1 and 2). The first series of analogs retain the naphthylmethylene substituent at the 3-position and contain various alkyl groups at the 1-position. Synthesis of these analogs began with conversion of 1-naphthalene acetyl chloride to pyrazolopyrimidine 4 in five steps (Scheme 1). (16)

Scheme 1.

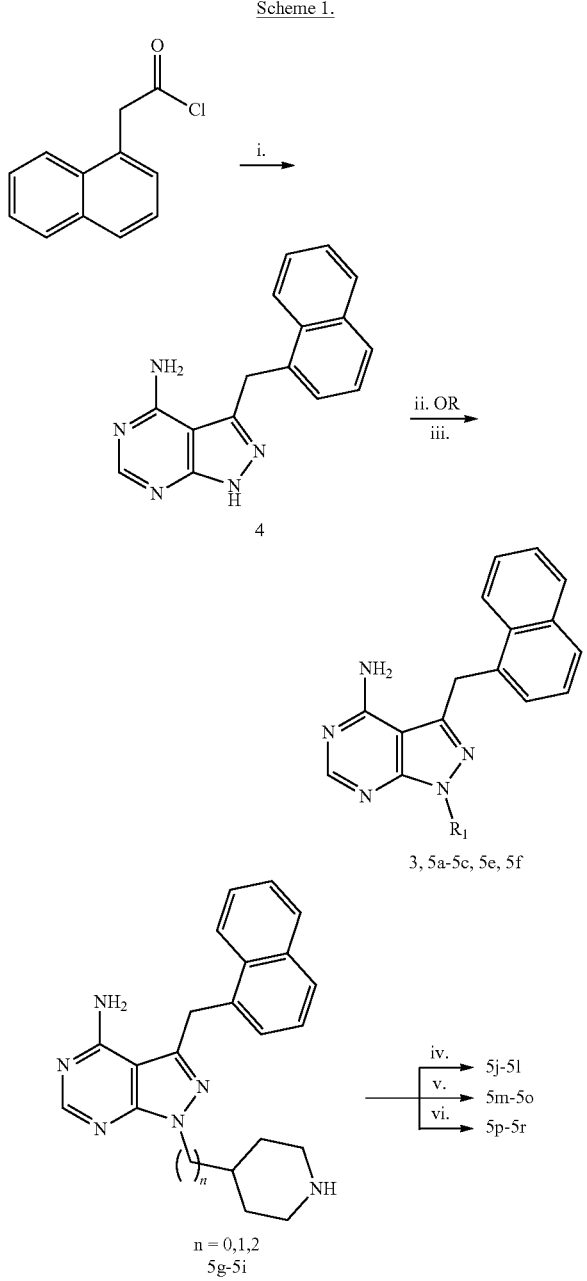

3, 5a-5c, 5e, 5f 5g-5i
n = 0,1,2 i: (a) Malononitrile, NaH, THF; (b) Dimethyl Sulfate, NaHCO$_3$; (c) H$_2$NNH$_2$, EtOH, heat; (d) Formamide, 180° C. ii: R$_2$-Br, K$_2$CO$_3$, DMF iii: (a) R$_2$-OH, PS-PPh$_3$, DEAD, THF; (b) TFA, DCM. iv: Ac$_2$O, DIPEA, DMF v: CH$_3$CHO, NaHB(OAc)$_3$. vi: Methylsulfonyl chloride, DIPEA, DMF.

To introduce various alkyl substituents at the 1-position, 4 can be derivatized with alkyl halides by direct nucleophilic displacement (5a-5e) or with alcohols using standard Mitsunobu reaction conditions (5a-5e). (17,18) Notably, the use of support-bound triphenylphosphine for the Mitsunobu reaction can expedite the purification of alkylated products. (19) The N-Boc protecting groups can be removed from piperidine analogues 5f-5h and the resultant free amines can be acetylated, sulfonylated, or alkylated.

The second series of derivatives can be generated with a synthetic route that allows various substituents to be introduced at the 3-position of the pyrazolopyrimidine core (Scheme 2).

Scheme 2.

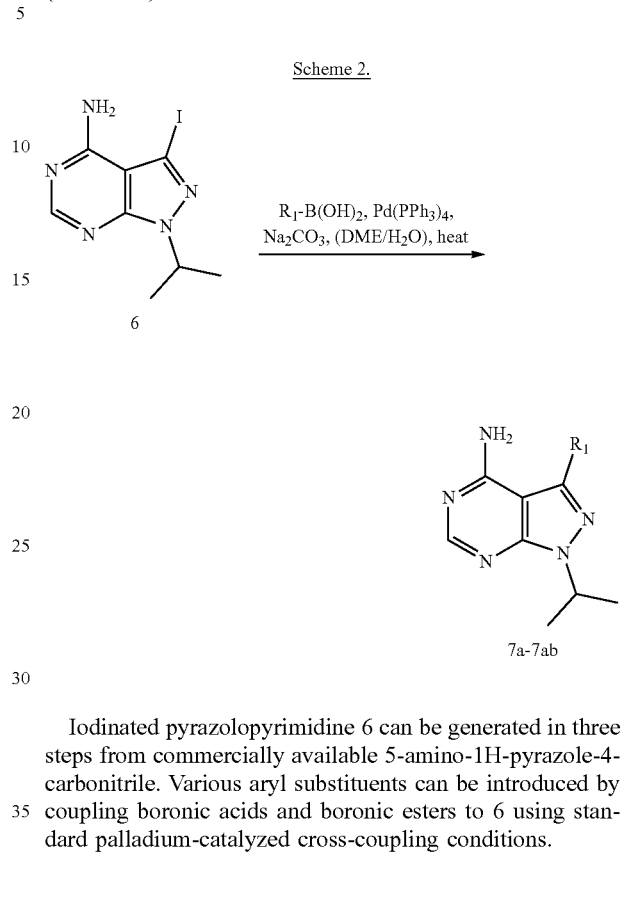

Iodinated pyrazolopyrimidine 6 can be generated in three steps from commercially available 5-amino-1H-pyrazole-4-carbonitrile. Various aryl substituents can be introduced by coupling boronic acids and boronic esters to 6 using standard palladium-catalyzed cross-coupling conditions.

SYNTHETIC EXAMPLES

Commercially available reagents and anhydrous solvents were used without further purification unless otherwise specified. The final purity of all compounds was determined by analytical HPLC with an Agilent ZORBAX SB-C18 column (2.1 mm×150 mm). Analytical HPLC data were generated by injecting 20 μL of sample solution in methanol and acetonitrile to a reverse phase HPLC system run over 30 min (2-100% acetonitrile/water with 0.05% TFA and 2-100% methanol/water with 0.05% TFA). The products were detected by UV at the detection frequency of 254 nm. All compounds were determined to be >95% pure by this method. Flash chromatography was performed on prepacked columns of silica gel (Varian SF10-4g, Si 50) by IntelliFlash with EtOAc/hexanes or MeOH/CH$_2$Cl$_2$ as eluent. The purification by preparative HPLC was performed on Varian Dynamax Microsorb 100-5 C18 column (250 mm×21.4 mm) with CH$_3$CN/H$_2$O or MeOH/H$_2$O and 0.05% TFA as eluent. The mass spectra were recorded with the Bruker Esquire Liquid Chromatograph—Ion Trap Mass Spectrometer. NMR spectra were recorded with either a Bruker 300 MHz spectrometer or Bruker 500 MHz spectrometer at ambient temperature with the residual solvent peaks as internal standards. The chemical shifts are given in ppm (δ) and coupling constants are reported in Hz. $^1$H resonances are referenced to CDCl$_3$ (7.26 ppm), DMSO-d$_6$ (2.54) or CD$_3$OD (3.34).

Example 1 Preparation of Intermediate A

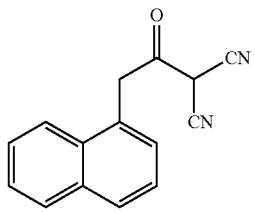 [SMILES: N#CC(C#N)C(=O)Cc1cccc2ccccc12]

To malononitrile (0.646 g, 9.8 mmol) in THF (15 mL) and sodium hydride (0.494 g, 19.5 mmol, 95% dispersion in paraffin oil), 1-naphthyleneacetyl chloride (2.0 g, 9.8 mmol) was added dropwise at 5-10° C. After 3 h, the reaction mixture was warmed to room temperature and hydrochloric acid (45 mL) was added. The mixture was then extracted with ethyl acetate (3×75 mL) and the organic layer was dried over $Na_2SO_4$ to yield A (1.71 g, 75%). $^1$H NMR ($CDCl_3$, 300 MHz) δ 7.96-8.02 (m, 1H), 7.80-7.91 (m, 2H), 7.49-7.59 (m, 2H), 7.41-7.47 (m, 2H), 4.12 (s, 2H), 3.56 (s, 1H).

Example 2 Preparation of Intermediate B

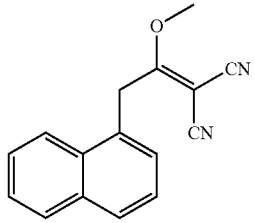 [SMILES: COC(Cc1cccc2ccccc12)=C(C#N)C#N]

To sodium hydrogen carbonate (6.112 g, 72.7 mmol) in 1,4-dioxane (12 mL) and water (2 mL), compound A (2.130 g, 9.1 mmol) and dimethyl sulfate (6.038 mL, 63.6 mmol) were added slowly. After stirring at 85° C. for 2.5 h, water (60 mL) was added. Extraction with tert-butyl methyl ether (4×50 mL), drying of the organic layer with $Na_2SO_4$, and silica gel chromatography using an ethyl acetate-hexanes gradient yielded B (0.964 g, 43%). $^1$H NMR ($CDCl_3$, 300 MHz) δ 8.08-8.13 (m, 1H), 7.99-8.03 (m, 1H), 7.92-7.97 (m, 1H), 7.58-7.70 (m, 2H), 7.49-7.56 (m, 1H), 7.25-7.30 (m, 1H), 4.63 (s, 2H), 3.98 (s, 3H).

Example 3 Preparation of Compound 4

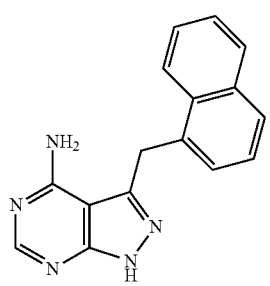 [SMILES: Nc1ncnc2[nH]nc(Cc3cccc4ccccc34)c12]

To compound B (0.908 g, 3.66 mmol) in ethanol (10 mL), hydrazine hydrate (222 μL, 3.66 mmol, 80% hydrazine hydrate) and triethylamine (501 μL, 3.66 mmol) were added. After refluxing for 3.5 h the solvent was evaporated and water was added. The solid was collected and without any further purification, was refluxed in formamide (6 mL) overnight. The cold reaction mixture was diluted with water and the precipitate was collected. This precipitate was redissolved in chloroform and then purified by silica gel chromatography using a methanol-chloroform gradient to yield 4 (456 mg, 45%). 1H NMR (DMSO-$d_6$, 300 MHz) δ 8.37 (s, 1H), 8.05-8.14 (m, 1H), 7.89-7.97 (m, 1H), 7.78-7.86 (m, 1H), 7.38-7.57 (m, 4H), 4.86 (s, 2H).

Example 4 General Procedure A

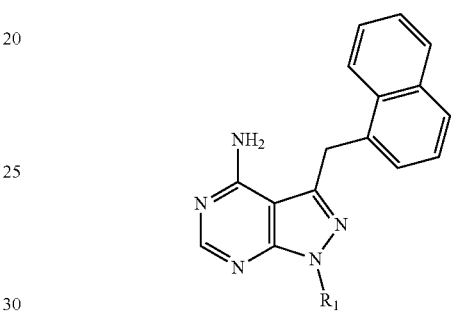

A mixture of 4 (0.073 mmol), $K_2CO_3$ (4.0 equiv), and the appropriate alkyl halide (1.1 equiv) were dissolved in dimethylformamide (400 μL) and acetonitrile (1 mL). The reaction was heated to 5° C. below the boiling point of the alkyl halide overnight. Preparative HPLC with a methanol/water gradient was used to yield the final compound.

Example 5 Preparation of Compound 3

3 was synthesized using isopropyl iodide as the alkyl halide in General Procedure A. $^1$H NMR ($CDCl_3$, 300 MHz) δ 8.04 (s, 1H), 7.98-8.03 (m, 1H), 7.84-7.92 (m, 2H), 7.40-7.56 (m, 3H), 7.30-7.36 (m, 1H), 5.14 (sept, J=6.9, 1H), 4.76 (s, 2H), 1.62 (d, J=6.9, 6H). MS (ESI) (M+H)$^+$=318.4.

Example 6 Preparation of Compound 5a 5a was synthesized using methyl iodide as the alkyl halide in General Procedure A. $^1$H NMR ($CDCl_3$, 300 MHz) δ 8.10 (s, 1H), 7.90-8.02 (m, 3H), 7.46-7.61 (m, 3H), 7.36-7.42 (m, 1H), 4.79 (s, 2H), 4.14 (s, 3H). (M+H)$^+$=290.4.

Example 7 Preparation of Compound 5b 5b was synthesized using propargyl bromide as the alkyl halide in General Procedure A. $^1$H NMR ($CDCl_3$, 300 MHz) δ 8.12 (s, 1H), 7.95-8.00 (m, 1H), 7.87-7.92 (m, 2H), 7.46-7.55 (m, 3H), 7.36-7.40 (m, 1H), 5.24 (m, 2H), 4.79 (s, 2H), 2.48 (m, 1H). MS (ESI) (M+H)$^+$=314.4.

Example 8 Preparation of Compound 5c 5c was synthesized using iodoacetamide as the alkyl halide in General Procedure A. $^1$H NMR ($CD_3OD$, 500 MHz) δ 8.31 (s, 1H), 8.08-8.11 (m, 1H), 7.88-7.92 (s, 1H), 7.81-7.84 (m, 1H), 7.50-7.54 (m, 2H), 7.41-7.46 (m, 1H), 7.26-7.30 (m, 1H), 5.06 (s, 2H), 4.79 (s, 2H). MS (ESI) (M+H)⁺=333.4.

Example 9 Preparation of Compound 5e 5e was synthesized using benzyl bromide as the alkyl halide in General Procedure A. ¹H NMR (CDCl₃, 300 MHz) δ 8.26 (s, 1H), 8.12-8.16 (m, 2H), 7.88-7.94 (m, 2H), 7.74-7.80 (m, 1H), 7.61-7.65 (m, 2H), 7.40 (m, 5H), 5.65 (s, 2H) 4.79 (s, 2H). MS (ESI) (M+H)⁺=366.5.

Example 10 Preparation of Compound 5f 5f was synthesized using cyclohexyl iodide as the alkyl halide in General Procedure A. ¹H NMR (CD₃OD, 300 MHz) δ 8.18-8.23 (m, 1H), 8.16 (s, 1H), 7.88-7.93 (m, 1H), 7.78-7.83 (m, 1H), 7.49-7.54 (m, 2H), 7.36-7.43 (m, 1H), 7.16-7.21 (m, 1H), 4.79 (s, 2H), 4.18-4.24 (m, 1H), 3.66-3.71 (m, 2H), 3.53-3.58 (m, 2H), 1.92-1.99 (m, 2H), 1.35-1.40 (m, 2H), 0.86-0.94 (m, 2H). MS (ESI) (M+H)⁺=358.5.

Example 11 General Procedure B

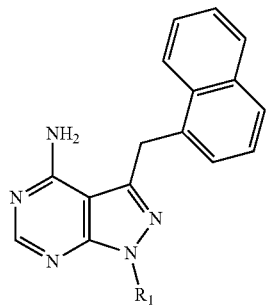

A mixture of 4 (0.073 mmol), polymer-supported triphenylphosphine (2 equiv of 1.52 mmol/g PL-TPP from Varian Polymer Laboratories) and the appropriate alcohol (1.0 equiv) were dissolved in dry THF (1 mL) and stirred under N₂. Diethyl azodicarboxylate (1.5 equiv) was then added at 0° C. After 15 min, the reaction mixture was warmed to room temperature and allowed to run overnight. The resin was filtered off and washed with dicholoromethane, concentrated in vacuo, and purified using reverse-phase preparative HPLC with a methanol/water gradient. The desired product was collected and subsequently deprotected by stirring in a mixture of trifluoroactetic acid (0.5 mL) and dicholoromethane (0.5 mL) for 2 h. The reaction mixture was concentrated in vacuo to yield the final compound.

Example 12 Preparation of Compound 5g 5g was synthesized using N-boc piperidine-4-ol as the alcohol in General Procedure B. ¹H NMR (DMSO-d₆, 300 MHz) δ 8.33 (s, 1H), 8.15-8.20 (m, 1H), 7.91-7.96 (m, 1H), 7.80-7.84 (m, 1H), 7.51-7.57 (m, 2H), 7.37-7.44 (m, 1H), 7.19-7.23 (m, 1H), 4.95 (m, 1H), 4.84 (s, 2H), 3.32-3.41 (m, 2H), 3.05-3.20 (m, 2H), 2.11-2.26 (m, 2H), 1.95-2.05 (m, 2H). MS (ESI) (M+H)⁺=359.4.

Example 13 Preparation of Compound 5h 5h was synthesized using N-boc piperidine-4-methanol as the alcohol in General Procedure B. ¹H NMR (CD₃OD, 500 MHz) δ 8.12 (s, 1H), 8.04-8.09 (m, 1H), 7.93-7.97 (m, 1H), 7.81-7.85 (m, 1H), 7.48-7.52 (m, 2H), 7.40-7.44 (m, 1H), 7.29-7.32 (m, 1H), 4.75 (s, 2H), 4.16 (d, J=7.0, 2H), 2.83-2.90 (m, 2H), 2.17-2.24 (m, 1H), 1.70-1.76 (m, 2H), 1.36-1.47 (m, 2H), 0.84-0.97 (m, 2H). MS (ESI) (M+H)⁺=373.5.

Example 14 Preparation of Compound 5i 5i was synthesized using N-boc piperidine-4-ethanol as the alcohol in General Procedure B. ¹H NMR (CD₃OD, 300 MHz) δ 8.25 (s, 1H), 7.98-8.02 (m, 1H), 7.86-7.90 (m, 1H), 7.78-7.82 (m, 1H), 7.44-7.49 (m, 2H), 7.38-7.42 (m, 1H), 7.28-7.32 (m, 1H), 4.81 (s, 2H), 4.30-4.35 (m, 2H), 3.57-3.62 (m, 2H), 2.50-2.61 (m, 2H), 1.90-2.01 (m, 2H), 1.75-1.85 (m, 5H). MS (ESI) (M+H)⁺=387.5.

Example 15 General Procedure C

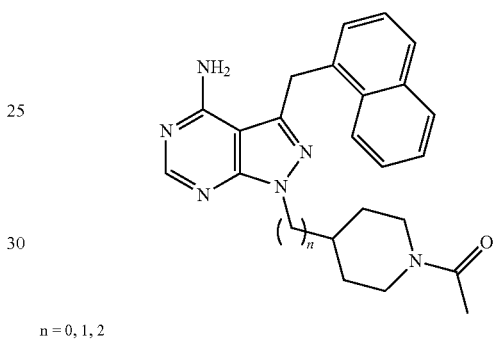

n = 0, 1, 2

Acetic anhydride (1 equiv) and diisopropylethylamine (3 equiv) were added to compounds 5g-5i (0.028 mmol) and dissolved in dimethylformamide (200 μL). The reaction was allowed to stir at room temperature overnight. The reaction mixture was diluted with methanol and water and purified using reverse-phase preparative HPLC with a methanol/water gradient.

Example 16 Preparation of Compound 5j 5j was synthesized using 5g in General Procedure C. ¹H NMR (CDCl₃, 300 MHz) δ 8.09 (s, 1H), 7.88-8.00 (m, 3H), 7.44-7.58 (m, 3H), 7.34-7.39 (m, 1H), 4.95-5.05 (m, 1H), 4.81-4.90 (m, 1H), 4.76 (s, 2H), 4.04-4.13 (m, 1H), 3.29-3.41 (m, 1H), 2.81-2.91 (m, 1H), 2.06-2.40 (m, 7H). MS (ESI) (M+H)⁺=401.5.

Example 17 Preparation of Compound 5k 5k was synthesized using 5h in General Procedure C. ¹H NMR (CD₃OD, 300 MHz) δ 8.25 (s, 1H), 8.04-8.10 (m, 1H), 7.88-7.93 (m, 1H), 7.81-7.85 (m, 1H), 7.47-7.52 (m, 2H), 7.39-7.45 (m, 1H), 7.29-7.33 (m, 1H), 4.78 (s, 2H), 4.38-4.46 (m, 1H), 4.24 (d, J=6.9, 2H), 3.79-3.87 (m, 1H), 2.95-3.05 (m, 1H), 2.45-2.58 (m, 1H), 2.10-2.20 (m, 1H), 2.05 (s, 3H), 1.46-1.60 (m, 2H), 1.32-1.40 (m, 2H). MS (ESI) (M+H)⁺=415.5.

Example 18 Preparation of Compound 5l 5l was synthesized using 5i in General Procedure C. ¹H NMR (CD₃OD, 300 MHz) δ 8.26 (s, 1H), 8.05-8.11 (m, 1H), 7.89-7.94 (m, 1H), 7.82-7.86 (m, 1H), 7.48-7.54 (m, 2H), 7.41-7.46 (m, 1H), 7.30-7.34 (m, 1H), 4.82 (s, 2H), 4.33-4.40 (m, 2H), 3.72-3.77 (m, 1H), 3.43-3.49 (m, 1H), 2.71-2.79 (m, 1H), 2.26-2.33 (m, 1H), 2.04 (s, 3H), 1.72-1.79 (m, 2H), 1.60-1.70 (m, 2H), 1.32-1.42 (m, 3H). MS (ESI) $(M+H)^+$=429.5.

Example 19 General Procedure D

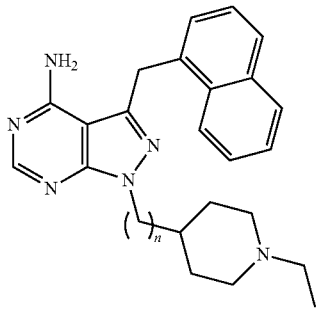

n = 0, 1, 2

Acetaldehyde (10 equiv), sodium triacetoxyborohydride (3 equiv), diisopropylethylamine (0.75 equiv), and a catalytic amount of acetic acid were added to 5g-5i (0.028 mmol) and dissolved in dichloroethane (200 μL). The reaction was allowed to stir at room temperature overnight. The reaction mixture was diluted with methanol and water and purified using reverse-phase preparative HPLC with a methanol/water gradient.

Example 20 Preparation of Compound 5m 5m was synthesized using 5g in General Procedure D. $^1$H NMR (CD$_3$OD, 300 MHz) δ 8.22 (s, 1H), 8.08-8.14 (m, 1H), 7.87-7.92 (m, 1H), 7.80-7.85 (m, 1H), 7.49-7.54 (m, 2H), 7.42-7.47 (m, 1H), 7.31-7.35 (m, 1H), 4.89-4.96 (m, 1H), 4.80 (s, 2H), 4.32-4.38 (m, 2H), 3.52-3.58 (m, 2H), 2.99-3.10 (m, 2H), 1.87-1.95 (m, 2H), 1.73-1.80 (m, 2H), 1.28-144 (m, 3H). MS (ESI) $(M+H)^+$=387.5.

Example 21 Preparation of Compound 5n 5n was synthesized using 5h in General Procedure D. $^1$H NMR (CD$_3$OD, 300 MHz) δ 8.22 (s, 1H), 8.08-8.14 (m, 1H), 7.89-7.93 (m, 1H), 7.81-7.85 (m, 1H), 7.48-7.54 (m, 2H), 7.39-7.45 (m, 1H), 7.28-7.33 (m, 1H), 4.78 (s, 2H), 4.23-4.27 (m, 2H), 3.64-3.69 (m, 2H), 3.10-3.19 (m, 2H), 2.80-2.87 (m, 1H), 2.17-2.24 (m, 2H), 1.78-1.84 (m, 2H), 1.57-1.66 (m, 2H), 1.28-1.42 (m, 3H). MS (ESI) $(M+H)^+$=401.5.

Example 22 Preparation of Compound 5o 5o was synthesized using 5i in General Procedure D. $^1$H NMR (CD$_3$OD, 300 MHz) δ 8.26 (s, 1H), 8.03-8.09 (m, 1H), 7.88-7.94 (m, 1H), 7.81-7.86 (m, 1H), 7.48-7.54 (m, 2H), 7.40-7.46 (m, 1H), 7.29-7.34 (m, 1H), 4.76 (s, 2H), 4.33-4.41 (m, 2H), 3.66-3.72 (m, 1H), 3.53-3.60 (m, 2H), 3.30-3.38 (m, 2H), 3.02-3.10 (m, 2H), 2.39-2.51 (m, 2H), 1.86-1.97 (m, 2H), 1.73-1.82 (m, 2H), 1.28-1.42 (m, 3H). MS (ESI) $(M+H)^+$=415.6.

Example 23 General Procedure E

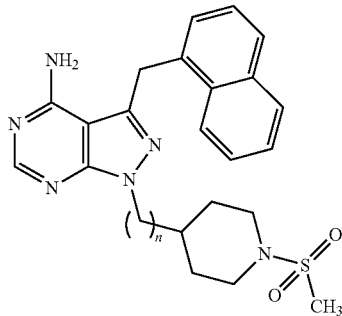

n = 0, 1, 2

Methylsulfonyl chloride (1.0 equiv) and diisopropylethylamine (3.0 equiv) were added to 5g-5i (0.028 mmol) and dissolved in dimethylformamide (200 μL). The reaction was allowed to stir at room temperature overnight. The reaction mixture was diluted with methanol and water and purified using reverse-phase preparative HPLC with a methanol/water gradient.

Example 24 Preparation of Compound 5g 5p was synthesized using 5g in General Procedure E. $^1$H NMR (CDCl$_3$, 300 MHz) δ 8.30 (s, 1H), 8.08-8.14 (m, 1H), 7.87-7.92 (m, 1H), 7.80-7.85 (m, 1H), 7.46-7.54 (m, 2H), 7.39-7.45 (m, 1H), 7.25-7.30 (m, 1H), 4.89-4.96 (m, 1H), 4.80 (s, 2H), 3.64-3.73 (m, 2H), 2.94-3.05 (m, 2H), 2.76 (s, 3H), 2.13-2.28 (m, 2H), 2.00-2.10 (m, 2H). MS (ESI) $(M+H)^+$=437.6.

Example 25 Preparation of Compound 5q 5q was synthesized using 5h in General Procedure E. $^1$H NMR (CD$_3$OD, 300 MHz) δ 8.26 (s, 1H), 8.04-8.11 (m, 1H), 7.88-7.94 (m, 1H), 7.80-7.86 (m, 1H), 7.48-7.54 (m, 2H), 7.39-7.45 (m, 1H), 7.29-7.35 (m, 1H), 4.78 (s, 2H), 4.26 (d, J=6.9, 2H), 3.59-3.69 (m, 2H), 2.78 (s, 3H), 2.57-2.68 (m, 2H), 1.98-2.06 (m, 1H), 1.55-1.63 (m, 2H), 1.34-1.40 (m, 2H). MS (ESI) $(M+H)^+$=451.6.

Example 26 Preparation of Compound 5r 5r was synthesized using 5i in General Procedure E. $^1$H NMR (CD$_3$OD, 300 MHz) δ 8.26 (s, 1H), 8.03-8.09 (m, 1H), 7.88-7.94 (m, 1H), 7.81-7.86 (m, 1H), 7.48-7.54 (m, 2H), 7.40-7.46 (m, 1H), 7.29-7.34 (m, 1H), 4.76 (s, 2H), 4.34-4.41 (t, J=6.9, 2H), 3.50-3.59 (m, 2H), 2.76 (s, 3H), 2.31-2.43 (m, 2H), 1.66-1.81 (m, 4H), 1.35-1.40 (m, 1H), 1.10-1.17 (m, 2H). MS (ESI) $(M+H)^+$=465.6.

Example 27 Preparation of Compound 5d

To compound B (0.107 g, 0.43 mmol) in ethanol (2 mL), t-butyl hydrazine hydrochloride (0.054 g, 0.43 mmol) and triethylamine (59 μL, 0.43 mmol) were added. After refluxing for 3.5 h, the solvent was evaporated and water was added. The solid was collected and then refluxed in formamide (6 mL) overnight. The cold reaction mixture was diluted with water and the precipitate was collected. This precipitate was re-dissolved in chloroform and then purified by silica gel chromatography using a methanol-chloroform gradient to yield 5d (0.025 g, 18%). $^1$H NMR (DMSO-d$_6$, 300 MHz) δ 8.24-8.32 (m, 2H), 7.93 (m, 1H), 7.81 (m, 1H), 7.52-7.58 (m, 2H), 7.39 (m, 1H), 7.13 (m, 1H), 4.81 (s, 2H), 1.66 (s, 9H). MS (ESI) (M+H)$^+$=332.4.

Example 28 Preparation of Intermediate C

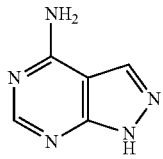

Commercially available 5-amino-1H-pyrazole-4-carbonitrile (2.0 g, 18.5 mmol) was mixed with formamide (10 mL) and heated to 180° C. overnight under nitrogen. The solution was cooled to rt, 60 mL of water was added, and the resulting precipitate was collected by vacuum filtration to yield C (2.367 g, 95%). $^1$H NMR (DMSO-d$_6$, 300 MHz) δ 8.13 (s, 1H), 8.06 (s, 1H).

Example 29 Preparation of Intermediate D

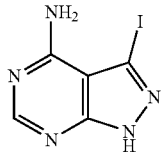

Compound C (2.367 g, 17.5 mmol) and N-iodosuccinimide (4.810 g, 21.4 mmol) were added to dimethylformamide (60 mL) and stirred at 50° C. for 24 hours. Another batch of N-iodosuccinimide (0.871 g, 3.8 mmol) was added to the reaction mixture and was allowed to stir for an additional 24 hours. The reaction mixture was cooled to room temperature and water (100 mL) was added, forming a precipitate that was collected by filtration to yield D (4.1 g, 89%). $^1$H NMR (DMSO-d$_6$, 300 MHz) δ 8.18 (s, 1H).

Example 30 Preparation of Compound 6

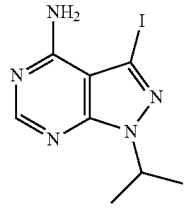

A mixture of D (1.0 g, 3.8 mmol), K$_2$CO$_3$ (2.135 g, 15.4 mmol), and isopropyl iodide (421 μL, 4.2 mmol) were dissolved in dimethylformamide (7.5 mL). The reaction was heated to 80° C. and left to run overnight. An extraction with saturated sodium acetate and ethyl acetate was performed. The organic layer was dried with sodium sulfate and concentrated in vacuo. The crude product was purified using silica gel chromatography with a methanol/dichloromethane gradient to yield 6 (673 mg, 58%). $^1$H NMR (DMSO-d$_6$, 300 MHz) δ 8.19 (s, 1H), 4.93-5.03 (m, 1H), 1.43 (d, J=6.9, 6H).

Example 31 General Procedure F

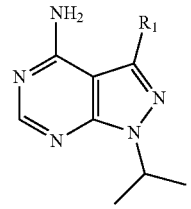

Compound 6 (1 equiv), tetrakis(triphenylphosphine) palladium(0) (0.05 equiv), and sodium carbonate (2.3 equiv) were added to the appropriate boronic acid or pinacol ester (1.1 equiv) in dimethoxyethane (1 mL) and water (0.5 mL). The reaction was performed in a microwave at 85° C. for one hour, followed by extraction with ethyl acetate and water. The organic layer was collected and concentrated in vacuo to yield the crude product. The crude product was then purified via flash chromatography with an ethyl acetate/hexanes gradient.

Example 32 Preparation of Compound 7a 7a was synthesized using 4-chlorophenylboronic acid in General Procedure F. $^1$H NMR (CDCl$_3$, 300 MHz) δ 8.32 (s, 1H), 7.57 (m, 4H), 5.19 (sep, J=6.8, 1H), 1.61 (d, J=6.8, 6H). MS (ESI) (M+H)$^+$=288.8.

Example 33 Preparation of Compound 7b 7b was synthesized using 3-chlorophenylboronic acid in General Procedure F. $^1$H NMR (CDCl$_3$, 300 MHz) δ 8.40 (s, 1H), 7.76 (s, 1H), 7.60 (m, 1H), 7.46-7.50 (m, 2H), 5.21 (sep, J=6.7, 1H), 1.62 (d, J=6.7, 6H). MS (ESI) (M+H)$^+$=288.8.

Example 34 Preparation of Compound 7c 7c was synthesized using 3,4-dichlorophenylboronic acid in General Procedure F. $^1$H NMR (CDCl$_3$, 300 MHz) δ 8.41 (s, 1H), 7.86 (s, 1H), 7.56-7.66 (m, 2H), 5.21 (sep, J=6.7, 1H), 1.61 (d, J=6.6, 6H). MS (ESI) (M+H)$^+$=323.3.

Example 35 Preparation of Compound 7d 7d was synthesized using 4-isopropylphenylboronic acid in General Procedure F. $^1$H NMR (CDCl$_3$, 300 MHz) δ 8.38 (s, 1H), 7.64 (d, J=8.0, 2H), 7.41 (d, J=8.0, 2H), 5.20 (sep, J=6.8, 1H), 3.01 (sep, J=6.8, 1H), 1.61 (d, J=6.6, 6H), 1.32 (d, J=6.9, 6H). MS (ESI) (M+H)$^+$=296.4.

Example 36 Preparation of Compound 7e 7e was synthesized using 3-isopropylphenylboronic acid in General Procedure F. $^1$H NMR (CDCl$_3$, 300 MHz) δ 8.38 (s, 1H), 7.38-7.68 (m, 4H), 5.20 (sep, J=6.8, 1H), 3.01 (sep, J=6.8, 1H), 1.62 (d, J=6.8, 6H), 1.32 (d, J=6.8, 6H). MS (ESI) (M+H)$^+$=296.4.

Example 37 Preparation of Compound 7f 7f was synthesized using 4-methylphenylboronic acid in General Procedure F. $^1$H NMR (CDCl$_3$, 300 MHz) δ 8.33 (s, 1H), 7.59 (d, J=7.7, 2H), 7.36 (d, J=7.7, 2H), 5.20 (sep, J=6.8, 1H), 2.46 (s, 3H), 1.62 (d, J=6.8, 6H). MS (ESI) (M+H)⁺=268.4.

Example 38 Preparation of Compound 7g 7g was synthesized using 3-methylphenylboronic acid in General Procedure F. ¹H NMR (CDCl₃, 300 MHz) δ 8.37 (s, 1H), 7.59 (m, 3H), 7.31 (s, 1H), 5.16 (sep, J=6.8, 1H), 2.43 (s, 3H), 1.61 (d, J=6.6, 6H). MS (ESI) (M+H)⁺=268.4.

Example 39 Preparation of Compound 7h 7h was synthesized using 3,4-dimethylphenylboronic acid in General Procedure F. ¹H NMR (CDCl₃, 300 MHz) δ 8.37 (s, 1H), 7.50 (m, 2H), 7.31 (s, 1H), 5.19 (sep, J=6.6, 1H), 2.37 (s, 3H), 2.35 (s, 3H), 1.61 (d, J=6.6, 6H). MS (ESI) (M+H)⁺=282.4.

Example 40 Preparation of Compound 7i 7i was synthesized using 4-fluoro-3-methylphenylboronic acid in General Procedure F. ¹H NMR (CDCl₃, 300 MHz) δ 8.38 (s, 1H), 7.45-7.58 (m, 2H), 7.15 (m, 1H), 5.19 (sep, J=6.8, 1H), 2.39 (s, 3H), 1.61 (d, J=6.7, 6H). MS (ESI) (M+H)⁺=286.4.

Example 41 Preparation of Compound 7j 7j was synthesized using 4-methoxyphenylboronic acid in General Procedure F. ¹H NMR (CDCl₃, 300 MHz) δ 8.37 (s, 1H), 7.59 (m, 2H), 7.08 (m, 2H), 5.19 (sept, J=6.8, 1H), 3.90 (s, 3H), 1.61 (d, J=6.8, 6H). MS (ESI) (M+H)⁺=284.4.

Example 42 Preparation of Compound 7k 7k was synthesized using 3,4-dimethoxyphenylboronic acid in General Procedure F. ¹H NMR (CDCl₃, 300 MHz) δ 8.38 (s, 1H), 7.21-7.27 (m, 2H), 7.02-7.06 (m, 1H), 5.19 (sep, J=6.9, 1H), 3.97 (m, 6H), 1.62 (d, J=6.9, 6H). MS (ESI) (M+H)⁺=314.4.

Example 43 Preparation of Compound 7l 7l was synthesized using 3,4,5-trimethoxyphenylboronic acid in General Procedure F. ¹H NMR (CDCl₃, 300 MHz) δ 8.39 (s, 1H), 6.91 (s, 2H), 5.22 (sep, J=6.9, 1H), 3.95 (s, 6H), 3.92 (s, 3H), 1.62 (d, J=6.9, 6H). MS (ESI) (M+H)⁺=344.5.

Example 44 Preparation of Compound 7m 7m was synthesized using 4-methoxy-3-methylphenylboronic acid in General Procedure F. ¹H NMR (CDCl₃, 300 MHz) δ 8.37 (s, 1H), 7.49 (m, 2H), 6.99 (m, 1H), 5.19 (sep, J=6.7, 1H), 3.91 (s, 3H), 2.32 (s, 3H), 1.61 (d, J=6.7, 6H). MS (ESI) (M+H)⁺=298.4.

Example 45 Preparation of Compound 7n 7n was synthesized using 3-acetylphenylboronic acid in General Procedure F. ¹H NMR (CDCl₃, 300 MHz) δ 8.41 (s, 1H), 8.32 (s, 1H), 8.08 (d, J=8.2, 1H), 7.95 (d, J=8.2, 1H), 7.67 (m, 1H), 5.23 (sep, J=6.8, 1H), 2.70 (s, 3H), 1.63 (d, J=6.6, 6H). MS (ESI) (M+H)⁺=296.4.

Example 46 Preparation of Compound 7o 7o was synthesized using naphthalene-1-boronic acid in General Procedure F. ¹H NMR (DMSO-d₆, 300 MHz δ 8.30 (s, 1H), 8.03-8.11 (m, 2H), 7.85-7.90 (m, 1H), 7.50-7.69 (m, 4H), 5.13 (septet, J=6.8, 1H), 1.53 (d, J=6.8, 6H). MS (ESI) (M+H)⁺=304.4.

Example 47 Preparation of Compound 7p 7p was synthesized using naphthalene-2-boronic acid in General Procedure F. ¹H NMR (CDCl₃, 300 MHz) δ 8.42 (s, 1H), 8.19 (s, 1H), 7.84-8.04 (m, 4H), 7.56-7.62 (m, 2H), 5.25 (septet, J=6.7, 1H), 1.66 (d, J=6.7, 6H). MS (ESI) (M+H)⁺=304.4.

Example 48 Preparation of Compound 7q 7q was synthesized using 6-methoxynaphthalene-2-boronic acid in General Procedure F. ¹H NMR (300 MHz, CDCl₃) δ 8.27 (s, 1H), 8.10 (s, 1H), 7.77-7.94 (m, 2H), 7.64-7.73 (m, 2H), 7.21 (s, 1H), 5.23 (septet, J=6.9, 1H), 3.98 (s, 3H), 1.65 (d, J=6.9, 6H). MS (ESI) (M+H)⁺=334.4.

Example 49 Preparation of Compound 7r 7r was synthesized using 6-ethoxynaphthalene-2-boronic acid in General Procedure F. ¹H NMR (CDCl₃, 300 MHz) δ 8.39 (s, 1H), 8.10 (s, 1H), 7.76-7.92 (m, 3H), 7.19-7.23 (m, 2H), 5.23 (sep, J=6.6, 1H), 4.21 (q, J=6.9, 2H), 1.61 (d, J=6.6, 6H), 1.52 (t, J=6.9, 3H). MS (ESI) (M+H)⁺=348.4.

Example 50 Preparation of Compound 7s 7s was synthesized using 2-methoxynapthalene-3-boronic acid in General Procedure F. ¹H NMR (CDCl₃, 300 MHz) δ 8.38 (s, 1H), 8.03 (s, 1H), 7.80-7.89 (m, 2H), 7.50-7.57 (m, 2H), 7.40-7.46 (m, 1H), 5.23 (sep, J=6.8, 1H), 3.98 (s, 3H), 1.66 (d, J=6.8, 6H). MS (ESI) (M+H)⁺=334.4.

Example 51 Preparation of Compound 7t 7t was synthesized using quinoline-3-boronic acid in General Procedure F. ¹H NMR (CDCl₃, 300 MHz) δ 9.27 (s, 1H), 8.46 (m, 1H), 8.38 (s, 1H), 8.17 (d, J=8.4, 1H), 7.91 (d, J=8.4, 1H), 7.77 (m, 1H), 7.62 (m, 1H), 5.22 (sep, J=6.9, 1H), 1.61 (d, J=6.9, 6H). MS (ESI) (M+H)⁺=305.4.

Example 52 Preparation of Compound 7u 7u was synthesized using 3,4-methylenedioxyphenylboronic acid in General Procedure F. ¹H NMR (CDCl₃, 300 MHz) δ 8.37 (s, 1H), 7.14-7.21 (m, 2H), 6.95-7.00 (m, 1H), 6.06 (s, 2H), 5.18 (sep, J=6.7, 1H), 1.61 (d, J=6.7, 6H). MS (ESI) (M+H)⁺=298.4.

Example 53 Preparation of Compound 7v 7v was synthesized using 1,4-benzodioxane-6-boronic acid in General Procedure F. ¹H NMR (CDCl₃, 500 MHz) δ 8.30 (s, 1H), 7.18 (s, 1H), 7.06-7.14 (m, 2H), 5.20 (sep, J=6.7, 1H), 4.36 (s, 4H), 1.63 (d, J=6.7, 6H). MS (ESI) (M+H)⁺=312.4.

Example 54 Preparation of Compound 7w 7w was synthesized using 3,4-dihydrochromen-6-ylboronic acid in General Procedure F. ¹H NMR (CDCl₃, 300 MHz) δ 8.35 (s, 1H), 7.35-7.41 (m, 2H), 6.92-6.98 (m, 1H), 5.18 (sep, J=6.7, 1H), 4.27 (t, J=5.2, 2H), 2.89 (t, J=5.2, 2H), 2.03-2.12 (m, 2H), 1.61 (d, J=6.7, 6H). MS (ESI) (M+H)$^+$=310.4.

Example 55 Preparation of Compound 7x 7x was synthesized using dibenzo[b,d]thiophen-4-ylboronic acid in General Procedure F. $^1$H NMR (CDCl$_3$, 500 MHz) δ 8.47 (s, 1H), 8.27 (s, 1H), 7.72 (d, J=7.6, 1H), 7.66 (d, J=7.6, 1H), 7.54 (s, 1H), 7.47 (t, J=7.6, 1H), 7.39 (t, J=7.6, 1H), 5.24 (sep, J=6.8, 1H), 1.65 (d, J=6.8, 6H). MS (ESI) (M+H)$^+$=360.5.

Example 56 Preparation of Compound 7y 7y was synthesized using 3-Benzylphenylboronic acid pinacol ester in General Procedure F. $^1$H NMR (CDCl$_3$, 300 MHz) δ 8.35 (s, 1H), 7.56 (m, 1H), 7.42-7.52 (m, 2H), 7.29-7.37 (m, 3H), 7.16-7.27 (m, 3H), 5.19 (sep, J=6.7, 1H), 4.08 (s, 2H), 1.61 (d, J=6.7, 6H). (ESI) (M+H)$^+$=344.4.

Example 57 Preparation of Compound 7z 7z was synthesized using 3-Biphenylboronic acid in General Procedure F. $^1$H NMR (CDCl$_3$, 300 MHz) δ 8.40 (s, 1H), 7.94 (s, 1H), 7.61-7.75 (m, 5H), 7.40-7.53 (m, 3H), 5.22 (sep, J=6.8, 1H), 1.64 (d, J=6.8, 6H). MS (ESI) (M+H)$^+$=330.4.

Example 58 Preparation of Compound 7aa

7aa was synthesized using 3-Benzyloxyphenylboronic acid in General Procedure F. $^1$H NMR (300 MHz, CDCl$_3$) δ 8.40 (s, 1H), 8.10 (s, 1H), 7.37-7.55 (m, 5H), 7.15-7.26 (m, 3H), 5.14-5.27 (m, 3H), 1.64 (d, J=6.8, 6H). MS (ESI) (M+H)$^+$=360.5.

Example 59 Preparation of Compound 7ab

7ab was synthesized using 3-Methylthiophenylboronic acid in General Procedure F. $^1$H NMR (CDCl$_3$, 300 MHz) δ 8.38 (s, 1H), 7.56 (s, 1H), 7.36-7.50 (m, 3H), 5.21 (sep, J=6.7, 1H), 2.56 (s, 3H), 1.63 (d, J=6.7, 6H). MS (ESI) (M+H)$^+$=300.4.

Example 60 General Procedure G (Compounds 1 and 2)

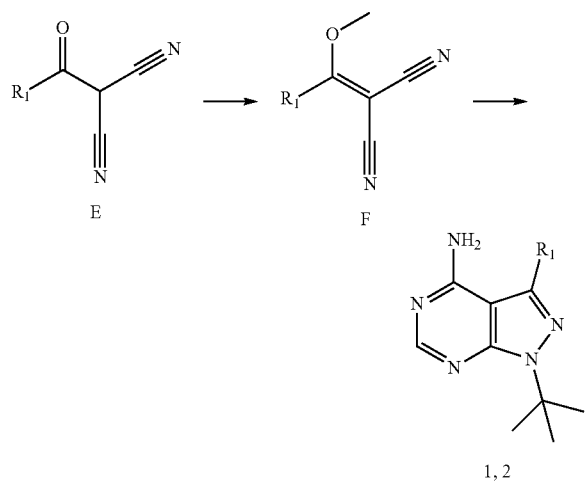

Intermediates E: To malononitrile (1.0 equiv) in THF (15 mL) and sodium hydride (2.0 equiv, 95% dispersion in paraffin oil), the appropriate acyl chloride (1.0 equiv) was added dropwise at 5-10° C. After 3 hours, the reaction mixture was warmed to room temperature and hydrochloric acid (45 mL) was added. The mixture was extracted with ethyl acetate (3×75 mL) and the organic layer was dried over Na2SO4 to yield intermediate E.

Intermediates F: To sodium hydrogen carbonate (8.0 equiv) in 1,4-dioxane (12 mL) and water (2 mL), compound E (1.0 equiv) and dimethyl sulfate (7.0 equiv) were added slowly. After stirring at 85° C. for 2.5 h, water (60 mL) was added. Extraction with tert-butyl methyl ether (4×50 mL), drying of the organic layer with Na2SO4, and silica gel chromatography using an ethyl acetate/hexanes gradient yielded intermediate F.

Compounds 1 and 2: To compound F (1.0 equiv) in ethanol (2 mL), t-butyl hydrazine hydrochloride (1.0 equiv) and triethylamine (1.0 equiv) were added. After refluxing for 3.5 h, the solvent was evaporated and water was added. The solid was collected and then refluxed in formamide (6 mL) overnight. The cold reaction mixture was diluted with water and the precipitate was collected. This precipitate was re-dissolved in chloroform and then purified by silica gel chromatography using a methanol-chloroform gradient to yield final compound.

1 was synthesized using 1-naphthoyl chloride as the acyl chloride in General Procedure G. $^1$H NMR (CDCl$_3$, 300 MHz) δ 8.25 (s, 1H), 7.97-8.10 (m, 2H), 7.77-7.85 (m, 1H), 7.55-7.67 (m, 4H), 1.91 (s, 9H). MS (ESI) (M+H)$^+$=318.4.

2 was synthesized using 2-naphthoyl chloride as the acyl chloride in General Procedure G. $^1$H NMR (DMSO-d$_6$, 300 MHz) δ 8.33 (s, 1H), 8.19 (s, 1H), 7.98-8.10 (m, 3H), 7.78-7.83 (m, 1H), 7.57-7.62 (m, 2H), 1.79 (s, 9H). MS (ESI) (M+H)$^+$=318.4.

Example 61 Preparation of Intermediate G

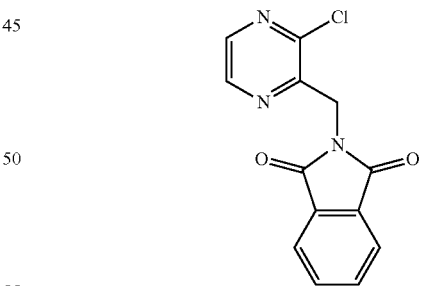

Phthalimide (354 mg, 2.35 mmol), 3-chloropyrazin-2-yl methanol (284 mg, 1.96 mmol), and resin bound triphenylphosphine (1.55 g, 2.35 mmol) were added to anhydrous THF. To this reaction mixture, DIAD (507 mg, 2.35 mmol) was added dropwise. After 12 h the reaction mixture was concentrated. The crude product was purified using silica gel chromatography with a hexane/dichloromethane gradient to yield Intermediate G (300 mg, 56% yield). $^1$H-NMR (300 MHz, CDCl$_3$) δ 5.17 (s, 2H), 7.77-7.83 (m, 2H), 7.87-7.97 (m, 2H), 8.29-8.34 (m, 2H). MS (ESI) (M+H)$^+$274.2.

Example 62 Preparation of Intermediate H

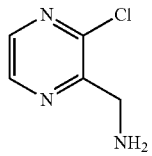

Anhydrous hydrazine (0.05 mL, 1.37 mmol) was added to a solution of Intermediate G (150 mg, 0.5 mmol) in 3.0 mL of dichloromethane at rt under an inert atmosphere. After 2.5 h, 4.5 mL of MeOH was added and the reaction mixture was stirred at reflux for 19 h. The reaction mixture was cooled to rt and the white precipitate that formed was filtered off. The precipitate was washed with ether (3×) and the filtrate was concentrated in vacuo. The resultant solid was re-dissolved in EtOAc and filtered again. The solution was concentrated to afford 77 mg (97% yield) of pure product. $^1$H-NMR (300 MHz, MeOD) δ 4.08 (s, 2H), 8.34 (d, 1H, J=2.7 Hz), 8.58 (d, 1H, J=2.7 Hz). MS (ESI) (M+H)$^+$143.9.

Example 63 Intermediate I

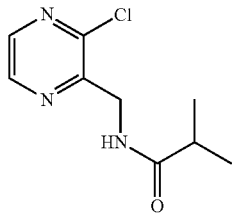

Intermediate H (26 mg, 0.19 mmol), isobutyric acid (0.02 mL, 0.2 mmol), EDCI (50 mg, 0.25 mmol), DIEA (0.1 mL, 0.5 mmol), and DMAP (5.7 mg, 0.038 mmol) were dissolved in 2.0 mL of dichloromethane. The reaction mixture was stirred at rt overnight and then concentrated in vacuo. The resultant residue was dissolved in EtOAc, washed with water (2×), NaHCO$_3$(1×), and brine (1×). The organic layer was dried over Na$_2$SO$_4$, and concentrated in vacuo to afford 37 mg (93% yield) of pure Intermediate I. $^1$H-NMR (300 MHz, CDCl$_3$) δ 1.21-1.26 (m, 6H), 2.46-2.59 (m, 1H), 4.69 (d, 2H, J=4.5 Hz), 8.32-8.34 (m, 1H), 8.46 (d, 1H, J=2.4 Hz).

Example 64 Intermediate J

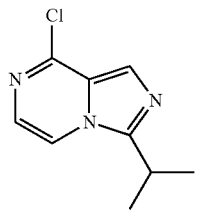

POCl$_3$ (0.08 ml, 0.90 mmol) was added to Intermediate I (37 mg, 0.18 mmol) dissolved in 0.78 mL of acetonitrile. A drop of DMF was added and the reaction mixture was stirred at 55° C. for 30 minutes. The reaction mixture was then concentrated in vacuo and the resultant solid was dissolved in 2 M ammonia in methanol followed by concentrating this solution in vacuo. The resultant solid was dissolved in a minimal amount of water and the product was extracted into dichloromethane (4×). The organic layers were combined and washed with saturated NaHCO$_3$, (1×), concentrated in vacuo, and dried over Na$_2$SO$_4$. Concentration of the solution afforded 33 mg (98% yield) of Intermediate J. $^1$H-NMR (300 MHz, CDCl$_3$) δ 1.46 (d, 6H, J=6.9 Hz), 3.29-3.38 (m, 1H), 7.33 (d, 1H, J=4.8 Hz), 7.61 (d, 1H, J=5.1 Hz), 7.82 (s, 1H). MS (ESI) (M+H)$^+$196.

Example 65 Intermediate K

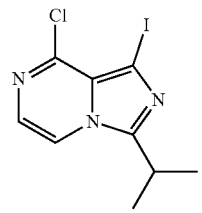

Intermediate J (33 mg, 0.17 mmol) dissolved in 0.18 mL of DMF was added to NIS (39 mg, 0.17 mmol) dissolved in 0.6 mL of DMF. The reaction mixture was heated to 60° C. for 3 h and then cooled to room temperature. The reaction mixture was partitioned between 1 M Na$_2$SO$_3$ and dichloromethane. The aqueous layer was then extracted with dichloromethane (3×). The organic layers were combined, dried over Na$_2$SO$_4$ and concentrated in vacuo to afford 34 mg (62% yield) of pure Intermediate K. $^1$H-NMR (300 MHz, CDCl$_3$) δ 1.41 (d, 6H, J=6.9 Hz), 3.20-3.31 (m, 1H), 7.28 (d, 1H, J=5.1 Hz), 7.65 (d, 1H, J=5.1 Hz). MS (ESI) (M+H)$^+$322.1.

Example 66 Intermediate L

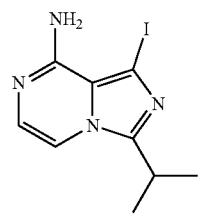

Intermediate K (33 mg, 0.10 mmol) and NH$_4$OH were heated to 80° C. for 6 h in a microwave. The reaction mixture was concentrated in vacuo and purified using silica gel chromatography with a hexane/EtOAc gradient to yield Intermediate L (33 mg, 66% yield). $^1$H-NMR (300 MHz, CDCl$_3$) δ 1.4 (d, 6H, J=5.4 Hz), 3.17-3.26 (m, 1H), 5.88 (br s, 2H), 7.02 (d, 1H, J=5.1 Hz), 7.23 (d, 1H, J=5.1 Hz). MS (ESI) (M+H)$^+$303.2.

Example 67 Intermediate M

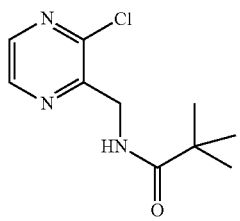

Intermediate H (104 mg, 0.76 mmol), pivalic acid (0.08 mL, 0.8 mmol), EDCI (200 mg, 1.0 mmol), DIEA (0.4 mL, 2.0 mmol), and DMAP (22 mg, 0.15 mmol) were dissolved in 8.0 mL of dichloromethane. The reaction mixture was stirred at rt overnight and then concentrated in vacuo. The resultant residue was dissolved in EtOAc, washed with water (2×), NaHCO$_3$(1×), and brine (1×). The organic layer was dried over Na$_2$SO$_4$, and concentrated in vacuo to afford 145 mg (94% yield) of pure Intermediate M. $^1$H-NMR (300 MHz, CDCl$_3$) δ 1.15 (s, 9H), 4.59 (d, 2H, J=4.8 Hz), 8.31-8.34 (m, 1H), 8.42 (d, 1H, J=2.4 Hz).

Example 68 Intermediate N

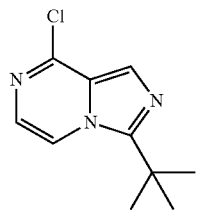

POCl$_3$ (0.12 ml, 1.35 mmol) was added to Intermediate M (54 mg, 0.27 mmol) dissolved in 1.2 mL of acetonitrile. A drop of DMF was added and the reaction mixture was stirred at 55° C. for 30 minutes. The reaction mixture was then concentrated in vacuo and the resultant solid was dissolved in 2 M ammonia in methanol followed by concentrating this solution in vacuo. The resultant solid was dissolved in a minimal amount of water and the product was extracted into dichloromethane (4×). The organic layers were combined and washed with saturated NaHCO$_3$(1×), concentrated in vacuo, and dried over Na$_2$SO$_4$. Concentration of the solution afforded 45 mg (95% yield) of Intermediate N. $^1$H-NMR (300 MHz, CDCl$_3$) δ 1.35 (s, 9H), 7.38 (m, 1H), 7.66 (m, 1H), 7.87 (s, 1H). MS (ESI) (M+H)$^+$210.1.

Example 69 Intermediate O

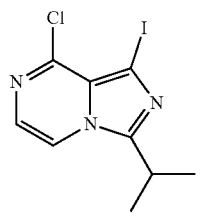

Intermediate N (45 mg, 0.25 mmol) dissolved in 0.23 mL of DMF was added to NIS (51 mg, 0.22 mmol) dissolved in 0.8 mL of DMF. The reaction mixture was heated to 60° C. for 3 h and then cooled to room temperature. The reaction mixture was partitioned between 1 M Na$_2$SO$_3$ and dichloromethane. The aqueous layer was then extracted with dichloromethane (3×). The organic layers were combined, dried over Na$_2$SO$_4$ and concentrated in vacuo to afford 49 mg (70% yield) of pure Intermediate O. $^1$H-NMR (300 MHz, CDCl$_3$) δ 1.31 (s, 9H), 7.23 (d, 1H, J=5.1 Hz), 7.67 (d, 1H, J=5.1 Hz). MS (ESI) (M+H)$^+$336.4.

Example 70 Intermediate P

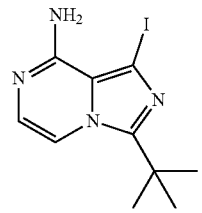

Intermediate O (76 mg, 0.22 mmol) and NH$_4$OH were heated to 80° C. for 6 h in a microwave. The reaction mixture was concentrated in vacuo and purified using silica gel chromatography with a hexane/EtOAc gradient to yield Intermediate P (76 mg, 66% yield). $^1$H-NMR (300 MHz, CDCl$_3$) δ 1.32 (s, 9H), 5.28 (br s, 2H), 7.06 (d, 1H, J=5.1 Hz), 7.21 (d, 1H, J=5.1 Hz). MS (ESI) (M+H)$^+$317.1.

Example 71 General Procedure H

Intermediates L or O (0.03 mmol), tetrakis(triphenylphosphine) palladium(0) (0.05 equiv), and sodium carbonate (2.3 equiv) were added to the appropriate boronic acid or pinacol ester (1.1 equiv) in dimethoxyethane (1 mL) and water (0.5 mL). The reaction was performed in a microwave at 85° C. for one hour, followed by extraction with ethyl acetate and water. The organic layer was collected and concentrated in vacuo to yield the crude product. The crude product was then purified via flash chromatography with an ethyl acetate/hexanes gradient.

Example 72 Preparation of Compounds 8-12 and 69-72

Compounds 8-12 and 69-72 (Table B) were generated with General Procedure H using the appropriate substituted boronic acid as is familiar to those skilled in the art.

Example 73 Preparation of Compounds 81-149

Compounds 81-149 were prepared according to the general procedures using the appropriate substituted boronic acid as is familiar to those skilled in the art.

| Compound No. | Structure |
|---|---|
| 81 | 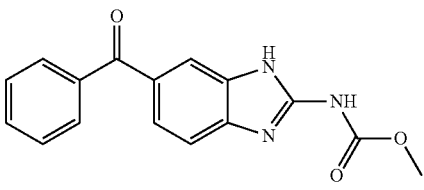 [SMILES: COC(=O)Nc1nc2ccc(C(=O)c3ccccc3)cc2[nH]1] |
| 82 | 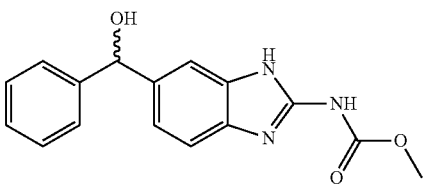 [SMILES: COC(=O)Nc1nc2ccc(C(O)c3ccccc3)cc2[nH]1] |
| 83 | 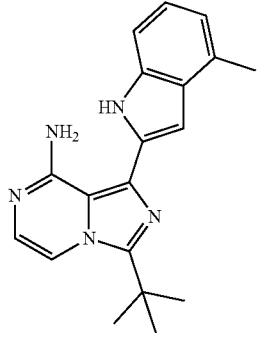 [SMILES: Cc1cccc2[nH]c(-c3nc(C(C)(C)C)n4ccnc(N)c34)cc12] |
| 84 | 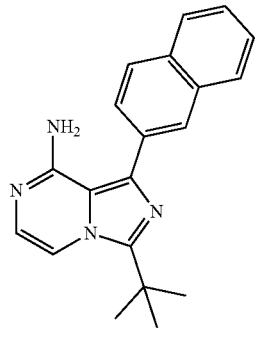 [SMILES: CC(C)(C)c1nc(-c2ccc3ccccc3c2)c2c(N)nccn12] |
| 85 | 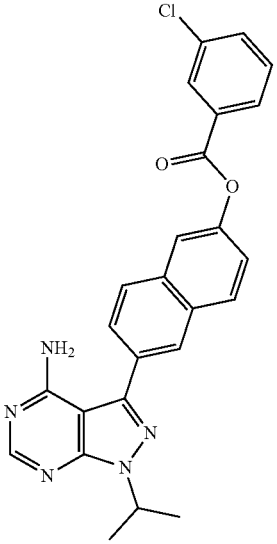 [SMILES: CC(C)n1nc(-c2ccc3cc(OC(=O)c4cccc(Cl)c4)ccc3c2)c2c(N)ncnc21] |

| Compound No. | Structure |
|---|---|
| 86 | 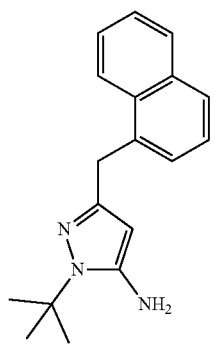 [SMILES: CC(C)(C)n1nc(Cc2cccc3ccccc23)cc1N] |
| 87 | 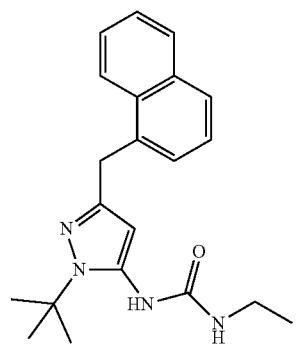 [SMILES: CCNC(=O)Nc1cc(Cc2cccc3ccccc23)nn1C(C)(C)C] |
| 88 | 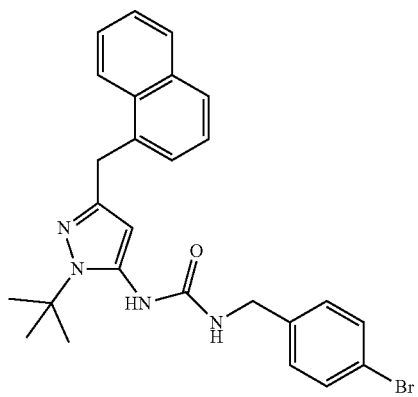 [SMILES: CC(C)(C)n1nc(Cc2cccc3ccccc23)cc1NC(=O)NCc1ccc(Br)cc1] |
| 89 | 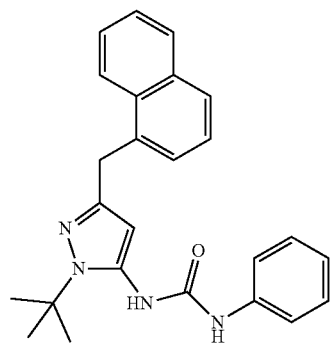 [SMILES: CC(C)(C)n1nc(Cc2cccc3ccccc23)cc1NC(=O)Nc1ccccc1] |

-continued
| Compound No. | Structure |
|---|---|
| 90 | 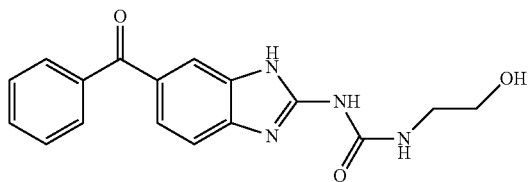 [SMILES: O=C(NCCO)Nc1nc2ccc(C(=O)c3ccccc3)cc2[nH]1] |
| 91 | 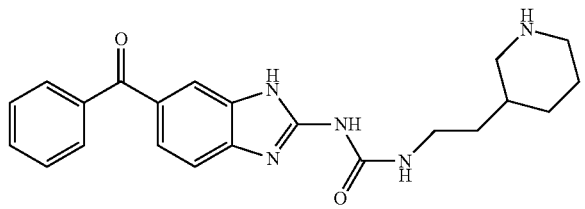 [SMILES: O=C(NCCC1CCCNC1)Nc1nc2ccc(C(=O)c3ccccc3)cc2[nH]1] |
| 92 | 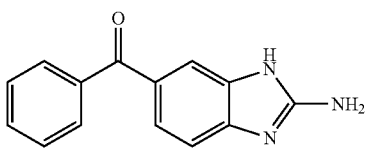 [SMILES: Nc1nc2ccc(C(=O)c3ccccc3)cc2[nH]1] |
| 93 | 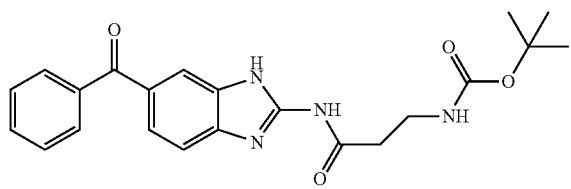 [SMILES: CC(C)(C)OC(=O)NCCC(=O)Nc1nc2ccc(C(=O)c3ccccc3)cc2[nH]1] |
| 94 | 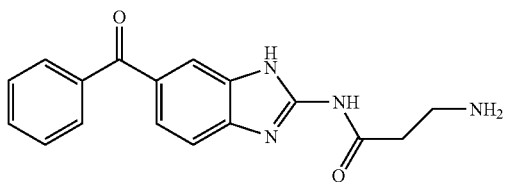 [SMILES: NCCC(=O)Nc1nc2ccc(C(=O)c3ccccc3)cc2[nH]1] |
| 95 | 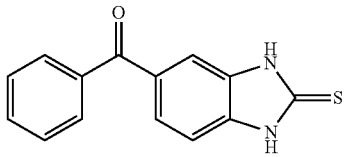 [SMILES: O=C(c1ccccc1)c1ccc2[nH]c(=S)[nH]c2c1] |
| 96 | 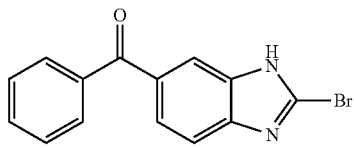 [SMILES: O=C(c1ccccc1)c1ccc2nc(Br)[nH]c2c1] |
| 97 | 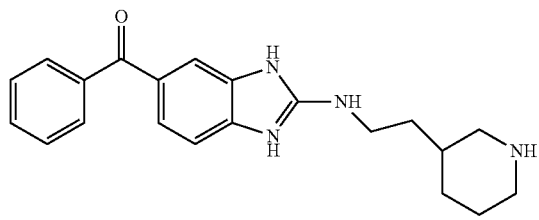 [SMILES: O=C(c1ccccc1)c1ccc2nc(NCCC3CCCNC3)[nH]c2c1] |

| Compound No. | Structure |
|---|---|
| 98 | 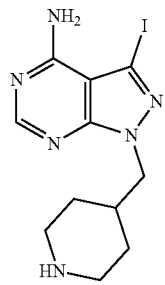 [SMILES: Nc1ncnc2c1c(I)nn2CC1CCNCC1] |
| 99 | 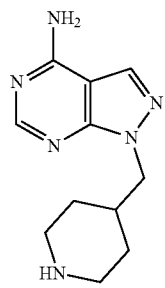 [SMILES: Nc1ncnc2c1cnn2CC1CCNCC1] |
| 100 | 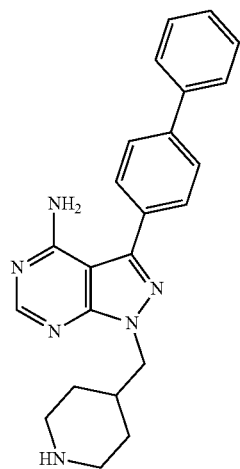 [SMILES: Nc1ncnc2c1c(-c1ccc(-c3ccccc3)cc1)nn2CC1CCNCC1] |
| 101 | 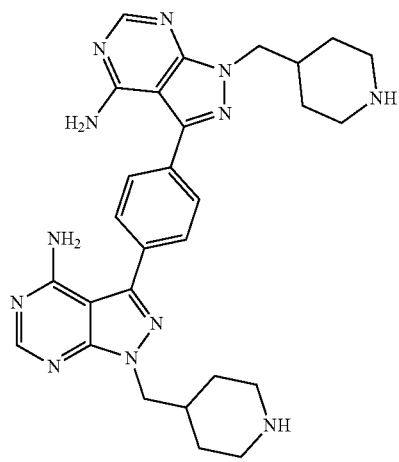 [SMILES: Nc1ncnc2c1c(-c1ccc(-c3nn(CC4CCNCC4)c4ncnc(N)c34)cc1)nn2CC1CCNCC1] |

-continued

| Compound No. | Structure |
|---|---|
| 102 | (structure) |
| 103 | (structure) |
| 104 | (structure) |
| 105 | (structure) |
| 106 | (structure) |
| 107 | (structure) |
| 108 | (structure) |
| 109 | (structure) |
| 110 | (structure) |

-continued
| Compound No. | Structure |
|---|---|
| 111 | 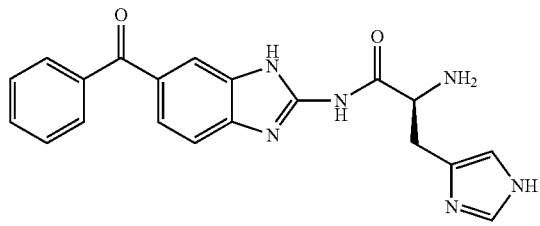 [SMILES: N[C@@H](Cc1c[nH]cn1)C(=O)Nc1nc2ccc(C(=O)c3ccccc3)cc2[nH]1] |
| 112 | 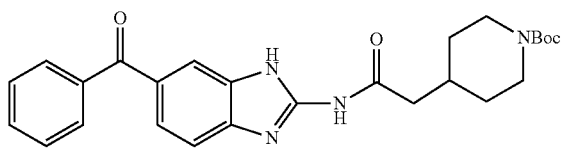 [SMILES: CC(C)(C)OC(=O)N1CCC(CC(=O)Nc2nc3ccc(C(=O)c4ccccc4)cc3[nH]2)CC1] |
| 113 | 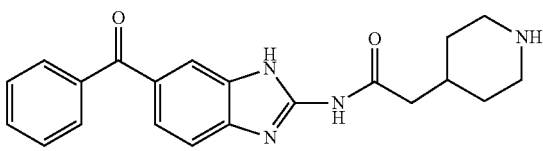 [SMILES: O=C(CC1CCNCC1)Nc1nc2ccc(C(=O)c3ccccc3)cc2[nH]1] |
| 114 | 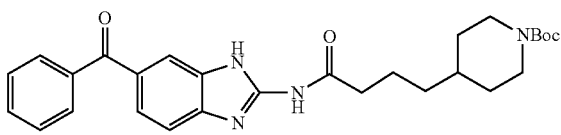 [SMILES: CC(C)(C)OC(=O)N1CCC(CCCC(=O)Nc2nc3ccc(C(=O)c4ccccc4)cc3[nH]2)CC1] |
| 115 | 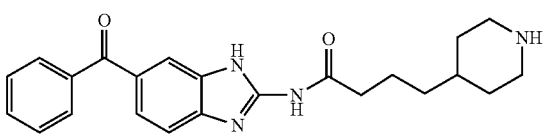 [SMILES: O=C(CCCC1CCNCC1)Nc1nc2ccc(C(=O)c3ccccc3)cc2[nH]1] |
| 116 | 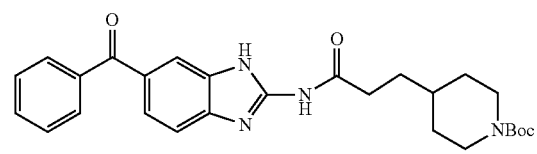 [SMILES: CC(C)(C)OC(=O)N1CCC(CCC(=O)Nc2nc3ccc(C(=O)c4ccccc4)cc3[nH]2)CC1] |
| 117 | 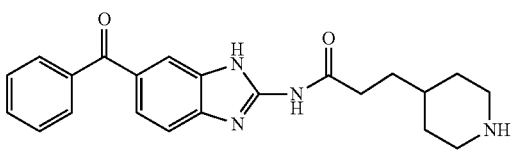 [SMILES: O=C(CCC1CCNCC1)Nc1nc2ccc(C(=O)c3ccccc3)cc2[nH]1] |

| Compound No. | Structure |
|---|---|
| 118 | 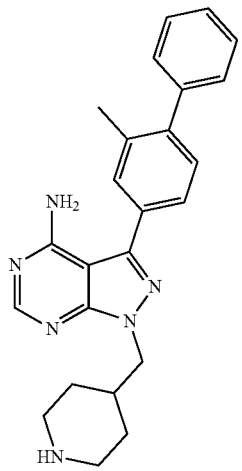 [SMILES: Cc1cc(-c2nn(CC3CCNCC3)c3ncnc(N)c23)ccc1-c1ccccc1] |
| 119 | 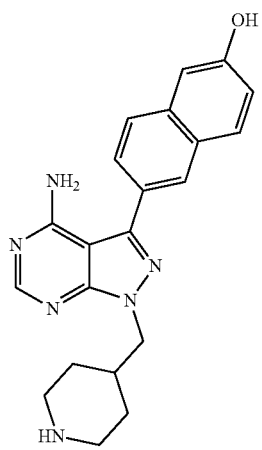 [SMILES: Nc1ncnc2c1c(-c1ccc3cc(O)ccc3c1)nn2CC1CCNCC1] |
| 120 | 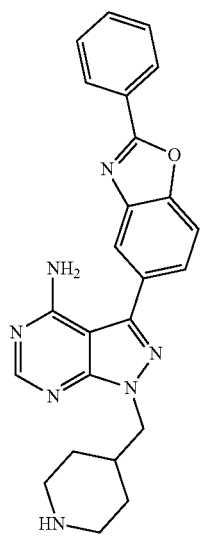 [SMILES: Nc1ncnc2c1c(-c1ccc3oc(-c4ccccc4)nc3c1)nn2CC1CCNCC1] |

-continued
| Compound No. | Structure |
|---|---|
| 121 | 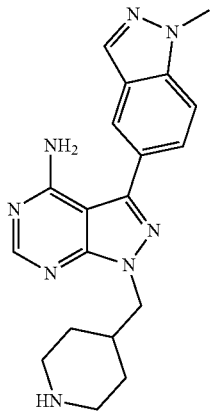 [SMILES: Cn1ncc2cc(-c3nn(CC4CCNCC4)c4ncnc(N)c34)ccc21] |
| 122 | 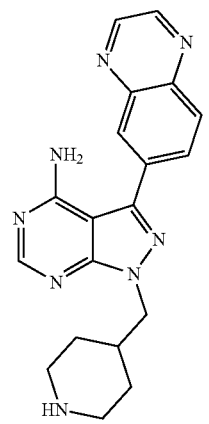 [SMILES: Nc1ncnc2c1c(-c1ccc3nccnc3c1)nn2CC1CCNCC1] |
| 123 | 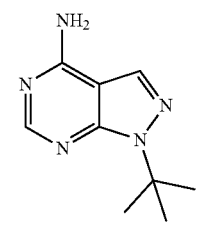 |
| 124 | 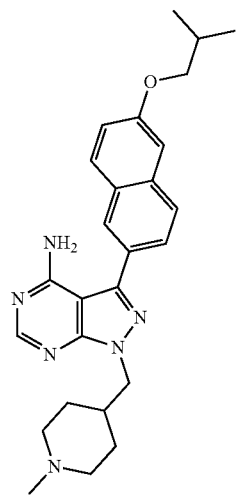 [SMILES: CC(C)COc1ccc2cc(-c3nn(CC4CCN(C)CC4)c4ncnc(N)c34)ccc2c1] |

-continued
| Compound No. | Structure |
|---|---|
| 125 | 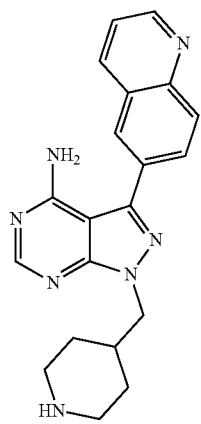 [SMILES: Nc1ncnc2c1c(-c1ccc3ncccc3c1)nn2CC1CCNCC1] |
| 126 | 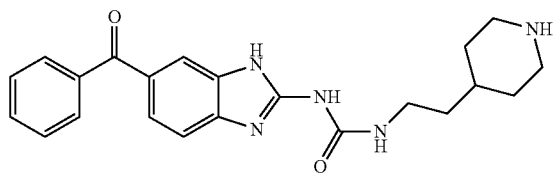 [SMILES: O=C(NCCC1CCNCC1)Nc1nc2ccc(C(=O)c3ccccc3)cc2[nH]1] |
| 127 | 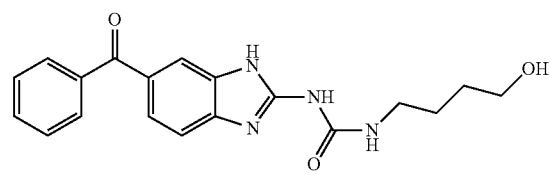 [SMILES: O=C(NCCCCO)Nc1nc2ccc(C(=O)c3ccccc3)cc2[nH]1] |
| 128 | 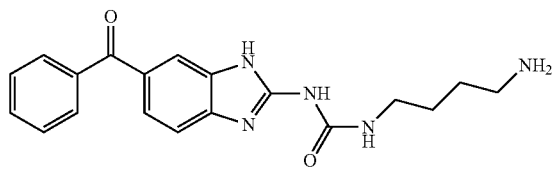 [SMILES: NCCCCNC(=O)Nc1nc2ccc(C(=O)c3ccccc3)cc2[nH]1] |
| 129 | 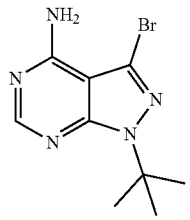 |

-continued
| Compound No. | Structure |
|---|---|
| 130 | 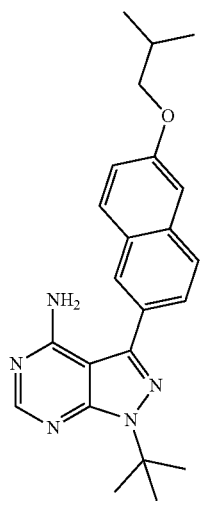 [SMILES: CC(C)COc1ccc2cc(-c3nn(C(C)(C)C)c4ncnc(N)c34)ccc2c1] |
| 131 | 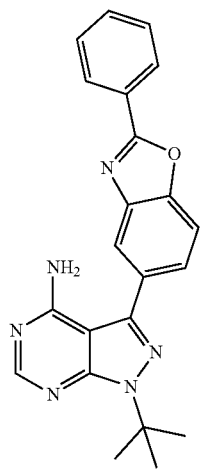 [SMILES: CC(C)(C)n1nc(-c2ccc3oc(-c4ccccc4)nc3c2)c2c(N)ncnc21] |
| 132 | 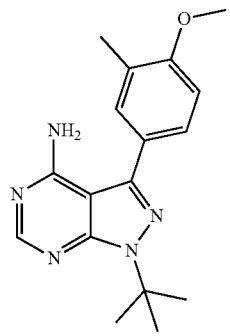 [SMILES: COc1ccc(-c2nn(C(C)(C)C)c3ncnc(N)c23)cc1C] |

-continued
| Compound No. | Structure |
|---|---|
| 133 | 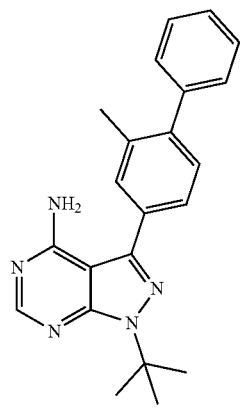 [SMILES: Cc1cc(-c2nn(C(C)(C)C)c3ncnc(N)c23)ccc1-c1ccccc1] |
| 134 | 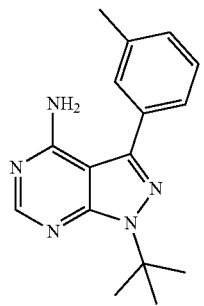 [SMILES: Cc1cccc(-c2nn(C(C)(C)C)c3ncnc(N)c23)c1] |
| 135 | 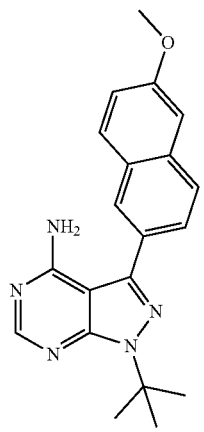 [SMILES: COc1ccc2cc(-c3nn(C(C)(C)C)c4ncnc(N)c34)ccc2c1] |
| 136 | 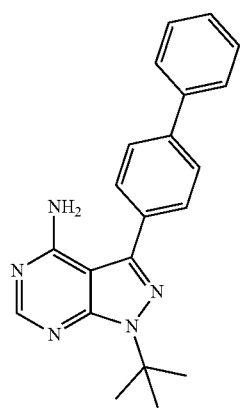 [SMILES: CC(C)(C)n1nc(-c2ccc(-c3ccccc3)cc2)c2c(N)ncnc21] |

-continued
| Compound No. | Structure |
|---|---|
| 137 | 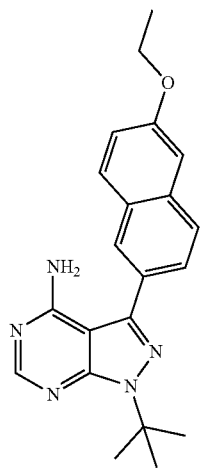 [SMILES: CCOc1ccc2cc(-c3nn(C(C)(C)C)c4ncnc(N)c34)ccc2c1] |
| 138 | 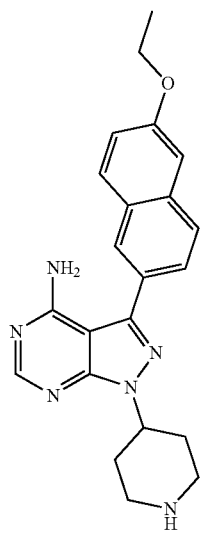 [SMILES: CCOc1ccc2cc(-c3nn(C4CCNCC4)c4ncnc(N)c34)ccc2c1] |
| 139 | 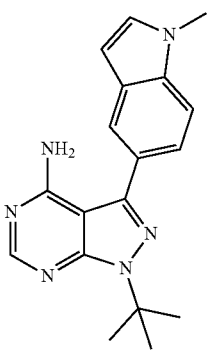 [SMILES: Cn1ccc2cc(-c3nn(C(C)(C)C)c4ncnc(N)c34)ccc21] |

| Compound No. | Structure |
|---|---|
| 140 | 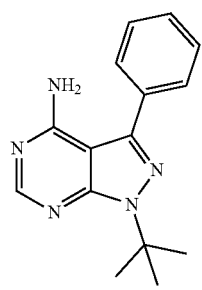 [SMILES: CC(C)(C)n1nc(-c2ccccc2)c2c(N)ncnc21] |
| 141 | 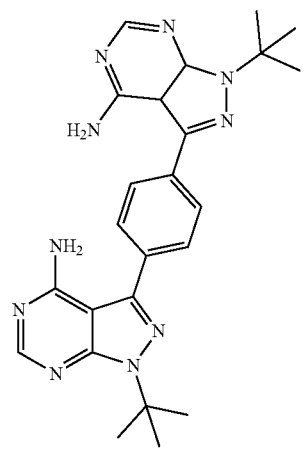 [SMILES: CC(C)(C)N1N=C(c2ccc(-c3nn(C(C)(C)C)c4ncnc(N)c34)cc2)C2C(N)=NC=NC21] |
| 142 | 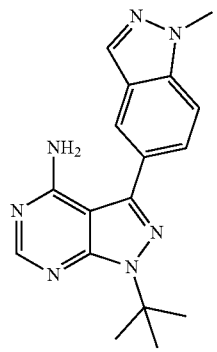 [SMILES: Cn1ncc2cc(-c3nn(C(C)(C)C)c4ncnc(N)c34)ccc21] |
| 143 | 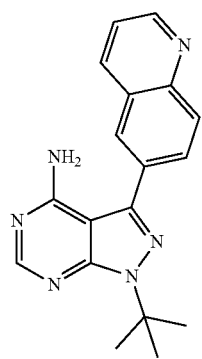 [SMILES: CC(C)(C)n1nc(-c2ccc3ncccc3c2)c2c(N)ncnc21] |

-continued
| Compound No. | Structure |
|---|---|
| 144 | 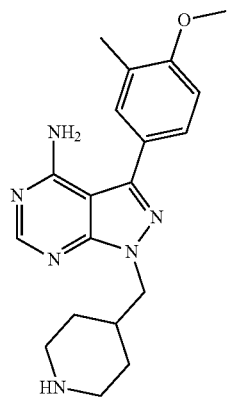 [SMILES: COc1ccc(-c2nn(CC3CCNCC3)c3ncnc(N)c23)cc1C] |
| 145 | 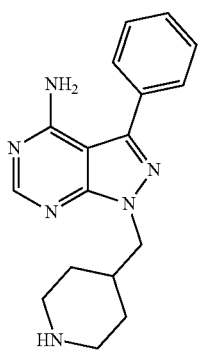 [SMILES: Nc1ncnc2c1c(-c1ccccc1)nn2CC1CCNCC1] |
| 146 | 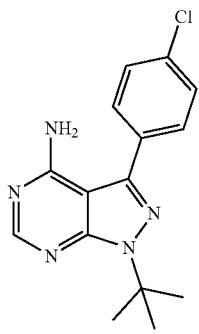 [SMILES: CC(C)(C)n1nc(-c2ccc(Cl)cc2)c2c(N)ncnc21] |
| 147 | 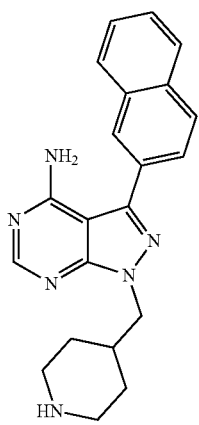 [SMILES: Nc1ncnc2c1c(-c1ccc3ccccc3c1)nn2CC1CCNCC1] |

-continued
| Compound No. | Structure |
|---|---|
| 148 | 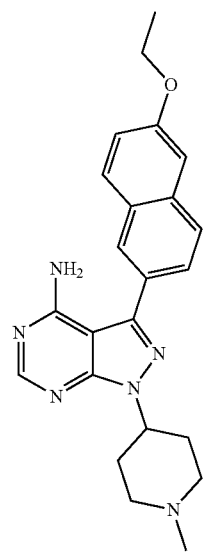 [SMILES: CCOc1ccc2cc(-c3nn(C4CCN(C)CC4)c4ncnc(N)c34)ccc2c1] |
| 149 | 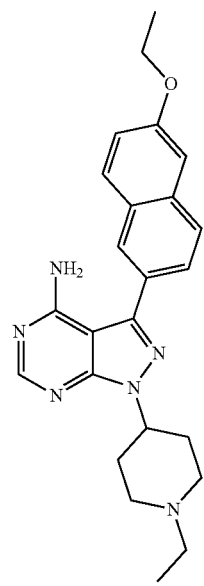 [SMILES: CCOc1ccc2cc(-c3nn(C4CCN(CC)CC4)c4ncnc(N)c34)ccc2c1] |

Example 74 Preparation of Compound 150

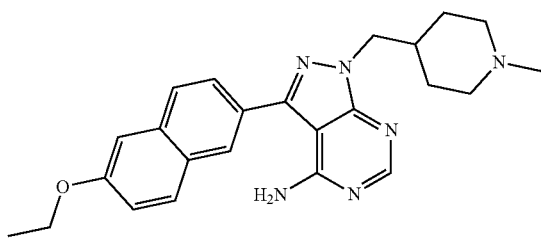 [SMILES: CCOc1ccc2cc(-c3nn(CC4CCN(C)CC4)c4ncnc(N)c34)ccc2c1]

3-(6-ethoxynaphthalen-2-yl)-1-((1-methylpiperidin-
4-yl)methyl)-1H-pyrazolo[3,4-d]pyrimidin-4-amine
(150)

This compound was synthesized as shown in the scheme below.

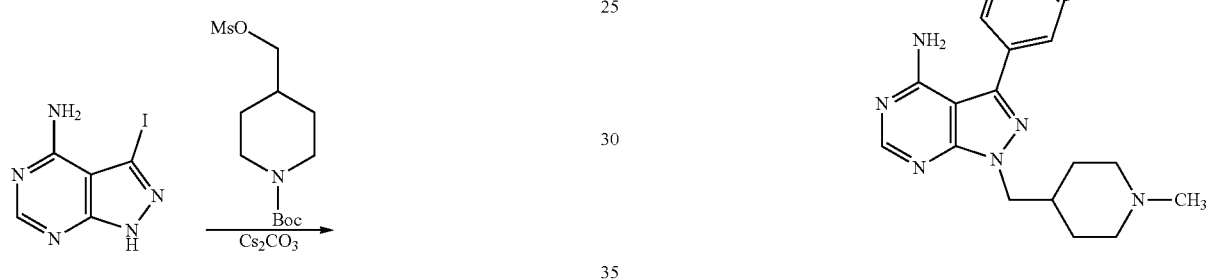

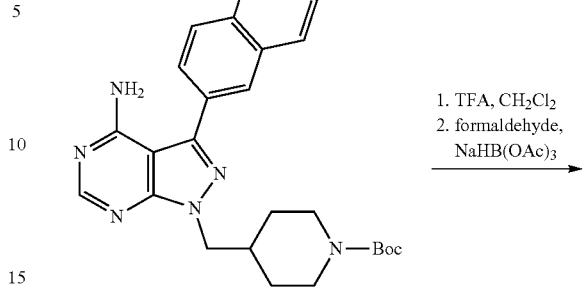

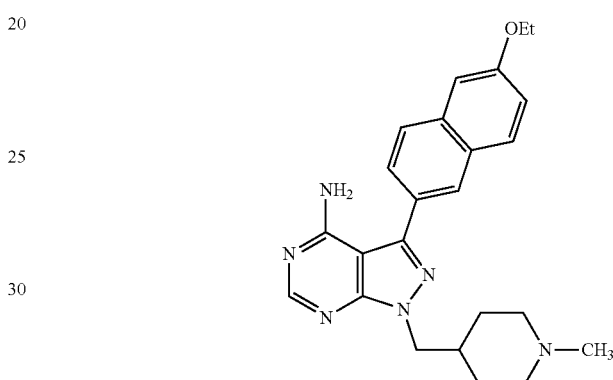

BIOLOGICAL EXAMPLES

Biological Example 1 Enzymology of TgCDPK1

Two types of enzyme assays were developed to follow TgCDPK1 activity, a radiometric scintillation proximity assay measured the labeled γ-phosphate of ATP added to a biotinylated peptide substrate and an ATP consumption assay where ATP consumption was monitored by luciferase and light production (KinaseGlo®, Promega Corp., Madison, Wis.). Both assays gave similar results for calcium dependence, $K_m$ of substrates (less than 2-fold differences in Km values; see Table 6 FIGS. 6, 7, 8, and 9), and inhibitor concentrations for 50% enzyme inhibition ($IC_{50}$s; see, Tables 6 and 7).

TABLE 6

$K_m$ and $IC_{50}$ values for TgCDPK1 enzyme

| | | Mean Substrate | | Inhibitor $IC_{50}$ values (μM)* | | |
|---|---|---|---|---|---|---|
| | Enzyme concn | $K_m$ | | NM-PP1 | NA-PP1 | NA-PP2 |
| Assay Type | (nM) | ATP | Peptide | (Cmpd 3) | (Cmpd 1) | (Cmpd 2) |
| SPA | 2 | 10 ± 2 | 12 ± 2 | 0.025 | 0.484 | 0.006 |
| KinaseGlo | 2 | 12.38 | 20.48 | 0.02 | 0.816 | 0.005 |

*ATP value of 12.4 μM and Peptide 10 μM

Note:
Enzyme concentrations are 10-fold less than shown in Table 7, substrate concentrations are different than Table 7, and the incubation time is 90 min instead of 30 min as shown in Table 7.

TABLE 7

Inhibitor IC$_{50}$ values at different TgCDPK1 enzyme concentrations

| Enzyme concn (nM) | incubation time (min) | IC$_{50}$ values (µM)# | | |
|---|---|---|---|---|
| | | NM-PP1 (Cmpd 3) | NA-PP1 (Cmpd 1) | NA-PP2 (Cmpd 2) |
| 20 | 30 | 0.066 | 0.989 | 0.018 |
| 2 | 90 | 0.039 | 0.978 | 0.008 |

TgCDPK1 data at ATP value of 10 µM and Peptide 40 µM, with coupled KinaseGlo assay. Note, a longer incubation time was necessary for the lower enzyme concentration to get reliable measurements for the IC$_{50}$ calculation.

As expected, activity of TgCDPK1 on the peptide substrates required addition of exogenous calcium (FIG. 1). Indeed, calcium titration revealed that a concentration of 4.7 µM gave 50% of TgCDPK1 kinase activity. The K$_m$ of ATP and peptide substrates were determined to be 10 and 14 µM, respectively.

Biological Example 2 Structure of TgCDPK1

We have determined X-ray crystal structures of Ca$^{2+}$-free TgCDPK1 in the apo form and in complex with two potent inhibitors (Table 1 and FIG. 2).

kinases[18]. The conformation represented by these structures is likely an inactive form of the enzyme since the calmodulin-like domain occludes the surface required for recognition of target proteins and peptides. Importantly, the ATP binding site remains accessible to small molecule substrates and inhibitors. The group of Raymond Hui at the Toronto Structural Genomics Consortium has shown that when TgCDPK1 is activated by calcium, the regulatory domain undergoes major structural rearrangement and is repositioned to lie against the opposite surface of the kinase domain (Wernimont et al. submitted for publication, PDB accession number 3hx4). This dramatic structural change allows access of the protein substrates to the active site.

Biological Example 3 Bumped Kinase Inhibitors (BKIs) and TgCDPK1

Most known kinase inhibitors bind in the ATP-binding pocket of the active site[19,20]. These inhibitors exploit many of the same hydrophobic contacts as the purine ring of ATP and make at least one conserved hydrogen bond to the hinge region. Potent inhibitors also occupy at least one hydrophobic pocket adjacent to the ATP-binding site. These additional hydrophobic interactions increase both binding affinity and

TABLE 1

Data collection and refinement statistics.

| | SAD (SeMet) | Apo (native) | NA-PP2 (SeMet) | NM-PP1 (native) |
|---|---|---|---|---|
| Data collection | | | | |
| Space group | P2$_1$ | P2$_1$ | P2$_1$ | P2$_1$ |
| Cell dimensions | | | | |
| a, b, c(Å) | 48.2, 72.0, 67.5 | 48.1, 71.9, 67.3 | 48.1, 72.5, 67.1 | 47.2, 72.9, 65.7 |
| α, β, γ (°) | 90.0, 102.9, 90.0 | 90.0, 103.0, 90.0 | 90.0, 103.8, 90.0 | 90.0, 98.8, 90.0 |
| Resolution (Å) | 90-2.30 (2.38-2.30)* | 50-2.04 (2.12-2.04) | 50-1.98 (2.06-1.98) | 50-1.99 (2.06-1.99) |
| Unique reflections | 20,099 (1,986) | 28,324 (2,799) | 30,0803 (2,996) | 30,350 (2,975) |
| R$_{merge}$ | 0.11 (0.95) | 0.05 (0.67) | 0.09 (0.70) | 0.06 (0.74) |
| I/σI | 13.1 (2.4) | 17.0 (2.4) | 8.4 (2.1) | 14.2 (1.9) |
| Completeness (%) | 100 (100) | 99.9 (100) | 98.1 (96.6) | 99.8 (98.1) |
| Redundancy | 7.7 (7.7) | 4.2 (4.2) | 3.7 (3.6) | 4.2 (4.1) |
| Wilson B factor (Å$^2$) | 43.7 | 34.8 | 26.6 | 29.7 |
| Refinement | | | | |
| Resolution (Å) | | 36.89-2.04 | 29.72-1.98 | 35.72-1.99 |
| No. reflections | | 26,871 | 29,224 | 28,797 |
| No. reflections test set | | 1,431 | 1,556 | 1,536 |
| R$_{work}$/R$_{free}$ | | 0.213/0.258 | 0.193/0.245 | 0.192/0.228 |
| No. atoms | | | | |
| Protein | | 3,674 | 3,776 | 3,743 |
| Nonprotein | | 79 | 194 | 167 |
| B-factors (Å$^2$) | | | | |
| Protein (Mean B$_{iso}$ + B$_{TLS}$) | | 60.2 | 42.5 | 48.7 |
| Nonprotein (Mean B$_{iso}$) | | 27.7 | 27.1 | 24.0 |
| R.m.s. deviations | | | | |
| Bond lengths (Å) | | 0.006 | 0.007 | 0.006 |
| Bond angles (°) | | 0.866 | 0.978 | 0.878 |
| PDB code | | 3i79 | 3i7c | 3i7b |

*Values in parentheses are for highest-resolution shell.

Figure 2A:
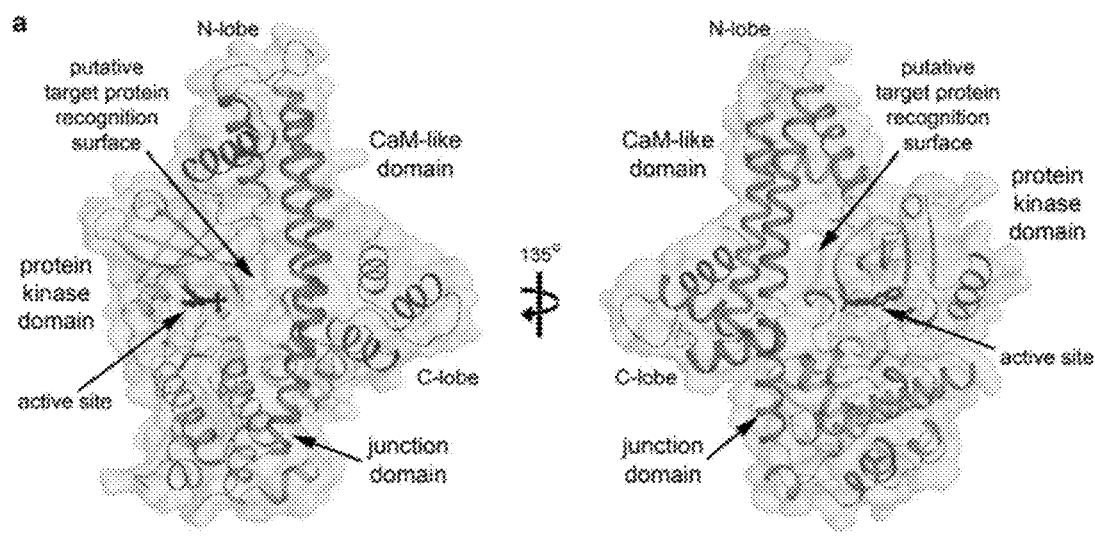

The structure of the catalytic domain is typical of serine/threonine type protein kinases. The two Ca$^{2+}$-binding EF-hand lobes and connecting extended helical stem of the calmodulin-like regulatory domain lie along one face of the kinase domain, adjacent to the active site (FIG. 2a). The kinase and regulatory domains are connected by an intervening helical junction domain characteristic of this class of target selectivity of the inhibitor because there is substantial heterogeneity among different kinases in these regions. Examination of the TgCDPK1 sequence in the vicinity of the ATP-binding pocket (FIG. 2b) shows that it contains a glycine residue at a position that has been termed the gatekeeper residue because it constrains access to the ATP-binding site[21-23]. The glycine at this position in TgCDPK1

(Gly128) is expected to create a much larger pocket off the ATP-binding site than is typically seen in protein kinases and comparison of the TgCDPK1 structure with other kinases shows that this is indeed the case. This difference in the active site architectures can be exploited for design of selective inhibitors against TgCDPK1.

Shokat and colleagues have shown that mutation of bulky gatekeeper residues to glycine renders mutant kinases uniquely susceptible to inhibition by a class of kinase inhibitors called "bumped kinase inhibitors" (BKIs). BKIs are analogs of 4-amino-1-tert-butyl-3-phenylpyrazolo[3,4-d]pyrimidine (Table 2) that are derivatized at C3 with bulky aromatic groups[24].

NM-PP1, a 550-fold difference between $IC_{50}$ values for wild type versus the G128M mutant (Table 2).

Figure 2C:
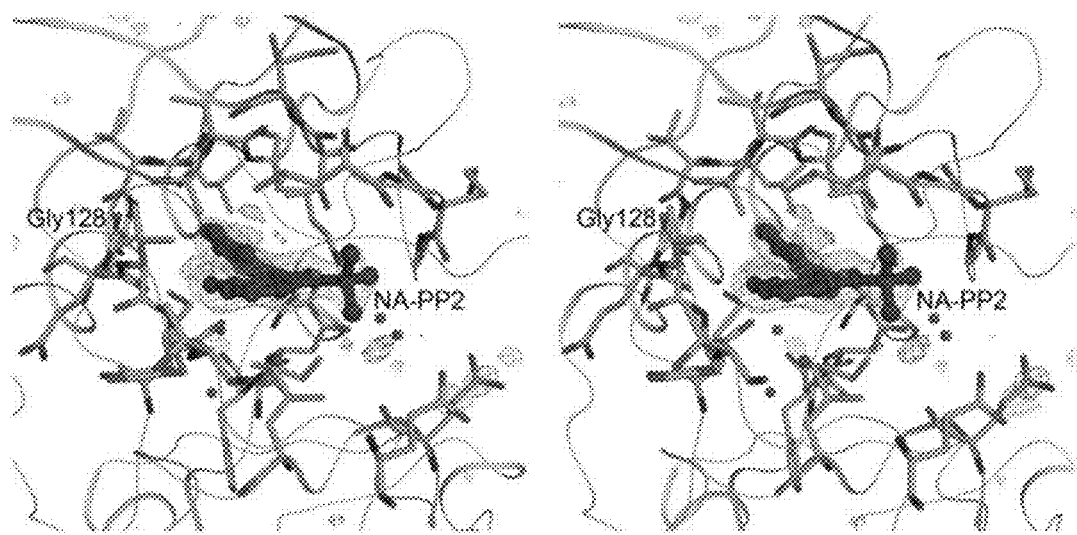
Figure 2D:
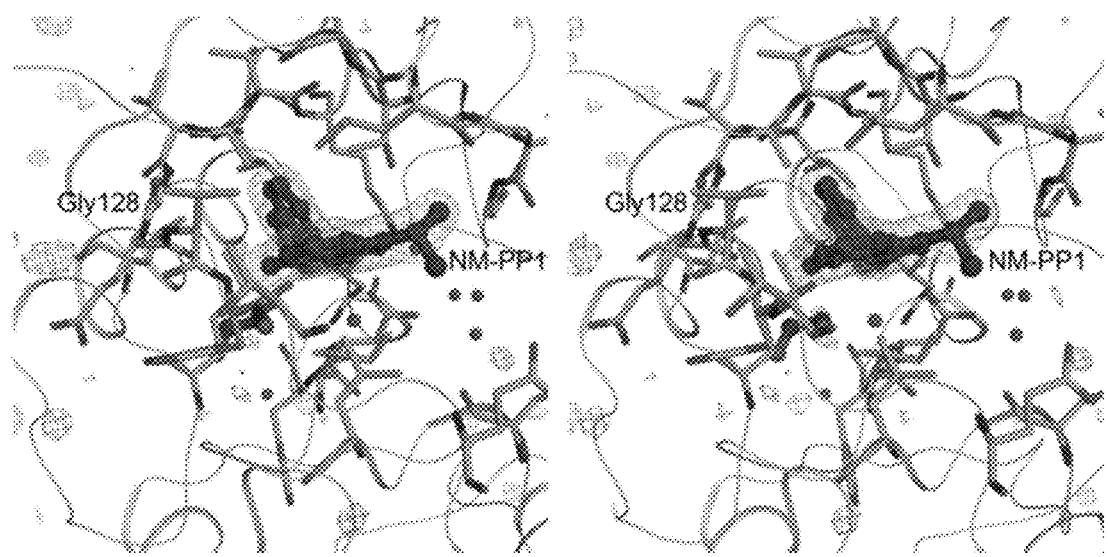
Figure 2E:
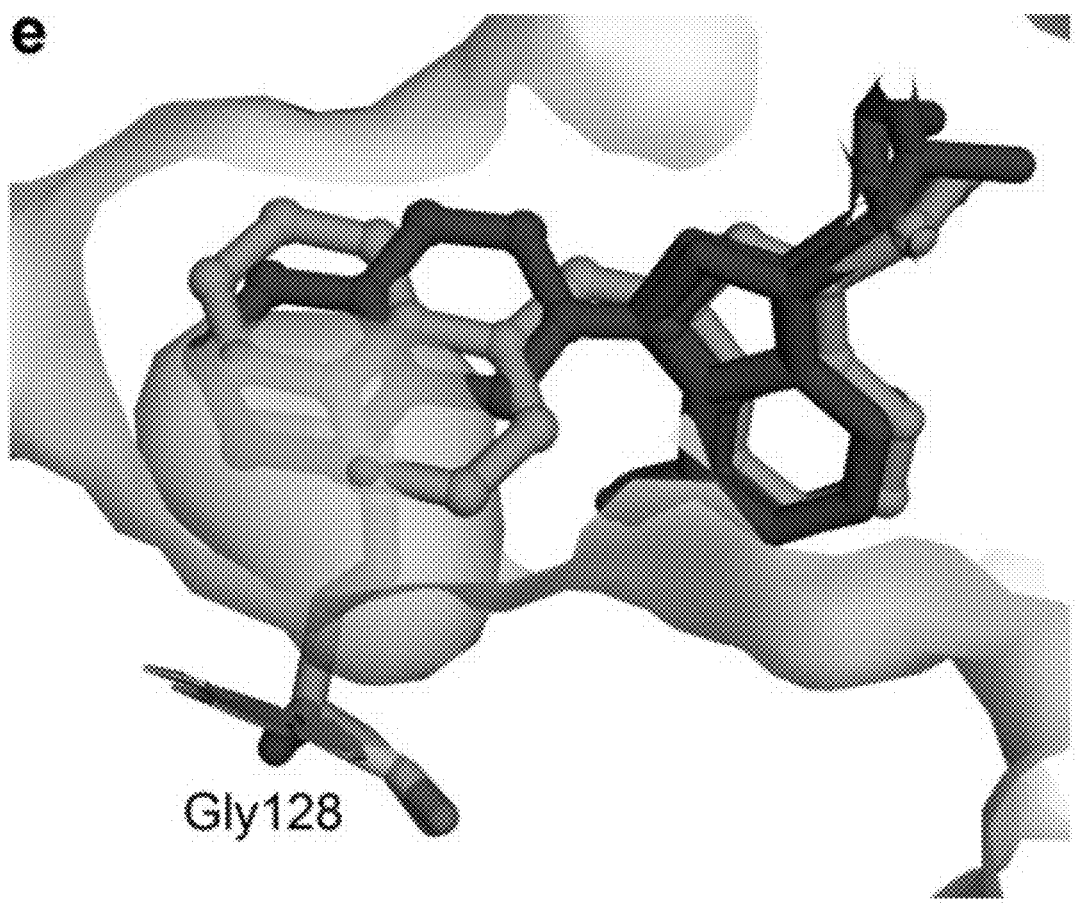

The crystal structure of TgCDPK1 in complex with two potent BKIs were determined (NA-PP2, FIG. 2c; NM-PP1, FIG. 2d) and, as predicted, these inhibitors bind in the ATP-binding site with the C3 bulky aromatic substituent occupying the pocket adjacent to the glycine gatekeeper. Superposition of an orthologous CDPK containing a methionine gatekeeper onto our BKI complexes showed impairment of the favorable binding mode observed for the BKIs in TgCDPK1 (FIG. 2e). The bulky gatekeeper sidechain clashes with the C3 bulky aromatic substituent providing a structural basis for the insensitivity of typical kinases

TABLE 2

Inhibition of wt TgCDPK1 and TgCDPK1 (Met gatekeeper) by bumped kinase inhibitors.*

| Inhibitor | NA-PP1 | NA-PP2 | NM-PP1 |
|---|---|---|---|
| Wild type TgCDPK1 (IC50 in μM) | 0.989 | 0.018 | 0.066 |
| G128M TgCDPK1 (IC50 in μM) | 173 | 21.44 | 36.18 |
| Chemical structure | 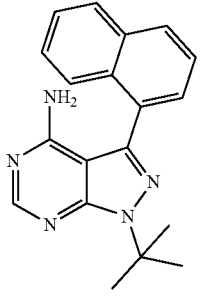 | 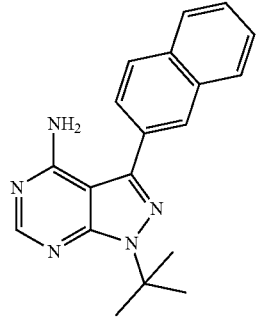 | 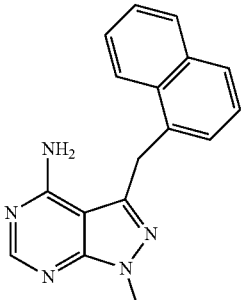 |

*The $IC_{50}$ values were calculated by non-lineaer regression using Prism (GraphPad Software).
The assay was performed three times and the mean IC50 is shown.
The assay was performed using coupling with KinaseGlo at 20 nM TgCDPK1, 10 μM ATP, 40 μM peptide, and an incubation time of 30 min.

The large sidechain of the gatekeeper residue in most kinases prevents access of the C3 bulky aromatic substituent to the more hydrophobic pocket at the back of the catalytic cleft rendering them insensitive to BKI inhibition[21,22]. Large gatekeeper amino acids like methionine or phenylalanine severely restrict access by the BKIs, while small residues such as the glycine present in TgCDPK1 are most permissive[22,23,25,26]. Studies with genetically engineered mice that express mutant kinases with small gatekeeper residues (glycine or alanine), have demonstrated that BKIs preferentially target the mutant kinases[27-29]. The well-documented lack of BKIs inhibition of mammalian kinases suggests that this class of compounds may be very selective for TgCDPK1 during *T. gondii* infection[27-29].

Based on structural and sequence analysis of the differences in ATP-binding sites of typical mammalian kinases and TgCDPK1 with a small gatekeeper (FIGS. 2a and 2b), we synthesized three BKIs and demonstrated that two of three were low double digit nanomolar inhibitors of TgCDPK1 (Table 2). To show that the glycine gatekeeper is the primary determinant of BKI inhibition, we created a glycine to methionine gatekeeper mutant of TgCDPK1 (G128M). Indeed the wild type enzyme was inhibited significantly better by individual BKIs compared to the G128M mutant enzyme (Table 2). For NA-PP1, there was a 175-fold difference, for NA-PP2, a 1200-fold difference and for NM-PP1, a 550-fold difference between $IC_{50}$ values for wild type versus the G128M mutant (Table 2). towards BKI inhibition, as verified experimentally with the G128M mutant of TgCDPK1 (Table 2). These results strongly implicate TgCDPK1 with its unique glycine gatekeeper as a drug target for selective treatment of toxoplasmosis.

Figure 3:
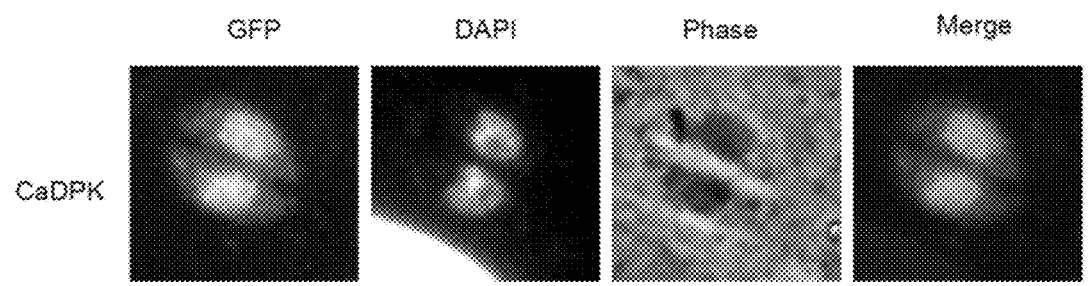
FIG. 3 is a graphical representation of the nuclear and cytosolic localization of TgCDPK1 in *T. gondii*. Live *T. gondii* cells transiently transfected with wild type TgCDPK1-GFP were fixed in 4% paraformaldehyde. Samples were probed with anti-GFP followed by anti-rabbit Ig coupled to Texas red, stained with DAPI and viewed. GFP, green; DAPI, blue.

Biological Example 4 TgCDPK1 Appears in the Cytoplasm and Nucleus of *T. gondii* Cells The mode of action of TgCDPK1 is unknown but its localization in the cell might provide clues to its cellular function. To this end, TgCDPK1 was fused with green fluorescent protein (GFP) to facilitate its localization within live intracellular *T. gondii*. TgCDPK1-GFP was found in both the cytosol and the nucleus (FIG. 3). Similar findings were obtained when the GFP tag was replaced with a C-terminal hemagglutinin (HA) tag. Thus CDPK1 may have targets in both cytosol and nucleus.

Biological Example 5 Effects of BKIs on Toxoplasma gondii Cell Entry and Growth

Figure 4A:
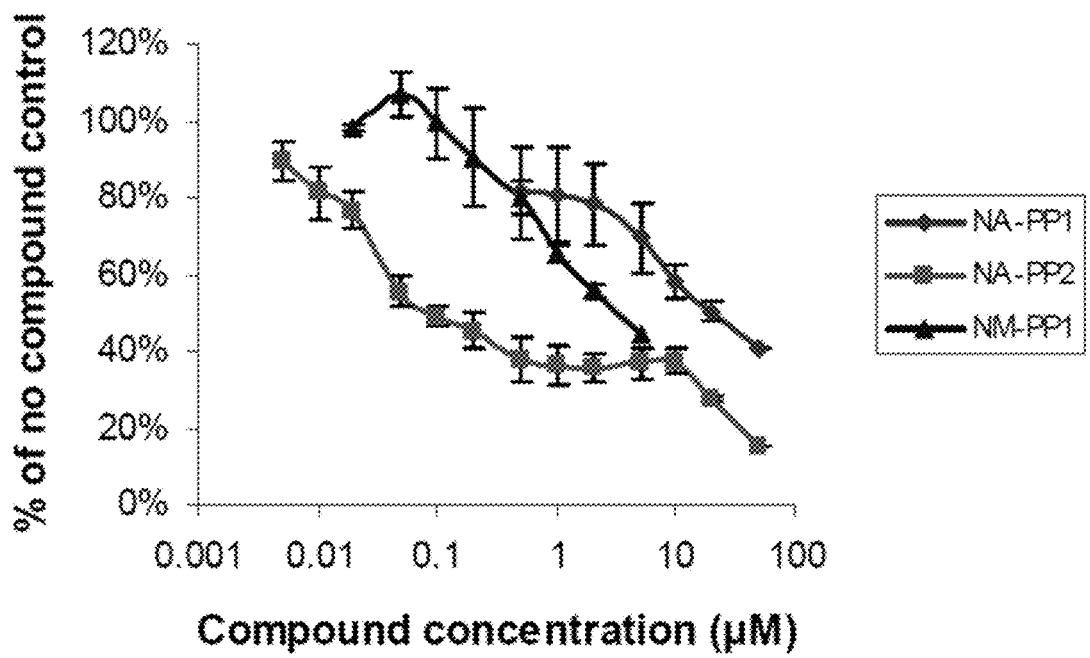
FIGS. 4a-4b are graphical representations demonstrating the effects of bumped kinase inhibitors on T. gondii binding to and invasion of mammalian cells. For these assays, T. gondii expressing β-galactosidase ($10^3$ per well) were allowed to infect fibroblasts in a 96 well plate. For "invasion" assays (FIG. 4a), compounds were added to the wells before infection with T. gondii. For "growth" assays (FIG. 4b), compounds were added to the indicated final concentration, four hours after infection with T. gondii cells. After 20 hours, the cells were lysed and β-galactosidase activity was assessed by adding 0.5 mM chlorophenol red-β-d-galactoside (CPRG), incubating at 37° C., and then measuring absorbance at 595 nm.
Figure 4B:
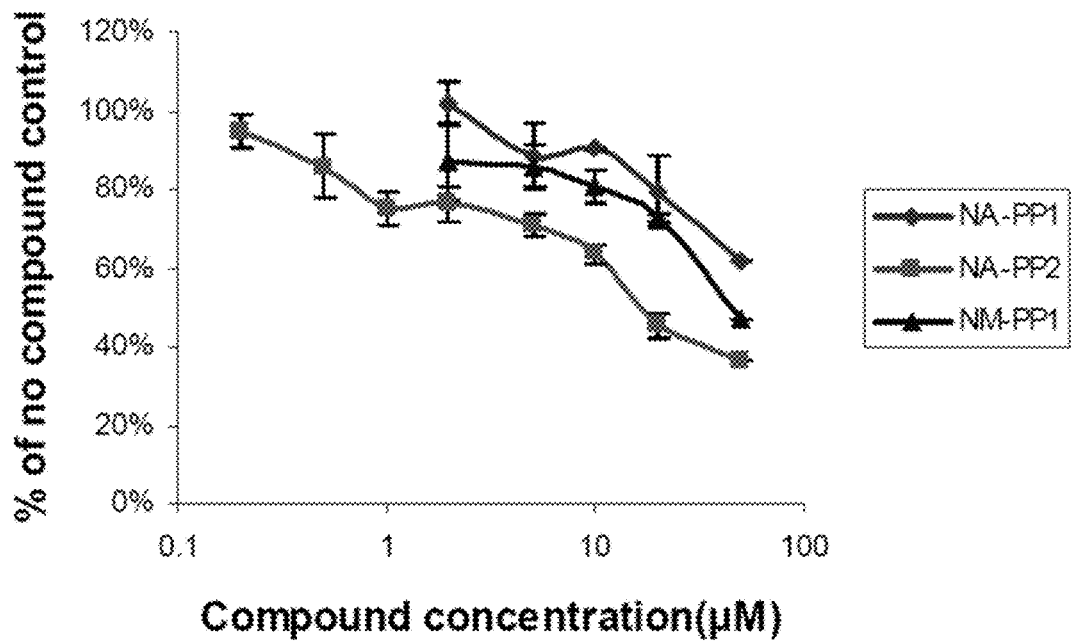

We tested three BKIs for effects on host cell invasion and parasite growth since earlier work on TgCDPK1[14] suggested a key role for this enzyme in *T. gondii* invasion. As shown in FIG. 4, BKIs profoundly reduced *T. gondii* proliferation if added simultaneously with cellular infection (FIG. 4a), and modestly reduced proliferation when added 4 hr after the start of invasion (FIG. 4b). Thus, inhibition of TgCDPK1 activity by BKIs has a stronger effect on invasion than on intracellular growth. This was confirmed by microscopic examination of invasion (see FIGS. 8(a)-8(c) and 9(a)-9(c)) and is consistent with previous observations on the role of TgCDPK1[12,14].

T. gondii expressing CDPK1-GFP, CDPK1(G128M)-GFP, or GFP were mixed with the indicated concentration of NA-PP2 and added to the fibroblast monolayer for 15 min at 4° C. to allow binding (Kafsack et al). The samples were then raised to 37° C. for 4 min to allow invasion. Samples were fixed, washed, and stained with antibody to T. gondii surface antigens (SAG, Argene) to identify extracellular parasites. FIG. 8(a) is a representative image from the untreated CDPK-GFP dataset. Intracellular parasites are marked by asterisks. FIG. 8(b) shows the change in the number of intracellular parasites upon drug treatment. The number of intracellular parasites was determined by subtracting the number of extracellular parasites (SAG+) by the number of total parasites (GFP+) and expressed as a ratio to the number of host cells observed (as measured by DAPI stained nuclei). Each sample was normalized to the untreated control of the same line. FIG. 8(c) shows the data used to derive the graph in panel b. Note that cells expressing the gatekeeper mutant CDPK1(G128M) are less sensitive to the drug. The drug additionally appears to affect adhesion.

T. gondii overexpressing CDPK1-GFP, CDPK1(G128M)-GFP, or GFP were mixed with wild type cells (105 of each) in medium with or without 1 µM NA-PP2. Parasites were allowed to infect fibroblasts on cover slips and grown overnight. Samples were stained with DAPI to identify host and parasite nuclei and vacuoles with 2 or more T. gondii cells (only fully invaded parasites can replicate) were counted. Each vacuole was assessed for GFP expression by the parasites. FIG. 9(a) is a representative set of images of CDPK1(G128M)-GFP mixed with wild type, in the absence of drug. Vacuoles containing multiple GFP-expressing parasites are marked with * and wild type vacuoles are marked with ◀. FIG. 9(b) shows the number of vacuoles with wild type (GFP−) or transfected parasites (GFP+), per host cell nucleus, in the absence and presence of drug for the three cell mixtures. FIG. 9(c) shows Data used to derive the graphs. Note that the parasite line overexpressing CDPK1 (G128M)-GFP was resistant to the effects of 1 µM NA-PP2, as compared to the co-cultured wild type control.

We expect that longer exposure to BKIs would increase the impact of the drug on T. gondii growth, as egressed parasites are prevented from invading new cells. Each BKI was tested for its effects on human fibroblast replication; the $EC_{50}$s were found to be approximately 1000-fold higher (not shown) than those seen in the T. gondii "invasion" assay.

Figure 5A:
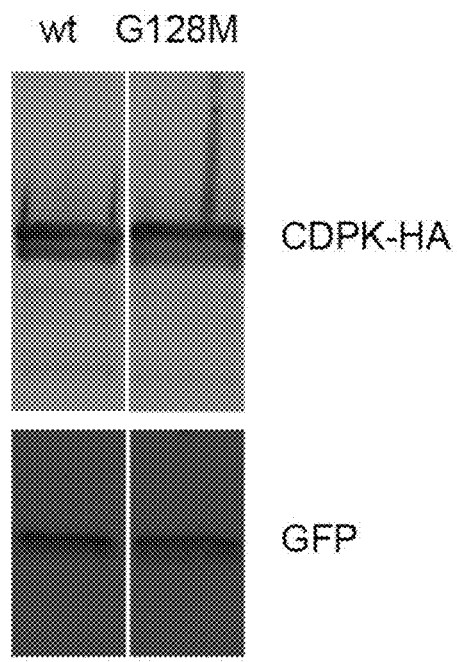
FIGS. 5a-5b are graphical representations demonstrating TgCDPK gatekeeper mutant reduction of sensitivity to BKIs. T. gondii clonal lines expressing HA-tagged versions of TgCDPK1 or a G128M mutant along with GFP and β-galactosidase were generated. Western blot (FIG. 5a) of protein separated on a 10% acrylamide gel and probed with anti-HA. Anti-GFP served as a loading control. Invasion assays were performed with increasing concentrations of BKIs NA-PP2 (FIG. 5b) using the parental cell line and the transfectants additionally expressing wild type TgCDPK1 and TgCDPK1 (G128M). Assays were done in triplicate and mean and standard deviations normalized to the no compound (vehicle alone) control are presented.
Figure 5B:
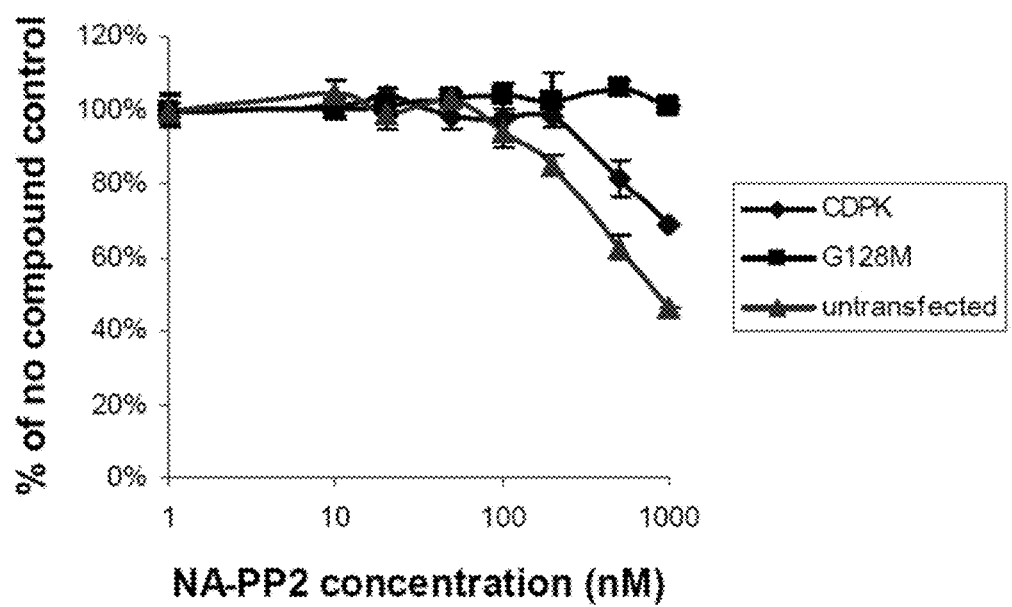
Figure 6:
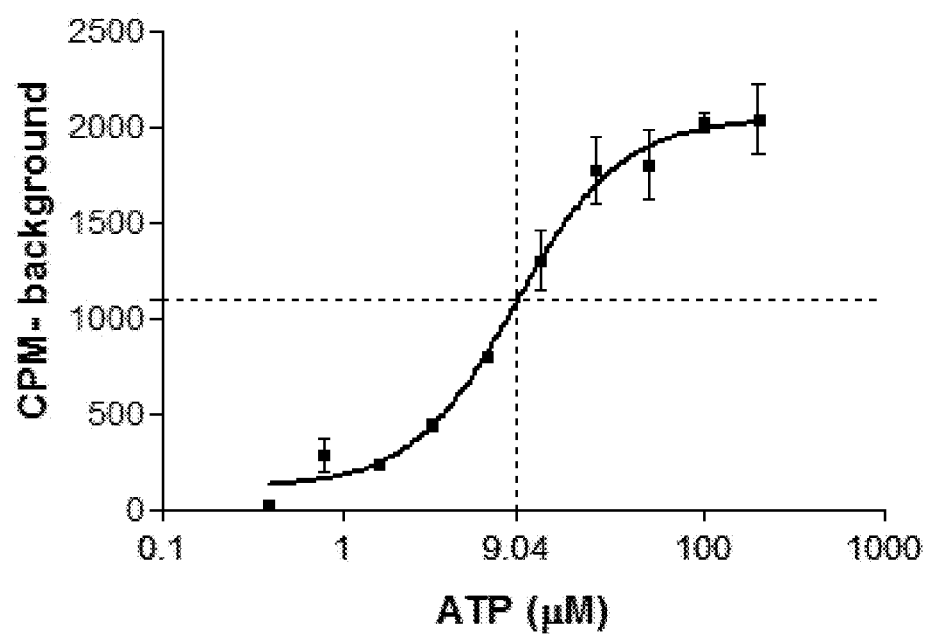
FIG. 6 is a $K_m$ plot of ATP for TgCDPK1 (2 nM) using the SPA assay to measure phosphorylation of a biotinylated peptide substrate by labeled γ-phosphate of ATP after 90 minutes incubation at 30° C.
Figure 7:
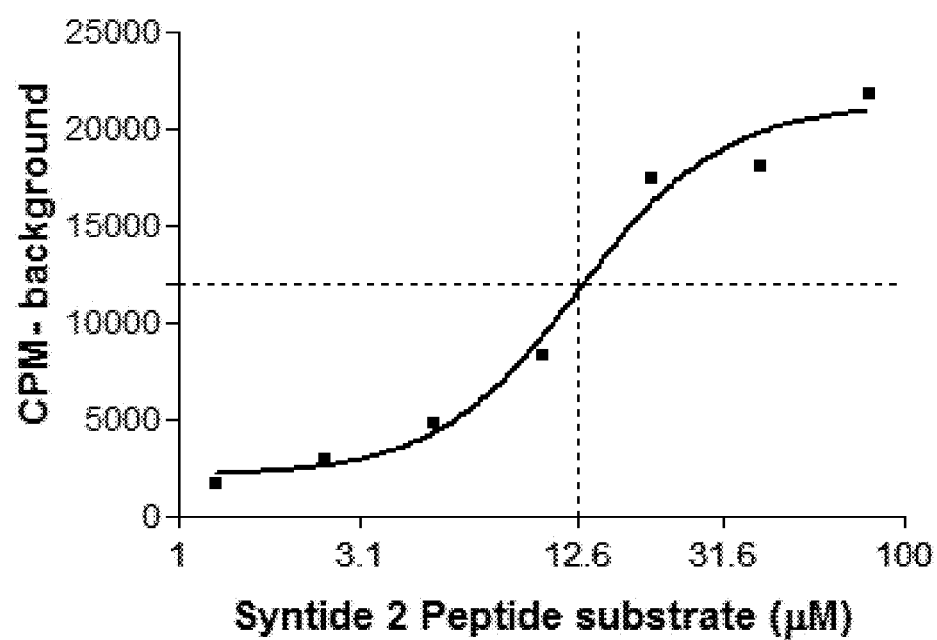
FIG. 7 is a $K_m$ plot of Syntide 2 substrate for TgCDPK1 (2 nM) using the SPA assay to measure phosphorylation of a biotinylated peptide substrate by labeled γ-phosphate of ATP after 90 minutes incubation at 30° C.
Figure 8:
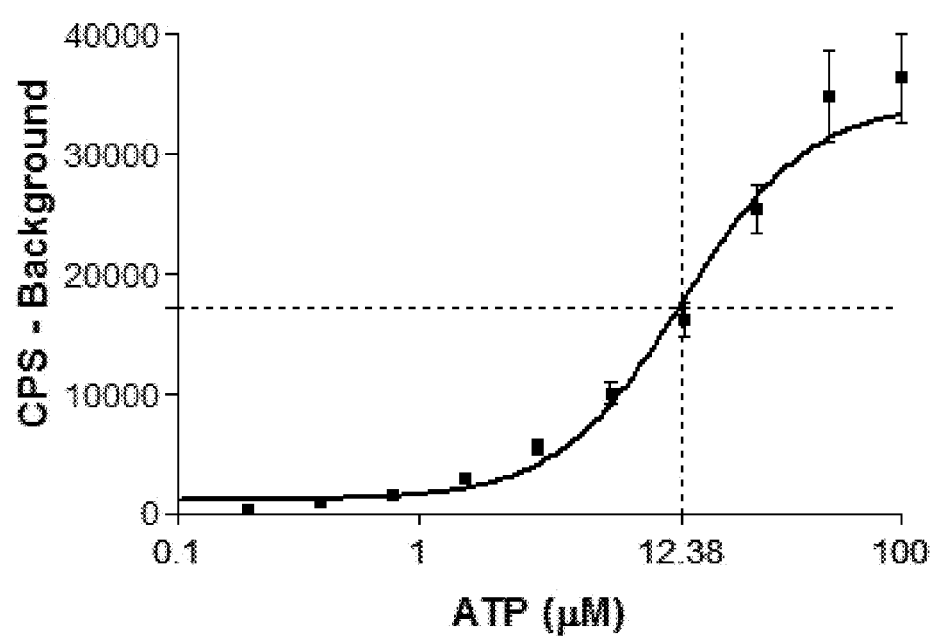
FIG. 8 is a $K_m$ plot of ATP using the luciferase based KinaseGlo assay that measures consumption of ATP after TgCDPK1 (2 nM) phosphorylation of peptide substrate Syntide 2 at 30° C. during a 90 minute reaction time. Remaining ATP in the reaction was measured after addition of KinaseGlo reagent by luminescence light production. Omitting peptide substrate or enzyme led to virtually no consumption of ATP (not shown).
Figure 9:
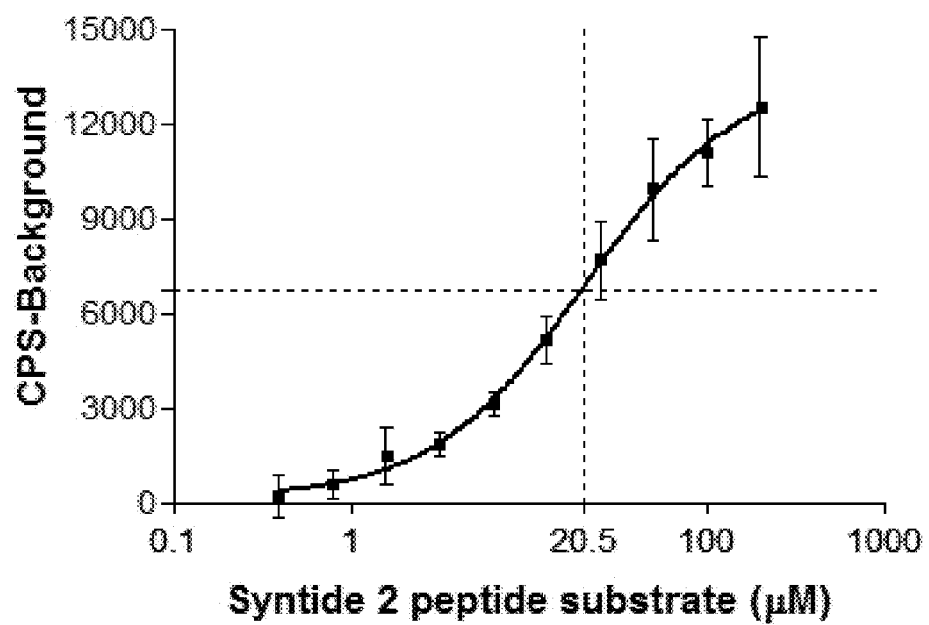
FIG. 9 is a $K_m$ plot of Syntide 2 substrate using the luciferase based KinaseGlo assay as described for FIG. 8.
Figure 10A:
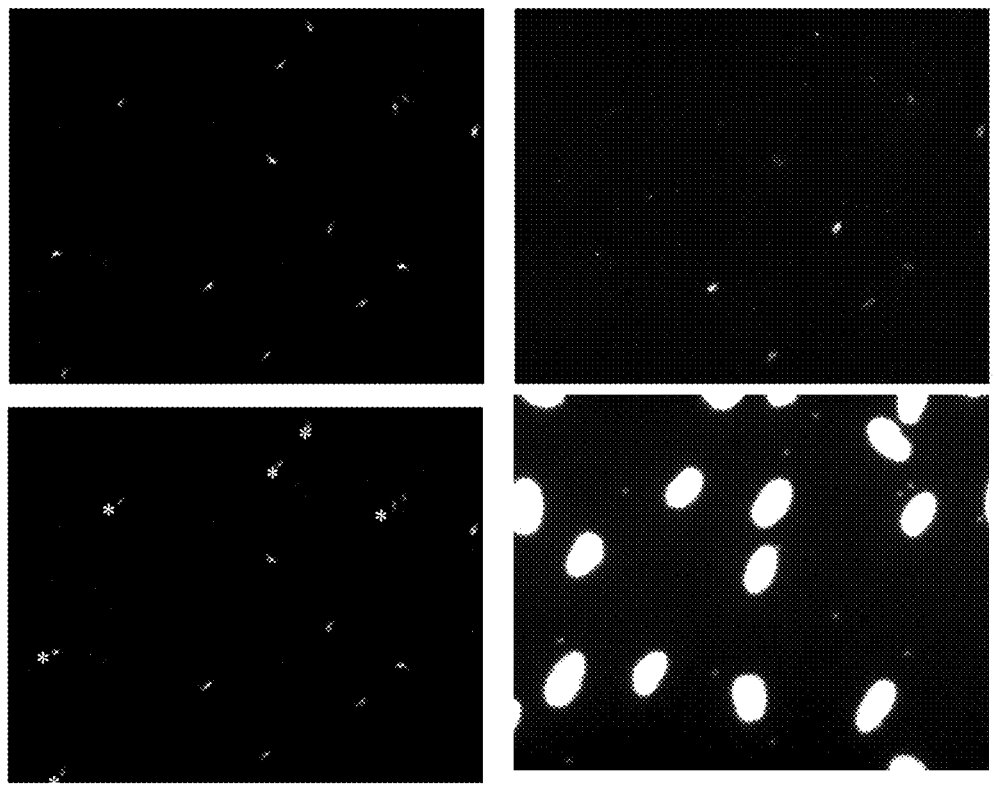
FIG. 10a is a representative image from the untreated CDPK-GFP dataset. Intracellular parasites are marked by asterisks.
Figure 10B:
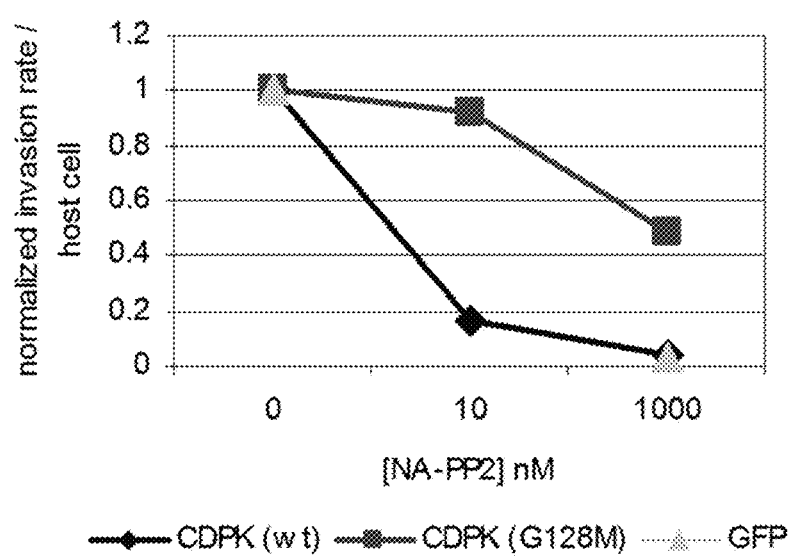
FIG. 10b shows the change in the number of intracellular parasites upon drug treatment. The number of intracellular parasites was determined by subtracting the number of extracellular parasites (SAG+) by the number of total parasites (GFP+) and expressed as a ratio to the number of host cells observed (as measured by DAPI stained nuclei). Each sample was normalized to the untreated control of the same line.
Figure 11A:
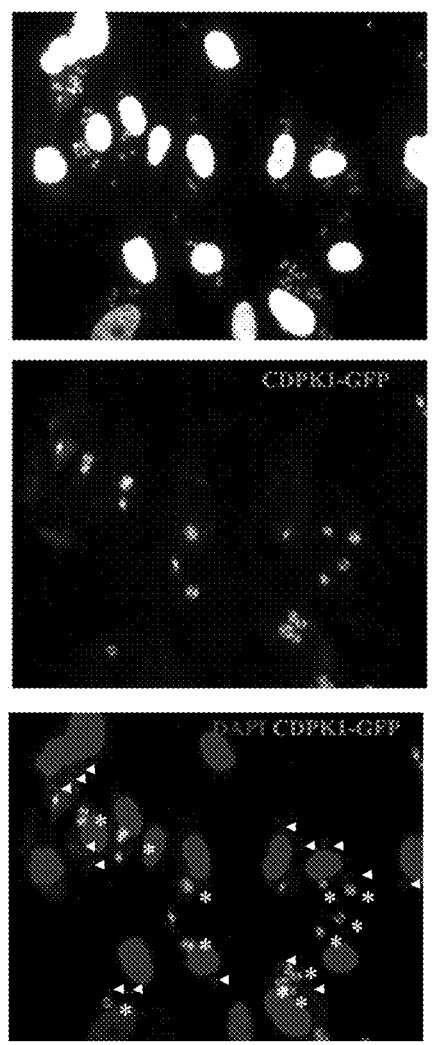
FIG. 11a is a representative set of images of CDPK1 (G128M)-GFP mixed with wild type, in the absence of drug. Vacuoles containing multiple GFP-expressing parasites are marked with * and wild type vacuoles are marked with ◄.
Figure 11B:
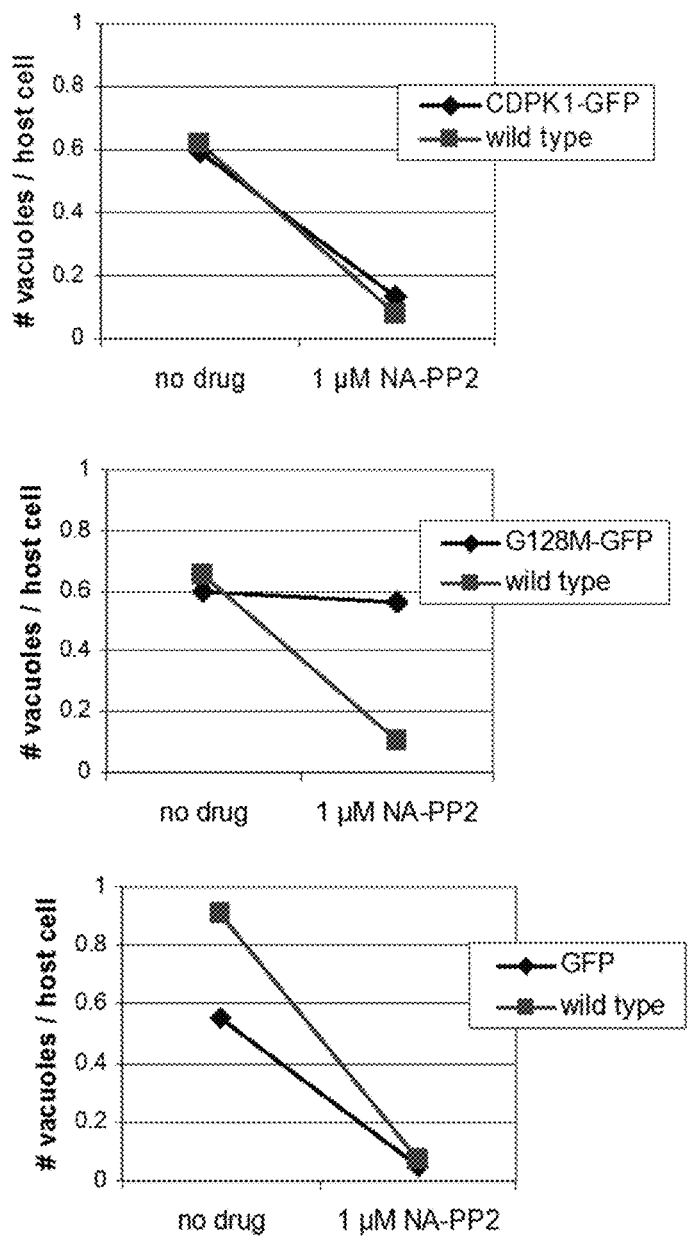
FIG. 11b shows the number of vacuoles with wild type (GFP−) or transfected parasites (GFP+), per host cell nucleus, in the absence and presence of drug for the three cell mixtures.

Biological Example 6 T. gondii Cell Expressing the G128M Gatekeeper Mutant Demonstrate that BKIs Act Through TgCDPK1 In Vivo We transfected the T. gondii cell line with expression plasmids encoding an HA tag fused to the C-terminus of either wild type TgCDPK1 or the G128M gatekeeper mutant. Immunoblot analysis showed that the wild type and G128M mutant TgCDPK1s were expressed to similar levels (FIG. 5a). Compared to the parental cell line, parasites expressing the G128M mutant were relatively resistant to BKIs NA-PP2 (FIG. 5b) and NM-PP1 (data not shown) added prior to invasion. In contrast, parasites overexpressing the wild type TgCDPK1 protein showed only a small shift in resistance. Although NA-PP2 was somewhat less effective against wild-type parasites in this experiment, the results were identical in the relative potency of the inhibitors, in that NA-PP2 was more potent than NM-PP1 in blocking T. gondii invasion, following the potency observed against TgCDPK1 enzyme. Furthermore, in both a microscopic assay of invasion (see FIGS. 8(a)-8(c))[30] and in a mixed cellular infection using wild type and TgCDPK1 (G128M) (see FIGS. 9(a)-9(c)), parasites expressing the gatekeeper mutant were markedly resistant to NA-PP2 while cells expressing either wild type TgCDPK1 or GFP controls were not. These findings demonstrate that BKIs are working primarily through the TgCDPK1 target to prevent T. gondii mammalian cell entry.

We have shown that TgCDPK1 is a promising drug target for the therapy of toxoplasmosis. Its kinase activity is uniquely sensitive to inhibition by BKIs, and BKI treatment in turn blocks entry of the parasite into mammalian cells. Blocking cell entry is important because T. gondii is an obligate intracellular parasite and cannot replicate without invasion. Moreover, these experimental findings address concerns about quantitative differences between enzyme inhibition and cellular effects thereby validating the utility of TgCDPK1 structures in complex with BKIs to drive drug development for toxoplasmosis therapy. The concept of using BKIs for the therapy of toxoplasmosis is bolstered by the fact that BKIs have been used in mouse studies with no demonstration of toxicity or troublesome effects to the animals[27-29]. Thus, BKIs have promise; as a selective drug for toxoplasmosis therapy because they are non-toxic to mammals but prevent cell entry and thus the replication of T. gondii.

Since the structure was determined for the inactive, $Ca^{2+}$-free form of TgCDPK, there may be some concern that this form would not be optimal to guide the design of small molecule inhibitors with improved potency and selectivity. It is apparent from structural and biochemical studies presented here, however, that small molecule inhibitors can still access the ATP-binding site of the $Ca^{2+}$-free conformation of TgCDPK1. Importantly, the structure of the active site near the ATP-binding pocket, particularly in the vicinity of the gatekeeper residue, is not significantly altered between the structures shown here and that of the $Ca^{2+}$-bound enzyme in complex with AMP-PNP (Wemimont et al. submitted for publication, PDB 3hx4). Thus, structure-guided optimization of small molecule inhibitors that target this region is possible using the inactive, $Ca^{2+}$-free form of TgCDPK1.

TgCDPK1 was localized in the cytoplasm, but also found in the nucleus. Some plant CDPKs are also partially localized to the nucleus. In those CDPKs, nuclear localization is mediated by a signal in the junction domain[18], but the T. gondii protein is not homologous in this region and no nuclear localization signal is predicted by standard programs. Since the size of the protein is above the threshold for free diffusion through the nuclear pore, we propose that the protein could bear a non-canonical nuclear localization sequence or piggyback into the nucleus on another protein. As noted earlier, Raymond Hui's group has demonstrated a $Ca^{2+}$-dependent structural rearrangement that repositions the regulatory domain to the opposite side of the catalytic domain (Wernimont et al. submitted for publication, PDB accession number 3hx4). This observation of $Ca^{2+}$-induced structural rearrangement raises the intriguing, but speculative, possibility that $Ca^{2+}$ could modulate localization by revealing or occluding the relevant region of the kinase. In any case, these results raise the possibility that TgCDPK1 phosphorylates specific nuclear proteins in addition to its presumably cytosolic targets involved in gliding motility.

Drug-resistant mutations of the TgCDPK1 gatekeeper to a bulky residue could eventually emerge under selective pressure of BKI therapy. One strategy to suppress the emergence of resistance is the co-administration of two drugs targeting different proteins. As TgCDPK1 is not the target of any existing drug, the development of an anti-TgCDPK1 compound could provide a partner drug for co-administration with another drug. Most transmission of T. gondii is not from person-to-person (although this can occur in pregnancy, transplantation, or transfusion), but rather through zoonotic cycles where drug pressure is not exerted[1]. This suggests that if drug resistance emerges it will largely be confined to the individual, posing little threat to the utility of the drug in other infected persons.

As other apicomplexan pathogens employ CDPK enzymes with a small gatekeeper residue, this work may have broader applicability. For instance, the TgCDPK1 ortholog in Cryptosporidium parvum also has a glycine residue at the gatekeeper position (FIG. 2b), suggesting that BKIs targeting T. gondii could also be effective for the therapy of cryptosporidiosis, another potentially life-threatening infection with poor therapeutics. Other parasite CDPKs have small gatekeeper residues, such as threonine. Indeed, an extended search of all reported human kinase ATP binding motifs found none with a glycine or alanine gatekeeper residue, and about ~20% with threonine[21]. Thus, these findings may have implications in the rational design of anti-apicomplexan CDPK agents devoid of toxic side effects to the host cells.

Biological Example 7 Expression, Purification and Assay of Recombinant Mutant and Wild Type TgCDPK1

TgCDPK1 (GI: 12484153, ToxoDB ID 162.m00001) or its G128M mutant, cloned into pAVA0421, was expressed in BL21*(DE3) E. coli (Invitrogen Corp. Carlsbad, USA) for 72 hours at 20° C. in a LEX Bioreactor (Harbinger Biotechnology & Engineering Corp. Ontario Canada). Cells collected from 2 liters of culture were lysed in 200 ml of 30 mM imidazole, 500 mM NaCl, 25 mM HEPES, 5% glycerol, 0.025% azide, 1 mM TCEP, 10 mM $MgCl_2$, 1 mM AEBSF, pH 7.0 and incubated with Benzonase® (Novagen, USA) for 30 min at room temperature before centrifugation at 14,000 rpm for 75 min and 4° C. Clarified supernatant was loaded onto 5 ml $Ni^{2+}$ HisTrap FF resin columns pre-equilibrated with 30 mM imidazole, 500 mM NaCl, 25 mM HEPES, 5% glycerol, 0.025% azide, 1 mM TCEP. Recombinant histidine-tagged protein was eluted in 220 mM imidazole pH 7.0. Fractions were subsequently separated on AKTA Prime size exclusion columns (HiLoad™ 26/60 Superdex 75™ prep grade) pre-equilibrated 500 mM NaCl, 25 mM HEPES, 5% glycerol, 0.025% azide, 2 mM DTT, pH 7.0. The N terminal hexahistidine tag was removed by 3 C protease cleavage at a 1:50 mg ratio and dialyzed overnight at 4° C. in 200 mM NaCl, 20 mM HEPES, 5% glycerol, 1 mM TCEP, pH 7.0 with final separation on $Ni^{2+}$ Sepharose™ 6 Fast Flow resin. Fractions were analyzed for purity by SDS-polyacrylamide gel electrophoresis and found to be >99% pure.

Two types of kinase assays were employed, an ATP consumption assay and a scintillation proximity assay. ATP consumption kinase assays were performed using a nonradioactive KinaseGlo® luciferase assay (Promega Corp., Madison, Wis., USA). Kinase phosphorylation reactions were performed in a buffered medium containing 20 mM HEPES pH 7.5 (KOH), 0.1% BSA, 10 mM $MgCl_2$, 1 mM EGTA (pH 7.2), plus or minus 2 mM $CaCl_2$[14]. The phosphorylation reaction mixture of 40 µM peptide substrate (Syntide-2, peptide sequence: Pro-Leu-Ala-Arg-Thr-Leu-Ser-Val-Ala-Gly-Leu-Pro-Gly-Lys-Lys (SEQ ID NO: 12)) (GenScript, Piscataway, USA), 19.48 nM of 14 TgCDPK1, 90 to 0.0005 µM serial dilutions of inhibitor in a total volume of 25 µl, was initiated by the addition of 10 µM ATP. The reaction was terminated after 30 minutes incubation at 30° C. by addition of excess EGTA (5 mM final concentration). Internal positive and negative controls were included in each assay run. No activity was detected when the peptide substrate was left out of the reaction mixture. Unused ATP was measured in luminescence based readout as counts per seconds on the Chameleon 425-104 multi-label plate scintillation counter (Hidex, Oy, Turku Finland). A second enzyme assay, based on the scintillation proximity assay, directly measured the attachment of γ-phosphate to peptide substrate. The scintillation proximity assay was used for confirmation of enzymatic characteristics like $K_m$ for ATP and substrate and for confirmation of IC50s of the inhibitors. Phosphorylation of biotinated peptide substrate, (Bio-Syntide-2, American Peptide Company, Inc. Sunnyvale, Calif.) was determined by serial titrations in scintillation proximity assays using streptavidin coated Beads and [γ-$^{33}$P] ATP (PerkinElmer, Boston, USA) as previously described[30].

Biological Example 8 Site-Directed Mutagenesis

Site-directed mutagenesis of the predicted gate keeper glycine residue to methionine was executed with Stratagene kit. PCR amplification of pAVA0421-TgCDPK1 plasmid DNA with page purified primers TgDPKmetS (GGC TAC TTC TAC CTC GTC ATG GAA GTG TAC ACG GGA GGC GAG TTG)(SEQ ID NO: 3) and TgDPKmetAS (CAA CTC GCC TCC CGT GTA CAC TTC CAT GAC GAG GTA GAA GTA GCC)(SEQ ID NO: 4) was carried out at 95° C. (30 seconds), 95° C. (30 seconds), 55° C. (1 minute), 68° C. (6:00 minutes) followed by 68° C. (6:00 minutes) repeated in 16 cycles. Dpn I digested PCR products was transformed into XL10-Gold ultracompetent E. coli cell (Stratagene) with selection on LB agar supplemented with 100 µg/ml ampicillin. Mutant plasmids was recovered with alkaline denaturation method using the QIAGEN plasmid purification kits and verified by nucleotide sequence analysis before transformation into protein expression E. coli strain BL21* (DE3) (Invitrogen Corp. Carlsbad, USA). Induction of expression and purification of mutant TgCDPK1(G128M) in E. coli BL21*(DE3) (Invitrogen Corp. Carlsbad, USA) was previously described[30].

Biological Example 9 Protein Crystallization

Purified TgCDPK1 protein was screened for crystallization leads using a Phoenix crystallization robot (Art Robbins Instruments, Sunnyvale, Calif.) and the JCSG+ Suite sparse matrix crystallization screen (Qiagen, Valencia, Calif.)[31]. A few leads were further optimized by finer grid screening around the initial hit using sitting-drop vapor diffusion at room temperature. Diffraction-quality crystals of native and selenomethionyl-derivatized (SeMet) protein (~18-26 mg/ml) were grown from mother liquor composed of 0.18-0.25 M (di- or tri-) ammonium citrate (pH 6.5-7.0), 22-26% polyethylene glycol (PEG) 3350, and 5 mM dithiothreitol. For inhibitor cocrystals, the crystallization drop was additionally supplemented with a final concentration of 4 mM inhibitor dissolved in dimethylsulfoxide. Thin pointed rods or plates approximately 50-150 μm long typically grew within one week. Crystals were mounted in cryoloops (Hampton Research, Aliso Viejo, Calif.) and directly frozen in liquid nitrogen or were first transferred to a fresh drop of mother liquor containing 10-20% ethylene glycol for, typically, less than 20 seconds prior to freezing. For inhibitor co-crystals, 2-4 mM inhibitor was maintained in the cryoprotection solution.

Biological Example 10 Structure Determination

Crystals of TgCDPK1 were screened at the Stanford Synchrotron Research Lightsource (SSRL) on beamline 9-2 using the SSRL automated mounting (SAM) system[32]. All data were collected at 100 K on a MarMosaic-325 CCD detector using the Blu-Ice software package[33]. Single-wavelength anomalous dispersion (SAD) data were collected from a single crystal of SeMet protein[34] at a wavelength of 0.9792 Å, the Se peak wavelength determined from a fluorescence scan of the crystal. All other datasets were also collected at or near the Se peak wavelength; apo (native) at 0.9792 Å, NA-PP2 complex (SeMet) at 0.9791 Å, and NM-PP1 complex (native) at 0.9795 Å. All data were processed using HKL2000[35]. Data collection statistics are presented in Table 1.

Initially, we were able to solve the structure of the kinase domain by molecular replacement (MR) using MOLREP[36] or Phaser[37] with the structure of the kinase domain of the orthologous protein from *Cryptosporidium parvum* (PDB ID 3dfa) as the search model. Although representing nearly two-thirds of the total protein content of the asymmetric unit, the resulting MR phases were not good enough to allow tracing of the novel calmodulin-like regulatory domain; despite significant effort at manual improvement of the MR solution and attempts to additionally place various calmodulin-like domains of very low sequence identity by MR. We thus turned to using SeMet protein in order to obtain experimental phase information to solve the complete structure. Using a SeMet SAD dataset, SOLVE[38] located 12 of 14 expected selenium atoms and produced initial phases to approximately 2.7 Å. The resulting phases were input into RESOLVE[38] using the RESOLVE_BUILD script (http://www.solve.lanl.gov/Resolve/html_resolve_manual/resolve_build.txt) for density modification and automated model building. The model was significantly improved by bootstrapping the results back into the RESOLVE_BUILD script two more times for rebuilding. Iterated manual model building and restrained refinement continued using Coot[39] and REFMAC5[40]. This model was transferred into the other datasets by MR using Phaser followed by a few rounds of model building and improvement in Coot and refinement with REFMAC5. The improved models were then submitted to ARP/wARP[41] for rebuilding using and continued cycles of building and restrained refinement ensued. Based on the initial, unbiased difference density present in the active sites of the cocrystal structures, it was immediately clear that the inhibitors had bound the enzyme. Ideal coordinates and refinement restraints for use in REFMAC5 and Coot for these ligands were created with the PRODRG server[42]. In the final cycles of refinement, perturbational displacement of the protein was described by a multi-group translation/libration/screw (TLS) model, with group boundaries suggested by the TLSMD server[43,44], that were refined prior to restrained refinement. Model quality was monitored and validated using Coot and MolProbity[45]. All final models display good Ramachandran statistics. For the final apo model, 97.6% of the residues are in favored regions of the Ramachandran plot with no outliers. The NA-PP2 complex model has 98.9% of residues in favored regions with no outliers and the NM-PP1 complex has 98.5% of residues in favored regions and Gly420 is an outlier. The CCP4 suite of programs[46,47] was used for all steps from data preparation through refinement. Model refinement statistics are presented in Table 1. Structural figures were created and rendered using PyMOL (Delano Scientific, Palo Alto, Calif.).

Atomic coordinates and structure factors have been deposited in the Protein Data Bank[48]. (http://www.pdb.org) with accession numbers 3i79 (apo), 3i7c (NA-PP2 complex), and 3i7b (NM-PP1 complex).

Biological Example 11 T. Gondii Growth/Invasion Assay and Expression of TgCDPK1-HA and TgCDPK1(G128M)

The TgCDPK1 coding region or its G128M mutant were amplified from the *E. coli* expression plasmids using primers to insert 3 adenine nucleotides before the start codon and mutate the second codon from glycine to alanine, allowing for enhanced expression in the parasite[49]. The products were inserted into the BglII/AvrII site of *T. gondii* transfection vector pCAT-GFP[50] or pHx-ACP-YFP[51] to yield in frame fusions with GFP or YFP, under the control of the tubA or Gra1 promoters respectively. Plasmids encoding HA-tagged versions of the molecules were created by replacing the YFP sequence with one that specifies four C-terminal HA epitopes. Linearized constructs were electroporated into RH strain *T. gondii* according to standard methods[52] and transfected parasites were used to infect human foreskin fibroblasts growing on cover slips. In some cases a *T. gondii* strain expressing β-galactosidase under control of the TubA promoter, as well as GFP under control of the GRA1 promoter, was employed (kind gift of Gustavo Arrizabalaga)[53].

Immunofluorescence analysis was performed as described[52] using rabbit anti-GFP (Invitrogen Corp. Carlsbad, USA) followed by goat anti-rabbit IgG coupled to Texas red (Southern Biotechnology). DNA was stained with DAPI. Samples were viewed on a Nikon Eclipse E600 using a Plan Apo 60×1.4 na objective.

*T. gondii* cells expressing β-galactosidase were grown in the presence of serial concentrations of BKIs. All assays were performed in triplicate and the mean and standard deviation are presented unless otherwise noted. In the growth assays, $10^3$ parasites were allowed to infect a confluent layer of fibroblasts in each well of a 96 well plate. After 4 hr, drug was added to the indicated final concentration. To assess effects on invasion, compounds were added prior to the addition of the parasites. The cultures were incubated for 20 hours at 37° C. and β-galactosidase was assayed as earlier described using chlorophenol red O-galactopyranose (CPRG, Sigma) as substrate[54]. Plates were developed at 37° C. for 4 hr (growth), 8 hr (invasion), or 10 hr (CDPK expression) and absorbance was measured at 595 nm on a Versamax microplate reader.

Cytotoxicity was analyzed by adding medium containing up to 50 μM of each compound to a confluent layer of fibroblasts; plates were incubated at 37° C. for 4 days. Alamar blue (Alamar Biosciences, Sacramento, Calif.) was added to each well and developed over night.

Biological Example 12 CpCDPK1

Figure 12:
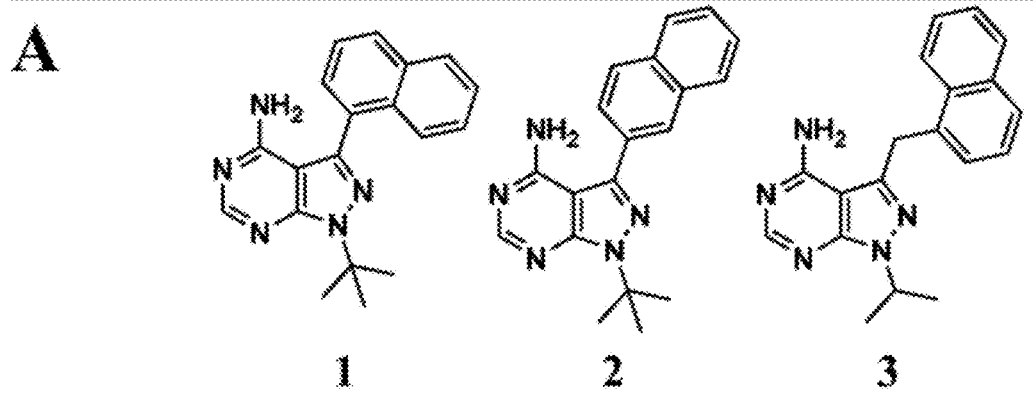
FIG. 12. (A) TgCDPK1 and CpCDPK1 inhibitors 1-3. $IC_{50}$ values shown are the average of three assays±(SEM). (B) C. parvum parasite numbers (Y axis) present after 24 hours of infection of human intestinal cells (HCT-8) with C. parvum sporozoites (1:1 ratio HCT-8 cells:C. parvum sporozoites) in the presence of varying concentrations of inhibitors 1-3. (left graph) Cultures were exposed to each inhibitor at the time of infection. (right graph) Cultures were exposed to each inhibitor 1 hour after infection.
Figure 12:
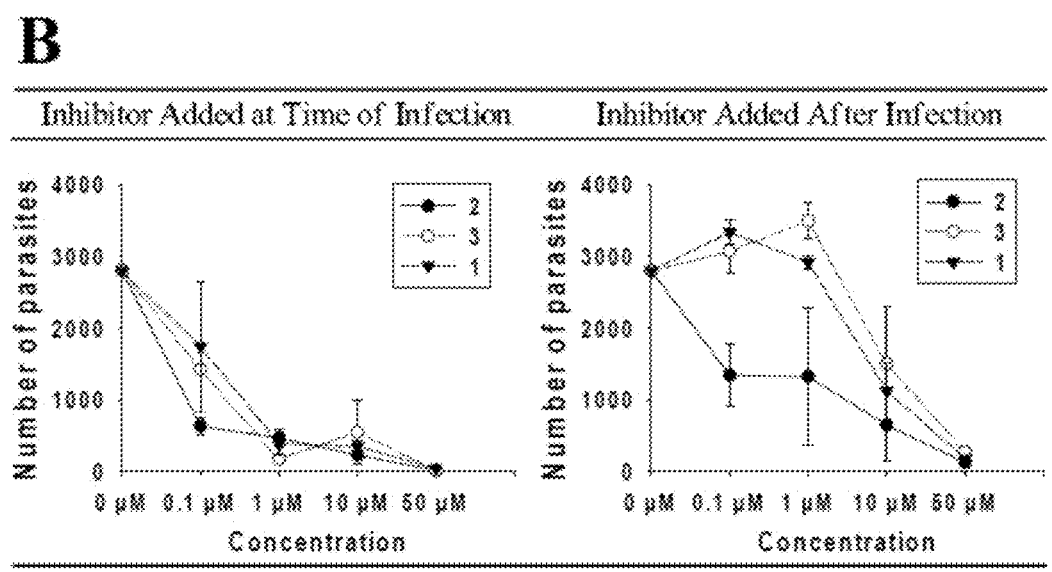

The sensitivity of CpCDPK1 to compounds 1-3 was determined with an in vitro activity assay (FIG. 12A). Both TgCDPK1 and CpCDPK1 show similar levels of inhibition by these compounds, with analog 2 as the most potent inhibitor. Next, the phenotypic response of C. parvum cells to compounds 1-3 was tested by measuring the amount of parasites present after 18 hours of infection of human intestinal cells (HCT-8) with C. parvum sporozoites in the presence of varying concentrations of these inhibitors. These assays were performed under two different sets of conditions: one in which the sporozoites were exposed to each inhibitor at the time of infection (FIG. 12B, left graph) and a second assay in which the sporozoites were exposed to each inhibitor one hour after infection (FIG. 12B, right graph). For each assay, the HCT-8 cells were lysed after 24 hours of culture and the amount of C. parvum rRNA was quantified using reverse transcriptase real time PCR. The amount of C. parvum rRNA was then related to the number of parasites using standard curves developed separately. Importantly, reduced levels of C. parvum sporozoites are observed with increasing concentrations of compounds 1-3 under both sets of conditions, with analogue 2 demonstrating the most potent effect on parasite proliferation similar to analogue 2's superior potency against CpCDPK1. The potencies of the pyrazolopyrimidine inhibitors were dramatically increased when they were added at the time of sporozoite infection rather than one hour after C. parvum had been incubated with HCT-8 host cells. This suggests that these inhibitors affect an early stage of C. parvum host cell invasion, which is similar to their effects on T. gondii invasion. In all cases, the relative ability of each inhibitor to block C. parvum proliferation correlates with its in vitro activity against CpCDPK1.

Based on the ability of pyrazolopyrimidine inhibitors to block T. gondii and C. parvum host cell invasion, compounds were further optimized based on this scaffold as potent and selective dual inhibitors of TgCDPK1 and CpCDPK1. Two synthetic routes were used to generate derivatives that contain varying substituents at the 1- and 3-positions of the pyrazolopyrimidine core as described in the preceding synthetic examples.

Inhibition of TgCDPK1 and CpCDPK1 was determined using a luminescent kinase assay which measures ATP depletion in the presence of the Syntide 2 peptide substrate (KinaseGlo). (U.S. Provisional Patent Application No. 61/299,286, and reference 9) Similar to TgCDPK1, exogenous calcium was necessary for CpCDPK1 to possess maximum catalytic activity (data not shown). Notably, both kinases were tested at the same ATP concentration which allows direct comparison of inhibitor potencies due to these enzymes possessing similar $K_m$s for this cofactor. (20)

Encouraged by the similar potency of inhibitor 3 against TgCDPK1 ($IC_{50}$=150±20 nM) and CpCDPK1 ($IC_{50}$=130±40 nM), pyrazolopyrimidine analogues that contain a naphthylmethylene group at the 3-position and various alkyl substituents at the 1-position were tested for their ability to inhibit both kinases (Table 3).

TABLE 3

In vitro activities of 3, 5a-5r against TgCDPK1 and CpCDPK1. Values shown are the average of three assays ± (SEM).

| R1= | Compound Number | CpCDPK1 $IC_{50}$ (nM) | TgCDPK1 $IC_{50}$ (nM) |
|---|---|---|---|
| isopropyl | 3 | 150 (20) | 130 (40) |
| —CH₃ | 5a | 410 (90) | 460 (240) |
| propargyl | 5b | 130 (30) | 990 (180) |
| —CH₂C(O)NH₂ | 5c | 2000 (400) | 1900 (100) |
| tert-butyl | 5d | 140 (50) | 31 (10) |
| benzyl | 5e | >3000 | 1800 (700) |
| cyclohexylmethyl | 5f | 2400 (300) | 1000 (300) |
| (piperidin-4-yl)methyl | 5g | 56 (16) | 59 (18) |
| piperidin-4-yl | 5h | 9.0 (0.5) | 15 (5) |

TABLE 3-continued

In vitro activities of 3, 5a-5r against TgCDPK1 and CpCDPK1.
Values shown are the average of three assays ± (SEM).

| R1= | Compound Number | CpCDPK1 IC$_{50}$ (nM) | TgCDPK1 IC$_{50}$ (nM) |
|---|---|---|---|
| (4-piperidinyl-ethyl, NH) | 5i | 34 (7) | 52 (17) |
| (4-(N-acetyl)piperidinyl-methyl) | 5j | 100 (10) | 91 (26) |
| (4-(N-acetyl)piperidinyl) | 5k | 360 (80) | 210 (20) |
| (4-(N-acetyl)piperidinyl-ethyl) | 5l | 180 (60) | 100 (10) |
| (4-(N-ethyl)piperidinyl-methyl) | 5m | 50 (7) | 36 (3) |
| (4-(N-ethyl)piperidinyl) | 5n | 160 (30) | 270 (30) |
| (4-(N-ethyl)piperidinyl-ethyl) | 5o | 100 (10) | 93 (4) |
| (4-(N-methanesulfonyl)piperidinyl-methyl) | 5p | 75 (18) | 54 (9) |
| (4-(N-methanesulfonyl)piperidinyl) | 5q | 700 (240) | 560 (10) |
| (4-(N-methanesulfonyl)piperidinyl-ethyl) | 5r | 200 (80) | 120 (30) |

Derivatives containing smaller alkyl groups (5a-5c) were found to have reduced potencies for both enzymes relative to 3. Furthermore, a significant increase in potency was not observed for inhibitors that contain bulkier substituents at the 1-position (5d-5f). However, the reduced potencies of compounds with larger substituents is not due to a size restriction in the ATP-binding pocket because derivatives that contain a basic piperidine group (derivatives 5g-5i) were found to be significantly more potent inhibitors of TgCDPK1 and CpCDPK1. Notably, compound 5h, which contains a methylene linkage between the pyrazolopyrimidine core and piperidine ring, has an 8-fold and 16-fold lower IC$_{50}$ for CpCDPK1 and TgCDPK1 than parent compound 3, respectively. Derivatization of 5g-5i with an acetyl (5j-5l), ethyl (5m-5o), or sulfonylmethyl (5p-5r) group reduces the enhanced potency that the piperidine substituent confers, with only modified versions of piperidine 5g showing similar inhibition as the parent compound. Notably, most compounds from this series are near equipotent inhibitors of both TgCDPK1 and CpCDPK1, demonstrating the overall similarity in this region of the ATP-binding pockets of both kinases.

To further probe the hydrophobic pocket adjacent to the gatekeeper residue (Hydrophobic Pocket II) a series of analogs that contain an isopropyl group at the 1-position and various aryl substituents at the 3-position were tested for their ability to inhibit both kinases (Table 4, compounds 7a-7ab). While many of these inhibitors were not expected to be as selective for CpCDPK1 and TgCDPK1 over mammalian kinases as naphthylmethylene derivatives 3 and 5a-5r, we felt that this series of compounds would provide insight into which substituents can be accommodated in this region. As shown in Table 4, a large number of aryl substituents are accommodated by both kinases. Almost all of the compounds from this series have an IC$_{50}$ less than 1 µM, with several inhibitors demonstrating very high potency against both enzymes. Inhibitors that contain aryl rings that are mono-substituted with smaller substituents at the meta (7b, 7e, 7g, and 7ab) or para positions (7a, 7d, 7f, and 7j) are accommodated in the ATP-binding sites of both kinases but are more potent against TgCDPK1 than CpCDPK1. However, neither kinase is inhibited by compounds that contain aryl rings that are meta-substituted with larger substituents at the 3-position (7y, 7z, and 7aa). Analogues that contain meta- and para-substituted aryl rings (7c, 7i, 7k, and 7m) are potent against both enzymes and show reduced selectivity for TgCDPK1. Consistent with this observation, pyrazolopyrimidine derivatives that contain a 2-naphthyl (7p-7r) or quinoline group (7t) are potent inhibitors of both enzymes. However, bicyclic substituents that are not planar show reduced potency (7u-7w). In general, most inhibitors from this series are 2- to 12-fold selective for TgCDPK1 over CpCDPK1. However, several compounds (for example, compounds 7l, 7q and 7t) are equipotent or slightly selective for CpCDPK1. This fact demonstrates that while the ATP-binding pockets of both kinases are very similar they are not identical.

TABLE 4

*In vitro* activities of 7a-5ab against TgCDPK1 and CpCDPK1. Values shown are the average of three assays ± (SEM).

| R1= | Compound Number | CpCDPK1 IC$_{50}$ (nM) | TgCDPK1 IC$_{50}$ (nM) |
|---|---|---|---|
| 4-Cl-phenyl | 7a | 220 (70) | 18 (4) |
| 3-Cl-phenyl | 7b | 120 (40) | 20 (6) |
| 3,4-diCl-phenyl | 7c | 13 (3) | 4.0 (1.0) |
| 4-iPr-phenyl | 7d | 210 (60) | 48 (14) |
| 3-iPr-phenyl | 7e | 59 (18) | 14 (5) |
| 4-Me-phenyl | 7f | 87 (25) | 13 (4) |
| 3-Me-phenyl | 7g | 114 (33) | 19 (9) |
| 3,4-diMe-phenyl | 7h | 22 (6) | 9.0 (3.0) |
| 3-Me-4-F-phenyl | 7i | 53 (9) | 9.0 (2.0) |
| 4-OMe-phenyl | 7j | 410 (130) | 40 (18) |
| 3,4-diOMe-phenyl | 7k | 170 (20) | 37 (11) |
| 3,4,5-triOMe-phenyl | 7l | 93 (7) | 420 (70) |
| 3-Me-4-OMe-phenyl | 7m | 17 (5) | 5.0 (1.0) |
| 3-acetyl-phenyl | 7n | 2100 (200) | 1500 (400) |

TABLE 4-continued

In vitro activities of 7a-5ab against TgCDPK1 and CpCDPK1.
Values shown are the average of three assays ± (SEM).

| R1= | Compound Number | CpCDPK1 IC$_{50}$ (nM) | TgCDPK1 IC$_{50}$ (nM) |
|---|---|---|---|
| 1-naphthyl | 7o | 620 (130) | 330 (80) |
| 2-naphthyl | 7p | 10 (3) | 5.0 (1.0) |
| 6-OMe-2-naphthyl | 7q | 5.0 (1.0) | 6.0 (1.0) |
| 6-OEt-2-naphthyl | 7r | 12 (4) | 5.0 (1.0) |
| 6-MeO-2-naphthyl (3-isomer) | 7s | 600 (100) | 900 (210) |
| 3-quinolinyl | 7t | 20 (4) | 24 (6) |
| benzo[1,3]dioxol-5-yl | 7u | 310 (20) | 45 (14) |
| 2,3-dihydrobenzo[1,4]dioxin-6-yl | 7v | 990 (70) | 180 (20) |
| chroman-6-yl | 7w | 110 (10) | 17 (6) |
| dibenzothiophen-3-yl | 7x | >3000 | >3000 |
| 3-benzyl-phenyl | 7y | 1400 (200) | 320 (90) |
| 3-Ph-phenyl | 7z | >3000 | 2200 (200) |
| 3-OBn-phenyl | 7aa | 1900 (400) | 1100 (200) |
| 3-SMe-phenyl | 7ab | 120 (30) | 56 (17) |

Key to the use of pyrazolopyrimidine-based kinase inhibitors as anti-parasitic agents is the potential to selectively inhibit TgCDPK1 and CpCDPK1 over mammalian kinases. To determine the potency of these compounds against mammalian kinases, a subset of inhibitors were tested against the tyrosine kinases SRC and ABL. We felt that these two kinases would be a suitable counter-screen because they both contain the most permissive gatekeeper residue found in mammalian kinases (threonine) and the pyrazolopyrimidine core was originally developed as a kinase inhibitor scaffold against SRC-family kinases. (21) As shown in Table 5, most of the pyrazolopyrimidines tested have limited activity against SRC and ABL. Consistent with earlier studies, previously-characterized "bumped" inhibitors 1 and 3 do not potently inhibit SRC or ABL kinase. Despite the increased activity of analogue 2 against TgCDPK1 and CpCDPK1, this compound only weakly inhibits SRC and ABL (IC$_{50}$>1 µM).

TABLE 5

Activities of various inhibitors against human kinases and human cell lines. Values shown are the average of three assays ± (SEM).

| Compound Number | IC$_{50}$ (μM) | | GI$_{50}$ (μM) | | | |
|---|---|---|---|---|---|---|
| | Abl | Src | CRL8155 | HL60 | HCC2998 | SF539 |
| 1 | >20 | 1.3 (0.2) | >10 | >10 | >10 | >10 |
| 2 | 6.0 (1.5) | 1.9 (0.2) | >10 | >10 | >10 | >10 |
| 3 | 7.9 (2.0) | 8.8 (0.8) | >10 | >10 | >10 | >10 |
| 5d | 7.7 (3.8) | 2.2 (0.5) | >10 | >10 | >10 | >10 |
| 5h | >20 | >20 | >10 | >10 | >10 | >10 |
| 5m | 0.36 (.05) | 0.21 (.06) | — | — | — | — |
| 5n | >20 | >20 | >10 | >10 | >10 | >10 |
| 5o | >20 | 4.2 (2.1) | — | — | — | — |
| 5p | 0.090 (.019) | 0.36 (.07) | >10 | >10 | >10 | >10 |
| 7c | 0.07 (.02) | 0.035 (.008) | >10 | >10 | >10 | >10 |
| 7e | 0.20 (.02) | 0.22 (.02) | — | — | — | — |
| 7p | 0.075 (.024) | 0.065 (.009) | >10 | >10 | ~10 | >10 |
| 7q | 0.82 (.04) | 0.77 (0.10) | >10 | >10 | >10 | >10 |
| 7r | 1.7 (0.5) | 0.20 (.03) | — | — | — | — |
| 7t | 0.86 (.06) | 2.7 (0.6) | >10 | >10 | >10 | >10 |

As expected, pyrazolopyrimidine inhibitors that contain smaller aryl groups at the 3-position (7c and 7e) are less selective for both parasite kinases due to their increased potency against SRC and ABL. However, analogues that contain a substituted naphthyl (7q and 7r) or quinoline (7t) substituent at the 3-position are much more selective due the increased size of these functional groups. Presumably, the larger threonine gatekeeper residues of SRC and ABL restrict access of these inhibitors to Hydrophobic Pocket II. While the substituent at the 3-position is the major contributor to inhibitor selectivity, substitution at the 1-position affects the potency of these compounds against TgCDPK1 and CpCDPK1 relative to SRC and ABL. For example, piperidine-containing analogues 5m and 5p are less selective for TgCDPK1 and CpCDPK1 than parent compound 1. However, several analogues restore the high selectivity of this class of compounds, with secondary piperidine 5h demonstrating over 1000-fold selectivity for the CDPKs. To test the overall toxicity of our pyrazolopyrimidines inhibitors, they were assayed for their ability to inhibit the growth of four human cell lines (Table 5): glioma derived (SF539), human lymphocyte (CRL8155), human promyelocytic leukemia (HL-60) and colorectal carcinoma (HC 2998). For all four cell lines tested, the inhibitors showed little or no growth inhibition at the highest concentration tested (10 μM).

Figure 13:
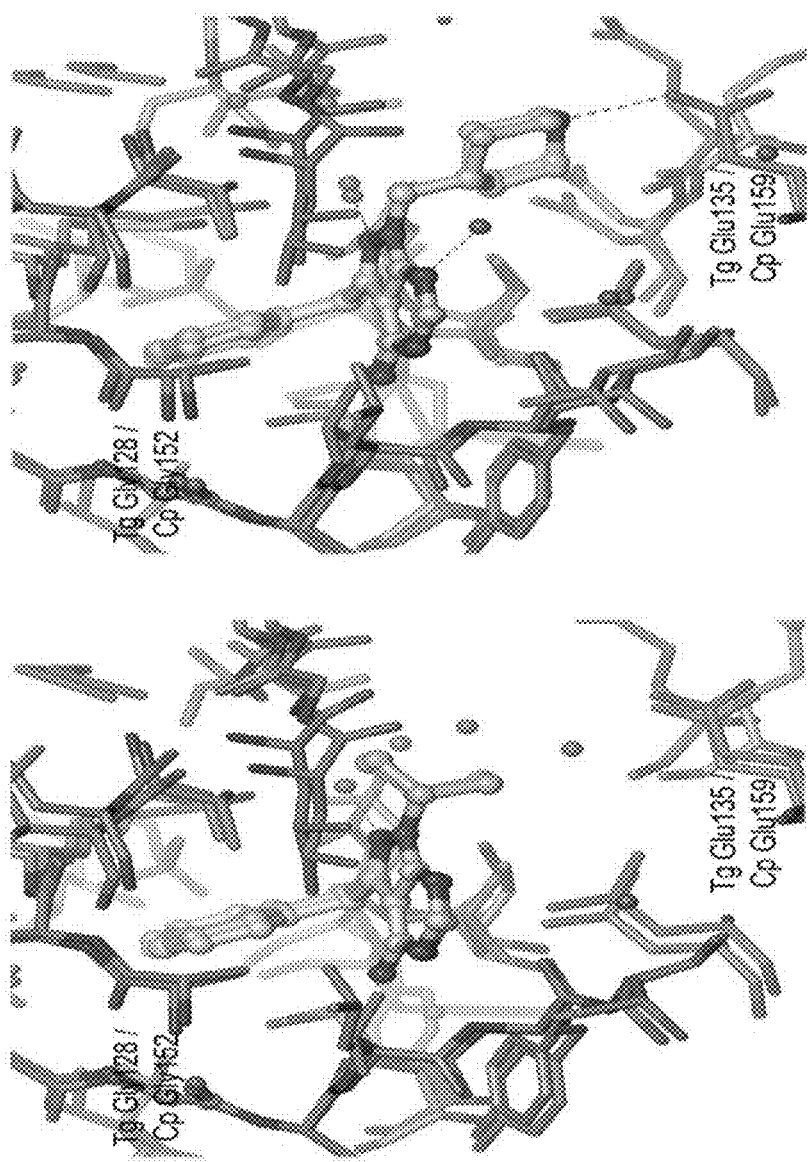
FIG. 13 is a graphical representation of the crystal structure of (left panel) Superposition of the active sites of TgCDPK1-3 (green sticks and light green ball-and-sticks) and CpCDPK1-3 (orange sticks and ball-and-sticks) complexes (Pdb entries 3i7b and 3ncg). (right panel) Overlay of the TgCDPK1·5h and CpCDPK1·5h complexes (Pdb entries 3n51 and 3mwu). Only residues within 6 Å of the bound inhibitors are shown and the unique glycine gatekeeper residue is shown as ball-and-sticks.
Figure 15:
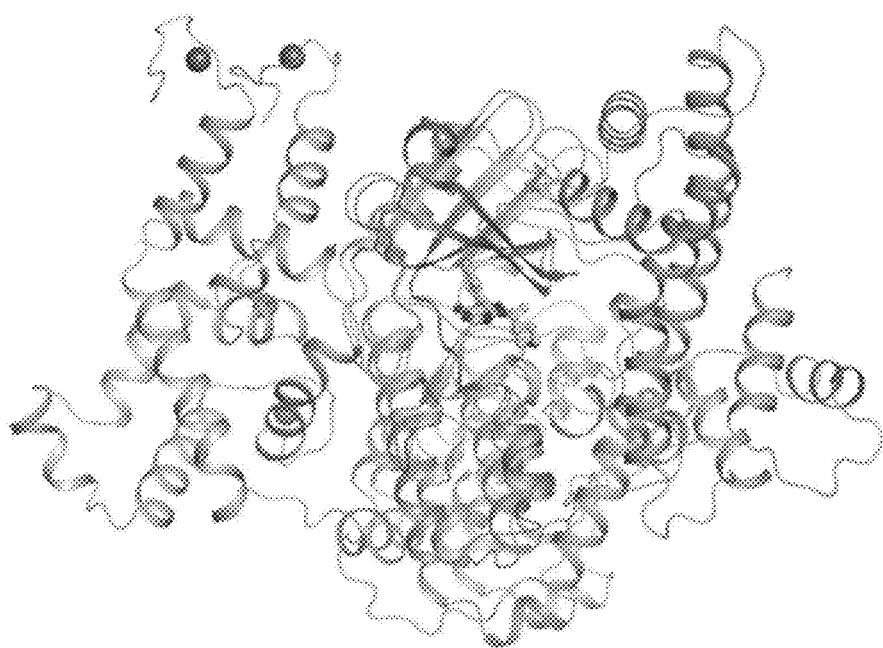
FIG. 15 shows the structure of calcium-free, inactive CDPK1 versus calcium bound, activated CDPK1. The kinase domains of calcium-free TgCDPK1 (green cartoon) and calcium-bound CpCDPK1 (orange cartoon) are superimposed to highlight the dramatic conformational change that occurs in the CDPK activating domain (CAD) upon calcium activation. In the absence of calcium, access to the active site (marked by bound inhibitors shown as ball-and-sticks) by protein substrates is occluded by the CAD (cyan cartoon). Upon binding calcium (gray spheres), the CAD (beige cartoon) is repositioned to the opposite surface of the kinase domain so that protein substrates may now bind. Despite this large conformational rearrangement of the CAD, the active site of the kinase domain in the vicinity of the bound inhibitors remains largely unchanged.
Figure 16:
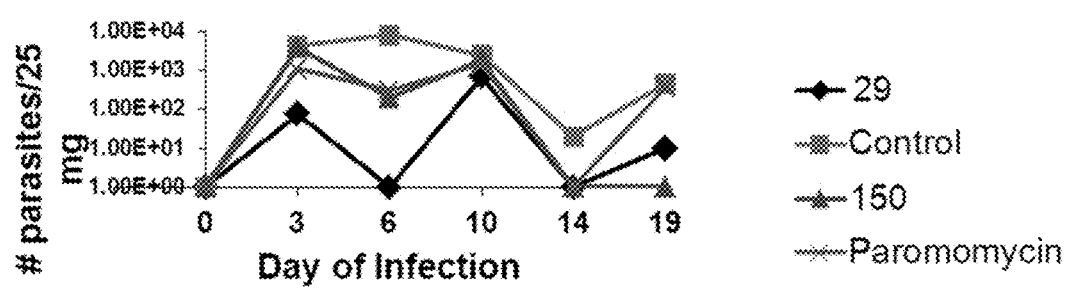
FIG. 16 shows activities of previously-described kinase inhibitors in the immunosuppressed mouse C. parvum model. SCID-beige C57BL6 mice were infected with 106 C. parvum oocysts on day 0. They were treated with once a day oral gavage with compound 29 (50 mg/kg/day, N=3), compound 150 (50 mg/kg/day, N=4), or Paromomycin (2 g/kg/day, N=3) on days 3-7 and 10-14. Infected controls (N=4) were gavaged with vehicle (3% tween80/7% EtOH/90% saline) alone. Shown are mean of the parasite numbers detected in 25 mg of stool from each mouse, by qRT-PCR. At the end of treatment, parasites were not detected in the drug treated groups, but the parasite burden quickly rebounded in the Paromomycin group, slowly with 29, and not with 150.

We have previously reported crystal structures of inhibitors 2 and 3 bound to TgCDPK1. (U.S. Provisional Patent Application No. 61/299,286, and reference 9) Similar to the structures of other pyrazolopyrimidines bound to tyrosine kinases, these inhibitors occupy the ATP-binding cleft of TgCDPK1. The pyrazolopyrimidine scaffold superimposes with the purine ring of ATP, with the exocyclic amine and nitrogen at the 5-position forming hydrogen-bonding interactions with the hinge region. In addition, the glycine gatekeeper residue of TgCDPK1 allows bulky substituents at the 3-position unobstructed access to Hydrophobic Pocket II. Replacing glycine with a larger amino acid at this position clearly creates a steric clash with the 2-naphthyl and 1-naphthylmethylene groups of inhibitors 2 and 3, respectively. (8) Based on the similar sensitivities of TgCDPK1 and CpCDPK1 to pyrazolopyrimidines we predicted that inhibitors of this class would bind in a similar orientation in both enzymes. The structure of compound 3 bound to CpCDPK1 shows that this is indeed the case (FIG. 13a). Superposition of the active sites of TgCDPK1 and CpCDPK1 bound to 3 shows that the inhibitor has an identical mode of binding in both kinases. Furthermore, all of the residues surrounding the inhibitor are nearly superimposable, which is remarkable because TgCDPK1 is in the calcium-free inactive conformation while CpCDPK1 is in the calcium-bound active conformation (FIG. 15).

It is therefore clear that the inhibitors are able to bind the ATP-binding site of CDPK1 whether it is active or not.

While structures of both enzymes bound to 2 and 3 provided direct insight into how large substituents can be accommodated at the 3-position, we were interested in further exploring how substitution at the 1-position affects the potencies of these inhibitors. Structures of inhibitor 5h bound to TgCDPK1 and CpCDPK1 show how increased potency can be obtained. While the pyrazolopyrimidine cores and 3-position substituents of inhibitors 3 and 5h make identical contacts with both enzymes, the piperidine ring of 5h forms a salt bridge with a glutamate residue that lines the ATP-binding cleft. Importantly, this interaction is present in the structures of 5h bound to both TgCDPK1 and CpCDPK1. Presumably, alkylation, acetylation or sulfonylation of the piperidine ring disrupts this interaction and accounts for the lower potency of compounds 5j-5r. Furthermore, the reduced potency of 5h against SRC and ABL demonstrates that these kinases cannot form a similar interaction.

In conclusion, we have demonstrated that selective pyrazolopyrimidine kinase inhibitors are indeed potent inhibitors of CpCDPK1 and that they are able to inhibit an early stage of C. parvum cell invasion. This class of compounds have a similar effect on the ability of T. gondii to invade human fibroblast cells. (U.S. Provisional Patent Application No. 61/299,286, and reference 9) Based on these results, a diverse panel of pyrazolopyrimidine analogues was generated and their activities against CpCDPK1 and TgCDPK1 were determined. By exploiting a unique sequence and structural variation in the ATP-binding clefts of TgCDPK1 and TgCDPK1 potent dual inhibitors of these enzymes were obtained. Importantly, many of these inhibitors show minimal inhibition of the tyrosine kinases SRC and ABL and are not toxic to human cell lines. Additionally, other derivatives of pyrazolopyrimidine may be useful and such variations on the compounds discussed herein are contemplated. For example, the potency and selectivity of these compounds and optimization their PK/ADME/Tox properties. Furthermore, optimized inhibitors may be able to be used to inhibit *C. parvum* host cell invasion.

Biological Example 13 TgCDPK1 and CpCDPK1 IC$_{50}$ Data

The following compounds were tested for inhibition of TgCDPK1 and CpCDPK1 (Table 8) according to the preceding methods:

TABLE 8

TgCDPK1 and CpCDPK1 IC$_{50}$ data

| Cmpd # | IC$_{50}$ (µM) TgCDPK1 | CpCDPK1 |
|---|---|---|
| 1 | 1.619 | >3.0 |
| 2 | 0.015 | 0.059 |
| 3 | 0.128 | 0.147 |
| 5a | 0.458 | 0.413 |
| 5b | 0.086 | 0.13 |
| 5c | 1.923 | 2.038 |
| 5d | 0.031 | 0.144 |
| 5e | 1.848 | >3.0 |
| 5f | 0.946 | 2.416 |
| 5g | 0.059 | 0.056 |
| 5h | 0.015 | 0.009 |
| 5i | 0.052 | 0.034 |
| 5j | 0.091 | 0.103 |
| 5k | 0.208 | 0.36 |
| 5l | 0.104 | 0.179 |
| 5m | 0.036 | 0.05 |
| 5n | 0.269 | 0.163 |
| 5o | 0.093 | 0.103 |
| 5p | 0.054 | 0.075 |
| 5q | 0.563 | 0.691 |
| 5r | 0.117 | 0.194 |
| 7a | 0.018 | 0.216 |
| 7b | 0.02 | 0.115 |
| 7c | 0.004 | 0.013 |
| 7d | 0.048 | 0.213 |
| 7e | 0.014 | 0.059 |
| 7f | 0.013 | 0.087 |
| 7g | 0.019 | 0.114 |
| 7h | 0.009 | 0.022 |
| 7i | 0.009 | 0.053 |
| 7j | 0.04 | 0.41 |
| 7k | 0.037 | 0.173 |
| 7l | 0.42 | 0.093 |
| 7m | 0.005 | 0.017 |
| 7n | 1.483 | 2.068 |
| 7o | 0.326 | 0.62 |
| 7p | 0.005 | 0.01 |
| 7q | 0.006 | 0.005 |
| 7r | 0.005 | 0.012 |
| 7s | 0.863 | 0.591 |
| 7t | 0.024 | 0.02 |
| 7u | 0.045 | 0.312 |
| 7v | 0.181 | 0.984 |
| 7w | 0.017 | 0.11 |
| 7x | >3.0 | >3.0 |
| 7y | 0.322 | 1.402 |
| 7z | 2.229 | >3.0 |
| 7aa | 1.058 | 1.894 |
| 7ab | 0.056 | 0.121 |
| 8 | 0.0048 | 0.0078 |
| 9 | 0.04 | 0.032 |
| 10 | 0.078 | 0.0336 |
| 11 | 0.0103 | 0.0573 |
| 12 | 0.0032 | 0.0532 |
| 13 | 0.553 | 0.894 |
| 14 | 0.627 | 0.953 |
| 15 | 0.149 | 0.265 |
| 16 | 0.9609 | >3.0 |
| 17 | 0.98 | 1.554 |
| 18 | >3.0 | >3.0 |
| 19 | 0.0638 | 0.3705 |

TABLE 8-continued

TgCDPK1 and CpCDPK1 IC$_{50}$ data

| Cmpd # | IC$_{50}$ (µM) TgCDPK1 | CpCDPK1 |
|---|---|---|
| 20 | 0.0036 | 0.003 |
| 21 | >3.0 | >3.0 |
| 22 | 1.142 | >3.0 |
| 23 | >3.0 | >3.0 |
| 24 | 0.0119 | 0.0704 |
| 25 | 0.0038 | 0.0073 |
| 26 | 0.0091 | 0.0162 |
| 27 | 0.0569 | 0.6231 |
| 28 | 0.0049 | 0.0023 |
| 29 | 0.0038 | 0.0035 |
| 30 | 0.1144 | 0.0837 |
| 31 | 0.1168 | 0.0936 |
| 32 | 0.0038 | 0.0051 |
| 33 | 0.0026 | 0.0046 |
| 34 | 0.0023 | 0.0021 |
| 35 | 0.0037 | 0.0044 |
| 36 | 0.003 | 0.0032 |
| 37 | 0.0013 | 0.0008 |
| 38 | 0.0007 | 0.0006 |
| 39 | 0.0007 | 0.0004 |
| 40 | 0.0008 | 0.0497 |
| 41 | 0.0006 | 0.0041 |
| 42 | 0.0009 | 0.054 |
| 43 | 0.0054 | 0.244 |
| 44 | 0.0037 | 0.0067 |
| 45 | 0.015 | 0.092 |
| 46 | 0.0106 | 0.1017 |
| 47 | 0.0055 | 0.2717 |
| 48 | 0.1366 | 1.5858 |
| 49 | 0.0186 | 0.2102 |
| 50 | 0.0522 | 1.0316 |
| 51 | 0.0159 | 0.2624 |
| 52 | 0.0043 | 0.3728 |
| 53 | 0.012 | 0.2723 |
| 54 | 0.0159 | 0.1471 |
| 55 | 0.0163 | 0.0307 |
| 56 | 0.004 | 0.1052 |
| 57 | 0.01 | 0.0134 |
| 58 | 0.1357 | 0.5877 |
| 59 | 0.0997 | 0.8319 |
| 60 | 0.0666 | 0.9289 |
| 61 | 0.0684 | 0.9269 |
| 62 | 0.0409 | 0.6918 |
| 63 | 0.0462 | 0.4168 |
| 64 | 0.1429 | 0.9285 |
| 65 | 0.1706 | 1.1576 |
| 66 | 0.1777 | 2.0183 |
| 67 | 0.1963 | 0.8222 |
| 68 | >3 | >3 |
| 69 | 0.0046 | 0.0107 |
| 70 | 0.0042 | 0.0022 |
| 71 | 0.0049 | 0.0053 |
| 72 | 0.0249 | 0.0123 |

Biological Example 14 Tyrosine Kinase IC$_{50}$ Data

The following compounds were tested for inhibition of human tyrosine kinases SrcKD, Src3D, AblKD, Abl3D, HckKD (Table 9) according to the preceding methods:

TABLE 9

Tyrosine Kinase IC$_{50}$ data

| Cmpd # | IC$_{50}$ (µM) | | | | |
|---|---|---|---|---|---|
| | SrcKD | Src3D | AblKD | Abl3D | HckKD |
| 1 | 1.3 | | >20.0 | | |
| 2 | 1.9 | | 6 | | |

TABLE 9-continued

Tyrosine Kinase IC$_{50}$ data

| | IC$_{50}$ (µM) | | | | |
|---|---|---|---|---|---|
| Cmpd # | SrcKD | Src3D | AblKD | Abl3D | HckKD |
| 3 | 8.8 | | 7.9 | | 1.382 |
| 5d | 2.2 | | 7.7 | | |
| 5h | >20.0 | | >20.0 | | >10.0 |
| 5m | 0.21 | | 0.36 | | |
| 5n | >20.0 | | >20.0 | | |
| 5o | 4.2 | | >20.0 | | |
| 5p | 0.36 | | 0.09 | | |
| 7c | 0.035 | | 0.07 | | |
| 7e | 0.22 | | 0.2 | | |
| 7p | 0.065 | | 0.075 | | |
| 7q | 0.77 | 0.576 | 0.82 | | 0.375 |
| 7r | 0.2 | 0.549 | 1.7 | | 0.218 |
| 7t | 0.2 | | 1.7 | | |
| 9 | | 0.686 | | 2.01 | |
| 11 | 0.475 | 0.628 | 2.36 | | 0.541 |
| 12 | 0.298 | 0.307 | 0.838 | | 0.244 |
| 20 | | 0.294 | | 0.238 | |
| 24 | | 1.45 | | 0.353 | |
| 25 | | 5.02 | | 0.969 | |
| 26 | | 1.242 | | 0.304 | |
| 28 | >20.0 | | >20.0 | | >10.0 |
| 29 | >20.0 | | >20.0 | | >10.0 |
| 30 | >20.0 | | >20.0 | | |
| 32 | >10.0 | | >10.0 | | >10.0 |
| 33 | >10.0 | | >10.0 | | >10.0 |
| 34 | 3.063 | | >10.0 | | 1.613 |
| 35 | >10.0 | | >10.0 | | >10.0 |
| 36 | >10.0 | | >10.0 | | >10.0 |
| 37 | 1.759 | | >10.0 | | |
| 38 | 0.375 | | 0.497 | | |
| 39 | 1.551 | | >10.0 | | |
| 40 | 0.038 | 0.043 | 0.316 | | |
| 41 | 0.199 | | 0.675 | | |
| 42 | | 0.784 | | 1.68 | |
| 43 | 0.263 | | 1.153 | | |
| 44 | >10.0 | | 7.34 | | |
| 45 | >10.0 | | 7.326 | | |
| 48 | | 0.8832 | | 1.701 | |
| 49 | | 0.1118 | | 0.0333 | |
| 50 | | 0.1966 | | 1.073 | |
| 51 | | 0.4003 | | 1.798 | |
| 52 | | 0.1067 | | 1.267 | |
| 53 | | 0.1911 | | 1.23 | |
| 54 | | 0.1254 | | 0.194 | |
| 55 | | 0.897 | | 0.6492 | |
| 57 | | >10 | | >10 | |
| 68 | | >10 | | >10 | |
| 69 | | 3.9 | | >10 | |
| 70 | | 2.38 | | 4.79 | |
| 71 | | 6.09 | | >10 | |
| 72 | | >10 | | 6.35 | |
| 83 | | >10 | | 4.159 | |
| 84 | | 1.287 | | 0.0862 | |
| 85 | | 0.0948 | | 0.403 | |
| 90 | | | | 0.094 | |
| 91 | | | | 0.01 | |
| 92 | >10 | | | ~10 | |
| 94 | >10 | | | 0.554 | |
| 99 | >10 | | >10 | | |
| 118 | >10 | | >10 | | |
| 120 | >10 | | >10 | | |
| 123 | >10 | | >10 | | |
| 124 | 3.78 | | 7.845 | | |
| 132 | 0.1773 | | 2.943 | | |
| 134 | 0.5796 | | 1.636 | | |
| 135 | 2.01 | | 4.861 | | |
| 137 | 2.21 | | 8.040 | | |
| 138 | 5.02 | | | | |
| 139 | 0.5210 | | 1.589 | | |
| 140 | 0.1286 | | 0.6356 | | |
| 142 | 2.10 | | | | |
| 143 | 4.13 | | | | |
| 144 | >10 | | 5.982 | | |
| 145 | >10 | | >10 | | |
| 146 | 0.0366 | | 0.172 | | |
| 148 | 5.58 | | | | |
| 149 | 8.68 | | | | |
| 150 | >10 | | >3 | | |

Biological Example 15 Expression, Purification and *P. falciparum* Enzyme Activity Assays Recombinant PfCDPK1 and PfCDPK4 proteins were expressed in *E. coli* (Rosetta Oxford strain) and lysed in 25 mM HEPES (pH 7.0), 500 mM NaCl, 500 glycerol, 0.500 CHAPS, 30 mMv imidazole, 1 mMv TCEP, 250 µg/ml AEBSF, 0.025% azide, and 2.5 U/mL benzonase nuclease (Novagen). Soluble recombinant enzymes were purified as earlier described by Ojo et al. (23), which is incorporated by reference herein in its entirety. A luminescence assay that measures the depletion of ATP in the presence of the peptide substrate, Syntide 2 (PLARTLSVAGLPGKK) (24,9), was used to determine the catalytic activity of these enzymes. Assays were performed with 10 µM ATP, 40 µM Syntide-2, and 6.6 nM or 22 nM of PfCDPK1 and PfCDPK4, respectively, in 20 mM HEPES (pH 7.5), 0.1% BSA (w/v), 10 mM MgCl$_2$, 1 mM EGTA, with or without 2 mM CaCl$_2$. The BKI compound library previously described by Murphy et al. (24), which is incorporated by reference herein in its entirety, was tested at serial concentrations between 3 µM and 1 nM.

Biological Example 16 PfCDPK4 Binding Mode Modeling

The kinase domain of PfCDPK4 was modeled by the I-TASSER server (25,26) using structures of TgCDPK1 available in the Protein Data Bank as a template. Subsequent docking of Compound 29 into the active site of this model was carried out using QXP/FLO (27) (version +0602). Compound 29 was initially placed in the active site of PfCDPK4 by SSM superposition (28) of an in-house TgCDPK1:Compound 29 co-crystal structure (PDB citation pending). The binding pocket was defined as all residues within 10 Å of the roughly-placed inhibitor. Protein atoms were fixed with the exception of sidechain atoms that project into the binding pocket. The two H-bonds between the pyrazolopyrimidine inhibitor scaffold and the hinge region of the kinase, which are conserved in most ATP/ATP-homolog:kinase complexes, were restrained. The interaction between the nitrogen of the R2 piperidine and the sidechain of Glu154 was also restrained because we see this interaction in >15 co-crystal structures of TgCDPK1/CpCDPK1 with BKIs containing the methylpiperidine R2 substituent (24). Docking of Compound 29 was subsequently carried out using 1100 cycles of Metropolis Monte Carlo conformational searching followed by energy minimization. The 25 lowest energy binding modes were visually inspected and favorable conformations were selected.

Biological Example 17 *P. berghei* Maintenance and Genetic Modification

The *P. berghei* ANKA wild type clone 2.34 and the transgenic lines derived from it were maintained in Theiler's Original (TO) or Swiss Webster outbred mice and infections monitored on Giemsa-stained blood films. The cdpk4⁻ mutant clone and its complementation with *P. berghei* cdpk4 were described previously by Billker et al., which is incorporated by reference herein in its entirety. A transfection vector for complementing the cdpk4⁻ mutant with Pfcdpk4 was generated by replacing the *P. berghei* sequence in plasmid p150 with a Pfcdpk4 sequence amplified by PCR from *P. falciparum* 3D7 gametocyte cDNA as an NheI-ApaI restriction fragment, placing it in frame with a carboxy terminal 2× myc epitope tag, a 3'UTR and terminator derived from the *P. berghei* dhfr/ts gene. Following verification of the Pfcdpk4 sequence, the plasmid was linearized in a unique HpaI site within the cdpk4 5' intergenic region and transfected into *P. berghei* cdpk4' using established protocols (29). Homologous insertion of the complementation vector into the upstream intergenic region of the cdpk4 mutant placed Pfcdpk4 under the control of the endogenous *P. berghei* promoter. Transgenic clones were genotyped by diagnostic PCR followed by Southern blot analysis.

Biological Example 18 Phenotypic Analysis of *P. berghei* Gametocytes Expressing PfCDPK4-2x-myc and Sensitivity to Compound 29

Expression of CDPK4-2x-myc proteins was verified by western blot analysis of mixed asexual parasite and gametocytes purified from peripheral blood of infected mice by ammonium chloride lysis. Parasites were suspended and lysed in SDS loading buffer containing 0.1 M DTT. Protein blots were probed with anti-myc mouse monoclonal antibody 9E10 (Sigma) at 1:2000 dilution. To assess the effect of complementation, exflagellation was quantified 3 to 4 days post infection by adding 4 µl of blood from a superficial tail vein to 150 µl exflagellation medium (RPMI1640 containing 25 mM HEPES (Sigma), 10% FCS, 100 µM xanthurenic acid, pH 7.5). Between 15 and 18 minutes after activation the number of exflagellating microgametocytes was counted in a haemocytometer and the red blood cell (RBC) count determined. The percentage of RBCs containing microgametocytes was assessed on Giemsa-stained blood smears and the number of exflagellations per 100 microgametocytes was then calculated. Ookinetes formation was analysed in-vitro largely as described (30), by culturing gametocyte-infected mouse blood in exflagellation medium for 24 h at 19° C. Conversion from macrogametocytes to ookinetes was assessed by staining live cultures with Cy3-conjugated monoclonal antibody 13.1 against the macrogamete/ookinete surface marker P28. The conversion rate was determined as the number of banana shaped ookinetes as a percentage of the total number of P28 expressing cells. For the experiments monitoring exflagellation after compound administration, mice bearing *P. berghei* gametocytes expressing PfCDPK4-2x-myc were treated with 50 mg/kg i.p. of BKI-2 or NA-PP2 or vehicle (90% saline 7% EtOH 3% DMSO), bled at the time points noted in FIG. 17c, exflagellation events determined as above, and compound concentration in the blood determined by quantitative liquid chromatography/mass spectrometry.

Biological Example 19 *P. berghei* Transmission Experiments

Mice were injected i.p. with drug or vehicle 3 days after an infection had been initiated with ~10⁶ *P. berghei* ANKA parasites constitutively expressing GFP (31). After 30 minutes treated mice were anaesthetized by i.p. injection of a mixture of ketamine (Ketalar®, 80 mg/kg) and xylazine (Rompun®, 8 mg/kg) and exposed to 25 female *A. stephensi* mosquitoes. After 5 days midguts were dissected, imaged using a fluorescence microscope and oocysts quantified.

Biological Example 20 *P. falciparum* Transmission Experiments

*P. falciparum* strain NF54 parasites were cultured in RPMI 1640 supplemented with 50 µM hypoxanthine and 10% A+ human serum. Cultures were started at 0.5% and grown for 16 days with daily media changes. Beginning on day 14 exflagellation was monitored. On Day 16, all cultures were pooled and re divided into 4 flasks to which BKIs were added for 30 minutes at 50 nM, 100 nM, 300 nM, 1 µM and 3 µM with one flask as a vehicle-only control and NA-PP2 flasks with 50 nM, 300 nM, and 3 µM. A wet mount was taken to check exflagellation and monitored beginning at 10 minutes and observed until 25 minutes had elapsed. Each flask of culture was fed to approximately 150 4 day old *A. stephensi* mosquitoes for 20 minutes. Ten days post feed ~50 mosquitoes from each cage was checked for midgut oocyst infection. On day 14 remaining mosquitoes in each cage were dissected and pooled to check for salivary gland sporozoites.

Figure 17A:
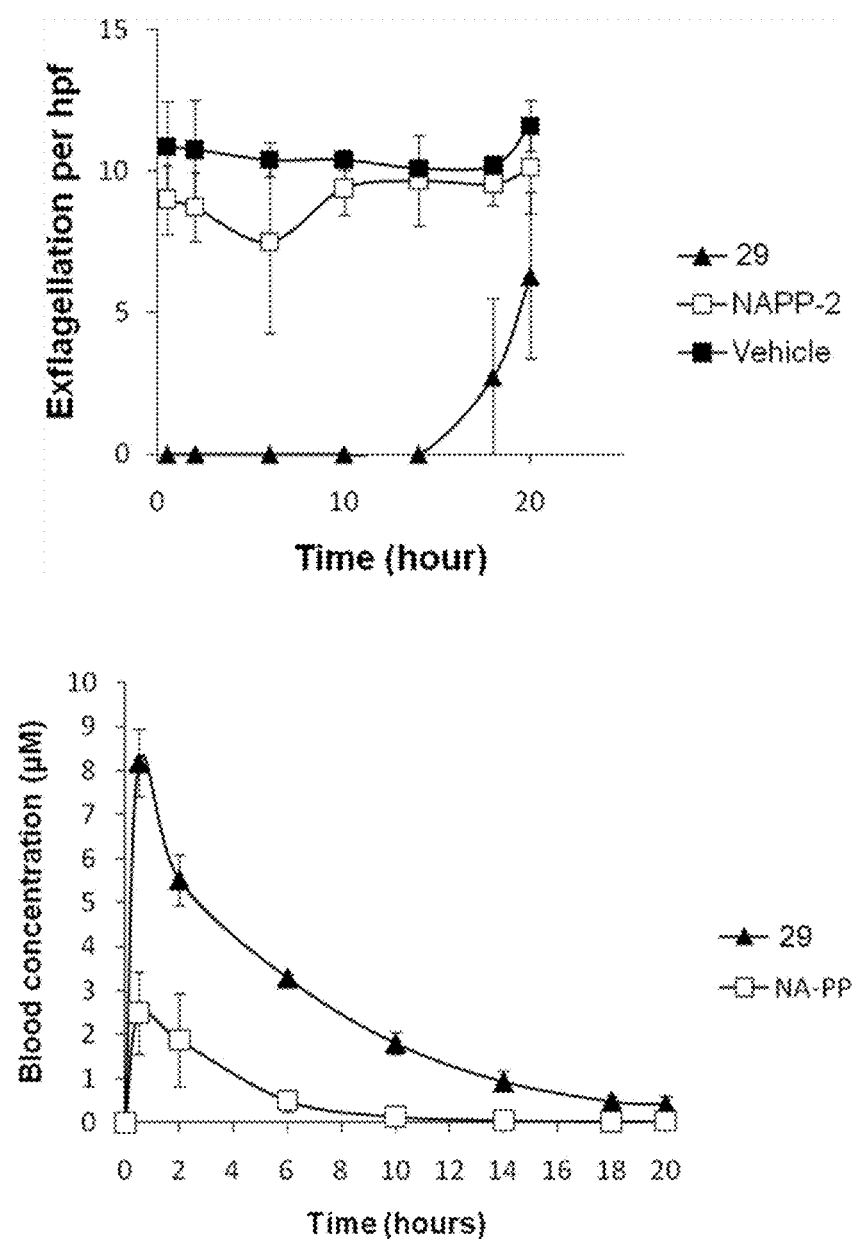
FIGS. 17a-17d are graphical representations demonstrating the blocking effects of Compound 29 on exflagellation of P. berghei and P. falciparum. For exflagellation blocking activities of Compound 29 in mouse blood (FIG. 17a), mice were infected with P. berghei expressing PfCDPK4-2x-myc, and treated i.p. with 50 mg/kg Compound 29 or NA-PP2 or vehicle control. Plots show the average number of exflagellation events per high powered field (error bars are standard error of the mean) and mouse blood Compound 29 or NA-PP2 concentration per time point. There was complete suppression of male gametocyte differentiation to exflagellating units for 14 hours in the presence of Compound 29 relative to NA-PP2 treated or untreated controls. Data are representative of three experiments. For in vitro studies (FIG. 17b), Compound 29's effects on exflagellation of *P. berghei* WT and *P. berghei* expressing PbCDPK4 or PfCDPK4 were studied. Exflagellation inducing medium containing different concentrations of Compound 29 or vehicle was mixed with gametocytes from wild type or cdpk4 complemented mutants in vitro. Exflagellation centers in 10 microscopic fields are expressed as a percentage of a solvent control. Error bars show standard deviations of triplicate measurements from 2 infected mice per parasite strain. For studies of the effect of treating mice with Compound 29 on *P. berghei* transmission to *A. stephensi* (FIG. 17c), mice were infected with *P. berghei* expressing GFP and treated with vehicle, 3 mg/kg, or 10 mg/kg Compound 29 or NA-PP2. The infectivity of mice was calculated as the geometric mean oocyst number on 8-20 dissected mosquito midguts. Each bar shows the arithmetic mean oocyst number generated by 3 infected mice. Error bars show standard deviations between mouse infections. Fluorescence micrographs illustrate typical infection levels in mosquitoes fed on control and Compound 29 treated mice. Scale bar=500 µM. Data are representative of three experiments. For studies of the effect of Compound 29 on *P. falciparum* exflagellation and infection of mosquitos (FIG. 17d), blood containing *P. falciparum* NF-54 strain gametocytes and 3 µM, 1 µM 0.3, 0.1, or 0.05 µM final concentration of Compound 29 or 3, 0.3 or 0.05 µM final concentration of NA-PP2, or no compound controls was fed to *A. stephensi*. A complete suppression of exflagellation was observed with 1 and 3 µM Compound 29. Blocking exflagellation with Compound 29 correlated well with the prevention of oocyst and infective sporozoites formation. Sexual stage development in mosquitoes fed with 0.1 µM was not completely but significantly reduced as shown by >86% reduction in the number of oocyst and infective sporozoites. In a repeat experiment, exflagellation events in the presence of Compound 29 were suppressed completely at 1 or 3 µM, and >90% at 0.3 µM.
Figure 17B:
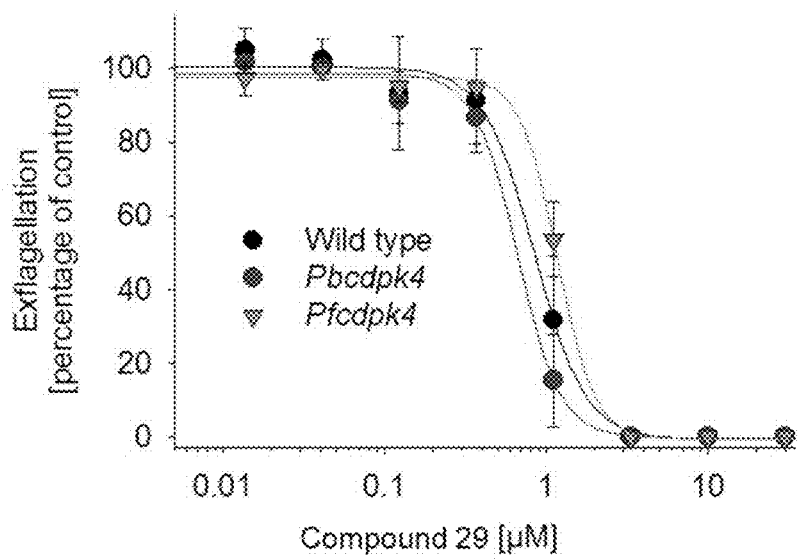

Administration of 50 mg/kg Compound 29 intraperitoneally (i.p.) resulted in a peak plasma concentration of 8.2 µM and plasma levels exceeding 0.4 µM for 20 hours post-treatment (FIG. 17a). When administered to infected mice at this dose, Compound 29 completely suppressed exflagellation in blood samples from treated mice 30 minutes post-injection and up to 14 hours later (FIG. 17a). However, 20 hours after dosing, when lower levels (0.41 µM) of Compound 29 could be detected, some exflagellation was observed (FIG. 17a), demonstrating that the effect of Compound 29 is reversible. Compound 29 blocked exflagellation of *P. berghei* WT and *P. berghei* exogenously expressing PbCDPK4 or PfCDPK4 with similar $IC_{50}$s in vitro (FIG. 17b).

Figure 17C:
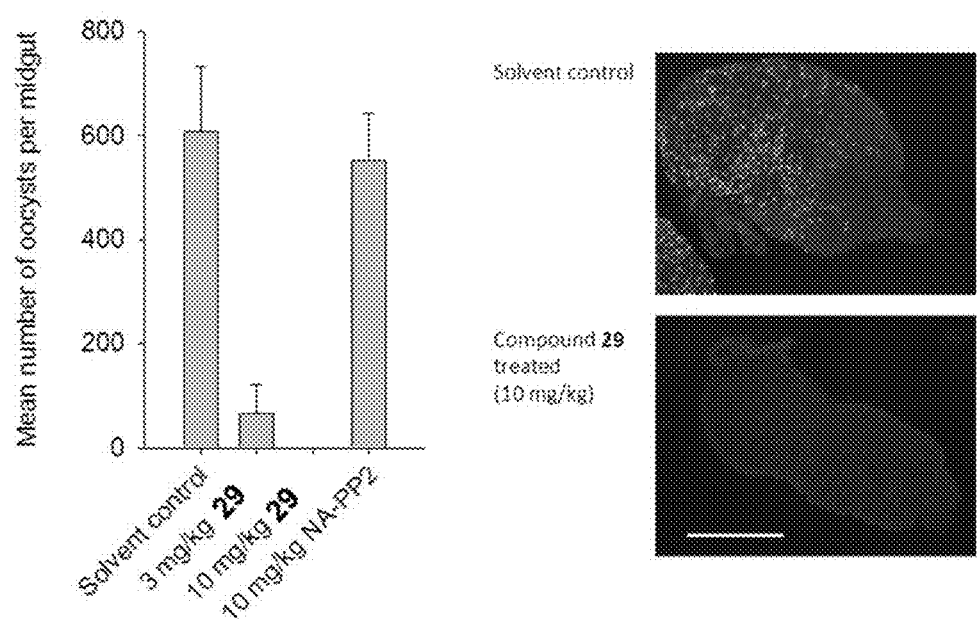
Figure 17D:
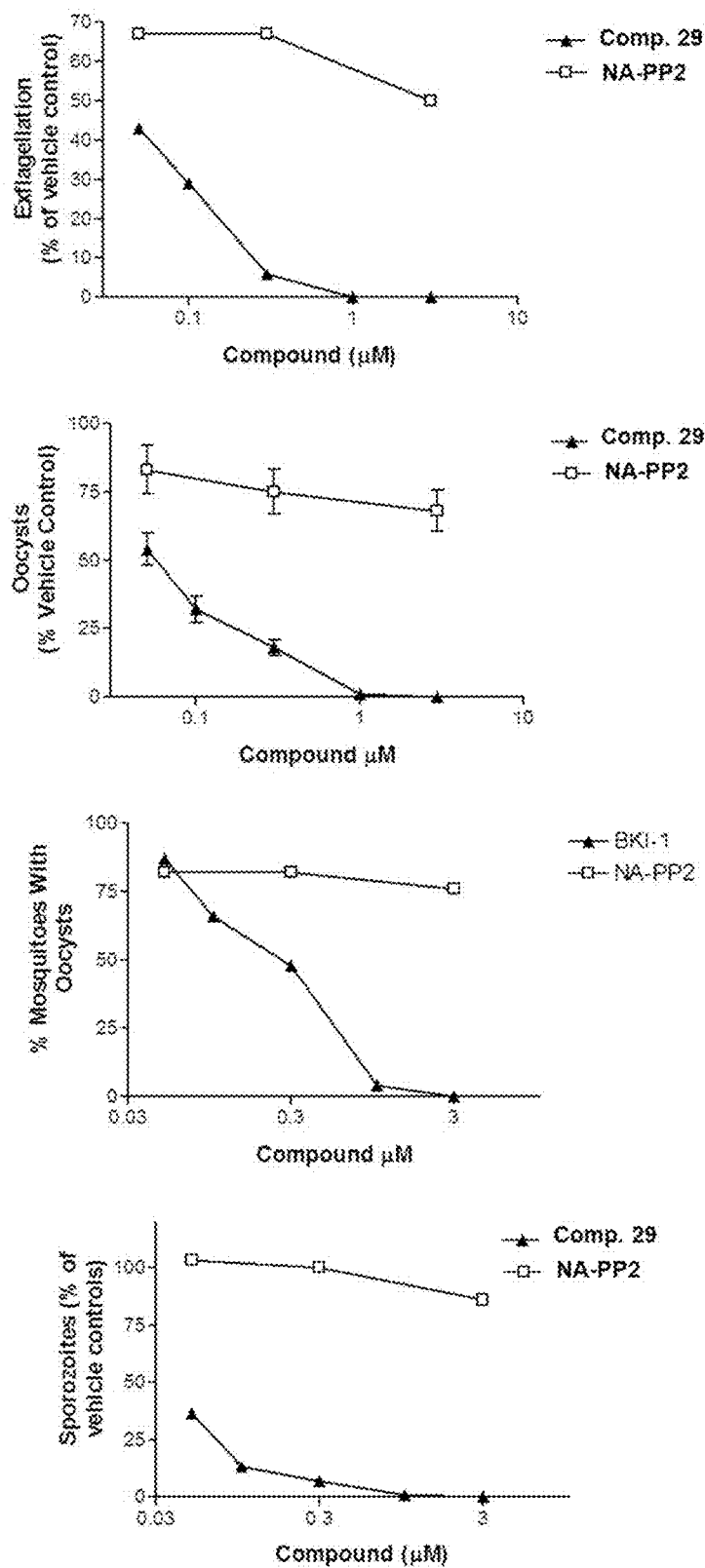

*P. berghei* gametocyte-infected mice was injected i.p. with Compound 29 at 10 mg/kg, a dose which has no impact on asexual parasitaemia or gametocyte rates, but is sufficient to block exflagellation (not shown) to assess its impact on malaria transmission to mosquitoes. *Anopheles stephensi* mosquitoes were allowed to feed on treated mice 30 minutes after dosing. We used *P. berghei* with WT expression of PbCDPK4, because of the results of FIG. 17b, but expressing GFP for ease of following oocyst production (FIG. 17c). Treatment of mice at 10 mg/kg completely blocked the formation of oocysts, while infected mice treated with vehicle or with control compound NA-PP2, gave rise to hundreds of oocysts per mosquito (FIG. 17c). Similarly, mixing Compound 29 (final concentrations of 1 µM or 3 µM) with human blood containing *P. falciparum* gametocytes, prevented the exflagellation of microgametes and the infection of *A. stephensi* midguts, compared to vehicle control (FIG. 17d). Furthermore, a complete absence of infective sporozoites was observed in dissected salivary glands of *A. stephensi* fed with 3 µM Compound 29 treated blood (FIG. 17d) which is consistent the absence of exflagellation at this concentration. At 100 nM, Compound 29 still reduced the prevalence of oocyst infections, and the sporozoite load in the few salivary glands that were infected was diminished by 86% relative to untreated controls (FIG. 17d). The observed overlap in phenotypic and developmental defects associated with CDPK4 inhibition in *P. berghei* and *P. falciparum* indicates that these enzymes have highly similar functional capacity. Compound 29 blocked exflagellation of *P. falciparum* microgametocytes and *P. berghei* microgametocytes expressing either PbCDPK4 or PfCDPK4 (FIG. 17b and 17d) indicating that CDPK4 of both species can be blocked by the compound. Further, the active site of *P. vivax* CDPK4 is highly homologous to that of PfCDPK4, so Compound 29 and related compounds may be useful in blocking *vivax* malaria.

Biological Example 21 Inhibition of *P. falciparum* Proliferation

The following compounds were tested for inhibition *P. falciparum* (PfCDPK1, PfCDPK4) enzymes and ability to block *P. falciparum* proliferation according to the preceding methods:

TABLE 10

Inhibition of *P. falciparum* proliferation

| Compound No. | Enzyme Inhibition (EC50, µM) | | | | Proliferation Blocking *P. falciparum* (EC$_{50}$, µM) |
|---|---|---|---|---|---|
| | PfCDPK1 (% inhibition @ 3 uM) | PfCDPK1 | PfCDPK4 (% inhibition @ 3 uM) | PfCDPK4 | |
| 8 | 92 | 0.1559 | 92 | 0.091 | |
| 9 | 76 | | 88 | | |
| 10 | 93 | 0.3804 | 94 | 0.3282 | |
| 1 | 51 | | 25 | | |
| 2 | | 1.25 | | 0.48 | 40 |
| 11 | 93 | 0.3729 | 87 | 0.5486 | |
| 12 | 95 | 0.6585 | 91 | 0.5256 | |
| 3 | 78 | | 76 | | >50 |
| 5f | | | 15 | | |
| 13 | | | 25 | | |
| 5e | | | 5 | | |
| 5a | | | 52 | | |
| 14 | | | 13 | | |
| 15 | | | 11 | | |
| 5b | | | 20 | | |
| 5c | 45 | | 23 | | |
| 16 | | | 13 | | |
| 17 | 44 | | 5 | | |
| 18 | | | 4 | | |
| 19 | | | 14 | | |
| 5d | 76 | | 86 | | |
| 5g | 56 | | 75 | | |
| 20 | | 0.309 | 93 | 0.2307 | |
| 7a | 97 | | 86 | | |
| 7b | 72 | | 85 | | |
| 7c | 93 | | 97 | | |
| 7d | 90 | | 80 | | |
| 7e | 74 | | 52 | | |
| 7f | 96 | | 85 | | |
| 7g | 72 | | 64 | | |
| 7h | 83 | | 85 | | |
| 7j | 87 | | 30 | | |
| 7m | 77 | | 85 | | |
| 7i | 79 | | 79 | | |
| 7n | 51 | | 10 | | |
| 7o | 58 | | 79 | | |
| 7p | 95 | 0.3805 | 98 | 0.1421 | |
| 7z | 79 | | 21 | | |
| 7ab | 85 | | 79 | | |
| 7t | 65 | 1.3569 | 83 | 0.1688 | |
| 5i | 58 | | 80 | 0.6029 | |
| 7q | | 0.2081 | | 0.0414 | >10 |
| 7aa | 75 | | 18 | | |
| 7r | 94 | 1.2874 | 99 | 0.4288 | >50 |
| 7s | 53 | | 20 | | |
| 21 | 68 | | 9 | | |
| 22 | 71 | | 9 | | |
| 5h | 66 | | 95 | 0.1543 | |
| 7k | 93 | 1.3614 | 43 | >3 | |
| 7u | 94 | 0.4219 | 77 | 1.105 | |
| 7l | 85 | | 31 | | |
| 23 | 75 | | 11 | | |
| 7v | | | 27 | | |
| 7x | | | 21 | | |
| 7w | | | 55 | | |
| 7y | | | 17 | | |
| 24 | | 0.4709 | 93 | 0.3366 | |
| 25 | | | 92 | 0.5785 | |
| 26 | | | 93 | 0.5438 | |
| 27 | | 0.8794 | 44 | >3 | |
| 5j | | | 48 | | |

TABLE 10-continued

Inhibition of *P. falciparum* proliferation

| Compound No. | Enzyme Inhibition (EC50, μM) | | | | Proliferation Blocking *P. falciparum* (EC$_{50}$, μM) |
|---|---|---|---|---|---|
| | PfCDPK1 (% inhibition @ 3 uM) | PfCDPK1 | PfCDPK4 (% inhibition @ 3 uM) | PfCDPK4 | |
| 5p | | | 53 | | |
| 5m | | | 42 | | |
| 5k | 69 | | 28 | | |
| 5q | 78 | | 15 | | |
| 5n | 49 | | 27 | | |
| 5l | 51 | | 41 | | |
| 5r | 55 | | 22 | | |
| 5o | 71 | | 37 | | |
| 28 | 92 | 0.7394 | 99 | 0.0188 | 31.9 |
| 29 | 97 | 0.3527 | 101 | 0.0139 | 6.16 |
| 30 | 82 | | 86 | | |
| 31 | 51 | | 40 | | |
| 32 | | 0.3652 | 96 | 0.0554 | |
| 33 | | 0.1959 | 98 | 0.0211 | >10 |
| 34 | | 0.0272 | 97 | 0.0302 | 5.83 |
| 35 | | 0.1514 | 99 | 0.0312 | >10 |
| 36 | | 0.1462 | 99 | 0.0157 | 11.7 |
| 37 | | 0.0958 | 96 | 0.0716 | |
| 38 | | 0.0452 | 96 | 0.0349 | 7 |
| 39 | 102 | 0.0211 | 98 | 0.0092 | 7 |
| 40 | 101 | 0.0963 | 84 | 0.5136 | |
| 41 | 101 | 0.0363 | 98 | 0.0192 | >10 |
| 42 | 101 | 0.1557 | 94 | 0.3084 | |
| 43 | 100 | 0.2775 | 78 | 1.2037 | |
| 44 | 100 | 0.1817 | 97 | 0.0583 | |
| 45 | 101 | 0.0565 | 82 | 0.3497 | |
| 46 | 95 | 0.4772 | 52 | >3 | |
| 47 | 91 | 1.2856 | 51 | 1.4322 | |
| 48 | 84 | 2.279 | 10 | >3 | |
| 49 | 88 | 0.688 | 22 | 2.3458 | |
| 50 | 83 | 2.0926 | 26 | >3 | |
| 51 | 86 | 1.5998 | 92 | 0.2595 | |
| 52 | 93 | 1.0749 | 62 | 1.2272 | 39.5 |
| 53 | 98 | 0.5317 | 57 | 1.6358 | |
| 54 | 101 | 0.0478 | 77 | 0.4376 | |
| 55 | 100 | 0.2160 | 94 | 0.1750 | |
| 56 | 93 | 1.1375 | 73 | 0.8877 | |
| 57 | 85 | 0.7055 | 82 | 0.2427 | |
| 58 | 97 | 0.2142 | 50 | 2.4330 | |
| 59 | 98 | 0.1107 | 79 | 0.4586 | |
| 60 | 98 | 0.0664 | 85 | 0.3257 | >10 |
| 61 | 101 | 0.0714 | 80 | 0.5146 | 7 |
| 62 | 102 | 0.0377 | 95 | 0.1402 | >10 |
| 63 | 103 | 0.0118 | 96 | 0.1355 | >10 |
| 64 | 101 | 0.1279 | 66 | 1.0831 | |
| 65 | 101 | 0.1012 | 53 | 2.8532 | |
| 66 | 100 | 0.2868 | 77 | 2.1832 | |
| 67 | 96 | 0.3249 | 49 | 1.9874 | |
| 68 | 70 | 2.2040 | 9 | >3 | |
| 69 | 101 | 0.1978 | 97 | 0.1320 | |
| 81 | 73 | | 75 | | |
| 82 | 56 | >3 | 4 | >3 | |
| 70 | 100 | 0.0538 | 96 | 0.0834 | |
| 71 | 101 | 0.0676 | 98 | 0.0652 | |
| 72 | 94 | 0.9484 | 91 | 0.2412 | |
| 73 | 87 | | 14 | | |
| 74 | 97 | 0.3473 | 68 | 1.0132 | |
| 75 | 75 | | 5 | | |
| 83 | 96 | 1.0779 | 93 | 0.3714 | |
| 84 | 101 | 0.0613 | 99 | 0.0551 | |
| 85 | 99 | 0.2287 | 72 | 0.4788 | |
| 90 | 77 | | 64 | | |
| 91 | 73 | | 59 | | |
| 92 | 68 | | 51 | | |
| 93 | 64 | | 49 | | |
| 94 | 71 | | 51 | | |
| 98 | 85 | | 9 | | |
| 99 | 70 | | 5 | | |
| 100 | 101 | 0.0749 | 68 | 0.9080 | |
| 101 | 79 | | 14 | | |
| 103 | 75 | | 58 | | |
| 105 | 71 | | 76 | | |

TABLE 10-continued

Inhibition of *P. falciparum* proliferation

| Compound No. | PfCDPK1 (% inhibition @ 3 uM) | PfCDPK1 | PfCDPK4 (% inhibition @ 3 uM) | PfCDPK4 | Blocking P. falciparum (EC$_{50}$, μM) |
|---|---|---|---|---|---|
| 107 | 65 | | 52 | | |
| 109 | 54 | | 30 | | |
| 111 | 63 | | 41 | | |
| 113 | 65 | | 61 | | |
| 115 | 71 | | 84 | | |
| 117 | 71 | | 74 | | |
| 118 | 97 | 0.5108 | 81 | 0.5116 | |
| 119 | 102 | 0.0769 | 101 | 0.0073 | |
| 120 | 101 | 0.0255 | 90 | 0.2135 | |
| 121 | 93 | 0.7017 | 93 | 0.1462 | |
| 122 | 97 | 0.4817 | 32 | >3 | |
| 123 | 62 | | 4 | | |
| 124 | 98 | 0.1193 | 93 | 0.1005 | |
| 125 | 89 | 1.0892 | 93 | 0.1130 | |
| 126 | 76 | | 65 | | |
| 127 | 68 | | 46 | | |
| 128 | 79 | | 64 | | |
| 129 | 79 | | 9 | | |
| 130 | 95 | 2.9475 | 47 | >3 | |
| 131 | 100 | 0.2659 | 38 | >3 | |
| 132 | 96 | >3 | 96 | 1.4865 | |
| 133 | 79 | | 26 | | |
| 134 | 89 | | 87 | | |
| 135 | 96 | 0.6679 | 97 | 0.1374 | |
| 136 | 90 | | 16 | | |
| 137 | 95 | 2.4325 | 95 | 0.9418 | |
| 139 | 99 | 1.1500 | 96 | 0.5658 | |
| 140 | 98 | 0.3375 | 90 | 0.3988 | |
| 141 | 92 | 1.4740 | 55 | 2.0305 | |
| 142 | 98 | 0.2942 | 97 | 0.0947 | |
| 143 | 97 | | 97 | | |
| 144 | 95 | | 94 | | |
| 145 | 93 | | 63 | | |
| 146 | 99 | | 95 | | |
| 147 | 100 | 0.0668 | 99 | 0.0172 | |
| 148 | | | | 0.0390 | |
| 149 | | | | 0.0816 | |
| 150 | | | | 0.0337 | |

Biological Example 22 Toxicity Data in Human Cell Lines

The following compounds were tested for toxicity in human cell lines according to the preceding methods:

TABLE 11

Toxicity data in human cell lines

Cell Toxicity LD50 Results (μM)

| Comp. No. | Observed HFF Toxicity | HL60 | CRL8155 | SF539 | HCC2998 |
|---|---|---|---|---|---|
| 1 | | <30% at 25 μM | <30% at 25 μM | <30% at 25 μM | <30% at 25 μM |
| 2 | | <30% at 25 μM; <30% at 30 μM | 37% at 25 μM; <30% at 30 μM | <30% at 25 μM | <30% at 25 μM |
| 11 | | <30% at 10 μM | <30% at 10 μM | <30% at 10 μM | <30% at 10 μM |
| 12 | | <30% at 10 μM | <30% at 10 μM | <30% at 10 μM | <30% at 10 μM |
| 3 | | <30% at 10 μM | <30% at 10 μM | <30% at 10 μM | <30% at 10 μM |
| 5d | | <30% at 10 μM | <30% at 10 μM | <30% at 10 μM | <30% at 10 μM |
| 5g | | <30% at 10 μM | <30% at 10 μM | <30% at 10 μM | <30% at 10 μM |
| 20 | | <30% at 10 μM | <30% at 10 μM | | |
| 7c | | 51% at 25 μM | 54% at 25 μM | 31% at 25 μM | <30% at 25 μM |
| 7p | | 50% at 25 μM; 35% at 10 μM | 46% at 25 μM | 84% at 25 μM; 54% at 10 μM | <30% at 25 μM |
| 7t | | <30% at 10 μM | <30% at 10 μM | <30% at 10 μM | <30% at 10 μM |
| 5i | | <30% at 10 μM; | <30% at 10 μM; | <30% at 10 μM | <30% at 10 μM |

TABLE 11-continued

Toxicity data in human cell lines

Cell Toxicity LD50 Results (μM)

| Comp. No. | Observed HFF Toxicity | HL60 | CRL8155 | SF539 | HCC2998 |
|---|---|---|---|---|---|
| | | <30% at 30 μM | <30% at 30 μM | | |
| 7q | | <30% at 10 μM | <30% at 10 μM | <30% at 10 μM | <30% at 10 μM |
| 7r | | <30% at 10 μM | <30% at 10 μM | <30% at 10 μM | <30% at 10 μM |
| 5h | | <30% at 10 μM | <30% at 10 μM | <30% at 10 μM | <30% at 10 μM |
| 25 | | 47% toxicity at 10 μM | 38% toxicity at 10 μM | | |
| 26 | | 45% toxicity at 10 μM | 38% toxicity at 10 μM | | |
| 5p | | <30% at 25 μM | <30% at 25 μM | <30% at 25 μM | <30% at 25 μM |
| 5n | | <30% at 10 μM | <30% at 10 μM | <30% at 10 μM | <30% at 10 μM |
| 28 | | <30% at 10 μM | <30% at 10 μM | <30% at 10 μM | <30% at 10 μM |
| | | <30% at 30 μM | <30% at 30 μM | | |
| 29 | | <30% at 10 μM | <30% at 10 μM | <30% at 10 μM | <30% at 10 μM |
| 30 | | <30% at 10 μM | <30% at 10 μM | <30% at 10 μM | <30% at 10 μM |
| | | <30% at 30 μM | <30% at 30 μM | | |
| 33 | T at 100 μM | <30% at 10 μM | <30% at 10 μM | <30% at 10 μM | 30% at 10 μM |
| 34 | T at 100 μM | <30% at 10 μM | <30% at 10 μM | 6; 104% at 10 μM | 30% at 10 μM |
| 35 | T at 25-100 μM | <30% at 10 μM | <30% at 10 μM | <30% at 10 μM | <30% at 10 μM |
| 36 | T at 100 μM | <30% at 10 μM | <30% at 10 μM | <30% at 10 μM | <30% at 10 μM |
| 37 | T at 100 μM | | | | |
| 38 | T at 100 μM | <30% at 10 μM | <30% at 10 μM | | |
| | | 98% at 30 μM | 98% at 30 μM | | |
| 40 | T at 100 μM | | | | |
| 41 | T at 100 μM | <30% at 10 μM | <30% at 10 μM | | |
| 42 | T at 100 μM | | | | |
| 44 | T at 100 μM | | | | |
| 46 | | <30% at 10 μM | <30% at 10 μM | | |
| 69 | T at 25 μM | <30% at 10 μM | <30% at 10 μM | | |
| 70 | | 40% at 10 μM | <30% at 10 μM | | |
| 71 | | <30% at 10 μM | <30% at 10 μM | | |
| 72 | | <30% at 10 μM | <30% at 10 μM | | |
| 83 | | 37% at 10 μM | <30% at 10 μM | | |
| | | 38% at 30 μM | 46% at 30 μM | | |
| 84 | | <30% at 10 μM | <30% at 10 μM | | |
| | | 50% at 30 μM | 48% at 30 μM | | |
| 90 | | <30% at 10 μM | <30% at 10 μM | | |
| 98 | | <30% at 10 μM | <30% at 10 μM | | |
| 105 | | <30% at 10 μM | <30% at 10 μM | | |
| 115 | | <30% at 10 μM | <30% at 10 μM | | |
| 118 | T at 6.25 & 25 μM | | | | |
| 119 | | <30% at 10 μM; <30% at 30 μM | <30% at 10 μM <30% at 30 μM | | |
| 120 | T at 25 μM | | | | |
| 121 | | <30% at 10 μM | <30% at 10 μM | | |
| 122 | | <30% at 10 μM | <30% at 10 μM | | |
| | | <30% at 30 μM | <30% at 30 μM | | |
| 124 | T at 6.25 & 25 μM | | | | |
| 147 | | 60% at 30 μM; 33% at 10 μM | <30% at 30 μM | | |
| 148 | | 49% at 30 μM; <30% at 10 μM | <30% at 30 μM | | |
| 149 | | <30% at 30 μM | <30% at 10 μM <30% at 30 μM | | |
| 150 | T at 25 μM | <30% at 10 μM <30% at 30 μM | <30% at 10 μM <30% at 30 μM | | |

Biological Example 23 Pharmacokinetics Properties

The following compounds were tested for their solubility properties in buffers of various pH:

TABLE 12

| | Pharmacokinetics properties | | | | | |
|---|---|---|---|---|---|---|
| | Experimental Solubility (μM) | | | PK/PD Analysis Results Oral Administration (IP Administration) | | |
| Compound No. | pH 2.0 | pH 6.5 | pH 7.4 | $C_{max}$ (μM) | $T_{max}$ (min) | AUC (μM-min) |
| 10 | | 29 | | 25.97 | 150 | 6725.59 |
| 2 | 43 | 2.4 | 1.5 | | | |
| 7a | | 45 | | | | |
| 7q | | | | 19.71 (3.8 IP) | 30 (30 IP) | 2120.14 (275.86 IP) |
| 7r | | 12 | | | | |
| 28 | 49 | 58 | 56 | 4.41 (84.06 IP) | 160 (40 IP) | 1228.15 (9050.27 IP) |
| 29 | 34 | 47 | 49 | 6.64 | 120 | 1200.96 |
| 34 | | 23 | | | | |
| 35 | | 45 | | | | |
| 36 | | | | 0.59 | 220 | 109.66 |
| 41 | | 4.4 | | 13.57 | 100 | 3172.19 |
| 42 | | 4.4 | | 10.69 | 160 | 2437.28 |
| 44 | 47 | 38 | 33 | 0.95 | 180 | 148.21 |
| 45 | | 62 | | | | |
| 69 | | 3 | | | | |
| 70 | | 5 | | | | |
| 71 | | 9 | | | | |
| 83 | | 36 | | | | |
| 84 | | 26 | | | | |
| 118 | | 40 | | | | |
| 119 | | 50 | | | | |
| 120 | | 44 | | | | |
| 121 | | 43 | | 0.19 | 90 | 26.69 |
| 124 | | 41 | | 1.84 | 180 | 399.24 |
| 125 | | 54 | | | | |
| 132 | | 3.8 | | | | |
| 134 | | 19.3 | | | | |
| 135 | | 3.0 | | | | |
| 137 | | 1.0 | | | | |
| 138 | | 51 | | | | |
| 139 | | 0.69 | | | | |
| 140 | | 22 | | | | |
| 142 | | 5.2 | | | | |
| 143 | | 17 | | | | |
| 144 | | 60 | | | | |
| 146 | | 9 | | | | |
| 147 | | 79 | | | | |
| 148 | | 56 | | | | |
| 149 | | 75 | | | | |
| 150 | | 82 | | | | |

Biological Example 24 Biological Properties of Compound Nos. 29 and 150

The compounds 29 and 150 were tested for their various biological properties according to the preceeding methods:

TABLE 13

| | Biological properties of Compound Nos. 29 and 150 | | | | | |
|---|---|---|---|---|---|---|
| | Enzymatic Assay $IC_{50}$ Results (μM) | | | Parasite Proliferation Assay $EC_{50}$ Results (μM) | | |
| Compound No. | Tg CDPK1 | Cp CDPK1 | Pf CDPK4 | T. gondii | C. parvum | P. falciparum Exflaggelation |
| 29 | 0.003 | 0.001 | 0.004 | 0.052 | 0.56 | 0.04 |
| 150 | 0.003 | 0.001 | 0.010 | 0.137 | 0.54 | 0.05 |

| | Stability $T_{1/2}$ (min) | Oral (10 mg/kg Dose) | | | Oral (50 mg/kg Dose) | | |
|---|---|---|---|---|---|---|---|
| Compound No. | Mouse Liver Microsomes | $C_{max}$ (μM) | $T_{max}$ (min) | AUC (μM-min) | $C_{max}$ (μM) | $T_{max}$ (min) | AUC (μM-min) |
| 29 | >60 | 0.2 | 140 | 57 | 1.1 | 160 | 311 |
| 150 | >60 | 0.8 | 129 | 430 | ND | ND | ND |

| | IP (10 mg/kg Dose) | | | IP (50 mg/kg Dose) | | |
|---|---|---|---|---|---|---|
| Compound No. | $C_{max}$ (μM) | $T_{max}$ (min) | AUC (μM-min) | $C_{max}$ (μM) | $T_{max}$ (min) | AUC (μM-min) |
| 29 | 0.7 | 30 | 191 | 8.2 | 30 | 1769 |
| 150 | 3 | 40 | 863 | ND | ND | ND |

Mice were dosed with 40 mg/kg of compound by oral gavages at 7 am, noon, and 3 μm on 4 consecutive days and blood levels determined by LC-MS. The first and fourth troughs refer to compound levels 17 hours after compound dosing taken at the beginning of d2 and d5. The first peak was 1 hr after the first dose. The fourth day peak was 1 hr after the third dose of d4. Mean±SD of N=3:

| Compound No. | Blood level (μM) | | | |
| --- | --- | --- | --- | --- |
| | First Peak | First Trough | Fourth D 4 Peak | Fourth Trough |
| 29 | 0.05 ± 0.08 | 0 ± 0 | 6.6 ± 1.6 | 0 ± 0 |
| 150 | 2.1 ± 1.2 | 2.0 ± 1.6 | 8.9 ± 3.4 | 6.3 ± 1.8 |

REFERENCES (BIOLOGICAL EXAMPLES 1-11)

The following references are herein incorporated by reference.

1. Montoya J G, Kovacs J A & Remington J S. *Principles and Practice of Infectious Diseases*. Chapter 276 Mandell, B. & D. (ed.) (Churchill Livingston, 2005).
2. Mead, P. S. et al. Food-related illness and death in the United States. *Emerging Infectious Diseases* 5, 607-625 (1999).
3. Baril, L. et al. Risk factors for *toxoplasma* infection in pregnancy: A case-control study in France. *Scandinavian Journal of Infectious Diseases* 31, 305-309 (1999).
4. Jones, J. L. et al. *Toxoplasma gondii* infection in the United States: Seroprevalence and risk factors. *American Journal of Epidemiology* 154, 357-365 (2001).
5. Wallace, M. R., Rossetti, R. J. & Olson, P. E. Cats and Toxoplasmosis Risk in Hiv-Infected Adults. *Jama—Journal of the American Medical Association* 269, 76-77 (1993).
6. Vastava, P. B. et al. MRI features of *toxoplasma* encephalitis in the immunocompetent host: a report of two cases. *Neuroradiology* 44, 834-838 (2002).
7. Hermentin, K., Hassl, A., Picher, O. & Aspock, H. Comparison of Different Serotests for Specific Toxoplasma Igm-Antibodies (Isaga, Spiha, Ifat) and Detection of Circulating Antigen in 2 Cases of Laboratory Acquired Toxoplasma Infection. *Zentralblatt fur Bakteriologie Mikrobiologie und Hygiene Series A-Medical Microbiology Infectious Diseases Virology Parasitology* 270, 534-541 (1989).
8. Bach, M. C. & Armstrong, R. M. Acute Toxoplasmic Encephalitis in A Normal Adult. *Archives of Neurology* 40, 596-597 (1983).
9. Pelphrey, P. M. et al. Highly efficient ligands for dihydrofolate reductase from *Cryptosporidium hominis* and *Toxoplasma gondii* inspired by structural analysis. *Journal of Medicinal Chemistry* 50, 940-950 (2007).
10. Dannemann, B. et al. Treatment of Toxoplasmic Encephalitis in Patients with Aids—A Randomized Trial Comparing Pyrimethamine Plus Clindamycin to Pyrimethamine Plus Sulfadiazine. *Annals of Internal Medicine* 116, 33-43 (1992).
11. JEFFREY M. JACOBSON et al. Pyrimethamine Pharmacokinetics in Human Immunodeficiency Virus-Positive Patients Seropositive for *Toxoplasma gondii*. *ANTIMICROBIAL AGENTS AND CHEMOTHERAPY* 40, 1360-1365 (1996).
12. Nagamune, K. & Sibley, L. D. Comparative genomic and phylogenetic analyses of calcium ATPases and calcium-regulated proteins in the apicomplexa. *Mol. Biol. Evol.* 23, 1613-1627 (2006).
13. Lovett, J. L. & Sibley, L. D. Intracellular calcium stores in *Toxoplasma gondii* govern invasion of host cells. *Journal of Cell Science* 116, 3009-3016 (2003).
14. Kieschnick, H., Wakefield, T., Narducci, C. A. & Beckers, C. *Toxoplasma gondii* attachment to host cells is regulated by a calmodulin-like domain protein kinase. *J Biol. Chem.* 276, 12369-12377 (2001).
15. Canduri, F., Perez, P. C., Caceres, R. A. & de Azevedo, W. F. Protein kinases as targets for antiparasitic chemotherapy drugs. *Current Drug Targets* 8, 389-398 (2007).
16. Doerig, C., Billker, O., Pratt, D. & Endicott, J. Protein kinases as targets for antimalarial intervention: kinomics, structure-based design, transmission-blockade, and targeting host cell enzymes. *Biophysica et Biochimica Acta—Proteins and Proteomics* 1754, 132-150 (2005).
17. Harper, J. F. & Harmon, A. Plants, symbiosis and parasites: A calcium signaling connection. *Nature Reviews Molecular Cell Biology* 6, 555-566 (2005).
18. Raichaudhuri, A., Bhattacharyya, R., Chaudhuri, S., Chakrabarti, P. & Dasgupta, M. Domain analysis of a groundnut calcium-dependent protein kinase: nuclear localization sequence in the junction domain is coupled with nonconsensus calcium binding domains. *J Biol. Chem.* 281, 10399-10409 (2006).
19. Noble, M. E., Endicott, J. A. & Johnson, L. N. Protein kinase inhibitors: insights into drug design from structure. *Science* 303, 1800-1805 (2004).
20. Knight, Z. A. & Shokat, K. M. Features of selective kinase inhibitors. *Chemistry &Biology* 12, 621-637 (2005).
21. Cohen, M. S., Zhang, C., Shokat, K. M. & Taunton, J. Structural bioinformatics-based design of selective, irreversible kinase inhibitors. *Science* 308, 1318-1321 (2005).
22. Liao, J. J. Molecular recognition of protein kinase binding pockets for design of potent and selective kinase inhibitors. *J. Med. Chem.* 50, 409-424 (2007).
23. Bishop, A. C. et al. A chemical switch for inhibitor-sensitive alleles of any protein kinase. *Nature* 407, 395-401 (2000).
24. Bishop, A. C. et al. Generation of monospecific nanomolar tyrosine kinase inhibitors via a chemical genetic approach. *Journal of the American Chemical Society* 121, 627-631 (1999).
25. Zhang, C. et al. A second-site suppressor strategy for chemical genetic analysis of diverse protein kinases. *Nat. Methods* 2, 435-441 (2005).
26. Bishop, A. C., Buzko, O. & Shokat, K. M. Magic bullets for protein kinases. *Trends Cell Biol.* 11, 167-172 (2001).
27. Johnson, A. W. et al. The brain-derived neurotrophic factor receptor TrkB is critical for the acquisition but not expression of conditioned incentive value. *European Journal of Neuroscience* 28, 997-1002 (2008).
28. Morgan, D. J. et al. Tissue-specific PKA inhibition using a chemical genetic approach and its application to studies on sperm capacitation. *Proceedings of the National Academy of Sciences of the United States of America* 105, 20740-20745 (2008).
29. Chen, X. et al. A chemical-genetic approach to studying neurotrophin signaling. *Neuron* 46, 13-21 (2005).
30. Ojo, K. K. et al. Glycogen synthase kinase 3 is a potential drug target for African trypansomiasis therapy. *Antimicrob. Agents Chemother.* 52, 3710-3717 (2008).
31. Newman, J. et al. Towards rationalization of crystallization screening for small- to medium-sized academic 31. laboratories: the PACT/JCSG plus strategy. *Acta Crystallographica Section D-Biological Crystallography* 61, 1426-1431 (2005).
32. Cohen, A. E., Ellis, P. J., Miller, M. D., Deacon, A. M. & Phizackerley, R. P. An automated system to mount cryo-cooled protein crystals on a synchrotron beamline, using compact sample cassettes and a small-scale robot. *Journal of Applied Crystallography* 35, 720-726 (2002).
33. McPhillips, T. M. et al. Blu-Ice and the Distributed Control System: software for data acquisition and instrument control at macromolecular crystallography beamlines. *Journal of Synchrotron Radiation* 9, 401-406 (2002).
34. Hendrickson, W. A., Horton, J. R. & Lemaster, D. M. Selenomethionyl Proteins Produced for Analysis by Multiwavelength Anomalous Diffraction (Mad)—A Vehicle for Direct Determination of 3-Dimensional Structure. *Embo Journal* 9, 1665-1672 (1990).
35. Otwinowski, Z. & Minor, W. Processing of X-ray diffraction data collected in oscillation mode. *Macromolecular Crystallography, Pt A* 276, 307-326 (1997).
36. Vagin, A. & Teplyakov, A. MOLREP: an automated program for molecular replacement. *Journal of Applied Crystallography* 30, 1022-1025 (1997).
37. Mccoy, A. J. et al. Phaser crystallographic software. *Journal of Applied Crystallography* 40, 658-674 (2007).
38. Terwilliger, T. SOLVE and RESOLVE: automated structure solution, density modification, and model building. *Journal of Synchrotron Radiation* 11, 49-52 (2004).
39. Emsley, P. & Cowtan, K. Coot: model-building tools for molecular graphics. *Acta Crystallographica Section D-Biological Crystallography* 60, 2126-2132 (2004).
40. Murshudov, G. N., Vagin, A. A. & Dodson, E. J. Refinement of macromolecular structures by the maximum-likelihood method. *Acta Crystallographica Section D-Biological Crystallography* 53, 240-255 (1997).
41. Cohen, S. X. et al. ARP/wARP and molecular replacement: the next generation. *Acta Crystallographica Section D-Biological Crystallography* 64, 49-60 (2008).
42. Schuttelkopf, A. W. & van Aalten, D. M. F. PRODRG: a tool for high-throughput crystallography of protein-ligand complexes. *Acta Crystallographica Section D Biological Crystallography* 60, 1355-1363 (2004).
43. Painter, J. & Merritt, E. A. Optimal description of a protein structure in terms of multiple groups undergoing TLS motion. *Acta Crystallographica Section D-Biological Crystallography* 62, 439-450 (2006).
44. Painter, J. & Merritt, E. A. TLSMD web server for the generation of multi-group TLS models. *Journal of Applied Crystallography* 39, 109-111 (2006).
45. Lovell, S. C. et al. Structure validation by C alpha geometry: phi, psi and C beta deviation. *Proteins-Structure Function and Genetics* 50, 437-450 (2003).
46. Bailey, S. The Ccp4 Suite—Programs for Protein Crystallography. *Acta Crystallographica Section D-Biological Crystallography* 50, 760-763 (1994).
47. Potterton, E., Briggs, P., Turkenburg, M. & Dodson, E. A graphical user interface to the CCP4 program suite. *Acta Crystallographica Section D-Biological Crystallography* 59, 1131-1137 (2003).
48. Berman, H. M. et al. The Protein Data Bank. *Nucleic Acids Research* 28, 235-242 (2000).
49. Matrajt, M., Nishi, M., Fraunholz, M. J., Peter, O. & Roos, D. S. Amino-terminal control of transgenic protein expression levels in *Toxoplasma gondii*. *Molecular and Biochemical Parasitology* 120, 285-289 (2002).
50. Striepen, B., He, C. Y. X., Matrajt, M., Soldati, D. & Roos, D. S. Expression, selection, and organellar targeting of the green fluorescent protein in *Toxoplasma gondii*. *Molecular and Biochemical Parasitology* 92, 325-338 (1998).
51. DeRocher, A., Hagen, C. B., Froehlich, J. E., Feagin, J. E. & Parsons, M. Analysis of targeting sequences demonstrates that trafficking to the *Toxoplasma gondii* plastid branches off the secretory system. *Journal of Cell Science* 113, 3969-3977 (2000).
52. Karnataki, A. et al. Cell cycle-regulated vesicular trafficking of Toxoplasma APT1, a protein localized to multiple apicoplast membranes. *Molecular Microbiology* 63, 1653-1668 (2007).
53. Fruth, I. A. & Arrizabalaga, G. *Toxoplasma gondii*: Induction of egress by the potassium ionophore nigericin. *International Journal for Parasitology* 37, 1559-1567 (2007).
54. Seeber, F. & Boothroyd, J. C. *Escherichia coli* beta-galactosidase as an in vitro and in vivo reporter enzyme and stable transfection marker in the intracellular protozoan parasite *Toxoplasma gondii*. *Gene* 169, 39-45 (1996).

REFERENCES (SYNTHETIC EXAMPLES AND BIOLOGICAL EXAMPLES 12 ETC.)

The following references are herein incorporated by reference.
1. White A C. Chapter 280: Cryptosporidiosis (*Cryptosporidium hominis, Cryptosporidium parvum*, and Other Species) in Mandell, Bennett, & Dolin: Principles and Practice of Infectious Diseases, 6th ed. Publ: Churchill Livingston (2005).
2. Samie, A.; Bessong, P. O.; Obi, C. L.; Sevilleja, J. E.; Stroup, S.; Houpt, E.; Guerrant, R. L. Cryptosporidium species: preliminary descriptions of the prevalence and genotype distribution among school children and hospital patients in the Venda region, Limpopo Province, South Africa. Exp. Parasitol. 114, 314-322 (2006).
3. Montoya J G, Kovacs J A, Remington J S. Chapter 276: *Toxoplasma gondii* in *Mandell, Bennett, &Dolin: Principles and Practice of Infectious Diseases*, 6th ed. Publ: Churchill Livingston (2005).
4. Nagamune K, Sibley L D. Comparative genomic and phylogenetic analyses of calcium ATPases and calcium-regulated proteins in the apicomplexa. *Mol. Biol. Evol.* 23, 1613-1627 (2006).
5. Billker O, Lourido S, Sibley L D. Cell Host Microbe. 2009 Jun. 18; 5(6):612-22. Calcium-dependent signaling and kinases in apicomplexan parasites.
6. Doerig C, Billker O, Pratt D, Endicott J. Protein kinases as targets for antimalarial intervention: kinomics, structure-based design, transmission-blockade, and targeting host cell enzymes. *Biophysica et Biochimica Acta—Proteins and Proteomics* 1754, 132-150 (2005).
7. Kieschnick H, Wakefield T, Narducci C A, Beckers, C. *Toxoplasma gondii* attachment to host cells is regulated by a calmodulin-like domain protein kinase. *J Biol. Chem.* 276, 12369-12377 (2001).
8. Chen X M, O'Hara S P, Huang B Q, Nelson J B, Lin J J C, Zhu G, Ward H D, LaRusso N F. Apical Organelle discharge by *Cryptosporidium parvum* is temperature, cytoskeleton, and intracellular calcium dependent and required for host cell invasion. *Infect. Immun.* 72, 6806-16 (2004).

9. Ojo K K, Larson, E T, Keyloun K R, Castaneda L J, DeRocher A E, Inampudi K K, Kim J E, Arakaki T, Murphy, R C, Zhang L, Napuli A J, Maly D J, Verlinde CLMJ, Buckner F S, Parsons M, Hol W G J, Merritt E A, Van Voorhis W C. *Toxoplasma gondii* calcium-dependent protein kinase 1 is a target for selective kinase inhibitors *Nat. Struct. Mol. Biol.* 17, 602-607 (2010).
10. Sugi T, Kato K, Kobayashi K, Watanabe S, Kurokawa H, Gong H, Pandey K, Takemae H, Akashi H. Use of the kinase inhibitor analog 1NM-PP1 reveals a role for *Toxoplasma gondii* CDPK1 in the invasion step. *Eukaryot. Cell* 9, 667-70 (2010).
11. Liao, J. J. Molecular recognition of protein kinase binding pockets for design of potent and selective kinase inhibitors. *J. Med. Chem.* 50, 409-424 (2007).
12. Zhang, C. et al. A second-site suppressor strategy for chemical genetic analysis of diverse protein kinases. *Nat. Methods* 2, 435-441 (2005).
13. Cohen, M. S. et al. Structural bioinformatics-based design of selective, irreversible kinase inhibitors. *Science* 308, 1318-1321 (2005).
14. Bishop, A. C. et al. A chemical switch for inhibitor-sensitive alleles of any protein kinase. *Nature* 407, 395-401 (2000).
15. Bishop, A. C. et al. Design of allele-specific inhibitors to probe protein kinase signaling. *Curr. Biol.* 8, 257-266 (1998).
16. Bishop, A C. et al. Generation of monospecific nanomolar tyrosine kinase inhibitors via a chemical genetic approach. *J. Am. Chem. Soc.* 121, 627-631 (1999).
17. Burchat A F, Calderwood D J, Friedman M M, Hirst G C, Li B, Rafferty P, Ritter K, Skinner B S. "Pyrazolo[3,4-d]pyrimidines containing an extended 3-substituent as potent inhibitors of Lck—a selectivity insight" *Bioorg. Med. Chem. Lett.,* 12, 1687-1690 (2002).
18. Apsel, B, Blair, J A, Gonzalez B, Nazif™, Feldman M E, Aizenstein B, Hoffman R, Williams R. L, Shokat K M, Knight Z A. "Targeted polypharmacology: discovery of dual inhibitors of tyrosine and phosphoinositide kinases" *Nat. Chem. Biol.,* 4, 691-699 (2008).
19. Valeur, E.; Roche, D. Efficient, mild, parallel and purification-free synthesis of aryl ethers via Mitsunobu reaction. *Tet. Lett.* 49, 4182-4185 (2008).
20. CpCDPK1's and TgCDPK1's $K_m$s for ATP are 9.0 μM and 10 μM, respectively
21. Hanke J H, Gardner J P, Dow R L, Changelian P L, Brissette W H, Weringer E J, Pollok B A, Connelly P A. "Discovery of a novel, potent, and Src family-selective tyrosine kinase inhibitor. Study of Lck- and FynT-dependent T cell activation." *J Biol. Chem.,* 271, 695-701 (1996).
22. Ajjampur, S. S.; Rajendran, P.; Ramani, S.; Banerjee, I.; Monica, B.; Sankaran, P.; Rosario, V.; Arumugam, R.; Sarkar, R.; Ward, H.; Kang, G. Closing the diarrhea diagnostic gap in Indian children by the application of molecular techniques. *J Med. Microbiol.* 57, 1364-1368 (2008).
23. K. K. Ojo et al., Structure determination of glycogen synthase kinase-3 from Leishmania major and comparative inhibitor structure-activity relationships with *Trypanosoma brucei* GSK-3. *Mol. Biochem. Parasitol.* 176, 98-108 (2011).
24. R. C. Murphy et al., Discovery of Potent and Selective Inhibitors of CDPK1 from *C. parvum* and *T. gondii*. *ACS Med. Chem. Lett.* 1, 331-335 (2010).
25. A. Roy, A. Kucukural, Y. Zhang, I-TASSER: a unified platform for automated protein structure and function prediction. *Nat. Protoc.* 5, 725-738 (2010).
26. Y. Zhang, I-TASSER server for protein 3D structure prediction. *BMC Bioinform.* 9, 40 (2008).
27. C. McMartin, R. S. Bohacek, QXP: powerful, rapid computer algorithms for structure-based drug design. *J. Comput. Aided Mol. Des* 11, 333-344 (1997).
28. E. Krissinel, K. Henrick, Secondary-structure matching (SSM), a new tool for fast protein structure alignment in three dimensions. *Acta Crystallogr. D Biol. Crystallogr.* 60, 2256-2268 (2004).
29. C. J. Janse, J. Ramesar, A. P. Waters, High-efficiency transfection and drug selection of genetically transformed blood stages of the rodent malaria parasite Plasmodium berghei. *Nat. Protoc.* 1, 346-356 (2006).
30. R. W. Moon et al., A cyclic GMP signalling module that regulates gliding motility in a malaria parasite. *PLoS Pathog.* 5, e1000599 (2009).
31. C. J. Janse, B. Franke-Fayard, A. P. Waters, Selection by flow-sorting of genetically transformed, GFP-expressing blood stages of the rodent malaria parasite, Plasmodium berghei. *Nat. Protoc.* 1, 614-623 (2006).

CONCLUSION

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize.

All of the references cited herein are incorporated by reference. Aspects of the disclosure can be modified, if necessary, to employ the systems, functions and concepts of the above references and application to provide yet further embodiments of the disclosure. These and other changes can be made to the disclosure in light of the detailed description.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure. Accordingly, the disclosure is not limited, except as by the appended claims.

The invention claimed is:
1. A compound of the formula

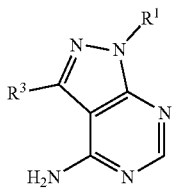

or a pharmaceutically acceptable salt thereof, wherein
R$^1$ is —C$_{1-4}$ alkyl-R$^{12}$, wherein
R$^{12}$ is —OR, —SR, —NR$_2$, —C(O)R, —C(O)OR, —C(O)NR$_2$, —S(O)$_2$R, —OC(O)R, —OC(O)OR, —OC(O)NR$_2$, —N(R)C(O)R, —N(R)C(O)OR, —N(R)C(O)NR$_2$, phenyl, monocyclic heteroaryl, C$_{3-8}$ cycloalkyl, or monocyclic heterocyclyl, wherein the aryl, heteroaryl, C$_{3-8}$ cycloalkyl, and heterocyclyl groups are each optionally substituted by one, two, or three groups that are each independently halogen, cyano, nitro, C$_{1-6}$ alkyl, C$_{1-6}$ haloalkyl, —OR, —SR, —NR$_2$, —C(O)R, —C(O)OR, —C(O)NR$_2$, —S(O)$_2$R, —OC(O)R, —OC(O)OR, —OC(O)NR$_2$, —N(R)C(O)R, —N(R)C(O)OR, or —N(R)C(O)NR$_2$;
R$^3$ is one of the formulas,

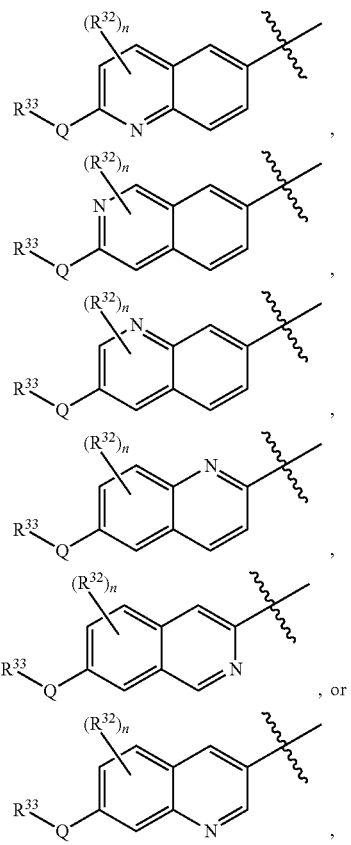

wherein
n is 0, 1, or 2;
Q is —O—, —S—, or —N(R$^Q$)—, wherein R$^Q$ is hydrogen or C$_{1-6}$ alkyl; and R$^{33}$ is C$_{1-6}$ alkyl, C$_{2-6}$ alkenyl, C$_{1-6}$ haloalkyl, C$_{3-8}$ cycloalkyl, heterocyclyl, aryl, arylC$_{1-6}$ alkyl, heteroaryl, or heteroarylC$_{1-6}$ alkyl wherein the alkyl, aryl, arylalkyl, heteroaryl, and heteroarylalkyl are optionally substituted with one, two, three, or four groups that are each independently halogen, cyano, nitro, C$_{1-6}$ alkyl, C$_{1-6}$ haloalkyl, —OR$^{20}$, —SR$^{20}$, —N(R$^{20}$)$_2$, —C(O)R$^{20}$, —C(O)OR$^{20}$, —C(O)N(R$^{20}$)$_2$, —S(O)$_2$R$^{20}$, —OC(O)R$^{20}$, —OC(O)OR$^{20}$, —OC(O)N(R$^{20}$)$_2$, —N(R$^{20}$)C(O)R$^{20}$, —N(R$^{20}$)C(O)OR$^{20}$, or —N(R$^{20}$)C(O)N(R$^{20}$)$_2$, wherein each R$^{20}$ is independently hydrogen or C$_{1-6}$ alkyl,
each R$^{32}$ is independently halogen, cyano, nitro, C$_{1-6}$ alkyl, C$_{1-6}$ haloalkyl, —OR$^{34}$, —SR$^{34}$, —N(R$^{34}$)$_2$, —C(O)R$^{34}$, —C(O)OR$^{34}$, —C(O)N(R$^{34}$)$_2$, —S(O)$_2$R$^{34}$, —OC(O)R$^{34}$, —OC(O)OR$^{34}$, —OC(O)N(R$^{34}$)$_2$, —N(R$^{34}$)C(O)R$^{34}$, —N(R$^{34}$)C(O)OR$^{34}$, or —N(R$^{34}$)C(O)N(R$^{34}$)$_2$, wherein each R$^{34}$ is independently hydrogen or C$_{1-6}$ alkyl;
and
R$^{35}$ is hydrogen or C$_{1-6}$ alkyl;
and
each R is independently hydrogen, C$_{1-6}$ alkyl, C$_{2-6}$ alkenyl, C$_{1-6}$ haloalkyl, C$_{3-8}$ cycloalkyl, heterocyclyl, aryl, arylC$_{1-6}$ alkyl, heteroaryl, or heteroarylC$_{1-6}$ alkyl wherein the alkyl, aryl, arylalkyl, heteroaryl, and heteroarylalkyl are optionally substituted with one, two, three, or four groups that are each independently halogen, cyano, nitro, C$_{1-6}$ alkyl, C$_{1-6}$ haloalkyl, —OR$^0$, —SR$^0$, —N(R$^0$)$_2$, —C(O)R$^0$, —C(O)OR$^0$, —C(O)N(R$^0$)$_2$, —S(O)$_2$R$^0$, —OC(O)R$^0$, —OC(O)OR$^0$, —OC(O)N(R$^0$)$_2$, —N(R$^0$)C(O)R$^0$, —N(R$^0$)C(O)OR$^0$, or —N(R$^0$)C(O)N(R$^0$)$_2$, wherein each R$^0$ is independently hydrogen or C$_{1-6}$ alkyl.

2. The compound of claim 1, wherein R$^3$ is

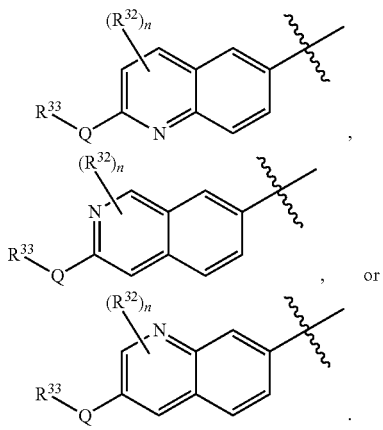

3. The compound of claim 1, wherein R$^3$ is

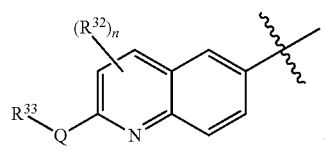

4. The compound of claim 3, wherein Q is —O— or —N(R$^Q$)—.

5. The compound of claim 4, wherein $R^{33}$ is $C_{1-6}$ alkyl, $C_{2-6}$ alkenyl, aryl$C_{1-6}$ alkyl, or heteroaryl$C_{1-6}$ alkyl, wherein the arylalkyl and heteroarylalkyl are optionally substituted with one, two, three, or four groups that are each independently halogen, cyano, nitro, $C_{1-6}$ alkyl, $C_{1-6}$ haloalkyl, —$OR^{20}$, —$SR^{20}$, —$N(R^{20})_2$, —$C(O)R^{20}$, —$C(O)OR^{20}$, —$C(O)N(R^{20})_2$, —$S(O)_2R^{20}$, —$OC(O)R^{20}$, —$OC(O)OR^{20}$, —$OC(O)N(R^{20})_2$, —$N(R^{20})C(O)R^{20}$, —$N(R^{20})C(O)OR^{20}$, or —$N(R^{20})C(O)N(R^{20})_2$, wherein each $R^{20}$ is independently hydrogen or $C_{1-6}$ alkyl.

6. The compound of claim 3, wherein $R^1$ is —$CH_2$—$R^{12}$.

7. The compound of claim 6, wherein $R^{12}$ is phenyl, monocyclic heteroaryl, $C_{3-8}$ cycloalkyl, or monocyclic heterocyclyl, wherein the phenyl, heteroaryl, $C_{3-8}$ cycloalkyl, and heterocyclyl groups are each optionally substituted by one, two, or three groups that are each independently halogen, cyano, nitro, $C_{1-6}$ alkyl, $C_{1-6}$ haloalkyl, —OR, —SR, —$NR_2$, —C(O)R, —C(O)OR, —$C(O)NR_2$, —$S(O)_2R$, —OC(O)R, —OC(O)OR, —$OC(O)NR_2$, —N(R)C(O)R, —N(R)C(O)OR, or —$N(R)C(O)NR_2$.

8. The compound of claim 6, wherein $R^{12}$ is piperidinyl optionally substituted by one or two groups that are each independently $C_{1-6}$ alkyl, —C(O)R, —C(O)OR, —$C(O)NR_2$, —$S(O)_2R$, —OC(O)R, —OC(O)OR, —$OC(O)NR_2$, —N(R)C(O)R, —N(R)C(O)OR, or —$N(R)C(O)NR_2$.

9. A compound, which is:
6-(4-amino-1-(piperidin-4-ylmethyl)-1H-pyrazolo[3,4-d]pyrimidin-3-yl)-N,N-dimethylquinolin-2-amine;
1-isopropyl-3-(quinolin-3-yl)-1H-pyrazolo[3,4-d]pyrimidin-4-amine;
1-(piperidin-4-ylmethyl)-3-(quinolin-3-yl)-1H-pyrazolo[3,4-d]pyrimidin-4-amine;

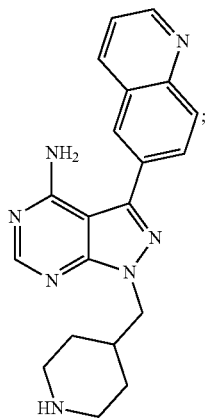 [SMILES: Nc1ncnc2c1c(-c1ccc3ncccc3c1)nn2CC1CCNCC1]

or
a pharmaceutically acceptable salt thereof.

10. A method for treating an apicomplexan protozoan related disease comprising providing to a patient in need of such treatment a therapeutically effective amount of a compound of claim 1, or a pharmaceutical composition comprising said compound and a pharmaceutically acceptable excipient, carrier, or diluent.

11. The method of claim 10, wherein the apicomplexan protozoan related disease is toxoplasmosis, cryptosporidiosis, coccidiosis, or malaria.

12. The compound of claim 1, wherein n is 0 or 1.

13. The compound of claim 12, wherein
$R^1$ is —$CH_2$—$R^{12}$; and
$R^3$ is

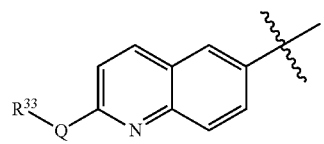

14. The compound of claim 13, wherein $R^{33}$ is $C_{1-6}$ alkyl, $C_{2-6}$ alkenyl, aryl$C_{1-6}$ alkyl, or heteroaryl$C_{1-6}$ alkyl, wherein the arylalkyl and heteroarylalkyl are each substituted with one or two groups that are each independently halogen, $C_{1-6}$ alkyl, or $C_{1-6}$ haloalkyl.

15. The compound of claim 14, wherein Q is —O— or —$N(R^Q)$—.

16. The compound of claim 15, wherein $R^{33}$ is $C_{1-6}$ alkyl.

17. The compound of claim 16, wherein $R^{12}$ is piperidinyl optionally substituted by one or two groups that are each independently $C_{1-6}$ alkyl, —C(O)R, —C(O)OR, —$C(O)NR_2$, —$S(O)_2R$, —OC(O)R, —OC(O)OR, —$OC(O)NR_2$, —N(R)C(O)R, —N(R)C(O)OR, or —$N(R)C(O)NR_2$.

18. The compound of claim 16, wherein $R^{12}$ is

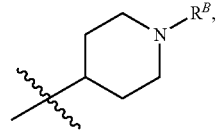

wherein $R^B$ is hydrogen, $C_{1-6}$ alkyl, —$C(O)R^A$, or —$S(O)_2R^A$, wherein each $R^A$ is independently hydrogen or $C_{1-6}$ alkyl.

19. The compound of claim 18, wherein Q is —O—.

20. The compound of claim 18, wherein $R^B$ is hydrogen or $C_{1-6}$ alkyl.

21. The compound of claim 20, wherein Q is —O—, —N(H)— or —$N(CH_3)$—.

22. The compound of claim 20, wherein Q is —O—.

* * * * *

SEQUENCE LISTING

<160> NUMBER OF SEQ ID NOS: 17

<210> SEQ ID NO 1
<211> LENGTH: 19
<212> TYPE: PRT
<213> ORGANISM: Toxoplasma gondii

<400> SEQUENCE: 1

Gly Tyr Phe Tyr Leu Val Gly Glu Val Tyr Thr Gly Gly Glu Leu Phe
1               5                   10                  15

Asp Glu Ile

<210> SEQ ID NO 2
<211> LENGTH: 19
<212> TYPE: PRT
<213> ORGANISM: Cryptosporidium parvum

<400> SEQUENCE: 2

Ser Ser Phe Tyr Ile Val Gly Glu Leu Tyr Thr Gly Gly Glu Leu Phe
1               5                   10                  15

Asp Glu Ile

<210> SEQ ID NO 3
<211> LENGTH: 45
<212> TYPE: DNA
<213> ORGANISM: Artificial Sequence
<220> FEATURE:
<223> OTHER INFORMATION: Synthetic

<400> SEQUENCE: 3
ggctacttct acctcgtcat ggaagtgtac acgggaggcg agttg        45

<210> SEQ ID NO 4
<211> LENGTH: 45
<212> TYPE: DNA
<213> ORGANISM: Artificial Sequence
<220> FEATURE:
<223> OTHER INFORMATION: Synthetic

<400> SEQUENCE: 4
caactcgcct cccgtgtaca cttccatgac gaggtagaag tagcc        45

<210> SEQ ID NO 5
<211> LENGTH: 19
<212> TYPE: PRT
<213> ORGANISM: Toxoplasma gondii

<400> SEQUENCE: 5

Arg Asn Tyr Tyr Leu Val Met Glu Val Tyr Arg Gly Gly Glu Leu Phe
1               5                   10                  15

Asp Glu Ile

<210> SEQ ID NO 6
<211> LENGTH: 19
<212> TYPE: PRT
<213> ORGANISM: Eimeria tenella

<400> SEQUENCE: 6

Gly Tyr Phe Tyr Leu Val Thr Glu Val Tyr Thr Gly Gly Glu Leu Phe
1               5                   10                  15

Asp Glu Ile

<210> SEQ ID NO 7
<211> LENGTH: 19
<212> TYPE: PRT
<213> ORGANISM: Plasmodium falciparum

<400> SEQUENCE: 7

```
Lys Tyr Phe Tyr Leu Val Thr Glu Phe Tyr Glu Gly Gly Glu Leu Phe
1               5                   10                  15

Glu Gln Ile

<210> SEQ ID NO 8
<211> LENGTH: 19
<212> TYPE: PRT
<213> ORGANISM: Plasmodium falciparum

<400> SEQUENCE: 8

Asn Tyr Tyr Tyr Leu Val Ser Asp Val Thr Thr Gly Gly Glu Leu Phe
1               5                   10                  15

Asp Glu Ile

<210> SEQ ID NO 9
<211> LENGTH: 19
<212> TYPE: PRT
<213> ORGANISM: Homo sapiens

<400> SEQUENCE: 9

Gly His Leu Tyr Leu Ile Met Gln Leu Val Ser Gly Gly Glu Leu Phe
1               5                   10                  15

Asp Arg Ile

<210> SEQ ID NO 10
<211> LENGTH: 19
<212> TYPE: PRT
<213> ORGANISM: Xenopus tropicalis

<400> SEQUENCE: 10

Gly Phe His Tyr Leu Val Phe Asp Leu Val Thr Gly Gly Glu Leu Phe
1               5                   10                  15

Glu Asp Ile

<210> SEQ ID NO 11
<211> LENGTH: 19
<212> TYPE: PRT
<213> ORGANISM: Macaca mulatta

<400> SEQUENCE: 11

Gly Phe His Tyr Leu Val Phe Asp Leu Val Thr Gly Gly Glu Leu Phe
1               5                   10                  15

Glu Asp Ile

<210> SEQ ID NO 12
<211> LENGTH: 15
<212> TYPE: PRT
<213> ORGANISM: Artificial Sequence
<220> FEATURE:
<223> OTHER INFORMATION: Synthetic

<400> SEQUENCE: 12

Pro Leu Ala Arg Thr Leu Ser Val Ala Gly Leu Pro Gly Lys Lys
1               5                   10                  15

<210> SEQ ID NO 13
<211> LENGTH: 507
<212> TYPE: PRT
<213> ORGANISM: Toxoplasma gondii

<400> SEQUENCE: 13

Met Gly Gln Gln Glu Ser Thr Leu Gly Gly Ala Ala Gly Glu Pro Arg
```

-continued

```
1               5                   10                  15
Ser Arg Gly His Ala Ala Gly Thr Ser Gly Gly Pro Gly Asp His Leu
                20                  25                  30
His Ala Thr Pro Gly Met Phe Val Gln His Ser Thr Ala Ile Phe Ser
                35                  40                  45
Asp Arg Tyr Lys Gly Gln Arg Val Leu Gly Lys Gly Ser Phe Gly Glu
                50                  55                  60
Val Ile Leu Cys Lys Asp Lys Ile Thr Gly Gln Glu Cys Ala Val Lys
65                  70                  75                  80
Val Ile Ser Lys Arg Gln Val Lys Gln Lys Thr Asp Lys Glu Ser Leu
                85                  90                  95
Leu Arg Glu Val Gln Leu Leu Lys Gln Leu Asp His Pro Asn Ile Met
                100                 105                 110
Lys Leu Tyr Glu Phe Phe Glu Asp Lys Gly Tyr Phe Tyr Leu Val Gly
                115                 120                 125
Glu Val Tyr Thr Gly Gly Glu Leu Phe Asp Glu Ile Ile Ser Arg Lys
                130                 135                 140
Arg Phe Ser Glu Val Asp Ala Ala Arg Ile Ile Arg Gln Val Leu Ser
145                 150                 155                 160
Gly Ile Thr Tyr Met His Lys Asn Lys Ile Val His Arg Asp Leu Lys
                165                 170                 175
Pro Glu Asn Leu Leu Leu Glu Ser Lys Ser Lys Asp Ala Asn Ile Arg
                180                 185                 190
Ile Ile Asp Phe Gly Leu Ser Thr His Phe Glu Ala Ser Lys Lys Met
                195                 200                 205
Lys Asp Lys Ile Gly Thr Ala Tyr Tyr Ile Ala Pro Glu Val Leu His
                210                 215                 220
Gly Thr Tyr Asp Glu Lys Cys Asp Val Trp Ser Thr Gly Val Ile Leu
225                 230                 235                 240
Tyr Ile Leu Leu Ser Gly Cys Pro Pro Phe Asn Gly Ala Asn Glu Tyr
                245                 250                 255
Asp Ile Leu Lys Lys Val Glu Lys Gly Lys Tyr Thr Phe Glu Leu Pro
                260                 265                 270
Gln Trp Lys Lys Val Ser Glu Ser Ala Lys Asp Leu Ile Arg Lys Met
                275                 280                 285
Leu Thr Tyr Val Pro Ser Met Arg Ile Ser Ala Arg Asp Ala Leu Asp
                290                 295                 300
His Glu Trp Ile Gln Thr Tyr Thr Lys Glu Gln Ile Ser Val Asp Val
305                 310                 315                 320
Pro Ser Leu Asp Asn Ala Ile Leu Asn Ile Arg Gln Phe Gln Gly Thr
                325                 330                 335
Gln Lys Leu Ala Gln Ala Ala Leu Leu Tyr Met Gly Ser Lys Leu Thr
                340                 345                 350
Ser Gln Asp Glu Thr Lys Glu Leu Thr Ala Ile Phe His Lys Met Asp
                355                 360                 365
Lys Asn Gly Asp Gly Gln Leu Asp Arg Ala Glu Leu Ile Glu Gly Tyr
                370                 375                 380
Lys Glu Leu Met Arg Met Lys Gly Gln Asp Ala Ser Met Leu Asp Ala
385                 390                 395                 400
Ser Ala Val Glu His Glu Val Asp Gln Val Leu Asp Ala Val Asp Phe
                405                 410                 415
Asp Lys Asn Gly Tyr Ile Glu Tyr Ser Glu Phe Val Thr Val Ala Met
                420                 425                 430
```

Asp Arg Lys Thr Leu Leu Ser Arg Glu Arg Leu Glu Arg Ala Phe Arg
        435                 440                 445

Met Phe Asp Ser Asp Asn Ser Gly Lys Ile Ser Ser Thr Glu Leu Ala
    450                 455                 460

Thr Ile Phe Gly Val Ser Asp Val Asp Ser Glu Thr Trp Lys Ser Val
465                 470                 475                 480

Leu Ser Glu Val Asp Lys Asn Asn Asp Gly Glu Val Asp Phe Asp Glu
                485                 490                 495

Phe Gln Gln Met Leu Leu Lys Leu Cys Gly Asn
            500                 505

<210> SEQ ID NO 14
<211> LENGTH: 538
<212> TYPE: PRT
<213> ORGANISM: Cryptosporidium parvum

<400> SEQUENCE: 14

Met Gly Asn Thr Ala Val Gly Asn Thr Gly Thr Arg Leu Arg Ala Pro
1               5                   10                  15

Val Asp Ala Val Val Asn Thr Thr Asn Lys Lys Ala Pro Val Ser Glu
            20                  25                  30

Lys Pro Ser Gln Pro Gln Ile Pro Asn Lys Thr Ser Asp Val Lys Lys
        35                  40                  45

Gly Gly Thr Met Gly Gly Glu Arg Gly Ser Val Thr Thr Gly Met Phe
    50                  55                  60

Val Gln Ser Gly Ser Gly Thr Phe Ala Glu Arg Tyr Asn Ile Val Cys
65                  70                  75                  80

Met Leu Gly Lys Gly Ser Phe Gly Glu Val Leu Lys Cys Lys Asp Arg
                85                  90                  95

Ile Thr Gln Gln Glu Tyr Ala Val Lys Val Ile Asn Lys Ala Ser Ala
            100                 105                 110

Lys Asn Lys Asp Thr Ser Thr Ile Leu Arg Glu Val Glu Leu Leu Lys
        115                 120                 125

Lys Leu Asp His Pro Asn Ile Met Lys Leu Phe Glu Ile Leu Glu Asp
    130                 135                 140

Ser Ser Ser Phe Tyr Ile Val Gly Glu Leu Tyr Thr Gly Gly Glu Leu
145                 150                 155                 160

Phe Asp Glu Ile Ile Lys Arg Lys Arg Phe Ser Glu His Asp Ala Ala
                165                 170                 175

Arg Ile Ile Lys Gln Val Phe Ser Gly Ile Thr Tyr Met His Lys His
            180                 185                 190

Asn Ile Val His Arg Asp Leu Lys Pro Glu Asn Ile Leu Leu Glu Ser
        195                 200                 205

Lys Glu Lys Asp Cys Asp Ile Lys Ile Ile Asp Phe Gly Leu Ser Thr
    210                 215                 220

Cys Phe Gln Gln Asn Thr Lys Met Lys Asp Arg Ile Gly Thr Ala Tyr
225                 230                 235                 240

Tyr Ile Ala Pro Glu Val Leu Arg Gly Thr Tyr Asp Glu Lys Cys Asp
                245                 250                 255

Val Trp Ser Ala Gly Val Ile Leu Tyr Ile Leu Leu Ser Gly Thr Pro
            260                 265                 270

Pro Phe Tyr Gly Lys Asn Glu Tyr Asp Ile Leu Lys Arg Val Glu Thr
        275                 280                 285

Gly Lys Tyr Ala Phe Asp Leu Pro Gln Trp Arg Thr Ile Ser Asp Asp

```
        290                 295                 300
Ala Lys Asp Leu Ile Arg Lys Met Leu Thr Phe His Pro Ser Leu Arg
305                 310                 315                 320

Ile Thr Ala Thr Gln Cys Leu Glu His Pro Trp Ile Gln Lys Tyr Ser
                325                 330                 335

Ser Glu Thr Pro Thr Ile Ser Asp Leu Pro Ser Leu Glu Ser Ala Met
            340                 345                 350

Thr Asn Ile Arg Gln Phe Gln Ala Glu Lys Lys Leu Ala Gln Ala Ala
        355                 360                 365

Leu Leu Tyr Met Ala Ser Lys Leu Thr Thr Leu Asp Glu Thr Lys Gln
370                 375                 380

Leu Thr Glu Ile Phe Arg Lys Leu Asp Thr Asn Asn Asp Gly Met Leu
385                 390                 395                 400

Asp Arg Asp Glu Leu Val Arg Gly Tyr His Glu Phe Met Arg Leu Lys
                405                 410                 415

Gly Val Asp Ser Asn Ser Leu Ile Gln Asn Glu Gly Ser Thr Ile Glu
            420                 425                 430

Asp Gln Ile Asp Ser Leu Met Pro Leu Leu Asp Met Asp Gly Ser Gly
        435                 440                 445

Ser Ile Glu Tyr Ser Glu Phe Ile Ala Ser Ala Ile Asp Arg Thr Ile
450                 455                 460

Leu Leu Ser Arg Glu Arg Met Glu Arg Ala Phe Lys Met Phe Asp Lys
465                 470                 475                 480

Asp Gly Ser Gly Lys Ile Ser Thr Lys Glu Leu Phe Lys Leu Phe Ser
                485                 490                 495

Gln Ala Asp Ser Ser Ile Gln Met Glu Glu Leu Glu Ser Ile Ile Glu
            500                 505                 510

Gln Val Asp Asn Asn Lys Asp Gly Glu Val Asp Phe Asn Glu Phe Val
        515                 520                 525

Glu Met Leu Gln Asn Phe Val Arg Asn Glu
530                 535

<210> SEQ ID NO 15
<211> LENGTH: 1617
<212> TYPE: DNA
<213> ORGANISM: Cryptosporidium parvum

<400> SEQUENCE: 15
atgggaaata ctgcagtagg gaatacagga acaaggctta gagcaccagt agatgccgta    60
gtaaacacta ctaataagaa agcacctgta agtgaaaagc catctcaacc acaaatacca   120
aacaaaactt ctgatgttaa aaagggagga actatgggag agagagagg aagtgtaaca   180 actggtatgt tgttcagag tggtagcggg acctttgcag aaaggtacaa tattgtatgt   240
atgcttggca aggttctttt tggagaagtt ttgaaatgta agacagaat cactcaacaa   300 gaatatgctg tcaaggttat taacaaagct agtgcaaaga acaaggatac tagtacaatt   360
ttgagagaag ttgagctttt aaagaagctt gatcatccaa atattatgaa gctattcgag   420
attttggaag attcatctag cttctacatt gtaggagagc tttacacagg aggagaactc   480
tttgatgaaa ttattaagag aaaaagattt agtgagcatg atgctgctag aattattaaa   540
caagtatttt caggaattac ttacatgcat aaacataaca ttgtacatag agatttaaag   600
ccagaaaaca tacttttaga gtctaaagaa aaagactgtg atattaaaat tatagatttt   660
ggattatcaa catgcttcca gcaaaatacc aagatgaagg atagaatagg aacagcctac   720
```

```
tatatagctc cagaagtttt gagaggtact tatgatgaga aatgtgatgt atggtcagct    780
ggagtaattc tatatattct cttatctgga cacctccat tctatggaaa aaatgaatat    840
gatattttga agagagtcga gacaggaaag tatgcttttg accttccaca atggagaact   900
atttctgatg atgccaagga tttaataaga aagatgttaa ctttccatcc ttctttgaga   960
attactgcaa cacaatgttt agaacatcca tggattcaaa atattcaag tgagactcca   1020 acaattagtg acttaccttc attagaatct gctatgacaa atattcgtca attccaagca   1080
gaaaagaaac ttgctcaagc agctctacta tatatggcaa gtaaattgac aacattggac   1140
gaaacaaagc aacttacaga gatctttagg aagttagata ctaataatga tggtatgtta   1200
gatagagatg agctcgttcg tggttatcat gaatttatga gattgaaagg agtagattct   1260
aattctttaa ttcagaatga aggatcaaca atagaggatc aaattgatag cttaatgcca   1320
ttgttagata tggatggatc gggttctata gaatattcag aatttattgc atctgcaata   1380
gatagaacaa ttttgttgag tagagaaaga atggaaagag ctttaaaat gtttgataaa   1440 gatggttctg gtaagatttc tacaaaggaa cttttaaac tcttttccca ggcagatagc   1500
agtattcaga tggaggagtt ggaatcaata attgaacaag ttgacaacaa taaggatggg   1560
gaagtagact ttaatgagtt tgtagaaatg cttcagaatt ttgtcaggaa tgaataa     1617

<210> SEQ ID NO 16
<211> LENGTH: 1617
<212> TYPE: DNA
<213> ORGANISM: Cryptosporidium parvum

<400> SEQUENCE: 16
atgggaaata ctgcagtagg gaatacagga acaaggctta gagcaccagt agatgccgta    60
gtaaacacta ctaataagaa agcacctgta agtgaaaagc catctcaacc acaaatacca   120
aacaaaactt ctgatgttaa aaagggagga actatgggag agagagagg aagtgtaaca   180 actggtatgt ttgttcagag tggtagcggg acctttgcag aaaggtacaa tattgtatgt   240
atgcttggca aaggttcttt tggagaagtt ttgaaatgta aagacagaat cactcaacaa   300
gaatatgctg tcaaggttat taacaaagct agtgcaaaga acaaggatac tagtacaatt   360
ttgagagaag ttgagctttt aaagaagctt gatcatccaa atattatgaa gctattcgag   420
attttggaag attcatctag cttctacatt gtaggagagc tttacacagg aggagaactc   480
tttgatgaaa ttattaagag aaaaagattt agtgagcatg atgctgctag aattattaaa   540
caagtatttt caggaattac ttacatgcat aaacataaca ttgtacatag agatttaaag   600
ccagaaaaca tacttttaga gtctaaagaa aaagactgtg atattaaaat tatagatttt   660
ggattatcaa catgcttcca gcaaaatacc aagatgaagg atagaatagg aacagcctac   720
tatatagctc cagaagtttt gagaggtact tatgatgaga aatgtgatgt atggtcagct   780
ggagtaattc tatatattct cttatctgga cacctccat tctatggaaa aaatgaatat   840
gatattttga agagagtcga gacaggaaag tatgcttttg accttccaca atggagaact   900
atttctgatg atgccaagga tttaataaga aagatgttaa ctttccatcc ttctttgaga   960
attactgcaa cacaatgttt agaacatcca tggattcaaa atattcaag tgagactcca   1020 acaattagtg acttaccttc attagaatct gctatgacaa atattcgtca attccaagca   1080
gaaaagaaac ttgctcaagc agctctacta tatatggcaa gtaaattgac aacattggac   1140
gaaacaaagc aacttacaga gatctttagg aagttagata ctaataatga tggtatgtta   1200
gatagagatg agctcgttcg tggttatcat gaatttatga gattgaaagg agtagattct   1260
```

-continued

| | |
|---|---|
| aattctttaa ttcagaatga aggatcaaca atagaggatc aaattgatag cttaatgcca | 1320 |
| ttgttagata tggatggatc gggttctata gaatattcag aatttattgc atctgcaata | 1380 |
| gatagaacaa ttttgttgag tagagaaaga atggaaagag cttttaaaat gtttgataaa | 1440 |
| gatggttctg gtaagatttc tacaaaggaa cttttaaac tcttttccca ggcagatagc | 1500 |
| agtattcaga tggaggagtt ggaatcaata attgaacaag ttgacaacaa taaggatggg | 1560 |
| gaagtagact ttaatgagtt tgtagaaatg cttcagaatt ttgtcaggaa tgaataa | 1617 |

<210> SEQ ID NO 17
<211> LENGTH: 1617
<212> TYPE: DNA
<213> ORGANISM: Cryptosporidium parvum

<400> SEQUENCE: 17

| | |
|---|---|
| atgggaaata ctgcagtagg gaatacagga acaaggctta gagcaccagt agatgccgta | 60 |
| gtaaacacta ctaataagaa agcacctgta agtgaaaagc catctcaacc acaaatacca | 120 |
| aacaaaactt ctgatgttaa aaagggagga actatgggag gagagagagg aagtgtaaca | 180 |
| actggtatgt tgttcagag tggtagcggg acctttgcag aaaggtacaa tattgtatgt | 240 |
| atgcttggca aaggttcttt tggagaagtt ttgaaatgta aagacagaat cactcaacaa | 300 |
| gaatatgctg tcaaggttat taacaaagct agtgcaaaga acaaggatac tagtacaatt | 360 |
| ttgagagaag ttgagctttt aaagaagctt gatcatccaa atattatgaa gctattcgag | 420 |
| attttggaag attcatctag cttctacatt gtaggagagc tttacacagg aggagaactc | 480 |
| tttgatgaaa ttattaagag aaaaagattt agtgagcatg atgctgctag aattattaaa | 540 |
| caagtatttt caggaattac ttacatgcat aaacataaca ttgtacatag agatttaaag | 600 |
| ccagaaaaca tacttttaga gtctaaagaa aaagactgtg atattaaaat tatagatttt | 660 |
| ggattatcaa catgcttcca gcaaaatacc aagatgaagg atagaatagg aacagcctac | 720 |
| tatatagctc cagaagtttt gagaggtact tatgatgaga aatgtgatgt atggtcagct | 780 |
| ggagtaattc tatatattct cttatctgga acacctccat tctatggaaa aaatgaatat | 840 |
| gatattttga agagagtcga gacaggaaag tatgcttttg accttccaca atggagaact | 900 |
| atttctgatg atgccaagga tttaataaga aagatgttaa ctttccatcc ttctttgaga | 960 |
| attactgcaa cacaatgttt agaacatcca tggattcaaa atattcaag tgagactcca | 1020 |
| acaattagtg acttaccttc attagaatct gctatgacaa atattcgtca attccaagca | 1080 |
| gaaaagaaac ttgctcaagc agctctacta tatatggcaa gtaaattgac aacattggac | 1140 |
| gaaacaaagc aacttacaga gatctttagg aagttagata ctaataatga tggtatgtta | 1200 |
| gatagagatg agctcgttcg tggttatcat gaatttatga gattgaaagg agtagattct | 1260 |
| aattctttaa ttcagaatga aggatcaaca atagaggatc aaattgatag cttaatgcca | 1320 |
| ttgttagata tggatggatc gggttctata gaatattcag aatttattgc atctgcaata | 1380 |
| gatagaacaa ttttgttgag tagagaaaga atggaaagag cttttaaaat gtttgataaa | 1440 |
| gatggttctg gtaagatttc tacaaaggaa cttttaaac tcttttccca ggcagatagc | 1500 |
| agtattcaga tggaggagtt ggaatcaata attgaacaag ttgacaacaa taaggatggg | 1560 |
| gaagtagact ttaatgagtt tgtagaaatg cttcagaatt ttgtcaggaa tgaataa | 1617 |